US009492540B2

(12) United States Patent
Korman et al.

(10) Patent No.: US 9,492,540 B2
(45) Date of Patent: *Nov. 15, 2016

(54) METHODS FOR TREATING CANCER USING ANTI-PD-1 ANTIBODIES

(71) Applicants: E. R. SQUIBB & SONS, L.L.C., Princeton, NJ (US); Ono Pharmaceutical Co., LTD., Osaka (JP)

(72) Inventors: Alan J. Korman, Piedmont, CA (US); Mohan Srinivasan, Cupertino, CA (US); Changyu Wang, Union City, CA (US); Mark J. Selby, San Francisco, CA (US); Bingliang Chen, Alameda, CA (US); Josephine M. Cardarelli, San Carlos, CA (US); Haichun Huang, San Carlos, CA (US)

(73) Assignees: Ono Pharmaceutical Co., Ltd., Osaka (JP); E.R. Squibb & Sons, L.L.C., Princeton, NJ (US)

( * ) Notice: Subject to any disclaimer, the term of this patent is extended or adjusted under 35 U.S.C. 154(b) by 226 days.

This patent is subject to a terminal disclaimer.

(21) Appl. No.: 14/270,750

(22) Filed: May 6, 2014

(65) Prior Publication Data

US 2014/0328833 A1    Nov. 6, 2014

Related U.S. Application Data

(60) Division of application No. 13/210,137, filed on Aug. 15, 2011, now Pat. No. 8,779,105, which is a continuation of application No. 11/913,217, filed as application No. PCT/JP2006/309606 on May 2, 2006, now Pat. No. 8,008,449.

(60) Provisional application No. 60/679,466, filed on May 9, 2005, provisional application No. 60/738,434, filed on Nov. 21, 2005, provisional application No. 60/748,919, filed on Dec. 8, 2005.

(51) Int. Cl.

| | | |
|---|---|---|
| A61K 39/395 | (2006.01) | |
| C07K 16/28 | (2006.01) | |
| C07K 16/18 | (2006.01) | |
| A61K 47/48 | (2006.01) | |
| C07K 16/46 | (2006.01) | |
| A61K 51/10 | (2006.01) | |
| A61K 39/00 | (2006.01) | |

(52) U.S. Cl.
CPC ..... *A61K 39/39558* (2013.01); *A61K 39/3955* (2013.01); *A61K 47/48561* (2013.01); *A61K 51/10* (2013.01); *C07K 16/18* (2013.01); *C07K 16/28* (2013.01); *C07K 16/2818* (2013.01); *C07K 16/468* (2013.01); *A61K 2039/505* (2013.01); *C07K 2316/96* (2013.01); *C07K 2317/21* (2013.01); *C07K 2317/24* (2013.01); *C07K 2317/52* (2013.01); *C07K 2317/56* (2013.01); *C07K 2317/565* (2013.01); *C07K 2317/73* (2013.01); *C07K 2317/732* (2013.01); *C07K 2317/74* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,324,514 A | 6/1994 | Sipos |
| 5,629,204 A | 5/1997 | Honjo et al. |
| 5,698,520 A | 12/1997 | Honjo et al. |
| 5,897,862 A | 4/1999 | Hardy et al. |
| 6,051,227 A | 4/2000 | Allison et al. |
| 6,632,927 B2 | 10/2003 | Adair et al. |
| 6,632,976 B1 | 10/2003 | Tomizuka et al. |
| 6,803,192 B1 | 10/2004 | Chen |
| 6,808,710 B1 | 10/2004 | Wood et al. |
| 6,936,704 B1 | 8/2005 | Freeman et al. |
| 7,029,674 B2 | 4/2006 | Carreno et al. |

(Continued)

FOREIGN PATENT DOCUMENTS

| | | |
|---|---|---|
| AU | 774391 B2 | 6/2004 |
| EP | 0 670 369 | 6/1995 |

(Continued)

OTHER PUBLICATIONS

Berman, D., et al., "The Development of Immunomodulatory Monoclonal Antibodies as a New Therapeutic Modality for Cancer: The Bristol-Myers Squibb Experience," *Pharmacology and Therapeutics* 148:132-153, Elsevier, Inc., England (Apr. 2015).

(Continued)

*Primary Examiner* — Ilia Ouspenski
(74) *Attorney, Agent, or Firm* — Sterne, Kessler, Goldstein & Fox P.L.L.C.

(57) ABSTRACT

The present invention provides isolated monoclonal antibodies, particularly human monoclonal antibodies, that specifically bind to PD-1 with high affinity. Nucleic acid molecules encoding the antibodies of the invention, expression vectors, host cells and methods for expressing the antibodies of the invention are also provided. Immunoconjugates, bispecific molecules and pharmaceutical compositions comprising the antibodies of the invention are also provided. The invention also provides methods for detecting PD-1, as well as methods for treating various diseases, including cancer and infectious diseases, using anti-PD-1 antibodies. The present invention further provides methods for using a combination immunotherapy, such as the combination of anti-CTLA-4 and anti-PD-1 antibodies, to treat hyperproliferative disease, such as cancer. The invention also provides methods for altering adverse events related to treatment with such antibodies individually.

79 Claims, 58 Drawing Sheets

(56) References Cited

U.S. PATENT DOCUMENTS

| | | | |
|---|---|---|---|
| 7,041,474 | B2 | 5/2006 | Kingsbury |
| 7,101,550 | B2 | 9/2006 | Wood et al. |
| 7,105,328 | B2 | 9/2006 | Wood et al. |
| 7,122,372 | B2 | 10/2006 | Hardy et al. |
| 7,329,639 | B2 | 2/2008 | Hardy et al. |
| 7,332,582 | B2 | 2/2008 | Hardy et al. |
| 7,423,128 | B2 | 9/2008 | Gazit-Bornstein et al. |
| 7,488,802 | B2 | 2/2009 | Collins et al. |
| 7,563,869 | B2 | 7/2009 | Honjo et al. |
| 7,595,048 | B2 | 9/2009 | Honjo et al. |
| 7,794,710 | B2 | 9/2010 | Chen et al. |
| 7,858,746 | B2 | 12/2010 | Honjo et al. |
| 8,008,449 | B2 | 8/2011 | Korman et al. |
| 8,168,179 | B2 | 5/2012 | Honjo et al. |
| 8,728,474 | B2 | 5/2014 | Honjo et al. |
| 8,779,105 | B2 | 7/2014 | Korman et al. |
| 9,067,999 | B1 | 6/2015 | Honjo et al. |
| 9,073,994 | B2 | 7/2015 | Honjo et al. |
| 9,084,776 | B2 | 7/2015 | Korman et al. |
| 2002/0164600 | A1 | 11/2002 | Freeman et al. |
| 2003/0232323 | A1 | 12/2003 | Freeman et al. |
| 2004/0073957 | A1 | 4/2004 | Tomizuka et al. |
| 2004/0175380 | A1 | 9/2004 | Allison et al. |
| 2004/0241745 | A1 | 12/2004 | Honjo et al. |
| 2006/0110383 | A1 | 5/2006 | Honjo et al. |
| 2007/0065427 | A1 | 3/2007 | Freeman et al. |
| 2007/0202100 | A1 | 8/2007 | Wood et al. |
| 2008/0025979 | A1 | 1/2008 | Honjo et al. |
| 2011/0081341 | A1 | 4/2011 | Honjo et al. |
| 2013/0133091 | A1 | 5/2013 | Korman et al. |
| 2014/0212422 | A1 | 7/2014 | Korman et al. |
| 2014/0294852 | A1 | 10/2014 | Korman et al. |
| 2014/0314714 | A1 | 10/2014 | Honjo et al. |
| 2014/0348743 | A1 | 11/2014 | Korman et al. |
| 2015/0093380 | A1 | 4/2015 | Honjo |
| 2015/0165025 | A1 | 6/2015 | Korman et al. |
| 2015/0197572 | A1 | 7/2015 | Honjo et al. |

FOREIGN PATENT DOCUMENTS

| | | |
|---|---|---|
| EP | 0 742 795 | 9/1998 |
| EP | 1 445 264 | 8/2004 |
| EP | 1 537 878 | 6/2005 |
| EP | 1 591 527 | 11/2005 |
| EP | 2206517 A1 | 7/2010 |
| EP | 2243493 A1 | 10/2010 |
| EP | 2161336 B1 | 7/2013 |
| JP | 07291996 A | 11/1995 |
| JP | 2002-194491 | 7/2002 |
| JP | 2003-029846 | 6/2003 |
| JP | 2004512005 A | 4/2004 |
| WO | WO/97/07671 | 3/1997 |
| WO | WO 00/32231 | 6/2000 |
| WO | WO 00/71078 | 11/2000 |
| WO | WO 01/14424 | 3/2001 |
| WO | WO 01/14557 | 3/2001 |
| WO | WO-0139722 A2 | 6/2001 |
| WO | WO-0183750 A2 | 11/2001 |
| WO | WO-0183750 A3 | 11/2001 |
| WO | WO 02/00692 | 1/2002 |
| WO | WO 02/00730 | 1/2002 |
| WO | WO-0232378 A2 | 4/2002 |
| WO | WO-0234205 A2 | 5/2002 |
| WO | WO 02/078731 | 10/2002 |
| WO | WO 02/079499 | 10/2002 |
| WO | WO 02/086083 | 10/2002 |
| WO | WO 03/006636 | 1/2003 |
| WO | WO 03/011911 | 2/2003 |
| WO | WO 03/033644 | 4/2003 |
| WO | WO 03/042402 | 5/2003 |
| WO | WO 03/099196 | 12/2003 |
| WO | WO 2004/004771 | 1/2004 |
| WO | WO 2004/056875 | 7/2004 |
| WO | WO 2004/072286 | 8/2004 |
| WO | WO 2005/003298 A2 | 1/2005 |
| WO | WO 2006/021955 | 3/2006 |
| WO | WO 2006/121168 | 11/2006 |
| WO | WO 2006/124269 | 11/2006 |
| WO | WO-2007005874 A2 | 1/2007 |
| WO | WO-2013173223 A1 | 11/2013 |

OTHER PUBLICATIONS

Complaint, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Case 1:15-cv-00560-GMS, United States District Court for the District of Delaware, Jun. 30, 2015, 49 pages.

Complaint, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Case 1:15-cv-00572-GMS, United States District Court for the District of Delaware, Jul. 7, 2015, 48 pages.

Declaration of James L. Riley, Ph.D., Aug. 10, 2015, 6 pages, submitted with Response to Grounds of Appeal, in European Patent No. 1537878.

Greenwald, R.J., et al., "Negative Co-receptors on Lymphocytes," *Current Opinion in Immunology* 14(3):391-396, Elsevier Science Ltd., England (Jun. 2002).

Minutes of the Oral Proceedings of Dec. 17, 2014, in European Patent No. EP 0921183, 3 pages.

Notice of Pre-grant Opposition mailed Jul. 21, 2015, in IN Patent Application No. 5057/CHENP/2007, Indian Pharmaceuticals Alliance, filed May 2, 2006.

Response to Grounds of Appeal, dated Aug. 12, 2015, in European Patent No. EP 1537878, 76 pages.

"Summary of a list of clinical trials available from the website ClinicalTrials.gov of the US National Institutes of Health," dated Aug. 10, 2015, 18 pages, submitted with Response to Grounds of Appeal in European Patent No. EP 1537878.

Brief Supporting Motion to Dismiss, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Case 1:15-cv-00560-GMS, United States District Court for the District of Delaware, Aug. 21, 2015, 25 pages.

Brief Supporting Motion to Dismiss, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Case 1:15-cv-00572-GMS, United States District Court for the District of Delaware, Aug. 28, 2015, 24 pages.

Declaration of Andrew C. Mayo, Aug. 21, 2015, 2 pages.

Declaration of John G. Day, Aug. 28, 2015, 2 pages.

Motion to Dismiss, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Case 1:15-cv-00560-GMS, United States District Court for the District of Delaware, Aug. 21, 2015. 3 pages.

Motion to Dismiss, *Bristol-Myers Squibb Co., E.R. Squibb & Sons L.L.C., Ono Pharmaceutical Co., Ltd., and Tasuku Honjo v. Merck &. Co., Inc. and Merck Sharp & Dohme Corp.*, Case 1:15-cv-00572-GMS, United States District Court for the District of Delaware, Aug. 28, 2015, 3 pages.

Nema, S., et al., "Excipients and Their Use in Injectable Products," *PDA J Pharm Sci Technol.* 51(4):166-171, Pda (Parenteral Drug Association), United States (1997).

Plaintiff's Objections and Responses Admission, *Bristol-Myers Squibb Co., E.R. Squibb & Sons L.L.C., Ono Pharmaceutical Co., Ltd., and Tasuku Honjo v Merck & Co., Inc. and Merck Sharp & Dohme Corp.*, C.A. No. 14-cv-1131-GMS, United States District Court for the District of Delaware, Jul. 1, 2015, 11 pages.

Van Dijk, M.A. and Van De Winkel J.G., "Human antibodies as next generation therapeutics," *Curr Opin Chem Biol.* 5(4)368-374, Elsevier Ltd., England (2001).

Office action mailed Nov. 18, 2015, in U.S. Appl. No. 14/227,733, inventors Korman. A., et al., filed Mar. 27, 2014.

Abbas, A.K., et al., Cellular and Molecular Immunobiology, 2nd ed., pp. 8, 47-50, W.B. Saunders Company, United States (1991).

(56) References Cited

OTHER PUBLICATIONS

Alignment of Amino Acid Sequences for Extracellular Domain of Wild-Type (UniProt Q15116) Human PD-1, Wild-Type (MednaBio) PD-1 ECD, C62S Variant of Wild-Type Human PD-1 ECD, and A101L Variant of Wild-Type Human PD-1 ECD, 1 pages, submitted with Opposition to EP Pat. No. 2161336 on Apr. 30, 2014.

Allison, J.P. and Krummel, M.F., "The Yin and Yang of T Cell Costimulation," Science 270(5238):932-933, American Association for the Advancement of Science, United States (1995).

Amended Complaint, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, C.A. No. 14-cv-1131-GMS, United States District Court for the District of Delaware, Nov. 21, 2014, 11 pages.

Andre, E., et al., "Precise Characterization of the Epitope Recognized by a Monoclonal Antibody Against *Escherichia coli* RNA Polymerase," Hybridoma 24(1):1-5, Mary Ann Liebert, Inc., United States (Feb. 2005).

Ansell, S.M., et al., "PD-1 Blockade with Nivolumab in Relapsed or Refractory Hodgkin's Lymphoma," The New England Journal of Medicine 372(4):311-319, Massachusetts Medical Society, United States (Jan. 22, 2015).

Answer to Complaint, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, C.A. No. 14-cv-1131-GMS, United States District Court for the District of Delaware, Oct. 31, 2014, 15 pages.

Answer to Plaintiffs' Amended Complaint, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, C.A. No. 14-cv-1131-GMS, United States District Court for the District of Delaware, Dec. 8, 2014, 17 pages.

Anti-Human CD279 (PD-1) Datasheet, 14-2799, J105, eBioscience, Sep. 6, 2013, 1 page.

Anti-Human CD279 (PD-1) Datasheet, 14-9989, J116, eBioscience, Sep. 6, 2013, 1 page.

Anti-Human CD279 (PD-1) Purchase Receipts, eBioscience, Oct. 8, 2013, 4 pages.

Antonia, S.J., et al., "Association of tumor PD-L1 Expression and Immune Biomarkers with Clinical Activity in Patients with Non-small Cell Lung Cancer (NSCLC) Treated with Nivolumab (Anti-PD-1; BMS-936558; ONO-4538)," 15th World Conference on Lung Cancer, Sydney, Australia, 15th WCLC: Best of Posters 1—IASLC Selection, P2.11-035, Oct. 27-30, 2013, accessed at http://web.oncoletter.ch/kongressberichte-videos-slides-Onkologie/id-15th-world-conference-on-lung-cancer-conference/conference-highlights.html, accessed on Jan. 8, 2015, 6 pages.

Appendix to Declaration of Vassiliki A. Boussiotis, Apr. 28, 2014, Data and Records for Example Experiments 21 and 22, 18 pages.

Armand, P., et al., "289 Nivolumab in Patients with Relapsed or Refractory Hodgkin Lymphoma—Preliminary Safety, Efficacy and Biomarker Results of a Phase I Study," 56th ASH Annual Meeting and Exposition, Abstracts & Program, San Francisco, CA, Dec. 6-9, 2014.

Berg, J.M., et al., "The Immune System," in Biochemistry 5th ed., pp. 921-950, W.H. Freeman and Company, United States (2002).

Biacore, "Application Note 1: Characterization of monoclonal antibody epitope specificity using Biacore's SPR technology," Biacore AB, 8 pages (2002).

Biacore, Sensor Surface Handbook, BR-1005-71, edition AB, pp. 1-98, GE Healthcare (Feb. 2005).

Biacore, "The SPR signal, " "Interpreting experimental data," and "BIA application areas," in BIAtechnology Handbook, version AB, chapters 4-6, 34 pages, Biacore AB (1998).

Campbell, A.M., "Characterisation of monoclonal antibodies," in Laboratory Techniques in Biochemistry and Molecular Biology, Monoclonal Antibody Technology: The Production and Characterization of Rodent and Human Hybridomas, vol. 13, pp. 186-215, Elsevier, the Netherlands (1984).

CD279/PD-1, D132-3/J110 Datasheet, MBL Medical & Biological Laboratories Co., Ltd., Sep. 6, 2013, 2 pages.

Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).

Communication pursuant to Article 94(3) EPC mailed on Dec. 22, 2014, in European Application No. 11 178 187.8-1410, European Patent Office, Germany.

Communication pursuant to Article 94(3) EPC mailed on Dec. 22, 2014, in European Application No. 11 178 191.0-1410, European Patent Office, Germany.

Communication pursuant to Rule 114(2) EPC, mailed Jul. 17, 2014, Third Party Observations (Article 115 EPC) for Application No. EP20110178187, European Patent Office, Germany.

Communication pursuant to Rule 114(2) EPC, mailed Jul. 17, 2014, Third Party Observations (Article 115 EPC) for Application No. EP20110178188, European Patent Office, Germany.

Communication pursuant to Rule 114(2) EPC, mailed Jul. 17, 2014, Third Party Observations (Article 115 EPC) for Application No. EP20110178191, European Patent Office, Germany.

Complaint, *Bristol-Myers Squibb Co. and Ono Pharmaceutical Co., Ltd. v. Merck & Co., Inc.*, 1:14-cv-01131-GMS, filed Sep. 4, 2014, 9 pages.

Co-pending U.S. Appl. No. 14/547,026, inventors Korman, A.J., et al., filed Nov. 18, 2014 (Not Published).

Co-pending U.S. Appl. No. 14/638,985, inventors Honjo, T., et al., filed Mar. 4, 2015 (Not Published).

Cragg, M.S., et al., "Complement-mediated lysis by anti-CD20 mAb correlates with segregation into lipid rafts," Blood 101(3):1045-1052, American Society of Hematology, United States (2003).

Creelan, B.C., "Update on Immune Checkpoint Inhibitors in Lung Cancer," Journal of the Moffitt Cancer Center 21(1):80-89, H. Lee Moffitt Cancer Center and Research Institute, United States (2014).

Cruse, J.M. and Lewis, R.E., "Antigens and Immunogens," in Atlas of Immunology, 2nd ed., pp. 105-126, CRC Press, United States (Dec. 29, 2003).

Curriculum Vitae of Brian T. Fife, Ph.D., 7 pages, submitted with Response to Oppositions against EP Pat. No. 2161336 on Feb. 16, 2015.

Curriculum Vitae of Dr. Robert J. Bloch, Apr. 11, 2012, 34 pages, submitted with Opposition to EP Pat. No. 2161336.

Curriculum Vitae of Vassiliki A. Boussiotis, Nov. 8, 2013, 24 pages, submitted with Opposition to EP Pat. No. 2161336.

Davies, D.R. and Cohen, G.H., "Interactions of protein antigens with antibodies," Proceedings of the National Academy of Sciences USA 93(1):7-12, National Academy of Sciences, United States (1996).

Declaration of Dr. Haidong Dong, Mar. 31, 2014, 15 pages, submitted with Opposition to EP Pat. No. 1537878.

Declaration of Professor Brian T. Fife, Feb. 12, 2015, 4 pages, submitted with Response to Oppositions against EP Pat. No. 2161336.

Del Rio, M-L., et al., "Antibody-mediated signaling through PD-1 costimulates T cells and enhances CD28-dependent proliferation," European Journal of Immunology 35(12):3545-3560, Wiley-VCH Verlag GmbH & Co. KGaA, Germany (Dec. 2005).

Dougan, D.A., et al., "Effects of substitutions in the binding surface of an antibody on antigen affinity," Protein Engineering 11(1):65-74, Oxford University Press, England (1998).

Email from MednaBio to Robert Bloch re: E1951MG1-Sequence Information, Apr. 25, 2014, 1 page.

ExPASy Bioinformatics Resource Portal calculation based on ECD of UniProt Sequence Q15116, accessed at http://web.expasy.org/cgi-bin/compute_pi/pi_tool, accessed on Apr. 28, 2014, 1 page.

Extended European Search Report for EP Application No. 06746353.9, European Patent Office, Germany, mailed on Mar. 6, 2009.

Extended European Search Report for EP Application No. 09013687.0, European Patent Office, Germany, mailed on Jan. 29, 2010.

(56) References Cited

OTHER PUBLICATIONS

Extended European Search Report for EP Application No. 10172772.5, European Patent Office, Netherlands, mailed on Sep. 9, 2010.

Extended European Search Report for EP Application No. 11178187.8, European Patent Office, Germany, mailed on Jun. 1, 2012.

Extended European Search Report for EP Application No. 11178188.6, European Patent Office, Germany, mailed on Jun. 27, 2013.

Extended European Search Report for EP Application No. 11178191.0, European Patent Office, Germany, mailed on Sep. 5, 2012.

Fivash, M., et al., "BIAcore for macromolecular interaction," Current Opinion in Biotechnology 9(1):97-101, Current Biology, England (1998).

Franklin, M.C., et al., "Insights into ErbB signaling from the structure of the ErbB2-pertuzumab complex," Cancer Cell 5(4):317-328, Cell Press, United States (Apr. 2004).

Freeman, G.J., et al., "Engagement of the PD-1 Immunoinhibitory by a Novel B7-Family Member Leads to Negative Regulation of Lymphocyte Activation," Blood 96(11):810a-811a, (Abstract No. 3502) (2000).

Ge, X., et al., "CD134-Allodepletion Allows Selective Elimination of Alioreactive Human T Cells without Loss of Virus-Specific and Leukemia-Specific Effectors," Biology of Blood and Marrow Transplantation 14(5):518-530, American Society for Blood and Marrow Transplantation, United States (2008).

Greenspan, N.S., "Epitopes, paratopes and other topes: do immunologists know what they are talking about?" Bulletin de l'Institut Pasteur 90(4):267-279, Elsevier, France (1992).

Harlow, E. and Lane, D., "Using Antibodies: A Laboratory Manual," Cold Spring Harbor Laboratory Press, Cold Spring Harbor, United States various pages (1999).

International Preliminary Report on Patentability for International Application No. PCT/JP2006/309606, The International Bureau of WIPO, Switzerland, issued on Nov. 13, 2007.

International Search Report for International Application No. PCT/JP03/08420, Japanese Patent Office, Japan, mailed Oct. 21, 2003.

International Search Report for International Application No. PCT/JP2006/309606, Japanese Patent Office, Japan, mailed on Aug. 15, 2006.

Ishima, R. and Torchia, D.A., "Protein Dynamics from NMR," Nature Structural Biology 7(9):740-743, Nature Publishing Company, United States (2000).

J105/D133-3 Datasheet, MBL Medical & Biological Laboratories Co., Ltd., Mar. 20, 2013, 2 pages.

J105/D133-3 Purchase Order, MBL Medical & Biological Laboratories Co., Ltd., Apr. 11, 2014, 1 page.

J105/D133-3 Purchase Receipts, Invoice MINV52635, MBL International Corporation, Oct. 2, 2013, 2 pages.

Jason-Moller, L., et al., "Overview of Biacore Systems and Their Applications," Current Protocols in Protein Science S45:19.13.1-19.13.14, John Wiley & Sons, Inc., United States (2006).

Johne, B., "Protocol: Epitope Mapping by Surface Plasmon Resonance in the BIAcore," Molecular Biotechnology 9(1):65-71, Humana Press, United States (1998).

Kanai, T., et al., "Blockade of B7-H1 Suppresses the Development of Chronic Intestinal Inflammation," The Journal of Immunology 171(8):4156-4163, American Association of Immunologists, Inc., United States (2003).

Ladner, R.C., "Mapping the Epitopes of Antibodies," Biotechnology and Genetic Engineering Reviews 24(1):1-30, Taylor & Francis, England (2007).

Laricchia-Robbio, L., et al., "Mapping of Monoclonal Antibody- and Receptor-Binding Domains on Human Granulocyte-Macrophage Colony-Stimulating Factor (rhGM-CSF) Using a Surface Plasmon Resonance-Based Biosensor," Hybridoma 15(5):343-350, Mary Ann Liebert, Inc., United States (1996).

Lesokhin, A.M., et al., "291 Preliminary Results of a Phase I Study of Nivolumab (BMS-936558) in Patients with Relapsed of Refractory Lymphoid Malignancies," 56th ASH Annual Meeting and Exposition, Abstracts & Program, San Francisco, CA, United States, Dec. 6-9, 2014.

Lewis, D.E., et al., "Tumor Necrosis Factor-$\alpha$ and CD80 Modulate CD28 Expression through a Similar Mechanism of T-cell Receptor-Independent Inhibition of Transcription," The Journal of Biological Chemistry 279(28):29130-29138, The American Society for Biochemistry and Molecular Biology, Inc., United States (Jul. 2004).

Li, L., et al., "A pathway regulated by cell cycle inhibitor p27Kip1 and checkpoint inhibitor Smad3 is involved in the induction of T cell tolerance," Nature Immunology 7(11):1157-1165, Nature Publishing, United States (2006).

Li, L., et al., "CD4+CD25+ regulatory T-cell lines from human cord blood have functional and molecular properties and T-cell anergy," Blood 106(9):3068-3073, American Society of Hematology, United States (Nov. 2005).

Li, L., et al., "IL-1beta-Mediated Signals Preferentially Drive Conversion of Regulatory T Cells but Not Conventional T Cells into IL-17-Producing Cells," The Journal of Immunology 185(7):4148-4153, American Association of Immunologists, Inc., United States (2010).

Li, L., et al., "Rap1-GTP is a Negative Regulator of Th Cell Function and Promotes the Generation of CD4+CD103+ Regulatory T Cells in Vivo," The Journal of Immunology 175(5):3133-3139, American Association of Immunologists, Inc., United States (Sep. 2005).

Li, L., et al., "The cyclin dependent kinase inhibitor (R)-roscovitine prevents alloreactive T cell clonal expansion and protects against acute GvHD," Cell Cycle 8(11):1794-1802, Landes Bioscience, United States (2009).

"List of Clinical Trials with Nivolumab from the website ClinicalTrials.gov of U.S. National Institutes of Health" submitted with Response to Oppositions against EP Pat. No. 2161336, mailed on Feb. 16, 2015, 11 pages.

Lute, K.D., et al., "Human CTLA4 knock-in mice unravel the quantitative link between tumor immunity and autoimmunity induced by anti-CTLA-4 antibodies," Blood 106(9):3127-3133, American Society of Hematology, United States (Nov. 2005).

May, K.F., Jr., et al., "Anti-human CTLA-4 monoclonal antibody promotes T-cell expansion and immunity in a hu-PBL-SCID model: a new method for preclinical screening of costimulatory monoclonal antibodies," Blood 105(3):1114-1120, American Society of Hematology, United States (Feb. 2005).

Nellore, A., et al., "The cyclin dependent kinase inhibitor (R)-roscovitine mediates selective suppression of alloreactive human T cells but preserves pathogen-specific and leukemia-specific effectors," Clinical Immunology 152(1-2):48-57 (May-Jun. 2014; Epub Mar. 12, 2014).

Nomi, T., et al., "Clinical significance and therapeutic potential of the programmed death-1 ligand/programmed death-1 pathway in human pancreatic cancer," Clinical Cancer Research 13(7):2151-2157, The Association, United States (2007).

Office Action mailed Apr. 13, 2015, in U.S. Appl. No. 14/638,985, inventors Honjo, T., et al., filed Mar. 4, 2015.

Office Action mailed Jan. 7, 2015, in U.S. Appl. No. 14/550,585, inventors Honjo, T., et al., filed Nov. 21, 2014.

Ono Pharmaceutical Co., Ltd Research Center Search Research Institute, Ryoji Yagi (Test Director), "Study of the Antitumor Effects of Anti-mouse PD-1 (J43) in Mouse J558 Cell (myeloma) Subcutaneous Implantation Methods," Final Report, Test No. E03CT011, (planned test period: 2003-2004), 34 pages.

Ozaki, S., et al., "Immunotherapy of Multiple Myeloma with a Monoclonal Antibody Directed Against a Plasma Cell-specific Antigen, HM1.24," Blood 90(8):3179-3186, American Society of Hematology, United States (1997).

Pardoll, D.M., "The blockade of immune checkpoints in cancer immunotherapy," Nature Reviews Cancer 12(4):252-264, Nature Publishing Group, England (2012).

Patent Assignment Abstract of Title for U.S. Pat. No. 8,008,449, USPTO Assignments on the Web, accessed on Apr. 30, 2014, 2 pages.

(56) References Cited

OTHER PUBLICATIONS

Patsoukis, N., et al., "Selective Effects of PD-1 on Akt and Ras Pathways Regulate Molecular Components of the Cell Cycle and Inhibit T Cell Proliferation," Science Signaling 5(230): ra46, pp. 1-14, American Association for the Advancement of Science, United States (Jun. 2012).

Patsoukis, N., et al., "PD-1 Increases PTEN Phosphatase Activity While Decreasing PTEN Protein Stability by Inhibiting Casein Kinase 2," Molecular and Cellular Biology 33(16):3091-3098, American Society for Microbiology, United States (Aug. 2013).

Patsoukis, N., et al., "PD-1 inhibits T cell proliferation by upregulating p27 and p15 and suppressing Cdc25A," Cell Cycle 11(23):1-5, Landes Bioscience, United States (Dec. 2012).

Polyak, M.J. and Deans, J.P., "Alanine-170 and proline-172 are critical determinants for extracellular CD20 epitopes; heterogeneity in the fine specificity of CD20 monoclonal antibodies is defined by additional requirements imposed by both amino acid sequence and quaternary structure," Blood 99(9):3256-3262, American Society of Hematology, United States (2002).

Press Release from Bristol-Myers Squibb, "Bristol-Myers Squibb Receives Accelerated Approval of Opdivo (nivolumab) from the U.S. Food and Drug Administration," Dec. 22, 2014, 6 pages.

Press Release from ESMO, "ESMO 2014 Press Release: Nivolumab Shows Signs of Superior Response Rate Compared to Standard Chemotherapy in Advanced Melanoma," Sep. 29, 2014, 2 pages.

Press Release from Ono Pharmaceuticals Co., Ltd., "Human Antihuman PD-1 Monoclonal Antibody "OPDIVO(R) Intravenous Infusion 20 mg/100 mg" Receives Manufacturing and Marketing Approval in Japan for the Treatment of Unresectable Melanoma," Jul. 4, 2014, 2 pages.

Press-Release from Bristol-Myers Squibb, "CheckMate-017, A Phase 3 Study of Opdivo (Nivolumab) Compared to Docetaxel in Patients with Second-Line Squamous Cell Non-small Cell Lung Cancer, Stopped Early," Jan. 11, 2015, 5 pages.

Press-Release from Bristol-Myers Squibb, "Phase 3 First-Line Melanoma Study of Nivolumab, an Investigational PD-1 Checkpoint Inhibitor, Demonstrates Superior Overall Survival Compared to Dacarbazine; Study Stopped Early," Jun. 24, 2014, 3 pages.

Product Insert for Keytruda(R) (pembrolizumab), Merck & Co., Inc., United States, issued 2014.

Product Insert for Opdivo(R) (nivolumab), Bristol-Myers Squibb Company, United States, issued Mar. 2015.

Product Specifications for AffiniPure Goat Anti-Human IgG, Fcγ Fragment Specific (minimal cross-reaction to Bovine, Horse, and Mouse Serum Proteins), Code No. 109-005-098, Lot No. 111632, Jackson ImmunoResearch Laboratories, Inc., Sep. 12, 2013, 1 page.

Product Specifications for AffiniPure Goat Anti-Mouse IgG, Fcγ Fragment Specific (minimal cross-reaction to Human, Bovine, and Horse Serum), Code No. 115-005-071, Lot No. 111143, Jackson ImmunoResearch Laboratories, Inc., Sep. 12, 2013, 1 page.

Response to Oppositions, mailed Feb. 16, 2015, in European Patent No. EP 2161336, Ono Pharmaceutical Co., Ltd. and Medarex, Inc., 27 pages.

Riley, J.L. and June, C.H., "The CD28 family: a T-cell rheostat for therapeutic control of T-cell activation," Blood 105(1):13-21, American Society of Hematology, United States (Jan. 2005).

Schmidt, M., et al., "Synergistic Interaction Between an Antip185HER-2 pseudomonas Exotoxin Fusion Protein [scFv(FRP5)-ETA] and Ionizing Radiation for Inhibiting Growth of Ovarian Cancer Cells that Overexpress HER-2," Gynecologic Oncology 80(2):145-155, Academic Press, United States (2001).

Second Declaration of Andrea Van Elsas, Ph.D., including exhibits 1-3, Jan. 22, 2015, submitted with Statement of Grounds of Appeal for EP Pat. No. 1537878, mailed on Feb. 3, 2015, 67 pages.

Sho, M., et al., "Effect of Blocking T Cell Negative Pathway on Cancer Metastasis," Article for the Annual Meeting of the Japanese Cancer Association 64:59 (W-102) (Aug. 2005).

Sho, M., et al., "Possibility of Clinical Applications for Novel Cancer Immunotherapy via Inhibition of T-cell Negative Pathway," Magazine of the Japan Society of Clinical Oncology 40(2):590 (PS22-5) (Sep. 2005).

Soh, E.Y., et al., "Neutralizing vascular endothelial growth factor activity inhibits thyroid cancer growth in vivo," Surgery 128(6):1059-1066, Mosby, United States (2000).

Statement of Grounds of Appeal mailed Feb. 3, 2015 for European Patent No. EP 1 537 878, European Patent Office, Munich, Germany, 107 pages.

Summary of Clinical Trial List, Search of: Nivolumab, ClinicalTrials.gov, accessed at https://www.clinicaltrials.gov/ct2/results?term—nivolumab&pg=1, accessed on Sep. 2, 2015, 7 pages.

Tchekmedyian, S., et al., Abstract 56, p. 15a and Davis, T.A., et al., Abstract 74, p. 19a, Proceedings of the American Society of Clinical Oncology, Thirty-Eighth Annual Meeting, Abstracts, Orlando, Florida, United States (May 18-21, 2002).

Teeling, J.L., et al., "Characterization of new human CD20 monoclonal antibodies with potent cytolytic activity against non-Hodgkin lymphomas," Blood 104(6):1793-1800, American Society of Hematology, United States (Sep. 2004).

Topalian, S., et al., "Nivolumab (anti-PD-1; BMS-936558; ONO-4538) in patients with advanced solid tumors: Survival and long-term safety in a phase I trial," accessed at http://meetinglibrary.asco.org/content/113543-132, accessed on Feb. 2, 2015, 2 pages.

Topalian, S., "Q&A: Suzanne Topalian on Immune Therapies", Cancer Discovery 3(7):712, American Association for Cancer Research, United States, published online Jun. 27, 2013.

Topalian, S.I., et al., "Safety, Activity, and Immune Correlates of Anti-PD-1 Antibody in Cancer," The New England Journal of Medicine 366(26):2443-2454, Massachusetts Medical Society, United States (2012).

Tsai, C.-J., et al., "Protein allostery, signal transmission and dynamics: a classification scheme of allosteric mechanisms," Molecular BioSystems 5(3):207-216, Royal Society of Chemistry, England (2009).

UniProtKB/Swiss-Prot Database entry, PDCD 1_HUMAN, accessed at http://www.uniprot.org/uniprot/Q15116.txt, accessed on Apr. 29, 2014, 5 pages.

Unpublished 2003 Data Compilation ONK014_004_0000003, 446 pages.

Unpublished 2003 Data Compilation ONK015_001_0000003, 50 pages.

Unpublished 2003 Data Compilation, UBIC_Control_00010079343, 38 pages.

Unpublished 2003-2004 Data Compilation ONK23_005_0000003, 476 pages.

Unpublished 2004-2005 Data Compilation ONK014_005_0000003, 538 pages.

Van Regenmortel, M.H.V., "The Recognition of Proteins and Peptides by Antibodies," Journal of Immunoassay 21(2-3):85-108, Taylor & Francis, England (2000).

Van Regenmortel, M.H.V., "Structural and functional approaches to the study of protein antigenicity," Immunology Today 10(8):266-272, Elsevier Science Publishers, England (1989).

Weber, J.S., et al., "Safety, Efficacy, and Biomarkers of Nivolumab with Vaccine in Ipilimumab-Refractory or -Naive Melanoma," Journal of Clinical Oncology 31(34):4311-4318, American Society of Clinical Oncology, United States (2013).

Wilson, I.A. and Stanfield, R.L., "Antibody-antigen interactions," Current Opinion in Structural Biology 3:113-118, Current Biology, United States (1993).

Winslow, R., "New Cancer Drugs Harness Power of Immune System", The Wall Street Journal, May 15, 2013, accessed at http://www.wsj.com/articles/SB10001424127887323398204578485401089823868, accessed on Jan. 8, 2015, 4 pages.

Wolchok, J.D., et al., "Nivolumab plus Ipilimumab in Advanced Melanoma," The New England Journal of Medicine 369(2):122-133, Massachusetts Medical Society, United States (2013).

Wu, K-P., et al., "Structural Basis of a Flavivirus Recognized by Its Neutralizing Antibody: Solution Structure of the Domain III of the Japanese Encephalitis Virus Envelope Protein," The Journal of

(56) References Cited

OTHER PUBLICATIONS

Biological Chemistry 278(46):46007-46013, American Society for Biochemistry and Molecular Biology, Inc., United States (Nov. 2003).
Yi, J., et al., "Mapping the Epitope of an Inhibitory Monoclonal Antibody to the C-terminal DNA-binding Domain of HIV-I Integrase," The Journal of Biological Chemistry 277(14):12164-12174, American Society for Biochemistry and Molecular Biology, Inc., United States (2002).
Zou, W. and Chen, L., "Inhibitory B7-family Molecules in the Tumour Microenvironment," Nature Reviews Immunology 8(6):467-477, Nature Publishing Group, England (2008).
Notice of Opposition to European Patent No. EP 2 161 336, from Novartis AG, dated Apr. 25, 2014.
Notice of Opposition to European Patent No. EP 2 161 336, from 4-Antibody AG, dated Apr. 29, 2014.
Notice of Opposition to European Patent No. EP 2 161 336, from Janssen Biotech, Inc., dated Apr. 30, 2014.
Notice of Opposition to European Patent No. EP 2 161 336, from Merck & Co., Inc., dated Apr. 30, 2014.
Honjo, et al., Deposit receipt for Accession No. FERM BP-8392 mentioned in EP-A 1 537 878, 1 page (Jun. 5, 2003).
Carreno, et al., "The B7 family of ligands and its receptors: New pathways for costimulation and inhibition of immune responses", Annu Rev. Immunol., 20:29-53 (2002).
Leach, et al., "Enhancement of antitumor immunity by CTLA-4 blockade", Science, 271(5256):1734-1736 (1996).
Declarations by Dr. Robert J. Boleh including 2 Annex and 39 exhibits, 82 pages (Apr. 29, 2014).
Patentee's response to Examination Report dated Nov. 24, 2011 for European Patent Application No. 09013687.0-2405, filed Apr. 4, 2012.
Witness Statement by Mr. Hiroyuki Yamada including exhibits 1-7, (Apr. 16, 2014) (23 pages).
Witness Statement of Ms. Masako Ikeda including exhibits A-E, (Apr. 15, 2014) (20 pages).
Response to request further processing of application dated Jan. 13, 2014, for EP Application No. 11178191.0-1410, filed Mar. 20, 2014. (13 pages).
Park, et al., "Monoclonal antibody therapy", Advances in Protein Chemistry, 56:369-421 (2001).
Clark, "Antibody engineering IgG effector Mechanisms", Chemical Immunology, 65:88-110: enclosed is a reprint from http://www.path.cam.ac.uk/mrc7/publications/reprints/PP1997CI65_88.pdf (1997).
Iwai, et al., "PD-1 inhibits antiviral immunity at the effector phase on the liver", The Journal of Experimental Medicine, 198(1):39-50 (2003).
Adams, et al., "Monoclonal antibody therapy of cancer", Nature Biotechnology, 23(9):1147-1157 (2005).
Affidavit of Christopher Butler, 8 pages (Apr. 23, 2014).
Declaration of AndreaVan Elsas, Ph.D., in support of the opposition against EP-B1 2 161 336, 197 pages (Apr. 29, 2014).
Declaration of Vassiliki A. Boussiotis, in connection with the opposition against European Patent No. 2161336B1, 167 pages (Apr. 28, 2014).
Communication pursuant to Article 94(3) EPC for European Application No. 06786260.7-1412, dated Apr. 23, 2014.
Carreno, et al., "BTLA: A new inhibitory receptor with a B7-like ligand", TRENDS in Immunology, 24(10):524-527 (2003).
Chen, "Co-inhibitory molecules of the B7-CD28 family in the control of T-cell immunity", Nature, 4:336-347 (2004).
Shinohara, et al., Structural and chromosomal localization of the human PD-1 Gene (PDCD1), UniProt database entry Q15116, http://www.uniprot.org/uniprot/Q15116.txt. downloaded Apr. 29, 2014.
Exhibit 1 "Human anti-PD-1 antibodies: binding to PD-1, cross-competition with 5C4 and affinity to PD-1", 6 pages.
Carter, et al., "Cytotoxic T-lymphocyte antigen-4 and programmed death-1 function as negative regulators of lymphocyte activation", Immunologic Research, 28(1):49-59 (2003).
Kaveri, "Epitope and idiotope mapping using monoclonal antibodies", Antibody Engineering Protocols, Methods if Molecular Biology, 51(Chapter 11):171-181 (2005).
Zhang, et al., "Structural and functional analysis of the costimulatory receptor programmed death-1", Immunity, 20:337-347 (2004).
Sequence alignments between PD-1 and each of CTLA-4, CD28 and ICOS, retrieved on-line on Apr. 10, 2014, http://www.ebi.ac.uk/Tools/services/web/toolresult.ebi?jobId=clustalo-I20140410-15.
Ansari, et al., "The programmed death-1 (PD-1) pathway regulates autoimmune diabetes in nonobese diabetic (NOD) mice", J. Exp. Med, 198(1):63-69 (2003).
Janeway, et al., "Immunobiology: The immune system in health and disease", New York, Garland Science, Chapter 9: 367-408 (2005).
Nagler, et al., "Phase I clinical trial of CT-011, a humanized monoclonal antibody directed against a B7 family-associated protein, in patients with advanced hematological malignancies", Experimental Hematology, 33:97 (2005).
Cloeckaert, et al., "O-Polysaccharide epitopic heterogeneity at the surface of brucella spp. studied by enzyme-linked immunosorbent assay and flow cytometry", Clinical and Diagnostic Laboratory Immunology, 5(6):862-870 (1998).
Brahmer, et al., "Phase I study of single-agent anti-programmed death-1 (MDX-1106) in refractory solid tumors: Safety, clinical activity, pharmacodynamics, and immunologic correlates", Journal of Clinical Oncology, 28(19):3167-3175 (2005).
Declaration from Dr. Jennifer Mataraza, 11 pages (Apr. 28, 2014).
U.S. Appl. No. 14/227,733, filed Mar. 27, 2014.
U.S. Appl. No. 14/244,405, filed Apr. 3, 2014.
U.S. Appl. No. 14/248,462, filed Apr. 9, 2014.
U.S. Appl. No. 11/913,217, Apr. 22, 2011 Notice of Allowance.
U.S. Appl. No. 11/913,217, Jan. 25, 2011 Response to Non-Final Office Action.
U.S. Appl. No. 11/913,217, Oct. 25, 2010 Non-Final Office Action.
U.S. Appl. No. 13/210,137, Mar. 26, 2014 Notice of allowance and issue Fee payment.
U.S. Appl. No. 13/210,137, Mar. 4, 2014 Response to Non-Final Office Action.
U.S. Appl. No. 13/210,137, Feb. 21, 2014 Non-Final Office Action.
Extended European Search Report issued on Jun. 7, 2010 in counterpart EP application No. 10161767.8.
Extended European Search Report issued on Oct. 5, 2010 in counterpart EP application No. 10161767.8.
Communication from the Japanese Patent Office mailed Jul. 10, 2012, in Japanese counterpart application No. 2009-203514.
European Office Action issued Aug. 18, 2011, in corresponding European Patent Application No. 10172772.5 (in the name of Ono Pharmaceutical Co., Ltd.).
Partial European Search Report dated Oct. 26, 2006 in EP application No. 03741154.3.
EP application No. 03741154.3 Notice of Opposition dated Jul. 8, 2011, issued by the EPO in the name of Ono Pharmaceutical Co., Ltd. et al.
EP application No. 03741154.3 Response to the communication pursuant to Art. 96(2) EPC dated Jun. 25, 2007, 7 pages.
EP Publication No. 1 576 014, Excerpt from Register of European Patents, retrieved online from https://register.epo.org/espacenet/application?number=EP03780521 on May 27, 2011.
International Search Report for PCT/JP02/08420, dated Oct. 21, 2003.
"About the Internet Archive: General Information", Internet Archive, 2001, 10 pages, retrieved online from http://www.archive.org/about/about.php on Apr. 5, 2011.
Affinity purified anti-mouse PD-1 (PD1): Archived website information for J43 and J116 antibodies; eBioscience and Waybackmachine/org 2002, 4 pages, retrieved online from http://web.archive.org/web/20020301031217 http://ebioscience/specs/antibody14/14-9985 . . . on Jun. 14, 2011.
"Anti-Human CD 279 (PD-1) Functional Grade Purified: Murine anti-PD-1 antibody J116", eBioscience, Information Sheet, 2000, 2 pages.
Brown, et al., "Expression and functional consequences of PD-1 ligands on natural APCS and tumors", The FASEB Journal, 2001, 15(4):A345 (abstract No. 275.23).

(56) References Cited

OTHER PUBLICATIONS

Freeman, et al., "Engagement of the PD-1 immunoinhibitory receptor by a novel B7-family member leads to negative regulation of lymphocyte activation", Blood, 2000, 96(11):810a-811a (Abstract No. 3502).
Ozkaynak, et al., "Programmed death-1 targeting can promote allograft survival", The Journal of Immunology, 2002, 169:6546-6553.
Tamura, et al., "B7-H1 costimulation preferentially enhances CD28-independent T-helper cell function", 2001, Blood, 97(6):1809-1816.
Dong, et al., "Tumor-associated B7-H1 promotes T-cell apoptosis: A potential mechanism of immune evasion", 2002, Nature Medicine, 8(8):793-800.
Nishimura, et al., "Immunological studies on PD-1-deficient mice: implication of PD-1 as a negative regulator for B cell responses", 1998, International Immunology, 10(10):1563-1572.
Yamazaki, et al., "Expression of programmed death 1 ligands by murine T cells and APC", 2002, The Journal of Immunology, 169(10):5538-5545.
Zuberek, et al., "The role of in vivo PD-1/PD-L1 interactions in syngeneic and allogeneic antitumor responses in murine tumor models", 2001, Blood, 98(11):42B.
Brown, et al., Blockade of PD-1 ligands on dendritic cells enhances T cells activation and cytokine production, FASEB Journal, Mar. 2002, 16(4):A710-517.4.
Brahmer, et al., Safety and activity of MDX-1106 (ONO-4538) anti-PD-1 monoclonal antibody in patients with selected refractory or relapsed malignancies, 2008, J. Clin. Oncol., 26(May 20 Suppl; abstract No. 3006).
Huang, Structural chemistry and therapeutic intervention of protein-protein interactions in immune response, human immunodeficiency virus entry, apoptosis, Pharmacology and Therapeutics, 2000, 86:201-215.
Blazar, et al., "Infusion of Anti-B7.1 (CD80) and anti-B7.2 (CD86) monoclonal antibodies inhibits murine graft-versus-host-disease lethality in part via direct effects on CD4+ and CD8+ T cells", J. Immunol., 1996, 157:3250-3259.
Kasagi, et al., "Anti-Programmed Cell Death 1 antibody Reduces CD4+PD-1+T Cells and Relieves the Lupus-Like Nephritis of NZB/W F1 Mice", The Journal of Immunology, 184:2337-2347 (2010).
Hirano et al., "Blockade of B7-H1 and PD-1 by monoclonal antibodies potentiates cancer therapeutic immunity", Cancer Research, American Association for Cancer Research, 65(3): 1089-1096, Feb. 2005.
Agata, et al., 1996, "Expression of the PD-1 antigen on the surface of stimulation mouse T and B lymphocytes," Int Immunol, vol. 8: p. 765-772.
Bennett, et al., 2003, "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses," J Immunol, vol. 170: p. 711-718.
Berger et al., "Phase I safety and pharmacokinetic study of CT-011, a humanized antibody interacting with PD-1, in patients with advanced hematologic malignancies," Clin Cancer Res. (2008); 14(10):3044-51.
Blank et al., "PD-L1/B7H-1 Inhibits the Effector Phase of Tumor Rejection by T Cell Receptor (TCR) Transgenic CD8+ T Cells"; Cancer Research; (2004); 64:1140-1145.
Blank, et al., 2005, "Interaction of PD-L1 on tumor cells with PD-1 on tumor-specific T cells as a mechanism of immune evasion: implications for tumor immunotherapy," Cancer Immunol. Immunother., vol. 54: p. 307-314.
Brown, et al., 2003, "Blockade of Programmed Death-1 Ligands on Dendritic Cells Enhances T Cell Activation and Cytokine Production," J. Immunol., vol. 170: p. 1257-1266.

Carter, et al., 2002, "PD-1: PD-L inhibitory pathway affects both CD4+ and CD8+ T cells and is overcome by IL-2," Eur J Immunol, vol. 32: p. 634-643.
Cox et al., "A directory of human germ-line $V_\kappa$ segments reveals a strong bias in their usage"; Eur. J. Immunol.; (1994); 24:827-836.
Dong, et al., 2002, "Tumor-associated B7-H1 promotes T-cell apoptosis: A potential mechanism of immune evasion," Nat Med., vol. 8: p. 783-800.
Dong, H. and Chen, L., 2003, "B7-H1 pathway and its role in the evasion of tumor immunity," J Mol Med, vol. 81: p. 281-287.
Finger, et al., 1997, "The human PD-1 gene: complete eDNA, genomic organization, and developmentally regulated expression in B cell progenitors," Gene, vol. 197: p. 177-187.
Freeman, et al., 2000, "Engagement of the PD-1 Immunoinhibitory Receptor by a Novel B7 Family Member Leads to Negative Regulation of Lymphocyte Activation," J Exp Med, vol. 192: p. 1027-1034.
Hansen, et al., 1980, "Monoclonal Antibodies Identifying a Novel T-Cell Antigen and Ia Antigens of Human Lymphocytes," Immunogenics, vol. 10: p. 247-260.
He, et al., 2004, "Blocking Programmed Death-1 Ligand-PD-1 Interactions by Local Gene Therapy Results in Enhancement of Antitumor Effect of Secondary Lymphoid Tissue Chemokine," J. Immunol., vol. 173: p. 4919-4928.
Hutloff, et al., 1999, "ICOS is an inducible T-cell co-stimulator structurally and functionally related to CD28," Nature, vol. 397: p. 263-266.
Ishida, et al., 1992, "Induced expression of PD-1, a novel member of the immunoglobulin gene superfamily, upon programmed cell death," EMBO J., vol. 11: p. 3887-3895.
Iwai, et al., 2002, "Involvement of PD-Li on tumor cells in the escape from host immune system and tumor immunotherapy by PD-L1 blockade," Proc. Nat'l. Acad. Sci. USA, vol. 99: p. 12293-12297.
Iwai, et al., 2002, "Microanatomical localization of PD-1 in human tonsils," Immunology Letters, vol. 83, No. 3: p. 215-220.
Iwai, et al., 2005, "PD-1 blockade inhibits hematogenous spread of poorly immunogenic tumor cells by enhanced recruitment of effector T cells," Int. Immunol., vol. 17: p. 133-144.
Koga et al., "Blockade of the Interaction Between PD-1 and PD-L1 Accelerates Graft Arterial Disease in Cardiac Allografts"; Arterioscler. Thromb. Vasc. Biol.; (2004); 24(11):2057-2062.
Konishi, et al., 2004, "B7-H1 Expression on Non-Small Cell Lung Cancer Cells and Its Relationship with Tumor-Infiltrating Lymphocytes and Their PD-1 Expression," Clin. Cancer Res., vol. 10: p. 5094-5100.
Latchman, et al., 2001, "PD-L2 is a second ligand for PD-1 and inhibits T cell activation," Nat Immunol, vol. 2: p. 261-268.
Lonberg, et al., 1994, "Antigen-specific human antibodies from mice comprising four distinct genetic modifications," Nature, vol. 368, No. 6474: p. 856-859.
Nielsen, et al., 2004, "A putative regulatory polymorphism in PD-1 is associated with nephropathy in a population-based cohort of systemic lupus erythematosus patients," Lupus, vol. 13: p. 510-516.
Nishimura, et al., 1999, "Development of Lupus-like Autoimmune Disease by Disruption of the PD-1 Gene Encoding an ITIM Motif-Carrying Immunoreceptor," Immunity, vol. 11: p. 141-151.
Nishimura, et al., 2001, "Autoimmune Dilated Cardiomyopathy in PD-1 Receptor-Deficient Mice," Science, vol. 291: p. 319-322.
Okazaki, et al., 2001, "PD-1 immunoreceptor inhibits B cell receptor-mediated signaling by recruiting src homology 2-domain-containing tryosine phosphatase 2 to phosphotyrosine," PNAS, vol. 98: p. 13866-13871.
Okazaki, et al., 2002, "New regulatory co-receptors: inducible co-stimulator and PD-1," Curr. Opin. Immunol., vol. 41, No. 6: p. 779-782.
Panka et al., 1988, Proc. Natl. Acad. Sci. USA, 85:3080-3084.
Prokunina, L. and Alarcon-Riquelme, M., 2004, "The genetic basis of systemic lupus erythematosus-knowledge of today and thoughts for tomorrow," Hum Mol Genet, vol. 13: p. R143-R148.
Rudikoff et al., 1982, Proc. Natl. Acad. Sci. USA, 79:1979-1983.

(56) References Cited

OTHER PUBLICATIONS

Salama, et al., 2003, "Critical Role of the Programmed Death-1 (PD-1) Pathway in Regulation of Experimental Autoimmune Encephalomyelitis," *J Exp Med*, vol. 198: p. 71-78.
Shinohara, et al., 1994, "Structure and chromosomal localization of the human PD-1 gene (PDCD1)," *Genomics*, vol. 23: p. 704-706.
Thomas, M.L., 1995, "Of ITAMs and ITIMs: Turning on and Off the B Cell Antigen Receptor," *J Exp Med*, vol. 181 : p. 1953-1956.
Tomlinson et al., "The Repertoire of Human Germline $V_H$ Sequences Reveals about Fifty Groups of $V_H$ Segments with Different Hypervariable Loops"; *J. Mol. Biol.*; (1992); 227:776-798.
Vivier, E. and Daeron, M., "Immunoreceptor tyrosine-based inhibition motifs," *Immunol Today*, vol. 18: p. 286-291.
Wong RM et al., "Programmed death-1 blockade enhances expansion and functional capacity of human melanoma antigen-specific CTLs," *Int Immunol.* (2007), 19(10):1223-34.
Singer, et al., Genes and Genomes, *University Science Books*, 1:63-64 (1998).
Answering Brief including exhibits A, B and C, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Civil Action No. 1:15-cv-00560-GMS, United States District Court for the District of Delaware, Sep. 25, 2015, 70 pages.
Answering Brief including exhibits A, B and C, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Civil Action No. 1:15-cv-00572-GMS, United States District Court for the District of Delaware, Sep. 25, 2015, 70 pages.
Declaration of Andrew C. Mayo including exhibits 12-13, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Civil Action No. 1:15-cv-00560-GMS, United States District Court for the District of Delaware, Oct. 14, 2015, 73 pages.
Declaration of Andrew C. Mayo including exhibits 12-13, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Civil Action No. 1:15-cv-00572-GMS, United States District Court for the District of Delaware, Oct. 14, 2015, 73 pages.
Defendants *E.R. Squibb & Sons, L.L.C., and Bristol-Myers Squibb, Co.'s* Answer, *Dana-Farber Cancer Institute, Inc. v. Ono Pharmaceutical Co., Ltd., Tasuku Honjo, E.R. Squibb & Sons L.L.C and Bristol-Myers Squibb Co.*, Civil Action No. 1:15-cv-13443-MLW, United States District Court for the District of Massachusetts, Dec. 21, 2015, 15 pages.
Defendant *Tasuku Honjo's* Answer, *Dana-Farber Cancer Institute, Inc. v. Ono Pharmaceutical Co., Ltd., Tasuku Honjo, E.R. Squibb & Sons L.L.C., and Bristol-Myers Squibb Co.*, Civil Action No. 1:15-cv-13443-MLW, United States District Court for the District of Massachusetts, Dec. 21, 2015, 15 pages.
Dong, H., et al., "B7-H1, a third member of the B7 family, co-stimulates T-cell proliferation and interleukin-10 secretion," *Nature Medicine* 5(12):1365-1369, Nature America Inc., United States (1999).
Reply Brief Supporting Their Motion to Dismiss, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Civil Action No. 1:15-cv-00560-GMS, United States District Court for the District of Delaware, Oct. 14, 2015, 14 pages.
Reply Brief Supporting Their Motion to Dismiss, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Civil Action No. 1:15-cv-00572-GMS, United States District Court for the District of Delaware, Oct. 14, 2015, 14 pages.
Summons to attend oral proceedings pursuant to Rule 115(1) EPC for EP Application No. 09013687.0, European Patent Office, Munich, Germany, mailed on Dec. 14, 2015, 9 pages.
Office action mailed Dec. 14, 2015 in U.S. Appl. No. 14/244,405, Korman, A., et al., filed Apr. 3, 2014.

Allison, J.P., et al., "CTLA-4 Blockade in Tumor Immunotherapy," in *Principles and Practice of the Biologic Therapy of Cancer*, 3rd edition, Rosenberg, S.A., ed., pp. 890-895, Lippincott Williams & Wilkins, Philadelphia, United States (2000).
Approved Judgment before Mr. Justice Birss, Case Nos. HP-2014-0000388 and HP14 A 02748, *Merck vs. Ono*, dated Oct. 22, 2015, Royal Courts of Justice, London, England, 57 pages.
Communication pursuant to Article 94(3) EPC and Pending Claims for EP Application No. 10075561.1, European Patent Office, Germany, mailed on Jun. 2, 2015, 5 pages.
Exhibit 1, "Dichotomy of the activity of PD-L1 (B7-4) and how an anti-PD-1 antibody fits into it," in Response to Patentee's Aug. 12, 2015 Reply, mailed Dec. 21, 2015 for European Patent No. EP 1537878, filed Jul. 2, 2003, 1 page.
West, J.H., "CheckMate-057 Trial: The Future of PD-L1 as a Biomarker," medscape.com, accessed at http://www.medscape.com/viewarticle/845926, accessed on Sep. 17, 2015, 1 page (Jun. 5, 2015).
Response to Patentee's Aug. 12, 2015 Reply to Grounds of Appeal, mailed Dec. 21, 2015 in European Patent No. EP 1537878, Merck & Co., Inc., filed Jul. 2, 2003, Munchen, Germany, 92 pages.
Co-pending U.S. Appl. No. 15/000,863, inventors Honjo, T., et al., filed Jan. 19, 2016 (Not Published).
Co-pending U.S. Appl. No. 15/000,869, inventors Honjo, T., et al., filed Jan. 19, 2016 (Not Published).
Office action mailed Jan. 22, 2016 in U.S. Appl. No. 14/245,692, Honjo, et al., filed Apr. 4, 2014.
Claim Construction Chart, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Civil Action No. 1:14-cv-01131-GMS, United States District Court for the District of Delaware, Feb. 5, 2016, 21 pages.
Claim Construction Chart, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Civil Action No. 1:15-cv-00560-GMS, United States District Court for the District of Delaware, Feb. 5, 2016, 21 pages.
Claim Construction Chart, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, Civil Action No. 1:15-cv-00572-GMS, United States District Court for the District of Delaware, Feb. 5, 2016; 21 pages.
Office Action mailed Feb. 16, 2016 in U.S. Appl. No. 14/248,462, Korman, et al., filed Apr. 9, 2014.
Defendants' Claim Construction Opening Brief, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, C.A. No. 1:14-cv-01131-GMS, United States District Court for the District of Delaware, Feb. 25, 2016, 23 pages.
Plaintiffs' Claim Construction Opening Brief including exhibits A through D, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, C.A. No. 1:14-cv-01131-GMS, United States District Court for the District of Delaware, Feb. 25, 2016, 49 pages.
Declaration of Dr. Ulrich von Adrian including exhibits A through H, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, C.A. No. 1:14-cv-01131-GMS, United States District Court for the District of Delaware, Feb. 25, 2016, 437 pages.
Defendants' Claim Construction Opening Brief, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, C.A. No. 1:15-cv-00560-GMS, United States District Court for the District of Delaware, Feb. 25, 2016, 23 pages.
Plaintiffs' Claim Construction Opening Brief including exhibits A through D, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, C.A. No. 1:15-cv-00560-GMS, United States District Court for the District of Delaware, Feb. 25, 2016, 49 pages.

(56) References Cited

OTHER PUBLICATIONS

Declaration of Dr. Ulrich von Andrian including exhibits A through H, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, C.A. No. 1:15-cv-00560-GMS, United States District Court for the District of Delaware, Feb. 25, 2016, 437 pages.
Defendants' Claim Construction Opening Brief, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, C.A. No. 1:15-cv-00572-GMS, United States District Court for the District of Delaware. Feb. 25, 2016, 23 pages.
Plaintiffs° Claim Construction Opening Brief including exhibits A through D, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, C.A. No. 1:15-cv-00572-GMS, United States District Court for the District of Delaware, Feb. 25, 2016, 49 pages.
Declaration of Dr. Ulrich von Andrian including exhibits A through H, *Bristol-Myers Squibb Co., E.R. Squibb & Sons L.L.C., Ono Pharmaceutical Co., Ltd., and Tasuku Honjo* v. *Merck & Co., Inc, and Merck Sharp & Dohme Corp.*, C.A. No. 1:15-cv-00572-GMS, United States District Court for the District of Delaware, Feb. 25, 2016, 437 pages.
Amended Answer, E.R. Squibb & Sons L.L.C. and Bristol-Myers Squibb Co., C.A. No. 1:15-cv-13443-MLW, United States District Court for the District of Massachusetts, Feb. 3, 2016, 15 pages.
Amended Answer, Tasuku Honjo, C.A. No. 1:15-ev-13443-MLW, United States District Court for the District of Massachusetts, Feb. 3, 2016, 15 pages.
Complaint, *Dana-Farber Cancer Institute, Inc.* v. *Ono Pharmaceutical Co., Ltd., Tasuku Honjo, E.R. Squibb & Sons, L.L.C., and Bristol-Myers Squibb Co.*, 1:15-cv-13443-GMS, United States District Court for the District of Massachusetts, filed Sep. 25, 2015, 16 pages.
Order Denying Defendants' Motion to Dismiss, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, Case 1:15-cv-00560-GMS, United States District Court for the District of Delaware, Mar. 17, 2016, 3 pages.
Answer to Complaint, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, C.A. No. 1:15-cv-00560-GMS, United States District Court for the District of Delaware, Mar. 31, 2016, 16 pages.
Answer to Complaint, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, C.A. No. 1:15-cv-00572-GMS, United States District Court for the District of Delaware, Mar. 31, 2016, 16 pages.
Claim Construction Answering Brief filed by Bristol-Myers Squibb Co., E. R. Squibb & Sons, L.L.C., Ono Pharmaceutical Co., Ltd., and Tasuku Honjo, including exhibits A through I, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, Civil Action No. 1:14-cv-01131-GMS, United States District Court for the District of Delaware, Mar. 28, 2016, 98 pages.
Claim Construction Answering Brief filed by Bristol-Myers Squibb Co., E. R. Squibb & Sons, L.L.C., Ono Pharmaceutical Co., Ltd., and Tasuku Honjo, including exhibits A through I, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, Civil Action No. 1:15-cv-00560-GMS, United States District Court for the District of Delaware, Mar. 28, 2016, 98 pages.
Claim Construction Answering Brief filed by Bristol-Myers Squibb Co., E. R. Squibb & Sons, L.L.C., Ono Pharmaceutical Co., Ltd., and Tasuku Honjo, including exhibits A through I, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, Civil Action No. 1:15-cv-00572-GMS, United States District Court for the District of Delaware, Mar. 28, 2016, 98 pages.
Claim Construction Answering Brief filed by Merck & Co., Inc, and Merck Sharp & Dohme Corp., including exhibit I, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, Civil Action No. 1:14-cv-01131-GMS, United States District Court for the District of Delaware, Mar. 28, 2016, 30 pages.
Claim Construction Answering Brief filed by Merck & Co., Inc. and Merck Sharp & Dohme Corp., including exhibit I, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, Civil Action No. 1:15-cv-00560-GMS, United States District Court for the District of Delaware, Mar. 28, 2016, 30 pages.
Claim Construction Answering Brief filed by Merck & Co., Inc. and Merck Sharp & Dohme Corp., including exhibit 1, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, Civil Action No. 1:15-cv-00572-GMS, United States District Court for the District of Delaware, Mar. 28, 2016, 30 pages.
Declaration of Dr. Ulrich von Andrian including exhibits A through H, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, C.A. No. 1:14-cv-01131-GMS, United States District Court for the District of Delaware, Mar. 24, 2016, 438 pages.
Declaration of Dr. Ulrich von Andrian including exhibits A through H, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, C.A. No. 1:15-cv-00560-GMS, United States District Court for the District of Delaware, Mar. 24, 2016, 438 pages.
Declaration of Dr. Ulrich von Andrian including exhibits A through H, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, C.A. No. 1:15-cv-00572-GMS, United States District Court for the District of Delaware, Mar. 24, 2016, 438 pages.
Order denying Motion to Dismiss, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, Civil Action No. 1:15-cv-00572-GMS, United States District Court for the District of Delaware, Mar. 29, 2016, 3 pages.
Non-Final Office Action mailed Mar. 25, 2016, in U.S. Appl. No. 15/000,869, Honjo, et al., filed Jan. 19, 2016.
Complaint for Declaratory Judgment, *Merck Sharp & Dohme Corp.* v. *Bristol-Myers Squibb Co., E.R. Squibb & Sons L.L.C., and Ono Pharmaceutical Co., Ltd.*, C.A. No. 2:33-av-0001, United States District Court for the District of New Jersey, Apr. 15, 2016, 21 pages.

Anti-PD1 17D8 VH

V segment:   3-33
  D segment:   unknown
  J segment:   JH4b

```
        Q   V   Q   L   V   E   S   G   G   D   V   V   Q   P   G   G   S
        L
  1     CAG GTG CAG CTG GTG GAG TCT GGG GGA GAC GTG GTC CAG CCT GGG GGG TCC
        CTG
```

CDR1
                                                    ~~~~~~~~~~~~~~~~~~~~
```
        R   L   S   C   A   A   S   G   V   A   F   S   N   Y   G   M   H
        W
  55    AGA CTC TCC TGT GCA GCG TCT GGA GTC GCC TTC AGT AAC TAT GGC ATG CAC
        TGG
```

CDR2
~~~~~~~~~~~~~~~~~~~~
```
        V   R   Q   A   P   G   K   G   L   E   W   V   A   V   I   W   Y
        D
  109   GTC CGC CAG GCT CCC GGC AAG GGG CTG GAG TGG GTG GCA GTT ATC TGG TAT
        GAT
```

CDR2
~~~~~~~~~~~~~~~~~~~~~~~~~~~~~~~~~~~~~~~~~
```
        G   S   N   K   Y   Y   A   D   S   V   K   G   R   F   T   I   S
        R
  163   GGA AGT AAT AAA TAC TAT GCA GAC TCC GTG AAG GGC CGG TTC ACC ATC TCC
        AGA
```

```
        D   N   S   K   N   M   L   Y   L   Q   M   N   S   L   R   A   E
        D
  217   GAC AAT TCC AAG AAC ATG CTC TAT CTG CAA ATG AAC AGC CTG AGA GCC GAG
        GAC
```

CDR3
                                ~~~~~~~~~~~~~~~~~~~~
```
        T   A   M   Y   Y   C   A   R   N   D   D   Y   W   G   Q   G   T
        L
  271   ACG GCT ATG TAT TAC TGT GCG AGG AAC GAT GAC TAC TGG GGC CAG GGA ACC
        CTG
```
                                                    ↳ JH4b
```
        V   T   V   S   S
  325   GTC ACC GTC TCC TCA
```

Figure 1A

Anti-PD1 17D8 VK

V segment:    L6
    J segment:    JK4

```
          E   I   V   L   T   Q   S   P   A   T   L   S   L   S   P   G   E
          R
  1       GAA ATT GTG TTG ACA CAG TCT CCA GCC ACC CTG TCT TTG TCT CCA GGG GAA
          AGA
                                                    CDR1
                                          ~~~~~~~~~~~~~~~~~~~~~~~~~~~~~~~~~~
          A   T   L   S   C   R   A   S   Q   S   V   S   S   Y   L   A   W
          Y
  55      GCC ACC CTC TCC TGC AGG GCC AGT CAG AGT GTT AGC AGC TAC TTA GCC TGG
          TAC
                                                                        CDR2
~~~~~~~~~~~~~~~~~~~~~~
          Q   Q   K   P   G   Q   A   P   R   L   I   I   Y   D   A   S   N
          R
  109     CAA CAG AAA CCT GGC CAG GCT CCC AGG CTC ATC ATC TAT GAT GCA TCC AAC
          AGG

CDR2
          ~~~~~~~~
          A   T   G   I   P   A   R   F   S   G   S   G   S   G   T   D   F
          T
  163     GCC ACT GGC ATC CCA GCC AGG TTC AGT GGC AGT GGG TCT GGG ACA GAC TTC
          ACT

CDR3
          ~~~~~~~~
          L   T   I   S   S   L   E   P   E   D   F   A   V   Y   Y   C   Q
          Q
  217     CTC ACC ATC AGC AGC CTA GAG CCT GAA GAT TTT GCA GTT TAT TAC TGT CAG
          CAG

CDR3
          ~~~~~~~~~~~~~~~~~~~~~~~~~~~~~~~~~~~~
          R   S   N   W   P   L   T   F   G   G   G   T   K   V   E   I   K
  271     CGT AGC AAC TGG CCT CTC ACT TTC GGC GGA GGG ACC AAG GTG GAG ATC AAA
```

Figure 1B

Anti-PD-1 2D3 VH

V segment:    3-33
    D segment:   7-27
    J segment:    JH4b

```
           Q   V   Q   L   V   E   S   G   G   D   V   V   Q   P   G   R   S
           L
    1      CAG GTG CAG CTG GTG GAA TCT GGG GGA GAC GTG GTC CAG CCT GGG AGG TCC
           CTG

CDR1
                                                              ~~~~~~~~~~~~~~~
           R   L   S   C   A   A   S   G   L   T   F   T   N   Y   G   F   H
           W
   55      AGA CTC TCC TGT GCA GCG TCT GGA TTA ACC TTC ACT AAC TAT GGC TTC CAC
           TGG

CDR2
           ~~~~~~~~~~~~~~~~~~~
           V   R   Q   A   P   G   K   G   L   E   W   V   A   V   I   W   Y
           D
   109     GTC CGC CAG GCT CCA GGC AAG GGG CTG GAG TGG GTG GCT GTT ATA TGG TAT
           GAT

CDR2
           ~~~~~~~~~~~~~~~~~~~~~~~~~~~~~~~~~~~~~~~~~~~~~~~~
           G   S   K   K   Y   Y   A   D   S   V   K   G   R   F   T   I   S
           R
   163     GGA AGT AAG AAA TAT TAT GCA GAC TCC GTG AAG GGC CGA TTC ACC ATC TCC
           AGA

D   N   S   K   N   T   L   Y   L   Q   M   N   N   L   R   A   E
           D
   217     GAC AAT TCC AAG AAC ACG CTG TAT CTG CAA ATG AAC AAC CTG AGA GCC GAG
           GAC

CDR3
                                                   ~~~~~~~~~~~~~~~
           T   A   V   Y   Y   C   A   T   G   D   D   Y   W   G   Q   G   T
           L
   271     ACG GCT GTG TAT TAC TGT GCG ACT GGG GAT GAC TAC TGG GGC CAG GGA ACC
           CTG

V   T   V   S   S
   325     GTC ACC GTC TCC TCA
```

Figure 2A

Anti-PD-1 2D3 VK

V segment:    L6
    J segment:    JK4

```
              E   I   V   L   T   Q   S   P   A   T   L   S   L   S   P   G   E
              R
  1           GAA ATT GTG TTG ACA CAG TCT CCA GCC ACC CTG TCT TTG TCT CCA GGG GAA
              AGA

CDR1
                                      ~~~~~~~~~~~~~~~~~~~~~~~~~~~~~~~~~~~~~~~~~~~
              A   T   L   S   C   R   A   S   Q   S   V   S   S   Y   L   A   W
              Y
  55          GCC ACC CTG TCC TGC AGG GCC AGT CAG AGT GTT AGC AGC TAC TTA GCC TGG
              TAC

CDR2
              ~~~~~~~~~~~~~~~~~~~~                                      ~~~~~~~~~~~
              Q   Q   K   P   G   Q   A   P   R   L   L   I   Y   D   T   S   N
              R
  109         CAA CAG AAA CCT GGC CAG GCT CCC AGG CTC CTC ATC TAT GAT ACA TCC AAC
              AGG

CDR2
              ~~~~~~~~
              A   T   G   I   P   A   R   F   S   G   S   G   S   G   T   D   F
              T
  163         GCC ACT GGC ATC CCA GCC AGG TTC AGT GGC AGT GGG TCT GGG ACA GAC TTC
              ACT

CDR3
              ~~~~~~~~
              L   T   I   S   S   L   E   P   E   D   F   A   V   Y   Y   C   Q
              Q
  217         CTC ACC ATC AGC AGC CTA GAG CCT GAA GAT TTT GCA GTT TAT TAC TGT CAG
              CAG

CDR3
              ~~~~~~~~~~~~~~~~~~~~~~~~~~~~~~
              R   S   N   W   P   L   T   F   G   G   G   T   K   V   E   I   K
  271         CGT AGC AAC TGG CCG CTC ACT TTC GGC GGA GGG ACC AAG GTG GAG ATC AAA
```

Figure 2B

Anti-PD-1 4H1 VH

V segment: 3-33
D segment: undetermined
J segment: JH4b

```
        Q   V   Y   L   V   E   S   G   G   V   V   Q   P   G   R   S
      L
  1   CAG GTG TAC TTG GTA GAG TCT GGG GGA GGC GTG GTC CAG CCT GGG AGG TCC
      CTG

CDR1
                                                              ~~~~~~~~~~~~
        R   L   S   C   A   A   S   G   F   T   F   S   N   Y   G   M   H
      W
  55  AGA CTC TCC TGT GCA GCG TCT GGA TTC ACC TTC AGT AAC TAT GGC ATG CAC
      TGG

CDR2
      ~~~~~~~~~~~~~~~~~~~
        V   R   Q   A   P   G   K   G   L   E   W   V   A   L   I   W   Y
      D
 109  GTC CGC CAG GCT CCA GGC AAG GGG CTG GAG TGG GTG GCA CTT ATA TGG TAT
      GAT

CDR2
      ~~~~~~~~~~~~~~~~~~~~~~~~~~~~~~~~~~~~~~~~~~~~~~~~~~
        G   S   N   K   Y   Y   A   D   S   V   K   G   R   F   T   I   S
      R
 163  GGA AGT AAT AAA TAC TAT GCA GAC TCC GTG AAG GGC CGA TTC ACC ATC TCC
      AGA

D   N   S   K   N   T   L   Y   L   Q   M   T   S   L   R   V   E
      D
 217  GAC AAT TCC AAG AAC ACG CTG TAT CTG CAA ATG ACC AGT CTG AGA GTC GAG
      GAC

CDR3
                              ~~~~~~~~~~~~~~~~~~
        T   A   V   Y   Y   C   A   S   N   V   D   H   W   G   Q   G   T
      L
 271  ACG GCT GTG TAT TAT TGT GCG AGC AAC GTT GAC CAT TGG GGC CAG GGA ACC
      CTG

V   T   V   S   S
 325  GTC ACC GTC TCC TCA
```

Figure 3A

Anti-PD-1 4H1 VK

V segment:    L6
    J segment:    JK1

```
            E   I   V   L   T   Q   S   P   A   T   L   S   L   S   P   G   E
            R
    1   GAA ATT GTG TTG ACA CAG TCT CCA GCC ACC CTG TCT TTG TCT CCA GGG GAA
        AGA

CDR1
                        ~~~~~~~~~~~~~~~~~~~~~~~~~~~~~~~~~~~~~~~~~~~~~~~~~~~~
            A   T   L   S   C   R   A   S   Q   S   V   N   S   N   L   A   W
            Y
   55   GCC ACC CTC TCC TGC AGG GCC AGT CAG AGT GTT AAC AGT AAC TTA GCC TGG
        TAC

CDR2
        ~~~~~~~~~~~~~~~~~~~~                                ~~~~~~~~~~~~~~~~~
            Q   Q   K   P   G   Q   A   P   R   L   L   I   Y   D   A   S   N
            R
  109   CAA CAG AAA CCT GGC CAG GCT CCC AGG CTC CTC ATC TAT GAT GCA TCC AAC
        AGG

CDR2
        ~~~~~~~~
            A   T   G   I   P   A   R   F   S   G   S   G   S   G   T   D   F
            T
  163   GCC ACT GGC ATC CCA GCC AGG TTC AGT GGC AGT GGG TCT GGG ACA GAC TTC
        ACT

L   T   I   S   S   L   E   P   E   D   F   A   V   Y   Y   C   H
            C
  217   CTC ACC ATC AGC AGC CTA GAG CCT GAA GAT TTT GCA GTT TAT TAC TGT CAC
        TGT

CDR3
                ~~~~~~~~~~~~~~~~~~~~~~~~~~~~~~~
            Q   Q   R   S   N   W   W   T   F   G   Q   G   T   K   V   E   I
            K
  271   CAG CAG CGT AGC AAC TGG TGG ACG TTC GGC CAA GGG ACC AAG GTG GAA ATC
        AAA
```

Figure 3B

Anti-PD1 5C4 VH

V segment: 3-33
    D segment: unknown
    J segment: JH4b

```
       Q   V   Q   L   V   E   S   G   G   V   V   Q   P   G   R   S
                                                                       L
  1    CAG GTG CAG CTG GTG GAG TCT GGG GGA GGC GTG GTC CAG CCT GGG AGG TCC
                                                                       CTG

CDR1
                                                        ~~~~~~~~~~~~~~~~~
       R   L   D   C   K   A   S   G   I   T   F   S   N   S   G   M   H
                                                                       W
 55    AGA CTC GAC TGT AAA GCG TCT GGA ATC ACC TTC AGT AAC TCT GGC ATG CAC
                                                                       TGG

CDR2
       ~~~~~~~~~~~~~~~~~~~~
       V   R   Q   A   P   G   K   G   L   E   W   V   A   V   I   W   Y
                                                                       D
109    GTC CGC CAG GCT CCA GGC AAG GGG CTG GAG TGG GTG GCA GTT ATT TGG TAT
                                                                       GAT

CDR2
       ~~~~~~~~~~~~~~~~~~~~~~~~~~~~~~~~~~~~~~~~~~~~~~~~~
       G   S   K   R   Y   Y   A   D   S   V   K   G   R   F   T   I   S
                                                                       R
163    GGA AGT AAA AGA TAC TAT GCA GAC TCC GTG AAG GGC CGA TTC ACC ATC TCC
                                                                       AGA

D   N   S   K   N   T   L   F   L   Q   M   N   S   L   R   A   E
                                                                       D
217    GAC AAT TCC AAG AAC ACG CTG TTT CTG CAA ATG AAC AGC CTG AGA GCC GAG
                                                                       GAC

CDR3
                                    ~~~~~~~~~~~~~~~
       T   A   V   Y   Y   C   A   T   N   D   D   Y   W   G   Q   G   T
                                                                       L
271    ACC GCT GTG TAT TAC TGT GCG ACA AAC GAC GAC TAC TGG GGC CAG GGA ACC
                                                                       CTG
                                                  └──▶ JH4b

V   T   V   S   S
325    GTC ACC GTC TCC TCA
```

Figure 4A

Anti-PD1 5C4 VK

V segment: L6
J segment: JK1

```
         E   I   V   L   T   Q   S   P   A   T   L   S   L   S   P   G   E
         R
  1      GAA ATT GTG TTG ACA CAG TCT CCA GCC ACC CTG TCT TTG TCT CCA GGG GAA
         AGA
```

CDR1
                              ~~~~~~~~~~~~~~~~~~~~~~~~~~~~~~~~~~~~~~~~
```
         A   T   L   S   C   R   A   S   Q   S   V   S   S   Y   L   A   W
         Y
  55     GCC ACC CTC TCC TGC AGG GCC AGT CAG AGT GTT AGT AGT TAC TTA GCC TGG
         TAC
```

CDR2
```
         ~~~~~~~~~~~~~~~~~~~~
         Q   Q   K   P   G   Q   A   P   R   L   L   I   Y   D   A   S   N
         R
  109    CAA CAG AAA CCT GGC CAG GCT CCC AGG CTC CTC ATC TAT GAT GCA TCC AAC
         AGG
```

CDR2
    ~~~~~~~~
```
         A   T   G   I   P   A   R   F   S   G   S   G   S   G   T   D   F
         T
  163    GCC ACT GGC ATC CCA GCC AGG TTC AGT GGC AGT GGG TCT GGG ACA GAC TTC
         ACT
```

CDR3
    ~~~~~~~~
```
         L   T   I   S   S   L   E   P   E   D   F   A   V   Y   Y   C   Q
         Q
  217    CTC ACC ATC AGC AGC CTA GAG CCT GAA GAT TTT GCA GTT TAT TAC TGT CAG
         CAG
```

CDR3
         ~~~~~~~~~~~~~~~~~~~~~~~~~~
```
         S   S   N   W   P   R   T   F   G   Q   G   T   K   V   E   I   K
  271    AGT AGC AAC TGG CCT CGG ACG TTC GGC CAA GGG ACC AAG GTG AAA ATC AAA
                              └─→
```

Figure 4B

Anti-PD-1 4A11 VH

V segment:    4-39
    D segment:    3-9
    J segment:    JH4b

```
            Q   L   Q   L   Q   E   S   G   P   G   L   V   K   P   S   E   T
            L
  1         CAG CTG CAG CTG CAG GAG TCG GGC CCA GGA CTG GTG AAG CCT TCG GAG ACC
            CTG
                                                                          CDR1
            ~~~~~~~~~~~~~~~~~~~
            S   L   T   C   T   V   S   G   G   S   L   S   R   S   S   F   F
            W
  55        TCC CTC ACC TGC ACT GTC TCT GGT GGC TCC CTC AGC AGG AGT AGT TTC TTC
            TGG
            CDR1                                                          CDR2
            ~~~~
                ~~~~~~~~~~~~
            G   W   I   R   Q   P   P   G   K   G   L   E   W   I   G   S   I
            Y
  109       GGC TGG ATC CGT CAG CCC CCA GGG AAG GGA CTG GAG TGG ATT GGG AGT ATC
            TAT
                                CDR2
            ~~~~~~~~~~~~~~~~~~~~~~~~~~~~~~~~~~~~~~~~~~~~~~~~~~
            Y   S   G   S   T   Y   Y   N   P   S   L   K   S   R   V   T   I
            S
  163       TAT AGT GGG AGC ACC TAC TAC AAC CCG TCC CTC AAG AGT CGA GTC ACC ATA
            TCC

V   D   T   S   K   N   Q   F   S   L   K   L   S   S   V   T   A
            A
  217       GTA GAC ACG TCC AAG AAC CAG TTC TCC CTG AAG CTG AGC TCT GTG ACC GCC
            GCA
                                                                          CDR3
            ~~~~~~~~~~~~~~~~~~~~~~~~~~~~~~~~~~~~~~
            D   T   A   V   Y   Y   C   V   R   D   Y   D   I   L   T   G   D
            E
  271       GAC ACG GCT GTG TAT TAC TGT GTG AGA GAT TAC GAT ATT TTG ACT GGC GAC
            GAG
            CDR3
            ~~~~~~~~~~
            D   Y   W   G   Q   G   T   L   V   T   V   S   S
  325       GAC TAC TGG GGC CAG GGA ACC CTG GTC ACC GTG TCC TCA
```

Figure 5A

Anti-PD-1 4A11 VK

V segment:    L15
    J segment:    JK1

```
          D   I   Q   M   T   Q   S   P   S   S   L   S   A   S   V   G   D
          R
1         GAC ATC CAG ATG ACC CAG TCT CCA TCC TCA CTG TCT GCA TCT GTG GGA GAC
          AGA
                                              CDR1
                                              ~~~~~~~~~~~~~~~~~~~~~~~~~~~~~~
          V   S   I   T   C   R   A   S   Q   G   I   S   S   W   L   A   W
          Y
55        GTC TCC ATC ACT TGT CGG GCG AGT CAG GGT ATT AGC AGC TGG TTA GCC TGG
          TAT
                                                                          CDR2

~~~~~~~~~~~~~~~~~~~~~
          Q   Q   K   P   E   K   A   P   K   S   L   I   Y   A   A   S   N
          L
109       CAG CAG AAA CCA GAG AAA GCC CCT AAG TCC CTG ATC TAT GCT GCA TCC AAT
          TTA
              CDR2
              ~~~~~~~
          R   S   G   V   P   S   R   F   S   G   S   G   S   G   T   D   F
          T
163       CGA AGT GGG GTC CCA TCA AGG TTC AGC GGC AGT GGA TCT GGG ACA GAT TTC
          ACT

CDR3
              ~~~~~~~
          L   T   I   S   S   L   Q   P   E   D   F   A   T   Y   Y   C   Q
          Q
217       CTC ACC ATC AGC AGC CTG CAG CCT GAA GAT TTT GCA ACT TAT TAC TGC CAA
          CAG
                  CDR3
              ~~~~~~~~~~~~~~~~~~~~~~~~~~~
          Y   Y   S   Y   P   R   T   F   G   Q   G   T   K   V   E   I   K
271       TAT TAT AGT TAC CCT AGG ACG TTC GGC CAA GGG ACC AAG GTG GAA ATC AAA
```

Figure 5B

Anti-PD-1 7D3 VH

V segment: 3-33
D segment: 7-27
J segment: JH4b

```
      Q   V   Q   L   V   E   S   G   G   G   V   V   Q   P   G   R   S
      L
  1   CAG GTG CAG CTG GTG GAG TCT GGG GGA GGC GTG GTC CAG CCT GGG AGG TCC
      CTG
                                                                    CDR1
                                                                    ~~~~~~~~~~~~~~~
      R   L   S   C   T   T   S   G   I   T   F   S   S   Y   G   F   H
      W
 55   AGA CTC TCC TGT ACA ACG TCT GGA ATC ACC TTC AGT AGC TAT GGC TTT CAC
      TGG

CDR2
      ~~~~~~~~~~~~~~~~~~
      V   R   Q   A   P   G   K   G   L   E   W   V   A   V   I   W   Y
      D
109   GTC CGC CAG GCT CCA GGC AAG GGG CTG GAG TGG GTG GCA GTG ATA TGG TAT
      GAT
                      CDR2
      ~~~~~~~~~~~~~~~~~~~~~~~~~~~~~~~~~~~~~~~~~~~~~~~
      G   S   K   K   Y   Y   A   D   S   V   K   G   R   F   T   L   S
      R
163   GCA AGT AAA AAA TAC TAT GCA GAC TCC GTG AAG GGC CGA TTC ACC CTC TCC
      AGA

D   D   S   K   N   T   L   Y   L   Q   M   N   S   L   R   A   E
      D
217   GAC GAT TCC AAG AAC ACG CTG TAT CTG CAA ATG AAC AGC CTG AGA GCC GAG
      GAC
                                                  CDR3
                                                  ~~~~~~~~~~~~~~~~
      T   A   V   Y   Y   C   V   T   G   D   D   Y   W   G   Q   G   T
      L
271   ACG GCT GTG TAT TAC TGT GTT ACT GGG GAT GAC TAC TGG GGC CAG GGA ACC
      CTG

V   T   V   S   S
325   GTC ACC GTC TCC TCA
```

Figure 6A

Anti-PD-1 7D3 VK

V segment: L6
J segment: JK4

```
        E   I   V   L   T   Q   S   P   A   T   L   S   L   S   P   G   E
                                                                            R
1       GAA ATT GTG TTG ACA CAG TCT CCA GCC ACC CTG TCT TTG TCT CCA GGG GAA
        AGA
                                            CDR1
                                  ~~~~~~~~~~~~~~~~~~~~~~~~~~~~~~~~~~~~~~
        A   T   L   S   C   R   A   S   Q   S   V   S   S   Y   L   A   W
                                                                            Y
55      GCC ACC CTC TCC TGC AGG GCC AGT CAG AGT GTT AGC AGC TAC TTA GCC TGG
        TAC
                                                                    CDR2
        ~~~~~~~~~~~~~~~~~~~~
        Q   Q   K   P   G   Q   A   P   R   L   L   I   Y   D   A   S   N
                                                                            R
109     CAA CAG AAA CCT GGC CAG GCT CCC AGG CTC CTC ATC TAT GAT GCA TCC AAC
        AGG
        CDR2
        ~~~~~~~~
        A   T   G   I   P   A   R   F   S   G   S   G   S   G   T   D   F
                                                                            T
163     GCC ACT GGC ATC CCA GCC AGG TTC AGT GGC AGT GGG TCT GGG ACA GAC TTC
        ACT

CDR3
        ~~~~~~~~
        L   T   I   S   S   L   E   P   E   D   F   A   V   Y   Y   C   Q
                                                                            Q
217     CTC ACC ATC AGC AGC CTA GAG CCT GAA GAT TTT GCA GTT TAT TAC TGT CAG
        CAG
                CDR3
        ~~~~~~~~~~~~~~~~~~~~~~~~~~~
        R   S   N   W   P   L   T   F   G   G   G   T   K   V   E   I   K
271     CGT AGC AAC TGG CCT CTC ACT TTC GGC GGA GGG ACC AAG GTG GAG ATC AAA
```

Figure 6B

Anti-PD-1 5F4 VH

V segment: 4-39
D segment: 3-9
J segment: JH4b

```
        Q   L   Q   L   Q   E   S   G   P   G   L   V   K   P   S   E   T
        L
1       CAG CTG CAG CTG CAG GAG TCG GGC CCA GGA CTG GTG AAG CCT TCG GAG ACC
        CTG
```

CDR1

```
        ~~~~~~~~~~~~~~~~~~~~
        S   L   T   C   S   V   S   G   G   S   L   S   R   S   S   Y   F
        W
55      TCC CTC ACC TGC TCT GTC TCT GGT GGC TCC CTC AGC AGG AGT AGT TAC TTC
        TGG
```

CDR1                                                                CDR2
~~~
~~~~~~~~~~~~

```
        G   W   I   R   Q   P   P   G   K   G   L   E   W   I   A   S   I
        F
109     GGC TGG ATC CGC CAG CCC CCA GGG AAG GGG CTG GAG TGG ATT GCG AGT ATC
        TTT
```

CDR2
~~~~~~~~~~~~~~~~~~~~~~~~~~~~~~~~~~~~~~~~~~~~~~

```
        Y   S   G   E   T   Y   F   N   P   S   L   K   S   R   V   T   I
        S
163     TAT AGT GGG GAA ACC TAC TTC AAT CCG TCC CTC AAG AGT CGA GTC ACC ATA
        TCC
```

```
        V   D   T   S   R   N   Q   F   S   L   K   L   S   S   V   T   A
        A
217     GTA GAC ACG TCC AGG AAC CAG TTC TCC CTG AAG CTG AGC TCT GTG ACC GCC
        GCA
```

CDR3
~~~~~~~~~~~~~~~~~~~~~~~~~~~~~~~~~~

```
        D   T   A   V   Y   Y   C   A   R   D   Y   D   I   L   T   G   D
        E
271     GAC ACG GCT GTG TAT TAC TGT GCG AGA GAT TAC GAT ATT TTG ACT GGC GAC
        GAG
```

CDR3
~~~~~~~~

```
        D   Y   W   G   Q   G   T   L   V   T   V   S   S
325     GAC TAC TGG GGC CAG GGA ACC CTG GTC ACC GTC TCC TCA
```

Figure 7A

Anti-PD-1 5F4 VK

V segment:    L15
    J segment:    JK1

```
           D   I   Q   M   T   Q   S   P   S   S   L   S   A   S   V   G   D
           R
1          GAC ATC CAG ATG ACC CAG TCT CCA TCC TCA CTG TCT GCA TCT GTA GGA GAC
           AGA
                                                    CDR1
                                                    ~~~~~~~~~~~~~~~~~~~~~~~~~~~~
           V   T   I   T   C   R   A   S   Q   G   I   S   S   W   L   A   W
           Y
55         GTC ACC ATC ACT TGT CGG GCG AGT CAG GGT ATT AGC AGC TGG TTA GCC TGG
           TAT
                                                                        CDR2

~~~~~~~~~~~~~~~~~~~
           Q   Q   K   P   E   K   A   P   K   S   L   I   Y   A   A   S   S
           L
109        CAG CAG AAA CCA GAG AAA GCC CCT AAG TCC CTG ATC TAT GCT GCA TCC AGT
           TTG

CDR2
           ~~~~~~~
           Q   S   G   V   P   S   R   F   S   G   S   G   S   G   T   D   F
           T
163        CAA AGT GGG GTC CCA TCA AGG TTC AGC GGC AGT GGA TCT GGG ACA GAT TTC
           ACT

CDR3
           ~~~~~~~
           L   T   I   S   S   L   Q   P   E   D   F   A   T   Y   Y   C   Q
           Q
217        CTC ACC ATC AGC AGC CTG CAG CCT GAA GAT TTT GCA ACT TAT TAC TGC CAA
           CAG
                   CDR3
                   ~~~~~~~~~~~~~~~~~~~~~~~~~~~~~~~
           Y   Y   S   Y   P   R   T   F   G   Q   G   T   K   V   E   I   K
271        TAT TAT AGT TAC CCT AGG ACG TTC GGC CAA GGG ACC AAG GTG GAA ATC AAA
```

Anti-PD-1 4H1 and 5C4 VK Region

```
                          CDR1
L6 germline: E I V L T Q S P A T L S L S P G E R A T L S C R A S Q S V S S Y L A
4H1 VK:                                                                        
5C4 VK:

CDR2
L6 germline: W Y Q Q K P G Q A P R L L I Y D A S N R A T G I P A R F S G S G
4H1 VK:                                                                    
5C4 VK:

CDR3
L6 germline: T D F T L T I S S L E P E D F A V Y Y C Q Q R S N W P    W T F G Q G T
JK1 germline:                                                                 R
4H1 VK:                                                                       R
5C4 VK:

JK1 germline: K V E I K  (JK1)
4H1 VK:                  (JK1)
5C4 VK:
```

Figure 10

Anti-PD-1 4A11 and 5F4 VH regions

```
                                                          CDR1
4-39 germline:  Q L Q L Q E S G P G L V K P S E T L S L T C T V S G G S I S S Y Y W
4A11 VH:                                                          L       F
5F4 VH:                                                       R   R       F
                                           CDR2
4-39 germline:  G W I R Q P P G K G L E W I G Y I Y Y S G S T Y Y N P S L K S R V T I S
4A11 VH:                                       A                   F
5F4 VH:                                        A                   S 4-39 germline:  V D T S K N H F S L K L S S V T A A D T A V Y Y C A R
4A11 VH:                                                             D Y D I L T G D E
5F4 VH:             R                                                D Y D I L T G D E
                                                                           CDR3
JH4b germline:  D Y W G Q G T L V T V S S                 (JH4b)
4A11 VH:                                                  (JH4b)
5F4 VH:
```

Figure 11

Anti-PD-1 4A11 and 5F4 VK region

```
                                                    CDR1
L15 germline:  D I Q M T Q S P S S L S A S V G D R V T I T C R A S Q G I S S
4A11 VK:       - - - - - - - - - - - - - - - - - - - - - - - - - - - - - -
5F4 VK1:       - - - - - - - - - - - - - - - - - - - - - - - - - - - - - -

CDR2
L15 germline:  W L A W Y Q Q K P E K A P K S L I Y A A S S L Q S G V P S R F
4A11 VK:       - - N - - - - - - - - - - - - - - - - - - - T - - - - - - -
5F4 VK1:       - - - - - - - - - - - - - - - - - - - - - - N R - - - - - -

CDR3
L15 germline:  S G S G S G T D F T L T I S S L Q P E D F A T Y Y C Q Q Y N S
4A11 VK:       - - - - - - - - - - - - - - - - - - - - - - - - - - - - Y Y
5F4 VK1:       - - - - - - - - - - - - - - - - - - - - - - - - - - - - Y Y L15 germline:
JK1 germline:  Y P   T F G Q G T K V E I K       (JK1)
4A11 VK:           R                             (JK1)
5F4 VK1:           R
```

Figure 12

METHODS FOR TREATING CANCER USING ANTI-PD-1 ANTIBODIES

CROSS-REFERENCE TO RELATED APPLICATIONS

This application is a divisional of U.S. patent application Ser. No. 13/210,137 filed Aug. 15, 2011, which is a continuation of U.S. patent application Ser. No. 11/913,217 filed Jan. 29, 2009, issued as U.S. Pat. No. 8,008,449 on Aug. 30, 2011, which is a national stage of International Application Serial No. PCT/JP06/0309606 filed May 2, 2006, which claims priority to U.S. Provisional Patent Application Ser. No. 60/679,466 filed May 9, 2005, U.S. Provisional Patent Application Ser. No. 60/738,434 filed Nov. 21, 2005, and U.S. Provisional Patent Application Ser. No. 60/748,919 filed Dec. 8, 2005, the contents of each of which are incorporated by reference in their entirety, and to each of which priority is claimed.

REFERENCE TO A SEQUENCE LISTING SUBMITTED ELECTRONICALLY VIA EFS-WEB

The content of the electronically submitted substitute sequence listing (Name: 3338_0180008_2ndSubstituteSequenceListing.txt; Size: 50,897 bytes; and Date of Creation: Jun. 8, 2015) is herein incorporated by reference in its entirety.

TECHNICAL FIELD

The present invention relates generally to immunotherapy in the treatment of human disease and reduction of adverse events related thereto. More specifically, the present invention relates to the use of anti-PD-1 antibodies and the use of combination immunotherapy, including the combination of anti-CTLA-4 and anti-PD-1 antibodies, to treat cancer and/or to decrease the incidence or magnitude of adverse events related to treatment with such antibodies individually.

BACKGROUND OF THE INVENTION

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al. (2002) *Curr. Opin. Immunol.* 14: 391779-82; Bennett et al. (2003). *J Immunol* 170:711-8). The initial members of the family, CD28 and ICOS, were discovered by functional effects on augmenting T cell proliferation following the addition of monoclonal antibodies (Hutloff et al. (1999) *Nature* 397:263-266; Hansen et al. (1980) *Immunogenics* 10:247-260). PD-1 was discovered through screening for differential expression in apototic cells (Ishida et al. (1992) *EMBO J* 11:3887-95). The other members of the family, CTLA-4, and BTLA were discovered through screening for differential expression in cytotoxic T lymphocytes and TH1 cells, respectively. CD28, ICOS and CTLA-4 all have an unpaired cysteine residue allowing for homodimerization. In contrast, PD-1 is suggested to exist as a monomer, lacking the unpaired cysteine residue characteristic in other CD28 family members.

The PD-1 gene is a 55 kDa type I transmembrane protein that is part of the Ig gene superfamily (Agata et al. (1996) *Int Immunol* 8:765-72). PD-1 contains a membrane proximal immunoreceptor tyrosine inhibitory motif (ITIM) and a membrane distal tyrosine-based switch motif (ITSM) (Thomas, M. L. (1995) *J Exp Med* 181:1953-6; Vivier, E and Daeron, M (1997) *Immunol Today* 18:286-91). Although structurally similar to CTLA-4, PD-1 lacks the MYPPPY motif that is critical for B7-1 and B7-2 binding. Two ligands for PD-1 have been identified, PD-L1 and PD-L2, that have been shown to downregulate T cell activation upon binding to PD-1 (Freeman et al. (2000) *J Exp Med* 192:1027-34; Latchman et al. (2001) *Nat Immunol* 2:261-8; Carter et al. (2002) *Eur J Immunol* 32:634-43). Both PD-L1 and PD-L2 are B7 homologs that bind to PD-1, but do not bind to other CD28 family members. One ligand for PD-1, PD-L1 is abundant in a variety of human cancers (Dong et al. (2002) *Nat. Med.* 8:787-9). The interaction between PD-1 and PD-L1 results in a decrease in tumor infiltrating lymphocytes, a decrease in T-cell receptor mediated proliferation, and immune evasion by the cancerous cells (Doug et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1, and the effect is additive when the interaction of PD-1 with PD-L2 is blocked as well (Iwai et al. (2002) *Proc. Nat'l. Acad. Sci. USA* 99:12293-7; Brown et al. (2003) *J. Immunol.* 170:1257-66).

PD-1 is an inhibitory member of the CD28 family expressed on activated B cells, T cells, and myeloid cells (Agata et al., supra; Okazaki et al. (2002) *Curr Opin Immunol* 14: 391779-82; Bennett et al. (2003) *J Immunol* 170:711-8). PD-1 deficient animals develop various autoimmune phenotypes, including autoimmune cardiomyopathy and a lupus-like syndrome with arthritis and nephritis (Nishimura et al. (1999) *Immunity* 11:141-51; Nishimura et al. (2001) *Science* 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003) *J Exp Med* 198:71-78; Prokunina and Alarcon-Riquelme (2004) *Hum Mol Genet* 13:R143; Nielsen et al. (2004) *Lupus* 13:510). In a murine B cell tumor line, the ITSM of PD-1 was shown to be essential to block BCR-mediated $Ca^{2+}$-flux and tyrosine phosphorylation of downstream effector molecules (Okazaki et al, (2001) *PNAS* 98:13866-71).

Accordingly, agents that recognize PD-1, and methods of using such agents, are desired.

DISCLOSURE OF THE INVENTION

The present invention provides isolated monoclonal antibodies, in particular human monoclonal antibodies, that bind to PD-1 and that exhibit numerous desirable properties. These properties include, for example, high affinity binding to human PD-1, but lacking substantial cross-reactivity with either human CD28, CTLA-4 or ICOS. Still further, antibodies of the invention have been shown to modulate immune responses. Accordingly, another aspect of the invention pertains to methods of modulating immune responses using anti-PD-1 antibodies. In particular, the invention provides a method of inhibiting growth of tumor cells in vivo using anti-PD-1 antibodies.

In one aspect, the invention pertains to an isolated monoclonal antibody, or an antigen-binding portion thereof, wherein the antibody exhibits at least one of the following properties:

(a) binds to human PD-1 with a $K_D$ of $1\times10^{-7}$ M or less;
(b) does not substantially bind to human CD28, CTLA-4 or ICOS;
(c) increases T-cell proliferation in an Mixed Lymphocyte Reaction (MLR) assay;
(d) increases interferon-gamma production in an MLR assay;
(e) increases IL-2 secretion in an MLR assay;
(f) binds to human PD-1 and cynomolgus monkey PD-1;
(g) inhibits the binding of PD-L1 and/or PD-L2 to PD-1;
(h) stimulates antigen-specific memory responses;
(i) stimulates antibody responses;
(j) inhibits tumor cell growth in vivo.

Preferably the antibody is a human antibody, although in alternative embodiments the antibody can be, for example, a murine antibody, a chimeric antibody or humanized antibody.

In more preferred embodiments, the antibody binds to human PD-1 with a $K_D$ of $5\times10^{-8}$ M or less, binds to human PD-1 with a $K_D$ of $1\times10^{-8}$ M or less, binds to human. PD-1 with a $K_D$ of $5\times10^{-9}$ M or less, or binds to human PD-1 with a $K_D$ of between $1\times10^{-8}$ M and $1\times10^{-10}$ M.

In another embodiment, the invention provides an isolated monoclonal antibody, or antigen-binding portion thereof, wherein the antibody cross-competes for binding to PD-1 with a reference antibody comprising:
(a) a human heavy chain variable region comprises an amino acid sequence selected from the group consisting of SEQ ID NOs: 1, 2, 3, 4, 5, 6 and 7; and
(b) a human light chain variable region comprises an amino acid sequence selected from the group consisting of SEQ ID NOs: 8, 9, 10, 11, 12, 13 and 14.

In various embodiments, the reference antibody comprises:
(a) a heavy chain variable region comprising the amino acid sequence of SEQ ID NO: 1; and
(b) a light chain variable region comprising the amino acid sequence of SEQ ID NO: 8; or the reference antibody comprises:
(a) a heavy chain variable region comprising the amino acid sequence of SEQ ID NO: 2; and
(b) a light chain variable region comprising the amino acid sequence of SEQ ID NO: 9; or the reference antibody comprises:
(a) a heavy chain variable region comprising the amino acid sequence of SEQ ID NO: 3; and
(b) a light chain variable region comprising the amino acid sequence of SEQ ID NO: 10; or the reference antibody comprises:
(a) a heavy chain variable region comprising the amino acid sequence of SEQ ID NO: 4; and
(b) a light chain variable region comprising the amino acid sequence of SEQ ID NO: 11; or the reference antibody comprises:
(a) a heavy chain variable region comprising the amino acid sequence of SEQ ID NO: 5; and
(b) a light chain variable region comprising the amino acid sequence of SEQ ID NO: 12; or the reference antibody comprises:
(a) a heavy chain variable region comprising the amino acid sequence of SEQ ID NO: 6; and
(b) a light chain variable region comprising the amino acid sequence of SEQ ID NO: 13; or the reference antibody comprises:
(a) a heavy chain variable region comprising the amino acid sequence of SEQ ID NO: 7; and
(b) a light chain variable region comprising the amino acid sequence of SEQ ID NO: 14.

In another aspect, the invention pertains to an isolated monoclonal antibody, or an antigen-binding portion thereof, comprising a heavy chain variable region that is the product of or derived from a human $V_H$ 3-33 gene, wherein the antibody specifically binds PD-1. The invention further provides an isolated monoclonal antibody, or an antigen-binding portion thereof, comprising a heavy chain variable region that is the product of or derived from a human $V_H$ 4-39 gene, wherein the antibody specifically binds PD-1. The invention further provides an isolated monoclonal antibody, or an antigen-binding portion thereof, comprising a light chain variable region that is the product of or derived from a human $V_K$ L6 gene, wherein the antibody specifically binds PD-1. The invention further provides an isolated monoclonal antibody, or an antigen-binding portion thereof, comprising a light chain variable region that is the product of or derived from a human $V_K$ L15 gene, wherein the antibody specifically binds PD-1.

In a preferred embodiment, the invention provides an isolated monoclonal antibody, or an antigen-binding portion thereof, comprising:
(a) a heavy chain variable region of a human $V_H$ 3-33 gene; and
(b) a light chain variable region of a human $V_K$ L6 gene; wherein the antibody specifically binds to PD-1.

In another preferred embodiment, the invention provides an isolated monoclonal antibody, or an antigen-binding portion thereof, comprising:
(a) a heavy chain variable region of a human $V_H$ 4-39 gene; and
(b) a light chain variable region of a human $V_K$ L15 gene; wherein the antibody specifically binds to PD-1.

In another aspect, the invention provides an isolated monoclonal antibody, or antigen-binding portion thereof, comprising:
a heavy chain variable region that comprises CDR1, CDR2, and CDR3 sequences; and a light chain variable region that comprises CDR1, CDR2, and CDR3 sequences, wherein:
(a) the heavy chain variable region CDR3 sequence comprises an amino acid sequence selected from the group consisting of SEQ ID NOs: 29, 30, 31, 32, 33, 34 and 35, and conservative modifications thereat
(b) the light chain variable region CDR3 sequence comprises an amino acid sequence selected from the group consisting of SEQ ID NOs: 50, 51, 52, 53, 54, 55 and 56, and conservative modifications thereof; and
(c) the antibody specifically binds to human PD-1.

Preferably, the heavy chain variable region. CDR2 sequence comprises an amino acid sequence selected from the group consisting of amino acid sequences of SEQ ID NOs: 22, 23, 24, 25, 26, 27 and 28, and conservative modifications thereof; and the light chain variable region CDR2 sequence comprises an amino acid sequence selected from the group consisting of amino acid sequences of SEQ ID NOs: 43, 44, 45, 46, 47, 48 and 49, and conservative modifications thereof. Preferably, the heavy chain variable region CDR1 sequence comprises an amino acid sequence selected from the group consisting of amino acid sequences of SEQ ID NOs: 15, 16, 17, 18, 19, 20 and 21, and conservative modifications thereof; and the light chain variable region CDR1 sequence comprises an amino acid sequence selected from the group consisting of amino acid sequences of SEQ ID NOs: 36, 37, 38, 39, 40, 41 and 42, and conservative modifications thereof.

In yet another aspect, the invention provides an isolated monoclonal antibody, or antigen-binding portion thereof, comprising a heavy chain variable region and a light chain variable region, wherein:
- (a) the heavy chain variable region comprises an amino acid sequence that is at least 80% homologous to an amino acid sequence selected from the group consisting of SEQ ID NOs: 1, 2, 3, 4, 5, 6 and 7;
- (b) the light chain variable region comprises an amino acid sequence that is at least 80% homologous to an amino acid sequence selected from the group consisting of SEQ ID NOs: 8, 9, 10, 11, 12, 13 and 14;
- (c) the antibody binds to human PD-1 with a $K_D$ of $1\times10^{-7}$M or less; and
- (d) the antibody does not substantially bind to human CD28, CTLA-4 or ICOS.

In a preferred embodiment, the antibodies additionally comprise at least one of the following properties:
- (a) the antibody increases T-cell proliferation in an MLR assay;
- (b) the antibody increases interferon-gamma production in an MLR assay; or
- (c) the antibody increases IL-2 secretion in an MLR assay.

Additionally or alternatively, the antibody may comprise one or more of the other features listed above.

In preferred embodiments, the invention provides an isolated monoclonal antibody, or antigen-binding portion thereof; comprising:
- (a) a heavy chain variable region CDR1 comprising an amino acid sequence selected from the group consisting of SEQ ID NOs: 15, 16, 17, 18, 19, 20 and 21;
- (b) a heavy chain variable region CDR2 comprising an amino acid sequence selected from the group consisting of SEQ ID NOs: 22, 23, 24, 25, 26, 27 and 28;
- (c) a heavy chain variable region CDR3 comprising an amino acid sequence selected from the group consisting of SEQ ID NOs: 29, 30, 31, 32, 33, 34 and 35;
- (d) a light chain variable region CDR1 comprising an amino acid sequence selected from the group consisting of SEQ ID NOs: 36, 37, 38, 39, 40, 41 and 42;
- (e) a light chain variable region CDR2 comprising an amino acid sequence selected from the group consisting of SEQ ID NOs: 43, 44, 45, 46, 47, 48 and 49; and
- (f) a light chain variable region CDR3 comprising an amino acid sequence selected from the group consisting of SEQ ID NOs: 50, 51, 52, 53, 54, 55 and 56;

wherein the antibody specifically binds PD-1.

A preferred combination comprises:
- (a) a heavy chain variable region CDR1 comprising SEQ ID NO: 15;
- (b) a heavy chain variable region CDR2 comprising SEQ ID NO: 22;
- (c) a heavy chain variable region CDR3 comprising SEQ ID NO: 29;
- (d) a light chain variable region CDR1 comprising SEQ ID NO: 36;
- (e) a light chain variable region CDR2 comprising SEQ ID NO: 43; and
- (f) a light chain variable region CDR3 comprising SEQ ID NO: 50.

Another preferred combination comprises:
- (a) a heavy chain variable region CDR1 comprising SEQ ID NO: 16;
- (b) a heavy chain variable region CDR2 comprising SEQ ID NO: 23;
- (c) a heavy chain variable region. CDR3 comprising SEQ ID NO: 30;
- (d) a light chain variable region CDR1 comprising SEQ ID NO: 37;
- (e) a light chain variable region CDR2 comprising SEQ ID NO: 44; and
- (f) a light chain variable region CDR3 comprising SEQ ID NO: 51.

Another preferred combination comprises:
- (a) a heavy chain variable region CDR1 comprising SEQ ID NO: 17;
- (b) a heavy chain variable region CDR2 comprising SEQ ID NO: 24;
- (c) a heavy chain variable region CDR3 comprising SEQ ID NO: 31;
- (d) a light chain variable region CDR1 comprising SEQ ID NO: 38;
- (e) a light chain variable region CDR2 comprising SEQ ID NO: 45; and
- (f) a light chain variable region CDR3 comprising SEQ ID NO: 52.

An other preferred combination comprises:
- (a) a heavy chain variable region CDR1 comprising SEQ ID NO: 18;
- (b) a heavy chain variable region CDR2 comprising SEQ ID NO: 25;
- (c) a heavy chain variable region CDR3 comprising SEQ ID NO: 32;
- (d) a light chain variable region CDR1 comprising SEQ ID NO: 39;
- (e) a light chain variable region CDR2 comprising SEQ ID NO: 46; and
- (f) a light chain variable region CDR3 comprising SEQ ID NO: 53.

Another preferred combination comprises:
- (a) a heavy chain variable region CDR1 comprising SEQ ID NO: 19;
- (b) a heavy chain variable region CDR2 comprising SEQ ID NO: 26;
- (c) a heavy chain variable region CDR3 comprising SEQ ID NO: 33;
- (d) a light chain variable region CDR1 comprising SEQ ID NO: 40;
- (e) a light chain variable region CDR2 comprising SEQ ID NO: 47; and
- (f) a light chain variable region CDR3 comprising SEQ ID NO: 54.

Another preferred combination comprises:
- (a) a heavy chain variable region CDR1 comprising SEQ ID NO: 20;
- (b) a heavy chain variable region CDR2 comprising SEQ ID NO: 27;
- (c) a heavy chain variable region CDR3 comprising SEQ ID NO: 34;
- (d) a light chain variable region CDR1 comprising SEQ ID NO: 41;
- (e) a light chain variable region CDR2 comprising SEQ ID NO: 48; and
- (f) a light chain variable region CDR3 comprising SEQ ID NO: 55.

Another preferred combination comprises:
- (a) a heavy chain variable region CDR1 comprising SEQ ID NO: 21;
- (b) a heavy chain variable region CDR2 comprising SEQ ID NO: 28;
- (c) a heavy chain variable region CDR3 comprising SEQ ID NO: 35;
- (d) a light chain variable region CDR1 comprising SEQ ID NO: 42;

(e) a light chain variable region CDR2 comprising SEQ ID NO: 49; and (f) a light chain variable region CDR3 comprising SEQ ID NO: 56.

Other preferred antibodies of the invention, or antigen-binding portions thereof, comprise:
- (a) a heavy chain variable region comprising an amino acid sequence selected from the group consisting of SEQ ID NOs: 1, 2, 3, 4, 5, 6 and 7; and
- (b) a light chain variable region comprising an amino acid sequence selected from the group consisting of SEQ ID NOs: 8, 9, 10, 11, 12, 13 and 14; wherein the antibody specifically binds PD-1.

A preferred combination comprises:
- (a) a heavy chain variable region comprising the amino acid sequence of SEQ ID NO: 1; and
- (b) a light chain variable region comprising the amino acid sequence of SEQ ID NO: 8.

Another preferred combination comprises:
- (a) a heavy chain variable region comprising the amino acid sequence of SEQ ID NO: 2; and
- (b) a light chain variable region comprising the amino acid sequence of SEQ ID NO: 9.

Another preferred combination comprises:
- (a) a heavy chain variable region comprising the amino acid sequence of SEQ ID NO: 3; and
- (b) a light chain variable region comprising the amino acid sequence of SEQ ID NO: 10.

Another preferred combination comprises:
- (a) a heavy chain variable region comprising the amino acid sequence of SEQ ID NO: 4; and
- (b) a light chain variable region comprising the amino acid sequence of SEQ ID NO: 11.

Another preferred combination comprises:
- (a) a heavy chain variable region comprising the amino acid sequence of SEQ ID NO: 5; and
- (b) a light chain variable region comprising the amino acid sequence of SEQ ID NO: 12.

Another preferred combination comprises:
(a) a heavy chain variable region comprising the amino acid sequence of SEQ ID NO: 6; and
- (b) a light chain variable region comprising the amino acid sequence of SEQ ID NO: 13.

Another preferred combination comprises:
- (a) a heavy chain variable region comprising the amino acid sequence of SEQ ID NO: 7; and
- (b) a light chain variable region comprising the amino acid sequence of SEQ ID NO: 14.

The antibodies of the invention can be, for example, full-length antibodies, for example of an IgG1 or IgG4 isotype. Alternatively, the antibodies can be antibody fragments, such as Fab or Fab'2 fragments, or single chain antibodies.

The invention also provides an immunoconjugate comprising an antibody of the invention, or antigen-binding portion thereof, linked to a therapeutic agent, such as a cytotoxin or a radioactive isotope. The invention also provides a bispecific molecule comprising an antibody, or antigen-binding portion thereof, of the invention, linked to a second functional moiety having a different binding specificity than said antibody, or antigen-binding portion thereof.

Compositions comprising an antibody, or antigen-binding portion thereof, or immunoconjugate or bispecific molecule of the invention, and a pharmaceutically acceptable carrier, are also provided.

Nucleic acid molecules encoding the antibodies, or antigen-binding portions thereof, of the invention are also encompassed by the invention, as well as expression vectors comprising such nucleic acids and host cells comprising such expression vectors. Moreover, the invention provides a transgenic mouse comprising human immunoglobulin heavy and light chain transgenes, wherein the mouse expresses an antibody of the invention, as well as hybridomas prepared from such a mouse, wherein the hybridoma produces the antibody of the invention.

In yet another aspect, the invention provides a method of modulating an immune response in a subject comprising administering to the subject the antibody, or antigen-binding portion thereof, of the invention such that the immune response in the subject is modulated. Preferably, the antibody of the invention enhances, stimulates or increases the immune response in the subject.

In a further aspect, the invention provides a method of inhibiting growth of tumor cells in a subject, comprising administering to a subject a therapeutically effective amount of an anti-PD-1 antibody, or antigen-binding portion thereof. The antibodies of the invention are preferred for use in the method although other anti-PD-1 antibodies can be used instead (or in combination with an anti-PD-1 antibody of the invention). For example, a chimeric, humanized or fully human anti-PD-1 antibody can be used in the method of inhibiting tumor growth.

In a further aspect, the invention provides a method of treating an infectious disease in a subject, comprising administering to a subject a therapeutically effective amount of an anti-PD-1 antibody, or antigen-binding portion thereof. The antibodies of the invention are preferred for use in the method although other anti-PD-1 antibodies can be used instead (or in combination with an anti-PD-1 antibody of the invention). For example, a chimeric, humanized or fully human anti-PD-1 antibody can be used in the method of treating an infectious disease.

Still further, the invention provides a method of enhancing an immune response to an antigen in a subject, comprising administering to the subject: (i) the antigen; and (ii) an anti-PD-1 antibody, or antigen-binding portion thereof; such that an immune response to the antigen in the subject is enhanced. The antigen can be, for example, a tumor antigen, a viral antigen, a bacterial antigen or an antigen from a pathogen. The antibodies of the invention are preferred for use in the method although other anti-PD-1 antibodies can be used instead (or in combination with an anti-PD-1 antibody of the invention). For example, a chimeric, humanized or fully human anti-PD-1 antibody can be used in the method of enhancing an immune response to an antigen in a subject.

The invention also provides methods for making "second generation" anti-PD-1 antibodies based on the sequences of the anti-PD-1 antibodies provided herein. For example, the invention provides a method for preparing an anti-PD-1 antibody comprising:

(a) providing: (i) a heavy chain variable region antibody sequence comprising a CDR1 sequence that is selected from the group consisting of SEQ ID NOs: 15, 16, 17, 18, 19, 20 and 21, and/or a CDR2 sequence that is selected from the group consisting of SEQ ID NOs: 22, 23, 24, 25, 26, 27 and 28; and/or a CDR3 sequence that is selected from the group consisting of SEQ ID NOs: 29, 30, 31, 32, 33, 34 and 35; or (ii) a light chain variable region antibody sequence comprising a CDR1 sequence that is selected from the group consisting of SEQ ID NOs: 36, 37, 38, 39, 40, 41 and 42, and/or a CDR2 sequence that is selected from the group consisting of SEQ ID NOs: 43, 44, 45, 46, 47, 48 and 49, and/or a CDR3 sequence that is selected from the group consisting of SEQ ID NOs: 50, 51, 52, 53, 54, 55 and 56;

(b) altering at least one amino acid residue within at least one variable region antibody sequence, said sequence being selected from the heavy chain variable region antibody sequence and the light chain variable region antibody sequence, to create at least one altered antibody sequence; and (c) expressing the altered antibody sequence as a protein.

Other features and advantages of the instant invention will be apparent from the following detailed description and examples which should not be construed as limiting. The contents of all references, GenBank entries, patents and published patent applications cited throughout this application are expressly incorporated herein by reference.

BRIEF DESCRIPTION OF THE DRAWINGS

FIG. 1A shows the nucleotide sequence (SEQ ID NO: 57) and amino acid sequence (SEQ ID NO: 1) of the heavy chain variable region of the 17D8 human monoclonal antibody. The CDR1 (SEQ ID NO: 15), CDR2 (SEQ ID NO: 22) and CDR3 (SEQ ID NO: 29) regions are delineated and the V, D and J germline derivations are indicated.

FIG. 1B shows the nucleotide sequence (SEQ ID NO: 64) and amino acid sequence (SEQ ID NO: 8) of the light chain variable region of the 17D8 human monoclonal antibody. The CDR1 (SEQ ID NO: 36), CDR2 (SEQ ID NO: 43) and CDR3 (SEQ ID NO: 50) regions are delineated and the V and J germline derivations are indicated.

FIG. 2A shows the nucleotide sequence (SEQ ID NO: 58) and amino acid sequence (SEQ ID NO: 2) of the heavy chain variable region of the 2D3 human monoclonal antibody. The CDR1 (SEQ ID NO: 16), CDR2 (SEQ ID NO: 23) and CDR3 (SEQ ID NO: 30) regions are delineated and the V and J germline derivations are indicated.

FIG. 2B shows the nucleotide sequence (SEQ ID NO: 65) and amino acid sequence (SEQ ID NO: 9) of the light chain variable region of the 2D3 human monoclonal antibody. The CDR1 (SEQ ID NO: 37), CDR2 (SEQ ID NO: 44) and CDR3 (SEQ ID NO: 51) regions are delineated and the V and J germline derivations are indicated.

FIG. 3A shows the nucleotide sequence (SEQ ID NO: 59) and amino acid sequence (SEQ ID NO: 3) of the heavy chain variable region of the 4H1 human monoclonal antibody. The CDR1 (SEQ ID NO: 17), CDR2 (SEQ ID NO: 24) and CDR3 (SEQ ID NO: 31) regions are delineated and the V and J germline derivations are indicated.

FIG. 3B shows the nucleotide sequence (SEQ ID NO: 66) and amino acid sequence (SEQ ID NO: 10) of the light chain variable region of the 4H1 human monoclonal antibody. The CDR1 (SEQ ID NO: 38), CDR2 (SEQ ID NO: 45) and CDR3 (SEQ ID NO: 52) regions are delineated and the V and J germline derivations are indicated.

FIG. 4A shows the nucleotide sequence (SEQ ID NO: 60) and amino acid sequence (SEQ ID NO: 4) of the heavy chain variable region of the 5C4 human monoclonal antibody. The CDR1 (SEQ ID NO: 18), CDR2 (SEQ ID NO: 25) and CDR3 (SEQ ID NO: 32) regions are delineated and the V and J germline derivations are indicated.

FIG. 4B shows the nucleotide sequence (SEQ ID NO: 67) and amino acid sequence (SEQ ID NO: 11) of the light chain variable region of the 5C4 human monoclonal antibody. The CDR1 (SEQ ID NO: 39), CDR2 (SEQ ID NO: 46) and CDR3 (SEQ ID NO: 53) regions are delineated and the V and J germline derivations are indicated.

FIG. 5A shows the nucleotide sequence (SEQ ID NO: 61) and amino acid sequence (SEQ ID NO: 5) of the heavy chain variable region of the 4A11 human monoclonal antibody. The CDR1 (SEQ ID NO: 19), CDR2 (SEQ ID NO: 26) and CDR3 (SEQ ID NO: 33) regions are delineated and the V and J germline derivations are indicated.

FIG. 5B shows the nucleotide sequence (SEQ ID NO: 68) and amino acid sequence (SEQ ID NO: 12) of the light chain variable region of the 4A11 human monoclonal antibody. The CDR1 (SEQ ID NO: 40), CDR2 (SEQ ID NO: 47) and CDR3 (SEQ ID NO: 54) regions are delineated and the V and J germline derivations are indicated.

FIG. 6A shows the nucleotide sequence (SEQ ID NO: 62) and amino acid sequence (SEQ ID NO: 6) of the heavy chain variable region of the 7D3 human monoclonal antibody. The CDR1 (SEQ ID NO: 20), CDR2 (SEQ ID NO: 27) and CDR3 (SEQ ID NO: 34) regions are delineated and the V and J germline derivations are indicated.

FIG. 6B shows the nucleotide sequence (SEQ ID NO: 69) and amino acid sequence (SEQ ID NO: 13) of the light chain variable region of the 7D3 human monoclonal antibody. The CDR1 (SEQ ID NO: 41), CDR2 (SEQ ID NO: 48) and CDR3 (SEQ ID NO: 55) regions are delineated and the V and J germline derivations are indicated.

FIG. 7A shows the nucleotide sequence (SEQ ID NO: 63) and amino acid sequence (SEQ ID NO: 7) of the heavy chain variable region of the 5F4 human monoclonal antibody. The CDR1 (SEQ ID NO: 21), CDR2 (SEQ ID NO: 28) and CDR3 (SEQ ID NO: 35) regions are delineated and the V and J germline derivations are indicated.

FIG. 7B shows the nucleotide sequence (SEQ ID NO: 70) and amino acid sequence (SEQ ID NO: 14) of the light chain variable region of the 5F4 human monoclonal antibody. The CDR1 (SEQ ID NO: 42), CDR2 (SEQ ID NO: 49) and CDR3 (SEQ ID NO: 56) regions are delineated and the V and J germline derivations are indicated.

FIG. 8 shows the alignment of the amino acid sequence of the heavy chain variable region of 17D8, 2D3, 4H1, 5C4 and 7D3 with the human germline $V_H$ 3-33 amino acid sequence (SEQ ID NO: 71).

FIG. 10 shows the alignment of the amino acid sequence of the light chain variable region of 4H1 and 5C4 with the human germline $V_k$ L6 amino acid sequence (SEQ ID NO: 73).

FIG. 11 shows the alignment of the amino acid sequence of the heavy chain variable region of 4A11 and 5F4 with the human germline $V_n$ 4-39 amino acid sequence (SEQ ID NO: 72).

FIG. 12 shows the alignment of the amino acid sequence of the light chain variable region of 4A11 and 5F4 with the human germline $V_k$ L15 amino acid sequence (SEQ ID NO: 74).

FIG. 13A shows to the flow cytometry plot for 5C4. FIG. 13B shows the flow cytometry plot for 4H1. Thin line represents the binding to CHO cells and solid line represents the binding to CHO hPD-1 cells.

FIG. 15A shows binding to activated human T-cells. FIG. 15B shows the binding to cynomolgous monkey T-cells. FIG. 15C shows the binding to CHO transfected cells expressing PD-1.

FIG. 16A is a bar graph showing concentration dependent T-cell proliferation; FIG. 16B is a bar graph showing concentration dependent IFN-gamma secretion; FIG. 16C is a bar graph showing concentration dependent IL-2 secretion.

FIG. 17A is a graph showing inhibition of binding of PD-L1; FIG. 17B is a graph showing inhibition of binding of PD-L2.

FIG. 50A is a bar graph showing concentration dependent T-cell proliferation using HuMAb 5C4; FIG. 50B is a bar graph showing concentration dependent IFN-gamma secretion using HuMAb 5C4.

FIG. 51A is a bar graph showing concentration dependent T-cell proliferation using HuMAb 5C4; FIG. 51B is a bar graph showing concentration dependent IFN-gamma secretion using HuMAb 5C4.

DETAILED DESCRIPTION OF THE INVENTION

Figure 9:
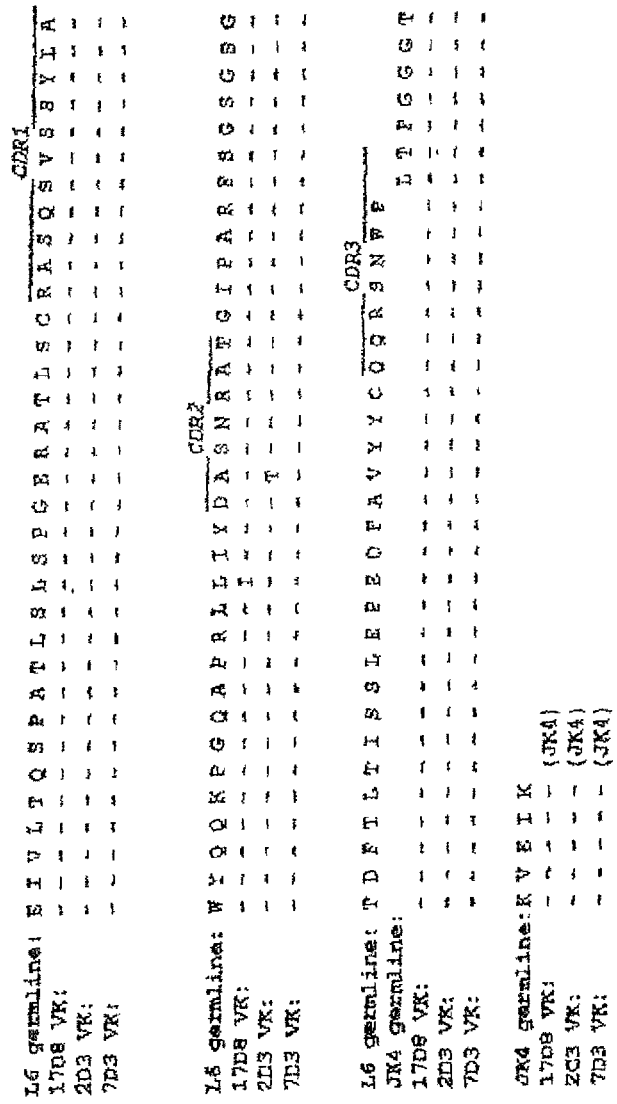
FIG. 9 shows the alignment of the amino acid sequence of the light chain variable region of 17D8, 2D3 and 7D3 with the human germline $V_k$ L6 amino acid sequence (SEQ ID NO: 73).

In one aspect, the present invention relates to isolated monoclonal antibodies, particularly human monoclonal antibodies, that bind specifically to PD-1. In certain embodiments, the antibodies of the invention exhibit one or more desirable functional properties, such as high affinity binding to PD-1, lack of cross-reactivity to other CD28 family members, the ability to stimulate T cell proliferation, IFN-γ and/or IL-2 secretion in mixed lymphocyte reactions, the ability to inhibit binding of one or more PD-1 ligands (e.g., PD-L1 and/or PD-L2), the ability to cross-react with cynomolgus monkey PD-1, the ability to stimulate antigen-specific memory responses, the ability to stimulate antibody responses and/or the ability to inhibit growth of tumor cells in vivo. Additionally or alternatively, the antibodies of the invention are derived from particular heavy and light chain germline sequences and/or comprise particular structural features such as CDR regions comprising particular amino acid sequences. In another aspect, the invention relates to the combined use of monoclonal antibodies that bind specifically to PD-1 and monoclonal antibodies that bind specifically to CTLA-4.

The invention provides, for example, isolated antibodies, methods of making such antibodies, immunoconjugates and bispecific molecules comprising such antibodies and pharmaceutical compositions containing the antibodies, immunconjugates or bispecific molecules of the invention.

In another aspect, the invention pertains to methods of inhibiting growth of tumor cells in a subject using anti-PD-1 antibodies. As demonstrated herein, anti-PD-1 antibodies are capable of inhibiting tumor cell growth in vivo. The invention also relates to methods of using the antibodies to modify an immune response, as well as to treat diseases such as cancer or infectious disease, or to stimulate a protective autoimmune response or to stimulate antigen-specific immune responses (e.g., by coadministration of anti-PD-1 with an antigen of interest).

In order that the present invention may be more readily understood, certain terms are first defined. Additional definitions are set forth throughout the detailed description.

The terms "Programmed Death 1," "Programmed Cell Death 1," "Protein PD-1," "PD-1," PD1," "PDCD1," "hPD-1" and "hPD-1" are used interchangeably, and include variants, isoforms, species homologs of human PD-1, and analogs having at least one common epitope with PD-1. The complete PD-1 sequence can be found under GenBank Accession No. U64863.

The terms "cytotoxic T lymphocyte-associated antigen-4," "CTLA-4," "CTLA4," "CTLA-4 antigen" and "CD152" (see, e.g., Murata, *Am. J. Pathol.* (1999) 155:453-460) are used interchangeably, and include variants, isoforms, species homologs of human CTLA-4, and analogs having at least one common epitope with CTLA-4 (see, e.g., Balzano (1992) *Int. J. Cancer Suppl.* 7:28-32). The complete CTLA-4 nucleic acid sequence can be found under GenBank Accession No. L15006.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the PD-1 receptor.

The term "antibody" as referred to herein includes whole antibodies and any antigen-binding fragment (i.e., "antigen-binding portion") or single chains thereof. An "antibody" refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., PD-1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds PD-1 is substantially free of antibodies that specifically bind antigens other than PD-1). An isolated antibody that specifically binds PD-1 may, however, have cross-reactivity to other antigens, such as PD-1 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human PD-1" is intended to refer to an antibody that binds to human PD-1 with a $K_D$ of $1\times10^{-7}$ M or less, more preferably $5\times10^{-8}$ M or less, more preferably $1\times10^{-8}$ M or less, more preferably $5\times10^{-9}$ M or less.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

The term "treatment" or "therapy" refers to administering an active agent with the purpose to cure, heal, alleviate, relieve, alter, remedy, ameliorate, improve, or affect a condition (e.g., a disease), the symptoms of the condition, or to prevent or delay the onset of the symptoms, complications, biochemical indicia of a disease, or otherwise arrest or inhibit further development of the disease, condition, or disorder in a statistically significant manner.

An "adverse event" (AE) as used herein is any unfavorable and generally unintended, even undesirable, sign (including an abnormal laboratory finding), symptom, or disease associated with the use of a medical treatment. For example, an adverse event may be associated with activation of the immune system or expansion of immune system cells (e.g., T cells) in response to a treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

As used herein, "hyperproliferative disease" refers to conditions wherein cell growth is increased over normal levels. For example, hyperproliferative diseases or disorders include malignant diseases (e.g., esophageal cancer, colon cancer, biliary cancer) and non-malignant diseases (e.g., atherosclerosis, benign hyperplasia, benign prostatic hypertrophy).

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer). For example, a subtherapeutic dose of CTLA-4 antibody is a single dose of the antibody at less than about 3 mg/kg, i.e., the known dose of anti-CTLA-4 antibody.

The use of the alternative (e.g., "or") should be understood to mean either one, both, or any combination thereof of the alternatives. As used herein, the indefinite articles "a" or "an" should be understood to refer to "one or more" of any recited or enumerated component.

As used herein, "about" or "comprising essentially of" mean within an acceptable error range for the particular value as determined by one of ordinary skill in the art, which will depend in part on how the value is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

As described herein, any concentration range, percentage range, ratio range or integer range is to be understood to include the value of any integer within the recited range and, when appropriate, fractions thereof (such as one tenth and one hundredth of an integer), unless otherwise indicated.

As used herein, the term "subject" includes any human or nonhuman animal. The term "nonhuman animal" includes all vertebrates, e.g., mammals and non-mammals, such as nonhuman primates, sheep, dogs, cats, horses, cows chickens, amphibians, reptiles, etc. Except when noted, the terms "patient" or "subject" are used interchangeably.

Various aspects of the invention are described in further detail in the following subsections.

Anti-PD-1 Antibodies

The antibodies of the invention are characterized by particular functional features or properties of the antibodies. For example, the antibodies bind specifically to PD-1 (e.g., bind to human PD-1 and may cross-react with PD-1 from other species, such as cynomolgus monkey). Preferably, an antibody of the invention binds to PD-1 with high affinity, for example with a $K_D$ of $1 \times 10^{-7}$ M or less. The anti-PD-1 antibodies of the invention preferably exhibit one or more of the following characteristics:

(a) binds to human PD-1 with a $K_D$ of $1 \times 10^{-7}$ M or less;
(b) does not substantially bind to human CD28, CTLA-4 or ICOS;
(c) increases T-cell proliferation in an Mixed Lymphocyte Reaction (MLR) assay;
(d) increases interferon-gamma production in an MLR assay;
(e) increases IL-2 secretion in an MLR assay;
(1) binds to human PD-1 and cynomolgus monkey PD-1;
(g) inhibits the binding of PD-L1 and/or PD-L2 to PD-1;
(h) stimulates antigen-specific memory responses;
(i) stimulates antibody responses;
(j) inhibits tumor cell growth in viva.

Preferably, the antibody binds to human PD-1 with a $K_D$ of $5 \times 10^{-8}$ M or less, binds to human PD-1 with a $K_D$ of $1 \times 10^{-8}$ M or less, binds to human PD-1 with a $K_D$ of $5 \times 10^{-9}$ M or less, or binds to human PD-1 with a $K_D$ of between $1 \times 10^{-8}$ M and $1 \times 10^{-10}$ M or less.

An antibody of the invention may exhibit any combination of the above-listed features, such as two, three, four, five or more of the above-listed features.

Standard assays to evaluate the binding ability of the antibodies toward PD-1 are known in the art, including for example, ELISAs, Western blots and RIAs. The binding kinetics (e.g., binding affinity) of the antibodies also can be assessed by standard assays known in the art, such as by Biacore analysis. Suitable assays for evaluating any of the above-described characteristics are described in detail in the Examples.

Monoclonal Antibodies 17D8, 2D3, 4H1, 5C4, 4A11, 7D3 and 5F4

Preferred antibodies of the invention are the human monoclonal antibodies 17D8, 2D3, 4H1, 5C4, 4A11, 7D3 and 5F4 isolated and structurally characterized as described in Examples 1 and 2. The $V_H$ amino acid sequences of 17D8, 2D3, 4H1, 5C4, 4A11, 7D3 and 5F4 are shown in SEQ ID NOs: 1, 2, 3, 4, 5, 6 and 7, respectively. The $V_L$ amino acid sequences of 17D8, 2D3, 4H1, 5C4, 4A11, 7D3 and 5F4 are shown in SEQ ID NOs: 8, 9, 10, 11, 12, 13 and 14, respectively.

Given that each of these antibodies can bind to PD-1, the $V_H$ and $V_L$ sequences can be "mixed and matched" to create other anti-PD-1 binding molecules of the invention. PD-1 binding of such "mixed and matched" antibodies can be tested using the binding assays described above and in the Examples (e.g., ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, the invention provides an isolated monoclonal antibody, or antigen-binding portion thereof comprising:

(a) a heavy chain variable region comprising an amino acid sequence selected from the group consisting of SEQ ID NOs: 1, 2, 3, 4, 5, 6 and 7; and
(b) a light chain variable region comprising an amino acid sequence selected from the group consisting of SEQ ID NOs: 8, 9, 10, 11, 12, 13 and 14;

wherein the antibody specifically binds PD-1, preferably human PD-1.

Preferred heavy and light chain combinations include:

(a) a heavy chain variable region comprising the amino acid sequence of SEQ ID NO: 1; and (b) a light chain variable region comprising the amino acid sequence of SEQ ID NO: 8; or (a) a heavy chain variable region comprising the amino acid sequence of SEQ ID NO: 2; and (b) a light chain variable region comprising the amino acid sequence of SEQ ID NO: 9; or (a) a heavy chain variable region comprising the amino acid sequence of SEQ ID NO: 3; and (b) a light chain variable region comprising the amino acid sequence of SEQ ID NO: 10; or (a) a heavy chain variable region comprising the amino acid sequence of SEQ ID NO: 4; and (b) a light chain variable region comprising the amino acid sequence of SEQ ID NO: 11; or (a) a heavy chain variable region comprising the amino acid sequence of SEQ ID NO: 5; and (b) a light chain variable region comprising the amino acid sequence of SEQ ID NO: 12; or (a) a heavy chain variable region comprising the amino acid sequence of SEQ ID NO: 6;
and (b) a light chain variable region comprising the amino acid sequence of SEQ ID NO: 13; or (a) a heavy chain variable region comprising the amino acid sequence of SEQ ID NO: 7;
and (b) a light chain variable region comprising the amino acid sequence of SEQ ID NO: 14.

In another aspect, the invention provides antibodies that comprise the heavy chain and light chain CDR1s, CDR2s and CDR3s of 17D8, 2D3, 4H1, 5C4, 4A11, 7D3 and 5F4, or combinations thereof. The amino acid sequences of the $V_H$ CDR1s of 17D8, 2D3, 4H1, 5C4, 4A11, 7D3 and 5F4 are shown in SEQ ID NOs: 15, 16, 17, 18, 19, 20 and 21, respectively. The amino acid sequences of the $V_H$ CDR2s of 17D8, 2D3, 4H1, 5C4, 4A11, 7D3 and 5F4 are shown in SEQ ID NOs: 22, 23, 24, 25, 26, 27 and 28, respectively. The amino acid sequences of the $V_H$ CDR3s of 17D8, 2D3, 4H1, 5C4, 4A11, 7D3 and 5F4 are shown in SEQ ID NOs: 29, 30, 31, 32, 33, 34 and 35, respectively. The amino acid sequences of the $V_k$ CDR1s of 17D8, 2D3, 4H1, 5C4, 4A11, 7D3 and 5F4 are shown in SEQ ID NOs: 36, 37, 38, 39, 40, 41 and 42, respectively. The amino acid sequences of the $V_k$ CDR2s of 17D8, 2D3, 4H1, 5C4, 4A11, 7D3 and 5F4 are shown in SEQ ID NOs: 43, 44, 45, 46, 47, 48 and 49, respectively. The amino acid sequences of the $V_k$ CDR3s of 17D8, 2D3, 4H1, 5C4, 4A11, 7D3 and 5F4 are shown in SEQ ID NOs: 50, 51, 52, 53, 54, 55 and 56, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to PD-1 and that antigen-binding specificity is provided primarily by the CDR1, CDR2, and CDR3 regions, the $V_H$ CDR1, CDR2, and CDR3 sequences and $V_k$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_k$ CDR1, CDR2, and CDR3) to create other anti-PD-1 binding molecules of the invention. PD-1 binding of such "mixed and matched" antibodies can be tested using the binding assays described above and in the Examples (e.g., ELISAs, Biacore analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 17D8, 2D3, 4H1, 5C4, 4A11, 7D3 and 5F4.

Accordingly, in another aspect, the invention provides an isolated monoclonal antibody, or antigen-binding portion thereof comprising:

(a) a heavy chain variable region CDR1 comprising an amino acid sequence selected from the group consisting of SEQ ID NOs: 15, 16, 17, 18, 19, 20 and 21;

(b) a heavy chain variable region CDR2 comprising an amino acid sequence selected from the group consisting of SEQ ID NOs: 22, 23, 24, 25, 26, 27 and 28;

(c) a heavy chain variable region CDR3 comprising an amino acid sequence selected from the group consisting of SEQ ID NOs: 29, 30, 31, 32, 33, 34 and 35;

(d) a light chain variable region CDR1 comprising an amino acid sequence selected from the group consisting of SEQ ID NOs: 36, 37, 38, 39, 40, 41 and 42;

(e) a light chain variable region CDR2 comprising an amino acid sequence selected from the group consisting of SEQ ID NOs: 43, 44, 45, 46, 47, 48 and 49; and (f) a light chain variable region CDR3 comprising an amino acid sequence selected from the group consisting of SEQ ID NOs: 50, 51, 52, 53, 54, 55 and 56;

wherein the antibody specifically binds PD-1, preferably human PD-1.

In a preferred embodiment, the antibody comprises:
(a) a heavy chain variable region CDR1 comprising SEQ ID NO: 15;
(b) a heavy chain variable region CDR2 comprising SEQ ID NO: 22;
(c) a heavy chain variable region CDR3 comprising SEQ ID NO: 29;
(d) a light chain variable region CDR1 comprising SEQ ID NO: 36;
(e) a light chain variable region CDR2 comprising SEQ ID NO: 43; and
(f) a light chain variable region CDR3 comprising SEQ ID NO: 50.

In another preferred embodiment, the antibody comprises:
(a) a heavy chain variable region CDR1 comprising SEQ ID NO: 16;
(b) a heavy chain variable region CDR2 comprising SEQ ID NO: 23;
(c) a heavy chain variable region CDR3 comprising SEQ ID NO: 30;
(d) a light chain variable region CDR1 comprising SEQ ID NO: 37;
(e) a light chain variable region CDR2 comprising SEQ ID NO: 44; and
(f) a light chain variable region CDR3 comprising SEQ ID NO: 51.

In another preferred embodiment, the antibody comprises:
(a) a heavy chain variable region CDR1 comprising SEQ ID NO: 17;
(b) a heavy chain variable region CDR2 comprising SEQ ID NO: 24;
(c) a heavy chain variable region CDR3 comprising SEQ ID NO: 31;
(d) a light chain variable region CDR1 comprising SEQ ID NO: 38;
(e) a light chain variable region CDR2 comprising SEQ ID NO: 45; and
(f) a light chain variable region CDR3 comprising SEQ ID NO: 52.

In another preferred embodiment, the antibody comprises:
(a) a heavy chain variable region CDR1 comprising SEQ ID NO: 18;
(b) a heavy chain variable region CDR2 comprising SEQ ID NO: 25;
(c) a heavy chain variable region CDR3 comprising SEQ ID NO: 32;
(d) a light chain variable region CDR1 comprising SEQ ID NO: 39;
(e) a light chain variable region CDR2 comprising SEQ ID NO: 46; and
(f) a light chain variable region CDR3 comprising SEQ ID NO: 53.

In another preferred embodiment, the antibody comprises:
(a) a heavy chain variable region CDR1 comprising SEQ ID NO: 19;
(b) a heavy chain variable region CDR2 comprising SEQ ID NO: 26;
(c) a heavy chain variable region CDR3 comprising SEQ ID NO: 33;
(d) a light chain variable region CDR1 comprising SEQ ID NO: 40;
(e) a light chain variable region CDR2 comprising SEQ ID NO: 47; and
(f) a light chain variable region CDR3 comprising SEQ ID NO: 54.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated monoclonal antibody, or an antigen-binding portion thereof, comprising a heavy chain variable region that is the product of or derived from a human $V_H$ 3-33 gene, wherein the antibody specifically binds PD-1, preferably human PD-1. In another preferred embodiment, the invention provides an isolated monoclonal antibody, or an antigen-binding portion thereof, comprising a heavy chain variable region that is the product of or derived from a human $V_H$ 4-39 gene, wherein the antibody specifically binds PD-1, preferably human PD-1. In yet another preferred embodiment, the invention provides an isolated monoclonal antibody, or an antigen-binding portion thereof, comprising a light chain variable region that is the product of or derived from a human $V_K$ L6 gene, wherein the antibody specifically binds PD-1, preferably human PD-1. In yet another preferred embodiment, the invention provides an isolated monoclonal antibody, or an antigen-binding portion thereof, comprising a light chain variable region that is the product of or derived from a human $V_K$ L15 gene, wherein the antibody specifically binds PD-1, preferably human PD-1. In yet another preferred embodiment, the invention provides an isolated monoclonal antibody, or antigen-binding portion thereof, wherein the antibody:

(a) comprises a heavy chain variable region that is the product of or derived from a human $V_H$ 3-33 or 4-39 gene (which gene encodes the amino acid sequence set forth in SEQ ID NO: 71 or 73, respectively);

(b) comprises a light chain variable region that is the product of or derived from a human $V_K$ L6 or L15 gene (which gene encodes the amino acid sequence set forth in SEQ ID NO: 72 or 74, respectively); and (c) specifically binds to PD-1.

Examples of antibodies having $V_H$ and $V_K$ of $V_H$ 3-33 and $V_K$ L6, respectively, are 17D8, 2D3, 4H1, 5C4, and 7D3. Examples of antibodies having $V_H$ and $V_K$ of $V_H$ 4-39 and $V_K$ L15, respectively are 4A11 and 5F4.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-PD-1 antibodies of the invention.

For example, the invention provides an isolated monoclonal antibody, or antigen-binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 1, 2, 3, 4, 5, 6 and 7;

(b) the light chain variable region comprises an amino acid sequence that is at least 80% homologous to an amino acid sequence selected from the group consisting of SEQ ID NOs: 8, 9, 10, 11, 12, 13 and 14; and the antibody exhibits one or more of the following properties:

(c) the antibody binds to human PD-1 with a $K_D$ of $1 \times 10^{-7}$M or less;

(d) the antibody does not substantially bind to human CD28, CTLA-4 or ICOS;

(e) the antibody increases T-cell proliferation in an MLR assay;

(f) the antibody increases interferon-gamma production in an MLR assay;

(g) the antibody increases 11-2 secretion in an MLR assay;

(h) the antibody binds to human PD-1 and cynomolgus monkey PD-1;

(i) the antibody inhibits the binding of PD-L1 and/or PD-L2 to PD-1;

(j) the antibody stimulates antigen-specific memory responses;

(k) the antibody stimulates antibody responses;

(l) the antibody inhibits tumor cell growth in vivo.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 57, 58, 59, 60, 61, 62, 63, 64, 65, 66, 67, 68, 69 and 70, followed by testing of the encoded altered antibody for retained function (i.e., the functions set forth in (c) through (l) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. (See www.ncbi.nlm.nih.gov).

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 17D8, 2D3, 41-11, 5C4, 4A11, 7D3 or 5F4), or conservative modifications thereof, and wherein the antibodies retain the desired functional properties of the anti-PD-1 antibodies of the invention. Accordingly, the invention provides an isolated monoclonal antibody, or antigen-binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 29, 30, 31, 32, 33, 34 and 35, and conservative modifications thereof;

(b) the light chain variable region CDR3 sequence comprises an amino acid sequence selected from the group consisting of amino acid sequence of SEQ ID NOs: 50, 51, 52, 53, 54, 55 and 56, and conservative modifications thereof, and the antibody exhibits one or more of the following properties:

(c) the antibody binds to human PD-1 with a $K_D$ of $1\times10^{-7}$ M or less;

(d) the antibody does not substantially bind to human CD28, CTLA-4 or ICOS;

(e) the antibody increases T-cell proliferation in an MLR assay;

(f) the antibody increases interferon-gamma production in an MLR assay;

(g) the antibody increases 11-2 secretion in an MLR assay;

(h) the antibody binds to human PD-1 and cynomolgus monkey PD-1;

(i) the antibody inhibits the binding of PD-L1 and/or PD-L2 to PD-1;

(j) the antibody stimulates antigen-specific memory responses;

(k) the antibody stimulates antibody responses;

(l) the antibody inhibits tumor cell growth in vivo.

In a preferred embodiment, the heavy chain variable region CDR2 sequence comprises an amino acid sequence selected from the group consisting of amino acid sequences of SEQ ID NOs: 22, 23, 24, 25, 26, 27 and 28, and conservative modifications thereof; and the light chain variable region CDR2 sequence comprises an amino acid sequence selected from the group consisting of amino acid sequences of SEQ ID NOs: 43, 44, 45, 46, 47, 48 and 49, and conservative modifications thereof. In another preferred embodiment, the heavy chain variable region CDR1 sequence comprises an amino acid sequence selected from the group consisting of amino acid sequences of SEQ ID NOs: 15, 16, 17, 18, 19, 20 and 21, and conservative modifications thereof; and the light chain variable region CDR1 sequence comprises an amino acid sequence selected from the group consisting of amino acid sequences of SEQ ID NOs: 36, 37, 38, 39, 40, 41 and 42, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (1) above) using the functional assays described herein.

Antibodies that Bind to the Same Epitope as Anti-PD-1 Antibodies of the Invention In another embodiment, the invention provides antibodies that bind to the same epitope on human PD-1 as any of the PD-1 monoclonal antibodies of the invention (i.e., antibodies that have the ability to cross-compete for binding to PD-1 with any of the monoclonal antibodies of the invention). In preferred embodiments, the reference antibody for cross-competition studies can be the monoclonal antibody 17D8 (having $V_H$ and $V_L$ sequences as shown in SEQ ID NOs: 1 and 8, respectively), or the monoclonal antibody 2D3 (having $V_H$ and $V_L$ sequences as shown in SEQ ID NOs: 2 and 9, respectively), or the monoclonal antibody 4H1 (having $V_H$ and $V_L$ sequences as shown in SEQ ID NOs: 3 and 10, respectively), or the monoclonal antibody 5C4 (having $V_H$ and $V_L$ sequences as shown in SEQ ID NOs: 4 and 11, respectively), or the monoclonal antibody 4A11 (having $V_H$ and $V_L$ sequences as shown in SEQ ID NOs: 5 and 12, or the monoclonal antibody 7D3 (having $V_H$ and $V_L$ sequences as shown in SEQ ID NOs: 6 and 13, or the monoclonal antibody 5F4 (having $V_H$ and $V_L$ sequences as shown in SEQ ID NOs: 7 and 14, respectively). Such cross-competing antibodies can be identified based on their ability to cross-compete with 17D8, 2D3, 4H1, 5C4, 4A11, 7D3 or 5F4 in standard PD-1 binding assays. For example, BIAcore analysis, ELISA assays or flow cytometry may be used to demonstrate cross-competition with the antibodies of the current invention. The ability of a test antibody to inhibit the binding of, for example, 17D8, 2D3, 4H1, 5C4, 4A11, 7D3 or 5F4, to human PD-1 demonstrates that the test antibody can compete with 17D8, 2D3, 4H1, 5C4, 4A11, 7D3 or 5F4 for binding to human PD-1 and thus binds to the same epitope on human PD-1 as 17D8, 2D3, 4H1, 5C4, or 4A11. In a preferred embodiment, the antibody that binds to the same epitope on human PD-1 as 17D8, 2D3, 4H1, 5C4, 4A11, 7D3 or 5E4 is a human monoclonal antibody. Such human monoclonal antibodies can be prepared and isolated as described in the Examples.

Engineered and Modified Antibodies

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl Acad. See. U.S.A.* 86:10029-10033; U.S. Pat. No. 5,225,539 to Winter, and U.S. Pat. Nos. 5,530,101; 5,585,089; 5,693,762 and U.S. Pat. No. 6,180,370 to Queen et al.)

Accordingly, another embodiment of the invention pertains to an isolated monoclonal antibody, or antigen-binding portion thereof, comprising a heavy chain variable region comprising CDR1, CDR2, and CDR3 sequences comprising an amino acid sequence selected from the group consisting of SEQ ID NOs: 15, 16, 17, 18, 19, 20 and 21, SEQ ID NOs: 22, 23, 24, 25, 26, 27 and 28, and SEQ ID NOs: 29, 30, 31, 32, 33, 34 and 35, respectively, and a light chain variable region comprising CDR1, CDR2, and CDR3 sequences comprising an amino acid sequence selected from the group consisting of SEQ ID NOs: 36, 37, 38, 39, 40, 41 and 42, SEQ ID NOs: 43, 44, 45, 46, 47, 48 and 49, and SEQ ID NOs: 50, 51, 52, 53, 54, 55 and 56, respectively. Thus, such antibodies contain the $V_H$ and $V_L$ CDR sequences of monoclonal antibodies 17D8, 2D3, 4H1, 5C4, 4A11, 7D3 or 5F4 yet may contain different framework sequences from these antibodies.

Such framework sequences can be obtained from public DNA databases or published references that include gemiline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the GenBank database. For example, the following heavy chain germline sequences found in the HCo7 HuMAb mouse are available in the accompanying GenBank accession numbers: 1-69 (NG_0010109, NT_024637 and BC070333), 3-33 (NG_0010109 and NT_024637) and 3-7 (NG_0010109 and NT 024637). As another example, the following heavy chain germline sequences found in the HCo12 HuMAb mouse are available in the accompanying GenBank accession numbers: 1-69 (NG_0010109, NT 024637 and BC070333), 5-51 (NG_0010109 and NT 024637), 4-34 (NG_0010109 and NT 024637), 3-30.3 (AJ1556644) and 3-23 (AJ406678).

Preferred framework sequences for use in the antibodies of the invention are those that are structurally similar to the framework sequences used by selected antibodies of the invention, e.g., similar to the $V_H$ 3-33 framework sequences (SEQ ID NO: 71) and/or the $V_H$ 4-39 framework sequences (SEQ ID NO: 73) and/or the $V_K$ L6 framework sequences (SEQ ID NO: 72) and/or the $V_K$ L15 framework sequences (SEQ ID NO: 74) used by preferred monoclonal antibodies of the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and U.S. Pat. No. 6,180, 370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in viva assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides isolated anti-PD-1 monoclonal antibodies, or antigen-binding portions thereof, comprising a heavy chain variable region comprising: (a) a $V_H$ CDR1 region comprising an amino acid sequence selected from the group consisting of SEQ ID NOs: 15, 16, 17, 18, 19, 20 and 21, or an amino acid sequence having one, two, three, four or five amino acid substitutions, deletions or additions as compared to SEQ ID NOs: 15, 16, 17, 18, 19, 20 and 21; (b) a $V_H$ CDR2 region comprising an amino acid sequence selected from the group consisting of SEQ ID NOs: 22, 23, 24, 25, 26, 27 and 28, or an amino acid sequence having one, two, three, four or five amino acid substitutions, deletions or additions as compared to SEQ ID NOs: 22, 23, 24, 25, 26, 27 and 28; (c) a $V_H$ CDR3 region comprising an amino acid sequence selected from the group consisting of SEQ ID NOs: 29, 30, 31, 32, 33, 34 and 35, or an amino acid sequence having one, two, three, four or five amino acid substitutions, deletions or additions as compared to SEQ ID NOs: 29, 30, 31, 32, 33, 34 and 35; (d) a $V_K$ CDR1 region comprising an amino acid sequence selected from the group consisting of SEQ ID NOs: 36, 37, 38, 39, 40, 41 and 42, or an amino acid sequence having one, two, three, four or five amino acid substitutions, deletions or additions as compared to SEQ ID NOs: 36, 37, 38, 39, 40, 41 and 42; (e) a $V_K$ CDR2 region comprising an amino acid sequence selected from the group consisting of SEQ ID NOs: 43, 44, 45, 46, 47, 48 and 49, or an amino acid sequence having one, two, three, four or five amino acid substitutions, deletions or additions as compared to SEQ ID NOs: 43, 44, 45, 46, 47, 48 and 49; and (f) a $V_K$ CDR3 region comprising an amino acid sequence selected from the group consisting of SEQ ID NOs: 50, 51, 52, 53, 54, 55 and 56, or an amino acid sequence having one, two, three, four or five amino acid substitutions, deletions or additions as compared to SEQ ID NOs: 50, 51, 52, 53, 54, 55 and 56.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the gennline sequence from which the antibody is derived. Such residues can be identified by comparing the antibody framework sequences to the germline sequences from which the antibody is derived.

For example, Table 1 below shows a number of amino acid changes in the framework regions of the anti-PD-1 antibodies 17D8, 2D3, 4H1, 5C4, 4A11, 7D3 and 5F4 that differ from the heavy chain parent germline sequence. To return one or more of the amino acid residues in the framework region sequences to their germline configuration, the somatic mutations can be "backmutated" to the germline sequence by, for example, site-directed mutagenesis or PCR-mediated mutagenesis.

Amino acid changes may occur in the framework regions of anti-PD-1 antibodies that differ from the light chain parent germline sequence. For example, for 17D8, amino acid residue #47 (within FR2) of $V_K$ is an isoleucine whereas this residue in the corresponding $V_K$ L6 germline sequence is a leucine. To return the framework region sequences to their germline configuration, the somatic mutations can be "back-mutated" to the germline sequence by, for example, site-directed mutagenesis or PCR-mediated mutagenesis (e.g., residue #47 (residue #13 of FR2) of the $V_K$ of 17D8 can be "backmutated" from isoleucine to leucine).

As another example, for 4A11, amino acid residue #20 (within FR1) of $V_K$ is a serine whereas this residue in the corresponding $V_K$ L15 germline sequence is a threonine. To return the framework region sequences to their germline configuration, for example, residue #20 of the $V_K$ of 4A11 can be "backmutated" from serine to threonine. Such "back-mutated" antibodies are also intended to be encompassed by the invention.

Figure 8:
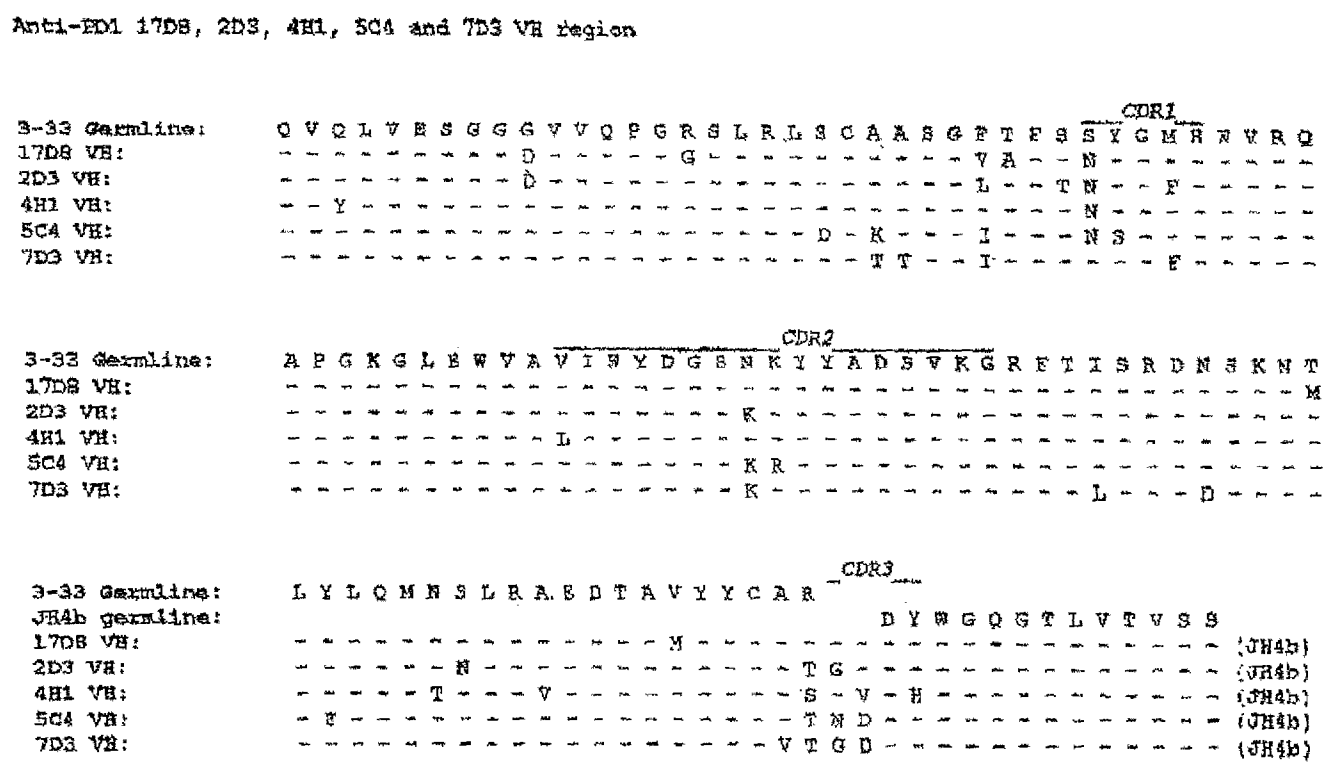

The alignment of $V_H$ regions for 17D8, 2D3, 4H1, 5C4 and 7D3, against the parent germline $V_H$ 3-33 sequence is shown in FIG. 8. The alignment of $V_H$ regions for 4A11 and 5F4 against the parent germline $V_H$ 4-39 sequence is shown in FIG. 11.

TABLE 1

Modifications to antibodies 17D8, 2D3, 4H1, 5C4, 4A11, 7D3 and 5F4 from the heavy chain germline configuration.

| Anti-PD-1 Ab | Amino acid position | Amino acid of antibody | Original amino acid of germline configuration |
|---|---|---|---|
| 17D8 | 10 | D | G |
|  | 16 | G | R |
|  | 27 | V | F |
|  | 28 | A | T |
|  | 78 | M | T |
|  | 93 | M | V |
| 2D3 | 10 | D | G |
|  | 27 | L | F |
|  | 30 | T | S |
|  | 85 | N | S |
|  | 98 | T | R |
| 4H1 | 3 | Y | Q |
|  | 84 | T | N |
|  | 88 | V | A |
|  | 98 | S | R |
| 5C4 | 21 | D | S |
|  | 23 | K | A |
|  | 27 | I | F |
|  | 80 | F | Y |
|  | 98 | T | R |
| 4A11 | 29 | L | I |
|  | 79 | Q | H |
|  | 98 | V | A |
| 7D3 | 23 | T | A |
|  | 24 | T | A |
|  | 27 | I | F |
|  | 70 | L | I |
|  | 74 | D | N |
|  | 97 | V | A |
|  | 98 | T | R |
| 5F4 | 23 | S | T |
|  | 29 | L | I |
|  | 51 | A | G |
|  | 77 | R | K |

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fe region, typically to alter one or more functional properties of the antibody, such as serum half-life, complement fixation, Fe receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in farther detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fe hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al, In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et at.

In yet another example, the Fc region is modified to increase the ability of the antibody to mediate antibody dependent cellular cytotoxicity (ADCC) and/or to increase the affinity of the antibody for an Fcy receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1, 4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the anti-PD-1 antibodies having $V_H$ and $V_K$ sequences disclosed herein can be used to create new anti-PD-1 antibodies by modifying the VH and/or $V_K$ sequences, or the constant region(s) attached thereto. Thus, in another aspect of the invention, the structural features of an anti-PD-1 antibody of the invention, e.g. 17D8, 2D3, 4141, 5C4, 4A11, 7D3 or 5F4, are used to create structurally related anti-PD-1 antibodies that retain at least one functional property of the antibodies of the invention, such as binding to human PD-1. For example, one or more CDR regions of 17D8, 2D3, 4111, 5C4, 4A11, 7D3 or 5F4, or mutations thereof, can be combined recombinantly with known framework regions and/or other CDRs to create additional, recombinantly-engineered, anti-PD-1 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-PD-1 antibody comprising:

(a) providing: (1) a heavy chain variable region antibody sequence comprising a CDR1 sequence selected from the group consisting of SEQ ID NOs: 15, 16, 17, 18, 19, 20 and 21, a CDR2 sequence selected from the group consisting of SEQ ID NOs: 22, 23, 24, 25, 26, 27 and 28, and/or a CDR3 sequence selected from the group consisting of SEQ ID NOs: 29, 30, 31, 32, 33, 34 and 35; and/or (ii) a light chain variable region antibody sequence comprising a CDR1 sequence selected from the group consisting of SEQ ID NOs: 36, 37, 38, 39, 40, 41 and 42, a CDR2 sequence selected from the group consisting of SEQ ID NOs: 43, 44, 45, 46, 47, 48 and 49, and/or a CDR3 sequence selected from the group consisting of SEQ ID NOs: 50, 51, 52, 53, 54, 55 and 56;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-PD-1 antibodies described herein, which functional properties include, but are not limited to:

(a) the antibody binds to human PD-1 with a $K_D$ of $1 \times 10^{-7}$ M or less;

(b) the antibody does not substantially bind to human CD28, CTLA-4 or ICOS;

(c) the antibody increases T-cell proliferation in an MLR assay;

(d) the antibody increases interferon-gamma production in an MLR assay;

(e) the antibody increases 11-2 secretion in an MLR assay;

(f) the antibody binds to human PD-1 and cynomolgus monkey PD-1;

(g) the antibody inhibits the binding of PD-L1 and/or PD-L2 to PD-1;

(h) the antibody stimulates antigen-specific memory responses;

(i) the antibody stimulates antibody responses;

(j) the antibody inhibits tumor cell growth in vivo.

The functional properties of the altered antibodies can be assessed using standard assays available in the art and/or described herein, such as those set forth in the Examples (e.g., flow cytometry, binding assays).

In certain embodiments of the methods of engineering antibodies of the invention, mutations can be introduced randomly or selectively along all or part of an anti-PD-1 antibody coding sequence and the resulting modified anti-PD-1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the 17D8, 2D3, 4H1, 5C4, 4A11, 7D3 or 5F4 monoclonal antibodies. DNA sequences encoding the VH sequences of 17D8, 2D3, 4H1, 5C4, 4A11, 7D3 and 5F4 are shown in SEQ ID NOs: 57, 58, 59, 60, 61, 62 and 63, respectively. DNA sequences encoding the VL sequences of 17D8, 2D3, 4H1, 5C4, 4A11, 7D3 and 5F4 are shown in SEQ ID NOs: 64, 65, 66, 67, 68, 69 and 70, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NTH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence (Gly$_4$-Ser)$_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693, 762 and U.S. Pat. No. 6,180,370 to Queen et al.).

In a preferred embodiment, the antibodies of the invention are human monoclonal antibodies. Such human monoclonal antibodies directed against PD-1 can be generated using transgenic or transchromosomic mice carrying parts of the human immune system rather than the mouse system. These transgenic and transchromosomic mice include mice referred to herein as HuMAb mice and KM Mice™, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HuMab mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-PD-1 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and U.S. Pat. No. 6,162,963 to Kucherlapati et al.

Moreover, alternative transchromosome animal systems expressing human immunoglobulin genes are available in the art and can be used to raise anti-PD-1 antibodies of the invention. For example, mice carrying both a human heavy chain transchromosome and a human light chain transchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-PD-1 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and U.S. Pat. No. 5,571,698 to Ladner et al; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and U.S. Pat. No. 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of PD-1 antigen and/or recombinant PD-1, or an PD-1 fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 µg) of PD-1 antigen can be used to immunize the human Ig mice intraperitoneally.

Detailed procedures to generate fully human monoclonal antibodies to PD-1 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-PD-1 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCol 2 transgene can be bred together into a single mouse having two different human heavy chain transgenes (HCo7/HCo12). Alternatively or additionally, the KM Mouse™ strain can be used, as described in Example 1.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Alternatively, the single cell suspensions of splenic lymphocytes from immunized mice can be fused using an electric field based electrofusion method, using a Cyto Pulse large chamber cell fusion electroporator (Cyto Pulse Sciences, Inc., Glen Burnie, Md.). Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/mi gentamycin and IX HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the tem "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or f3-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al. (1988) *Mol. Cell. Diol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr– host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to PD-1 by, for example, standard ELISA. Briefly, mierotiter plates are coated with purified PD-1 at 0.25 µg/ml in PBS, and then blocked with 5% bovine serum albumin in PBS. Dilutions of antibody (e.g., dilutions of plasma from PD-1-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with PD-1 immunogen. Hybridomas that bind with high avidity to PD-1 are subcloned and further characterized. One clone from each hybridoma, which retains the reactivity of the parent cells (by ELISA), can be chosen for making a 5-10 vial cell bank stored at −140° C., and for antibody purification.

To purify anti-PD-1 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-PD-1 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using PD-1 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-PD-1 human IgGs can be further tested for reactivity with PD-1 antigen by Western blotting. Briefly, PD-1 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Immunoconjugates

In another aspect, the present invention features an anti-PD-1 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromo-mannitol, streptozotocin, mitomycin C, and cis-dichlorodiamine platinum (II) (DDP) cisplatin), anthracyclines (e.g., daunorubicin (formerly daunomycin) and doxombicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-PD-1 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for PD-1 and a second binding specificity for a second target epitope. In a particular embodiment of the invention, the second target epitope is an Fe receptor, e.g., human FcγRI (CD64) or a human Fcα receptor (CD89). Therefore, the invention includes bispecific molecules capable of binding both to FcγR or FcαR expressing effector cells (e.g., monocytes, macrophages or polymorphonuclear cells (PMNs)), and to target cells expressing PD-1. These bispecific molecules target PD-1 expressing cells to effector cell and trigger Fc receptor-mediated effector cell activities, such as phagocytosis of an PD-1 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fe binding specificity and an anti-PD-1 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_C$ receptor or target cell antigen. The "anti-enhancement factor portion" can bind an $F_C$ receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ $M^{-1}$).

The production and characterization of certain preferred anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. H139469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fe receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. Fecal has medium affinity ($\approx 5\times 10^7$ $M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148:1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-PD-1 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) *Behring Ins. Mitt.* No. 78, 118-132; Brennan et al. (1985) *Science* 229:81-83), and Glennie et al. (1987) *J Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-PD-1 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-PD-1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-PD-1 antibody of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

In another aspect, the instant disclosure provides a pharmaceutical kit of parts comprising an anti-PD-1 antibody and an anti-CTLA-4 antibody, as described herein. The kit may also further comprise instructions for use in the treatment of a hyperproliferative disease (such as cancer as described herein). In another embodiment, the anti-PD-1 and anti-CTLA-4 antibodies may be co-packaged in unit dosage form.

In certain embodiments, two or more monoclonal antibodies with different binding specificities (e.g., anti-PD-1 and anti-CTLA-4) are administered simultaneously, in which case the dosage of each antibody administered falls within the ranges indicated. Antibody can be administered as a single dose or more commonly can be administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, T. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No.

5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994) 1 *Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Invention

The antibodies, antibody compositions and methods of the present invention have numerous in vitro and in vivo utilities involving, for example, detection of PD-1 or enhancement of immune response by blockade of PD-1. In a preferred embodiment, the antibodies of the present invention are human antibodies. For example, these molecules can be administered to cells in culture, in vitro or ex vivo, or to human subjects, e.g., in viva, to enhance immunity in a variety of situations. Accordingly, in one aspect, the invention provides a method of modifying an immune response in a subject comprising administering to the subject the antibody, or antigen-binding portion thereof, of the invention such that the immune response in the subject is modified. Preferably, the response is enhanced, stimulated or up-regulated.

As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo. To achieve antigen-specific enhancement of immunity, the anti-PD-1 antibodies can be administered together with an antigen of interest. When antibodies to PD-1 are administered together with another agent, the two can be administered in either order or simultaneously.

The invention further provides methods for detecting the presence of human PD-1 antigen in a sample, or measuring the amount of human PD-1 antigen, comprising contacting the sample, and a control sample, with a human monoclonal antibody, or an antigen-binding portion thereof, which specifically binds to human PD-1, under conditions that allow for formation of a complex between the antibody or portion thereof and human PD-1. The formation of a complex is then detected, wherein a difference complex formation between the sample compared to the control sample is indicative the presence of human PD-1 antigen in the sample.

Given the specific binding of the antibodies of the invention for PD-1, compared to CD28, ICOS and CTLA-4, the antibodies of the invention can be used to specifically detect PD-1 expression on the surface of cells and, moreover, can be used to purify PD-1 via immunoaffinity purification.

Cancer

Blockade of PD-1 by antibodies can enhance the immune response to cancerous cells in the patient. The ligand for PD-1, PD-L1, is not expressed in normal human cells, but is abundant in a variety of human cancers (Dong et al. (2002) *Nat Med* 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) *J Mol Med* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 to PD-L1 and the effect is additive when the interaction of PD-1 to PD-L2 is blocked as well (Iwai et al. (2002) *PNAS* 99:12293-7; Brown et al. (2003) *J. Immunol.* 170:1257-66). While previous studies have shown that T-cell proliferation can be restored by inhibiting the interaction of PD-1 to PD-L1, there have been no reports of a direct effect on cancer tumor growth in vivo by blocking the PD-1/PD-L1 interaction. In one aspect, the present invention relates to treatment of a subject in vivo using an anti-PD-1 antibody such that growth of cancerous tumors is inhibited. An anti-PD-1 antibody may be used alone to inhibit the growth of cancerous tumors. Alternatively, an anti-PD-1 antibody may be used in conjunction with other immunogenic agents, standard cancer treatments, or other antibodies, as described below.

Accordingly, in one embodiment, the invention provides a method of inhibiting growth of tumor cells in a subject, comprising administering to the subject a therapeutically effective amount of an anti-PD-1 antibody, or antigen-binding portion thereof. Preferably, the antibody is a human anti-PD-1 antibody (such as any of the human anti-human PD-1 antibodies described herein). Additionally or alternatively, the antibody may be a chimeric or humanized anti-PD-1 antibody.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention.

Examples of other cancers that may be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) *Int. Innnunol.* 17:133-144).

Optionally, antibodies to PD-1 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) *J Immunol.* 173:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF (discussed further below), In humans, some tumors have been shown to be immunogenic such as melanomas. It is anticipated that by raising the threshold of T cell activation by PD-1 blockade, we may expect to activate tumor responses in the host.

PD-1 blockade is likely to be most effective when combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) *Science* 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (i.e. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Soot, R & Srivastava, P (1995) *Science* 269:1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with PD-1 blockade to activate more potent anti-tumor responses.

PD-1 blockade may also be combined with standard cancer treatments. PD-1 blockade may be effectively combined with chemotherapeutic regimes. In these instances, it may be possible to reduce the dose of chemotherapeutic reagent administered (Mokyr, M. et al. (1998) *Cancer Research* 58: 5301-5304). An example of such a combination is an anti-PD-1 antibody in combination with decarbazine for the treatment of melanoma. Another example of such a combination is an anti-PD-1 antibody in combination with interleukin-2 (IL-2) for the treatment of melanoma. The scientific rationale behind the combined use of PD-1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-1 blockade through cell death are radiation, surgery, and hormone deprivation. Each of these protocols creates a source of tumor antigen in the host. Angiogenesis inhibitors may also be combined with PD-1 blockade. Inhibition of angiogenesis leads to tumor cell death which may feed tumor antigen into host antigen presentation pathways.

PD-1 blocking antibodies can also be used in combination with bispecific antibodies that target Fc alpha or Fc gamma receptor-expressing effectors cells to tumor cells (see, e.g., U.S. Pat. Nos. 5,922,845 and 5,837,243). Bispecific antibodies can be used to target two separate antigens. For example anti-Fe receptor/anti tumor antigen (e.g., Her-2/neu) bispecific antibodies have been used to target macrophages to sites of tumor. This targeting may more effectively activate tumor specific responses. The T cell arm of these responses would by augmented by the use of PD-1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Antibodies to each of these entities may be used in combination with anti-PD-1 to counteract the effects of the immunosuppressive agent and favor tumor immune responses by the host.

Other antibodies which may be used to activate host immune responsiveness can be used in combination with anti-PD-1. These include molecules on the surface of dendritic cells which activate DC function and antigen presentation. Anti-CD40 antibodies are able to substitute effectively for T cell helper activity (Ridge, J. et al. (1998) *Nature* 393: 474-478) and can be used in conjuction with PD-1 antibodies (Ito, N. et al. (2000) *Immunobiology* 201 (5)

527-40). Activating antibodies to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al, (1997) *Nature Medicine* 3: 682-685 (1997), and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-1 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. & Riddell, S. (1999) *Science* 285: 546-51). These methods may also be used to activate T cell responses to infectious agents such as CMV. Ex vivo activation in the presence of anti-PD-1 antibodies may be expected to increase the frequency and activity of the adoptively transferred T cells.

Infectious Diseases

Other methods of the invention are used to treat patients that have been exposed to particular toxins or pathogens. Accordingly, another aspect of the invention provides a method of treating an infectious disease in a subject comprising administering to the subject an anti-PD-1 antibody, or antigen-binding portion thereof, such that the subject is treated for the infectious disease. Preferably, the antibody is a human anti-human PD-1 antibody (such as any of the human anti-PD-1 antibodies described herein). Additionally or alternatively, the antibody can be a chimeric or humanized antibody.

Similar to its application to tumors as discussed above, antibody mediated PD-1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, Leishmania, *Staphylococcus aureus, Pseudomonas Aeruginosa*. PD-1 blockade is particularly useful against established infections by agents such as HIV that present altered antigens over the course of the infections. These novel epitopes are recognized as foreign at the time of anti-human PD-1 administration, thus provoking a strong T cell response that is not dampened by negative signals through PD-1.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections treatable by methods of the invention include *Candida (albicans, krusei, glabrata, tropicalis*, etc.), *Cryptococcus neofoimans, Aspergillus (fumigatus, niger*, etc.), Genus *Mucorales* (mucor, absidia, rhizophus), *Sporothrix schenkii, Blastomyces dennatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

In all of the above methods, PD-1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

Autoimmune Reactions

Anti-PD-1 antibodies may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B16 melanoma in van Elsas et al. supra; depigmentation in Trp-2 vaccinated mice (Overwijk, W. et al. (1999) *Proc. Natl. Acad. Sci. U.S.A.* 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) *J. Immunother Emphasis Tumor Immunol* 19 (1): 81-4).

Therefore, it is possible to consider using anti-PD-1 blockade in conjunction with various self proteins in order to devise vaccination protocols to efficiently generate immune responses against these self proteins for disease treatment. For example, Alzheimers disease involves inappropriate accumulation of Aβ peptide in amyloid deposits in the brain; antibody responses against amyloid are able to clear these amyloid deposits (Schenk et al., (1999) *Nature* 400: 173-177).

Other self proteins may also be used as targets such as IgE for the treatment of allergy and asthma, and TNFα for rhematoid arthritis. Finally, antibody responses to various hormones may be induced by the use of anti-PD-1 antibody. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-1 antibody can be used for induction of therapeutic autoimmune responses to treat patients having an inappropriate accumulation of other self-antigens, such as amyloid deposits, including Aβ in Alzheimer's disease, cytokines such as TNFα, and IgE.

Vaccines

Anti-PD-1 antibodies may be used to stimulate antigen-specific immune responses by coadministration of an anti-PD-1 antibody with an antigen of interest (e.g., a vaccine). Accordingly, in another aspect the invention provides a method of enhancing an immune response to an antigen in a subject, comprising administering to the subject: (i) the antigen; and (ii) an anti-PD-1 antibody, or antigen-binding portion thereof, such that an immune response to the antigen in the subject is enhanced. Preferably, the antibody is a human anti-human PD-1 antibody (such as any of the human anti-PD-1 antibodies described herein). Additionally or alternatively, the antibody can be a chimeric or humanized antibody. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-PD-1 antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-PD-1 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present invention are kits comprising the antibody compositions of the invention (e.g., human antibodies, bispecific or multispecific molecules, or immunoconugates) and instructions for use. The kit can further contain a least one additional reagent, or one or more additional human antibodies of the invention (e.g., a human antibody having a complementary activity which binds to an epitope in PD-1 antigen distinct from the first human antibody). Kits typically include a label indicating the intended use of the contents of the kit. The term label includes any writing, or recorded material supplied on or with the kit, or which otherwise accompanies the kit.

Combination Therapy

The present invention is based, in part, on the following experimental data. Mouse tumor models (MC38 colon cancer and SA1/N fibrosarcoma) were used to examine the in vivo effect of treating a tumor by combining immunostimulatory therapeutic antibodies—anti-CTLA-4 and anti-PD-1. The immunotherapeutic combination was provided either simultaneous with the implant of tumor cells (Examples 14 and 17) or after the tumor cells were implanted for a time sufficient to become an established tumor (Examples 15, 16 and 18). Regardless of the timing of antibody treatment, it was found that anti-CTLA-4 antibody treatment alone and anti-PD-1 antibody (chimeric antibody in which a rat anti-mouse PD-1 was modified with a mouse immunoglobulin Fc region, see Example 1) treatment alone had a modest effect on reducing tumor growth in the MC38 tumor model (see, e.g., FIGS. 21, 24 and 27). The anti-CTLA-4 antibody alone was quite effective in the SA1/N tumor model (see FIG. 30D), which required a lower anti-CTLA-4 antibody dose for the combination studies in this model. Nonetheless, the combination treatment of anti-CTLA-4 antibody and anti-PD-1 antibody showed an unexpected, significantly greater effect on reducing tumor growth as compared to treatment with either antibody alone (see, e.g., FIGS. 21D, 24D, 30F and 33H-J). In addition, the results of Examples 14, 16 and 18 show that the combination treatment of anti-CTLA-4 antibody and anti-PD-1 antibody had a significant (synergistic) effect on tumor growth even at sub-optimal therapeutic doses as compared to treatment with either antibody alone (i.e., the combination therapy was surprisingly more effective at subtherapeutic doses than either monotherapy). Without wishing to be bound by theory, it is possible that by raising the threshold of T cell activation by PD-1 and CTLA-4 blockade, anti-tumor responses may be activated in a host.

In one embodiment, the present invention provides a method for treating a hyperproliferative disease, comprising administering a PD-1 antibody and a CTLA-4 antibody to a subject. In further embodiments, the anti-PD-1 antibody is administered at a subtherapeutic dose, the anti-CTLA-4 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-PD-1 antibody and a subtherapeutic dose of anti-CTLA-4 antibody to a subject. In certain embodiments, the subject is human. In certain embodiments, the anti-CTLA-4 antibody is human sequence monoclonal antibody 10D1 and the anti-PD-1 antibody is human sequence monoclonal antibody, such as 17D8, 2D3, 4H1, 5C4 and 4A11. Human sequence monoclonal antibodies 17D8, 2D3, 4H1, 5C4 and 4A11 have been isolated and structurally characterized, as described in U.S. Provisional Patent No. 60/679,466.

The anti-CTLA-4 antibody and anti-PD-1 monoclonal antibodies (mAbs) and the human sequence antibodies of the invention can be produced by a variety of techniques, including conventional monoclonal antibody methodology, e.g., the standard somatic cell hybridization technique of Kohler and Milstein (1975) *Nature* 256:495. Any technique for producing monoclonal antibody can be employed, e.g., viral or oncogenic transformation of B lymphocytes. One animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known (see, e.g., Harlow and Lane (1988) *Antibodies, A Laboratory Manual*, Cold Spring Harbor Laboratory Press, Cold Spring Harbor N.Y.).

Anti-CTLA-4 antibodies of the instant invention can bind to an epitope on human CTLA-4 so as to inhibit CTLA-4 from interacting with a human B7 counterreceptor. Because interaction of human CTLA-4 with human B7 transduces a signal leading to inactivation of T-cells bearing the human CTLA-4 receptor, antagonism of the interaction effectively induces, augments or prolongs the activation of T cells bearing the human CTLA-4 receptor, thereby prolonging or augmenting an immune response. Anti-CTLA-4 antibodies are described in U.S. Pat. Nos. 5,811,097; 5,855,887; 6,051,227; in PCT Application Publication Nos. WO 01/14424 and WO 00/37504; and in U.S. Patent Publication No. 2002/0039581. Each of these references is specifically incorporated herein by reference for purposes of description of anti-CTLA-4 antibodies. An exemplary clinical anti-CTLA-4 antibody is human monoclonal antibody 10D1 as disclosed in WO 01/14424 and U.S. patent application Ser. No. 09/644,668. Antibody 10D1 has been administered in single and multiple doses, alone or in combination with a vaccine, chemotherapy, or interleukin-2 to more than 500 patients diagnosed with metastatic melanoma, prostate cancer, lymphoma, renal cell cancer, breast cancer, ovarian cancer, and HIV. Other anti-CTLA-4 antibodies encompassed by the methods of the present invention include, for example, those disclosed in: WO 98/42752; WO 00/37504; U.S. Pat. No. 6,207,156; Hurwitz et al. (1998) *Proc. Natl. Acad. Sci. USA* 95(17):10067-10071; Camacho et al. (2004) *J. Clin. Oncology* 22(145): Abstract No. 2505 (antibody CP-675206); and Mokyr et al. (1998) *Cancer Res.* 58:5301-5304. In certain embodiments, the methods of the instant invention comprise use of an anti-CTLA-4 antibody that is a human sequence antibody, preferably a monoclonal antibody and in another embodiment is monoclonal antibody 10D1.

In certain embodiments, the anti-CTLA-4 antibody binds to human CTLA-4 with a $K_D$ of $5 \times 10^{-8}$ M or less, binds to human CTLA-4 with a $K_D$ of $1 \times 10^{-8}$ M or less, binds to human CTLA-4 with a $K_D$ of $5 \times 10^{-9}$ M or less, or binds to human CTLA-4 with a $K_D$ of between $1 \times 10^{-8}$ M and $1 \times 10^{-10}$ M or less.

The combination of antibodies is useful for enhancement of an immune response against a hyperproliferative disease by blockade of PD-1 and CTLA-4. In a preferred embodiment, the antibodies of the present invention are human antibodies. For example, these molecules can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject an antibody combination, or a combination of antigen-binding portions thereof, of the invention such that the immune response in the subject is modified. Preferably, the response is enhanced, stimulated or up-regulated. In another embodiment, the instant disclosure provides a method of altering adverse events associated with treatment of a hyperproliferative disease with an immunostimulatory therapeutic agent, comprising administering an anti-PD-1 antibody and a subtherapeutic dose of anti-CTLA-4 antibody to a subject.

Blockade of PD-1 and CTLA-4 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include melanoma (e.g., metastatic malignant melanoma), renal cancer, prostate cancer, breast cancer, colon cancer and lung cancer. Examples of other cancers that may be treated using the methods of the instant disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers.

In certain embodiments, the combination of therapeutic antibodies discussed herein may be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. For example, an anti-CTLA-4 antibody and an anti-PD-1 antibody can be administered sequentially, such as anti-CTLA-4 being administered first and anti-PD-1 second, or anti-PD-1 being administered first and anti-CTLA-4 second. Furthermore, if more than one dose of the combination therapy is administered sequentially, the order of the sequential administration can be reversed or kept in the same order at each time point of administration, sequential administrations may be combined with concurrent administrations, or any combination thereof. For example, the first administration of a combination anti-CTLA-4 antibody and anti-PD-1 antibody may be concurrent, the second administration may be sequential with anti-CTLA-4 first and anti-PD-1 second, and the third administration may be sequential with anti-PD-1 first and anti-CTLA-4 second, etc. Another representative dosing scheme may involve a first administration that is sequential with anti-PD-1 first and anti-CTLA-4 second, and subsequent administrations may be concurrent.

Optionally, the combination of anti-PD-1 and anti-CTLA-4 antibodies can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF (discussed further below).

A combined PD-1 and CTLA-4 blockade can be further combined with a vaccination protocol. Many experimental strategies for vaccination against tumors have been devised (see Rosenberg, S. (2000) Development of Cancer Vaccines, ASCO Educational Book Spring: 60-62; Logothetis, C., 2000, ASCO Educational Book Spring: 300-302; Khayat, D. (2000) ASCO Educational Book Spring: 414-428; Foon, K. (2000) ASCO Educational Book Spring: 730-738; see also Restifo and Sznol, Cancer Vaccines, Ch. 61, pp. 3023-3043 in DeVita et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci U.S.A. 90: 3539-43).

The study of gene expression and large scale gene expression patterns in various tumors has led to the definition of so called tumor specific antigens (Rosenberg (1999) Immunity 10:281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. In certain embodiments, a combined PD-1 and CTLA-4 blockade using the antibody compositions described herein may be used in conjunction with a collection of recombinant proteins and/or peptides expressed in a tumor in order to generate an immune response to these proteins. These proteins are noimally viewed by the immune system as self-antigens and are, therefore, tolerant to them. The tumor antigen may also include the protein telomerase, which is required for the synthesis of telomeres of chromosomes and which is expressed in more than 85% of human cancers and in only a limited number of somatic tissues (Kim et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) Science 269:1585-1588; Tamura et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) Nature Medicine 4: 328-332). DCs may also be transduced by genetic means to express these tumor antigens as well. DCs have also been fused directly to tumor cells for the purposes of immunization (Kugler et al. (2000) Nature Medicine 6:332-336). As a method of vaccination, DC immunization may be effectively further combined with a combined PD-1 and CTLA-4 blockade to activate more potent anti-tumor responses.

A combined PD-1 and CTLA-4 blockade may also be further combined with standard cancer treatments. For example, a combined PD-1 and CTLA-4 blockade may be effectively combined with chemotherapeutic regimes. In these instances, as is observed with the combination of anti-PD-1 and anti-CTLA-4 antibodies, it may be possible to reduce the dose of other chemotherapeutic reagent administered with the combination of the instant disclosure (Mokyr et al. (1998) Cancer Research 58: 5301-5304). An example of such a combination is a combination of anti-PD-1 and anti-CTLA-4 antibodies further in combination with decarbazine for the treatment of melanoma. Another example is a combination of anti-PD-1 and anti-CTLA-4 antibodies further in combination with interleukin-2 (IL-2) for the treatment of melanoma. The scientific rationale behind the combined use of PD-1 and CTLA-4 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined PD-1 and CTLA-4 blockade through cell death include radiation, surgery, or hormone deprivation. Each of these protocols creates a source of tumor antigen in the host. Angiogenesis inhibitors may also be combined with a combined PD-1 and CTLA-4 blockade. Inhibition of angiogenesis leads to tumor cell death, which may also be a source of tumor antigen to be fed into host antigen presentation pathways.

A combination of PD-1 and CTLA-4 blocking antibodies can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of a combined PD-1 and CTLA-4 blockade. Alternatively, antigen may be delivered directly to DCs by the use of bispecific antibodies which bind to tumor antigen and a dendritic cell specific cell surface marker.

In another example, a combination of anti-PD-1 and anti-CTLA-4 antibodies can be used in conjunction with anti-neoplastic antibodies, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4 or PD-1. In an exemplary embodiment, a treatment of a hyperproliferative disease (e.g., a cancer tumor) may include an anti-cancer antibody in combination with anti-PD-1 and anti-CTLA-4 antibodies, concurrently or sequentially or any combination thereof, which may potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl, J. et al. (1986) J Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). In another example, antibodies to each of these entities may be further combined with an anti-PD-1 and anti-CTLA-4 combination to counteract the effects of immunosuppressive agents and favor anti-tumor immune responses by the host.

Other antibodies that may be used to activate host immune responsiveness can be further used in combination with an anti-PD-1 and anti-CTLA-4 combination. These include molecules on the surface of dendritic cells that activate DC function and antigen presentation. Anti-CD40 antibodies are able to substitute effectively for T cell helper activity (Ridge, J. et al. (1998) *Nature* 393: 474-478) and can be used in conjunction with an anti-PD-1 and anti-CTLA-4 combination (Ito, N. et al. (2000) *Immunobiology* 201 (5) 527-40). Activating antibodies to T cell costimulatory molecules, such as OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. A combined PD-1 and CTLA-4 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. & Riddell, S. (1999) *Science* 285: 546-51). These methods may also be used to activate T cell responses to infectious agents such as CMV. Ex vivo activation in the presence of anti-PD-1 and anti-CTLA-4 antibodies may be expected to increase the frequency and activity of the adoptively transferred T cells.

As set forth herein, organs can exhibit immune-related adverse events following immunostimulatory therapeutic antibody therapy, such as the GI tract (diarrhea and colitis) and the skin (rash and pruritis) after treatment with anti-CTLA-4 antibody. For example, non-colonic gastrointestinal immune-related adverse events have also been observed in the esophagus (esophagitis), duodenum (duodenitis), and ileum (ileitis) after anti-CTLA-4 antibody treatment.

In certain embodiments, the present invention provides a method for altering an adverse event associated with treatment of a hyperproliferative disease with an immunostimulatory agent, comprising administering a anti-PD-1 antibody and a subtherapeutic dose of anti-CTLA-4 antibody to a subject. For example, the methods of the present invention provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such an antibody, this entire patient population is suitable for therapy according to the methods of the present invention. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a combination PD-1 and CTLA-4 blockade (i.e., immunostimulatory therapeutic antibodies anti-PD-1 and anti-CTLA-4) can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the invention, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. The usual oral dosage of ENTOCORT EC® for the treatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR $58^{th}$ ed. 2004; 608-610.

In still further embodiments, a combination PD-1 and CTLA-4 blockade (i.e., immunostimulatory therapeutic antibodies anti-PD-1 and anti-CTLA-4) in conjunction with a non-absorbable steroid can be further combined with a salicylate. Salicylates include 5-ASA agents such as, for example: sulfasalazine (AZULFIDINE®, Pharmacia & UpJohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

In accordance with the methods of the present invention, a salicylate administered in combination with anti-PD-1 and anti-CTLA-4 antibodies and a non-absorbable steroid can includes any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies according to the present invention encompass administering a salicylate and a non-absorbable concurrently or sequentially (e.g., a salicylate is administered 6 hours after a non-absorbable steroid), or any combination thereof. Further, according to the present invention, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-PD-1 and anti-CTLA-4 antibodies.

The present invention is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against PD-1

Antigen

Immunization protocols utilized as antigen both (i) a recombinant fusion protein comprising the extracellular portion of PD-1 and (ii) membrane bound full-length PD-1. Both antigens were generated by recombinant transfection methods in a CHO cell line.

Transgenic HuMab and KM Mice™

Fully human monoclonal antibodies to PD-1 were prepared using the HCo7 strain of HuMab transgenic mice and the KM strain of transgenic transchromosomic mice, each of which express human antibody genes. In each of these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) *Nature Biotechnology* 14:845-851. The HCo7 strain carries the HCo7 human heavy chain transgene as described in U.S. Pat. Nos. 5,545,806; 5,625,825; and 5,545,807. The KM strain contains the SC20 transchromosome as described in PCT Publication WO 02/43478.

HuMab and KM Immunizations:

To generate fully human monoclonal antibodies to PD-1, HuMab mice and KM Mice™ were immunized with purified recombinant PD-1 fusion protein and PD-1-transfected CHO cells as antigen. General immunization schemes for HuMab mice are described in Lonberg, N. et al (1994) *Nature* 368(6474): 856-859; Fishwild, D. et al. (1996) *Nature Biotechnology* 14: 845-851 and PCT Publication WO 98/24884. The mice were 6-16 weeks of age upon the first infusion of antigen. A purified recombinant preparation (5-50 µg) of PD-1 fusion protein antigen and 5-10×10$^6$ cells were used to immunize the HuMab mice and KM Mice™ intraperitoneally, subcutaneously (Sc) or via footpad injection.

Transgenic mice were immunized twice with antigen in complete Freund's adjuvant or Ribi adjuvant IP, followed by 3-21 days IP (up to a total of 11 immunizations) with the antigen in incomplete Freund's or Ribi adjuvant. The immune response was monitored by retroorbital bleeds. The plasma was screened by ELISA (as described below), and mice with sufficient titers of anti-PD-1 human immunogolobulin were used for fusions. Mice were boosted intravenously with antigen 3 days before sacrifice and removal of the spleen. Typically, 10-35 fusions for each antigen were performed. Several dozen mice were immunized for each antigen.

Selection of HuMab or KM Mice™ Producing Anti-PD-1 Antibodies:

To select HuMab or KM Mice™ producing antibodies that bound PD-1, sera from immunized mice were tested by ELISA as described by Fishwild, D. et al. (1996). Briefly, microtiter plates were coated with purified recombinant PD-1 fusion protein from transfected CHO cells at 1-2 µg/ml in PBS, 100 µl/wells incubated 4° C. overnight then blocked with 200 µl/well of 5% fetal bovine serum in PBS/Tween (0.05%). Dilutions of sera from PD-1-immunized mice were added to each well and incubated for 1-2 hours at ambient temperature. The plates were washed with PBS/Tween and then incubated with a goat-anti-human IgG polyclonal antibody conjugated with horseradish peroxidase (HRP) for 1 hour at room temperature. After washing, the plates were developed with ABTS substrate (Sigma, A-1888, 0.22 mg/ml) and analyzed by spectrophotometer at OD 415-495. Mice that developed the highest titers of anti-PD-1 antibodies were used for fusions. Fusions were performed as described below and hybridoma supernatants were tested for anti-PD-1 activity by ELISA.

Generation of Hybridomas Producing Human Monoclonal Antibodies to PD-1:

The mouse splenocytes, isolated from the HuMab or KM mice, were fused to a mouse myeloma cell line either using PEG based upon standard protocols or electric field based electrofusion using a Cyto Pulse large chamber cell fusion electroporator (Cyto Pulse Sciences, Inc., Glen Burnie, Md.). The resulting hybridomas were then screened for the production of antigen-specific antibodies. Single cell suspensions of splenocytes from immunized mice were fused to one-fourth the number of SP2/0 nonsecreting mouse myeloma cells (ATCC, CRL 1581) with 50% PEG (Sigma). Cells were plated at approximately 1×10$^5$/well in flat bottom microtiter plate, followed by about two week incubation in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Individual wells were then screened by ELISA (described above) for human anti-PD-1 monoclonal IgG antibodies. Once extensive hybridoma growth occurred, medium was monitored usually after 10-14 days. The antibody-secreting hybridomas were replated, screened again and, if still positive for human IgG, anti-PD-1 monoclonal antibodies were subcloned at least twice by limiting dilution. The stable subclones were then cultured in vitro to generate small amounts of antibody in tissue culture medium for further characterization.

Hybridoma clones 17D8, 2D3, 4H1, 5C4, 4A11, 7D3 and 5F4 were selected for further analysis.

Example 2

Structural Characterization of Human Monoclonal Antibodies 17D8, 2D3, 4H1, 5C4, 4A11, 7D3 and 5F4

The cDNA sequences encoding the heavy and light chain variable regions of the 17D8, 2D3, 4H1, 5C4, 4A11, 7D3 and 5F4 monoclonal antibodies were obtained from the 17D8, 2D3, 4H1, 5C4, 4A11, 7D3 and 5F4 hybridomas, respectively, using standard PCR techniques and were sequenced using standard DNA sequencing techniques.

The nucleotide and amino acid sequences of the heavy chain variable region of 17D8 are shown in FIG. 1A and in SEQ ID NO: 57 and 1, respectively.

The nucleotide and amino acid sequences of the light chain variable region of 17D8 are shown in FIG. 1B and in SEQ ID NO: 64 and 8, respectively.

Comparison of the 17D8 heavy chain immunoglobulin sequence to the known human germline immunoglobulin heavy chain sequences demonstrated that the 17D8 heavy chain utilizes a VH segment from human germline VH 3-33, an undetermined D segment, and a JH segment from human germline 4b. The alignment of the 17D8 VH sequence to the germline VH 3-33 sequence is shown in FIG. 8. Further analysis of the 17D8 VH sequence using the Kabat system of CDR region determination led to the delineation of the heavy chain CDR1, CDR2 and CD3 regions as shown in FIGS. 1A and 8, and in SEQ ID NOs: 15, 22 and 29, respectively.

Comparison of the 17D8 light chain immunoglobulin sequence to the known human germline immunoglobulin light chain sequences demonstrated that the 17D8 light chain utilizes a VL segment from human germline VK L6 and a JK segment from human germline JK 4. The alignment of the 17D8 VL sequence to the germline VK L6 sequence is shown in FIG. 9. Further analysis of the 17D8 VL sequence using the Kabat system of CDR region determination led to the delineation of the light chain CDR1, CDR2 and CD3 regions as shown in FIGS. 1B and 9, and in SEQ ID NOs: 36, 43 and 50, respectively.

The nucleotide and amino acid sequences of the heavy chain variable region of 2D3 are shown in FIG. 2A and in SEQ ID NO: 58 and 2, respectively.

The nucleotide and amino acid sequences of the light chain variable region of 2D3 are shown in FIG. 2B and in SEQ ID NO: 65 and 9, respectively.

Comparison of the 2D3 heavy chain immunoglobulin sequence to the known human germline immunoglobulin heavy chain sequences demonstrated that the 2D3 heavy chain utilizes a VH segment from human germline VH 3-33, a D segment from human germline 7-27, and a JH segment from human germline JH 4b. The alignment of the 2D3 VH sequence to the germline VH 3-33 sequence is shown in FIG. 8. Further analysis of the 2D3 VH sequence using the Kabat system of CDR region determination led to the delineation of the heavy chain CDR1, CDR2 and CD3 regions as shown in FIGS. 2A and 8, and in SEQ ID NOs: 16, 23 and 30, respectively.

Comparison of the 2D3 light chain immunoglobulin sequence to the known human germline immunoglobulin light chain sequences demonstrated that the 2D3 light chain utilizes a VL segment from human germline VK L6 and a JK segment from human germline JK 4. The alignment of the 2D3 VL sequence to the germline VK L6 sequence is shown in FIG. 9. Further analysis of the 2D3 VL sequence using the Kabat system of CDR region determination led to the delineation of the light chain CDR1, CDR2 and CD3 regions as shown in FIGS. 2B and 9, and in SEQ ID NOs: 37, 44 and 51, respectively.

The nucleotide and amino acid sequences of the heavy chain variable region of 4H1 are shown in FIG. 3A and in SEQ ID NO: 59 and 3, respectively.

The nucleotide and amino acid sequences of the light chain variable region of 4H1 are shown in FIG. 3B and in SEQ ID NO: 66 and 10, respectively.

Comparison of the 4H1 heavy chain immunoglobulin sequence to the known human germline immunoglobulin heavy chain sequences demonstrated that the 4H1 heavy chain utilizes a VH segment from human germline VH 3-33, an undetermined D segment, and a JH segment from human germline JH 4b. The alignment of the 4H1 VH sequence to the germline VH 3-33 sequence is shown in FIG. 8. Further analysis of the 4H1 VH sequence using the Kabat system of CDR region determination led to the delineation of the heavy chain CDR1, CDR2 and CD3 regions as shown in FIGS. 3A and 8, and in SEQ ID NOs: 17, 24 and 31, respectively.

Comparison of the 4H1 light chain immunoglobulin sequence to the known human germline immunoglobulin light chain sequences demonstrated that the 4H1 light chain utilizes a VL segment from human germline VK L6 and a JK segment from human germline JK 1. The alignment of the 4H1 VL sequence to the germline VK L6 sequence is shown in FIG. 10. Further analysis of the 4H1 VL sequence using the Kabat system of CDR region determination led to the delineation of the light chain CDR1, CDR2 and CD3 regions as shown in FIGS. 3B and 10, and in SEQ ID NOs: 38, 45 and 52, respectively.

The nucleotide and amino acid sequences of the heavy chain variable region of 5C4 are shown in FIG. 4A and in SEQ ID NO: 60 and 4, respectively.

The nucleotide and amino acid sequences of the light chain variable region of 5C4 are shown in FIG. 4B and in SEQ ID NO: 67 and 11, respectively.

Comparison of the 5C4 heavy chain immunoglobulin sequence to the known human germline immunoglobulin heavy chain sequences demonstrated that the 5C4 heavy chain utilizes a VH segment from human germline VH 3-33, an undetermined D segment, and a JH segment from human germline JH 4b. The alignment of the 5C4 VH sequence to the germline VH 3-33 sequence is shown in FIG. 8. Further analysis of the 5C4 VH sequence using the Kabat system of CDR region determination led to the delineation of the heavy chain CDR1, CDR2 and CD3 regions as shown in FIGS. 4A and 8, and in SEQ ID NOs: 18, 25 and 32, respectively.

Comparison of the 5C4 light chain immunoglobulin sequence to the known human germline immunoglobulin light chain sequences demonstrated that the 5C4 light chain utilizes a VL segment from human germline VK L6 and a JK segment from human germline JK 1. The alignment of the 5C4 VL sequence to the germline VK L6 sequence is shown in FIG. 10. Further analysis of the 5C4 VL sequence using the Kabat system of CDR region determination led to the delineation of the light chain CDR1, CDR2 and CD3 regions as shown in FIGS. 4B and 10, and in SEQ ID NOs: 39, 46 and 53, respectively.

The nucleotide and amino acid sequences of the heavy chain variable region of 4A11 are shown in FIG. 5A and in SEQ ID NO: 61 and 5, respectively.

The nucleotide and amino acid sequences of the light chain variable region of 4A11 are shown in FIG. 5B and in SEQ ID NO: 68 and 12, respectively.

Comparison of the 4A11 heavy chain immunoglobulin sequence to the known human germline immunoglobulin heavy chain sequences demonstrated that the 4A11 heavy chain utilizes a VH segment from human germline VH 4-39, a D segment from human germline 3-9, and a JH segment from human germline JH 4b. The alignment of the 4A11 VH sequence to the germline VH 4-39 sequence is shown in FIG. 11. Further analysis of the 4A11 VH sequence using the Kabat system of CDR region determination led to the delineation of the heavy chain CDR1, CDR2 and CD3 regions as shown in FIGS. 5A and 11, and in SEQ ID NOs: 19, 26 and 33, respectively.

Comparison of the 4A11 light chain immunoglobulin sequence to the known human germline immunoglobulin light chain sequences demonstrated that the 4A11 light chain utilizes a VL segment from human germline VK L15 and a JK segment from human germline JK 1. The alignment of the 4A11 VL sequence to the germline VK L6 sequence is shown in FIG. 12. Further analysis of the 4A11 VL sequence using the Kabat system of CDR region determination led to the delineation of the light chain CDR1, CDR2 and CD3 regions as shown in FIGS. 5B and 12, and in SEQ ID NOs: 40, 47 and 54, respectively.

The nucleotide and amino acid sequences of the heavy chain variable region of 7D3 are shown in FIG. 7A and in SEQ ID NO: 62 and 6, respectively.

The nucleotide and amino acid sequences of the light chain variable region of 7D3 are shown in FIG. 7B and in SEQ ID NO: 69 and 13, respectively.

Comparison of the 7D3 heavy chain immunoglobulin sequence to the known human germline immunoglobulin heavy chain sequences demonstrated that the 7D3 heavy chain utilizes a VH segment from human germline VH 3-33, a human germline 7-27 D segment, and a JH segment from human germline JH 4b. The alignment of the 7D3 VH sequence to the germline VH 3-33 sequence is shown in FIG. 8. Further analysis of the 7D3 VH sequence using the Kabat system of CDR region determination led to the delineation of the heavy chain CDR1, CDR2 and CD3 regions as shown in FIGS. 6A and 8, and in SEQ ID NOs: 20, 27 and 34, respectively.

Comparison of the 7D3 light chain immunoglobulin sequence to the known human germline immunoglobulin light chain sequences demonstrated that the 7D3 light chain utilizes a VL segment from human germline VK L6 and a JK segment from human germline JK 4. The alignment of the 7D3 VL sequence to the germline VK L6 sequence is shown in FIG. 9. Further analysis of the 7D3 VL sequence using the Kabat system of CDR region determination led to the delineation of the light chain CDR1, CDR2 and CD3 regions as shown in FIGS. 6B and 9, and in SEQ ID NOs: 41, 48 and 55, respectively.

The nucleotide and amino acid sequences of the heavy chain variable region of 5F4 are shown in FIG. 7A and in SEQ ID NO: 63 and 7, respectively.

The nucleotide and amino acid sequences of the light chain variable region of 5F4 are shown in FIG. 7B and in SEQ ID NO: 70 and 14, respectively.

Comparison of the 5F4 heavy chain immunoglobulin sequence to the known human germline immunoglobulin heavy chain sequences demonstrated that the 5F4 heavy chain utilizes a VH segment from human germline VH 4-39, a D segment from human germline 3-9, and a JH segment from human germline JH 4b. The alignment of the 5F4 VH sequence to the germline VH 4-39 sequence is shown in FIG. 11. Further analysis of the 5F4 VH sequence using the Kabat system of CDR region determination led to the delineation of the heavy chain CDR1, CDR2 and CD3 regions as shown in FIGS. 7A and 11, and in SEQ ID NOs: 21, 28 and 35, respectively.

Comparison of the 5F4 light chain immunoglobulin sequence to the known human germline immunoglobulin light chain sequences demonstrated that the 5F4 light chain utilizes a VL segment from human germline VK L15 and a JK segment from human germline JK 1. The alignment of the 5F4 VL sequence to the germline VK L6 sequence is shown in FIG. 12. Further analysis of the 5F4 VL sequence using the Kabat system of CDR region determination led to the delineation of the light chain CDR1, CDR2 and CD3 regions as shown in FIGS. 7B and 12, and in SEQ ID NOs: 42, 49 and 56, respectively.

Example 3

Characterization of Binding Specificity and Binding Kinetics of Anti-PD-1 Human Monoclonal Antibodies In this example, binding affinity and binding kinetics of anti-PD-1 antibodies were examined by Biacore analysis. Binding specificity, and cross-competition were examined by flow cytometry.

Binding Affinity and Kinetics

Anti-PD-1 antibodies were characterized for affinities and binding kinetics by Biacore analysis (Biacore AB, Uppsala, Sweden). Purified recombinant human PD-1 fusion protein was covalently linked to a CM5 chip (carboxy methyl dextran coated chip) via primary amines, using standard amine coupling chemistry and kit provided by Biacore. Binding was measured by flowing the antibodies in HBS EP buffer (provided by Biacore AB) at a concentration of 267 nM at a flow rate of 50 µl/min. The antigen-antibody association kinetics was followed for 3 minutes and the dissociation kinetics was followed for 7 minutes. The association and dissociation curves were fit to a 1:1 Langmuir binding model using BIAevaluation software (Biacore AB). To minimize the effects of avidity in the estimation of the binding constants, only the initial segment of data corresponding to association and dissociation phases were used for fitting. The $K_D$, $k_{on}$ and $k_{off}$ values that were determined are shown in Table 2.

TABLE 2

Biacore binding data for PD-1 human monoclonal antibodies.

| Sample # | Sample ID | Affinity $K_D$ × $10^{-9}$ (M) | On rate $k_{on}$ × $10^5$ (1/Ms) | Off rate $k_{off}$ × $10^{-4}$ 1/s |
|---|---|---|---|---|
| 1 | 17D8 | 0.16 | 2.56 | 0.45 |
| 2 | 2D3 | 1.20 | 3.77 | 4.52 |
| 3 | 4H1 | 5.46 | 3.15 | 1.72 |
| 4 | 5C4 | 0.73 | 4.32 | 3.15 |
| 5 | 4A11 | 0.13 | 0.76 | 0.099 |
| 6 | 7D3 | 2.49 | 18.2 | 4.54 |
| 7 | 5F4 | 2.91 | 8.74 | 2.54 |

Binding Specificity by Flow Cytometry

Figure 13A:
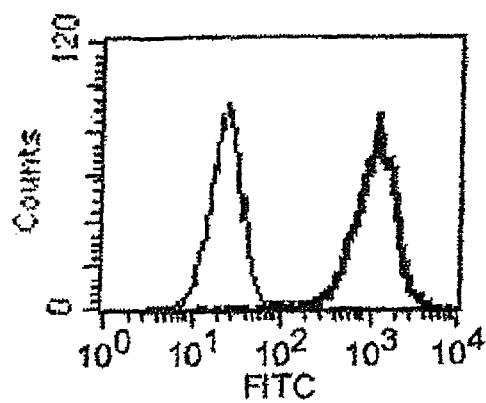
FIGS. 13A-13B show the results of flow cytometry experiments demonstrating that the human monoclonal antibodies 5C4 and 4H1, directed against human PD-1, binds the cell surface of CHO cells transfected with full-length human PD-1.
Figure 13B:
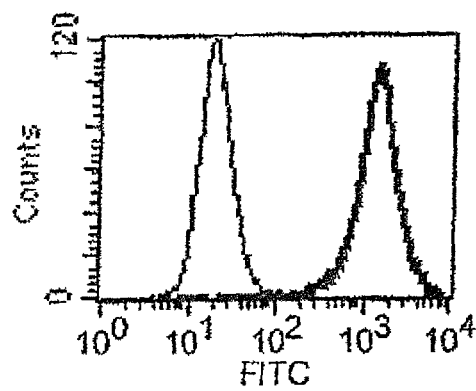

Chinese hamster ovary (CHO) cell lines that express recombinant human PD-1 at the cell surface were developed and used to determine the specificity of PD-1 human monoclonal antibodies by flow cytometry. CHO cells were transfected with expression plasmids containing full length cDNA encoding transmembrane forms of PD-1. Binding of the 5C4 and 4H1 anti-PD-1 human monoclonal antibodies was assessed by incubating the transfected cells with the anti-PD-1 human monoclonal antibodies at a concentration of 20 µg/ml. The cells were washed and binding was detected with a FITC-labeled anti-human IgG Ab. Flow cytometric analyses were performed using a FACScan flow cytometry (Becton Dickinson, San Jose, Calif.). The results are depicted in FIGS. 13A (5C4) and 13B (4H1). The anti-PD-1 human monoclonal antibodies bound to the CHO cells transfected with PD-1 but not to CHO cells that were not transfected with human PD-1. These data demonstrate the specificity of anti-PD-1 human monoclonal antibodies for PD-1.

Binding Specificity by ELISA Against Other CD28 Family Members

A comparison of the binding of anti-PD-1 antibodies to CD28 family members was performed by standard ELISA using four different CD28 family members to examine the specificity of binding for PD-1.

Figure 14:
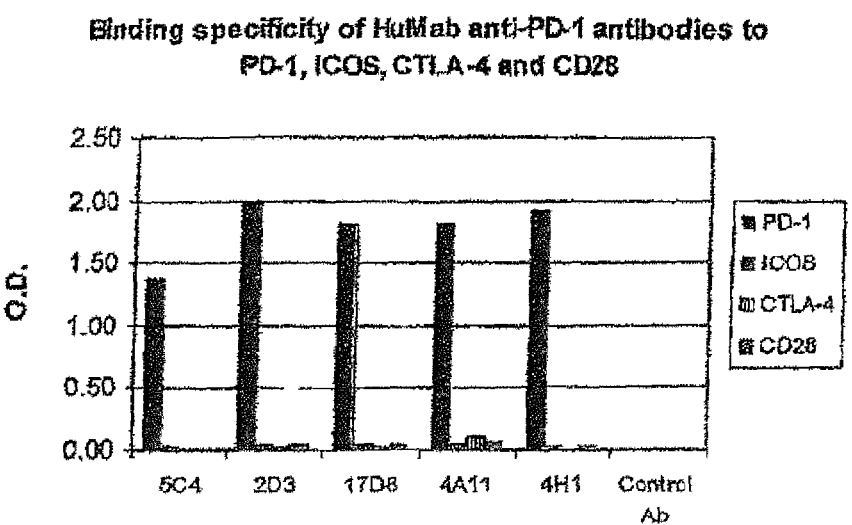
FIG. 14 shows a graph demonstrating that the human monoclonal antibodies 17D8, 2D3, 4H1, 5C4, and 4A11, directed against human PD-1, bind specifically to PD-1, and not to other members of the CD28

Fusion proteins of CD28 family members, ICOS, CTLA-4 and CD28 (R&D Biosystems) were tested for binding against the anti-PD-1 human monoclonal antibodies 17D8, 2D3, 4141, 5C4, and 4A11. Standard ELISA procedures were performed. The anti-PD-1 human monoclonal antibodies were added at a concentration of 20 µg/ml. Goat-anti-human IgG (kappa chain-specific) polyclonal antibody conjugated with horseradish peroxidase (HRP) was used as secondary antibody. The results are shown in FIG. 14. Each of the anti-PD-1 human monoclonal antibodies 17D8, 2D3, 4H1, 5C4, 4A11, 7D3 and 5F4 bound with high specificity to PD-1, but not to the other CD28 family members.

Example 4

Characterization of Anti-PD-1 Antibody Binding to PD-1 Expressed on the Surface of Human and Monkey Cells Anti-PD-1 antibodies were tested for binding to cells expressing PD-1 on their cell surface by flow cytometry.

Figure 15A:
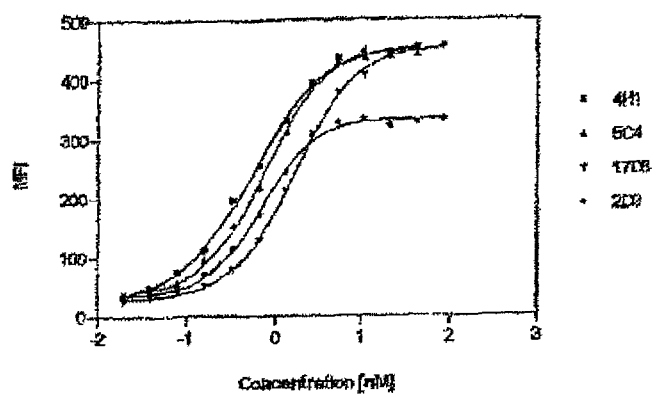
FIGS. 15A-15C show the results of flow cytometry experiments demonstrating that the human monoclonal antibodies 4H1 and 5C4, directed against human PD-1, binds to PD-1 on the cell surface.
Figure 15B:
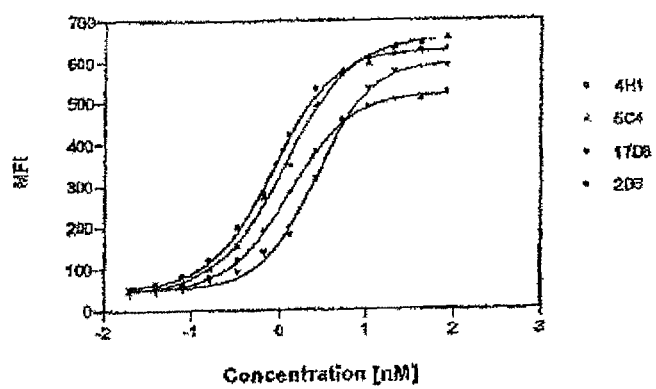
Figure 15C:
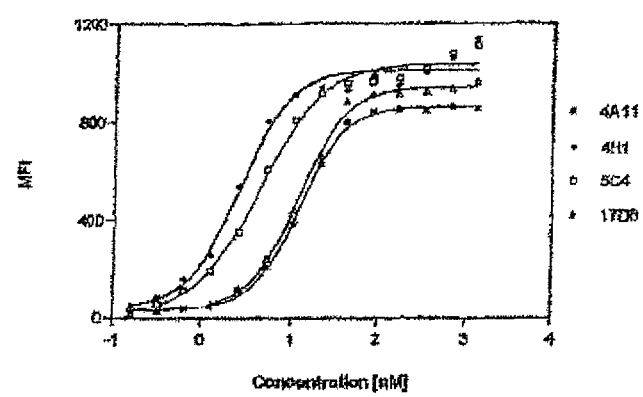

Activated human T-cells, monkey peripheral blood mononuclear cells (PBMC), and CHO cells transfected with PD-1 were each tested for antibody binding. Human T cells and cynomolgous PBMC were activated by anti-CD3 antibody to induce PD-1 expression on T cells prior to binding with a human anti-PD-1 monoclonal antibody. Binding of the 5C4 and 4H1 anti-PD-1 human monoclonal antibodies was assessed by incubating the transfected cells with either IgG1 or IgG4 forms of the anti-PD-1 human monoclonal antibodies at different concentrations. The cells were washed and binding was detected with a FITC-labeled anti-human IgG Ab. Flow cytometric analyses were performed using a FACScan flow cytometry (Becton Dickinson, San Jose, Calif.). The results are shown in FIGS. 15A (activated human T cells), 15B (cynomolgous monkey PBMC) and 15C (PD-1-transfected CHO cells). The anti-PD-1 monoclonal antibodies 5C4 and 4H1 bound to activated human T cells, activated monkey PBMCs, and CHO cells transfected with human PD-1, as measured by the mean fluorescent intensity (MFI) of staining. These data demonstrate that the anti-PD-1 HuMAbs bind to both human and cynomolgous monkey cell surface PD-1.

Example 5

Effect of Human Anti-PD-1 Antibodies on Cell Proliferation and Cytokine Production in a Mixed Lymphocyte Reaction A mixed lymphocyte reaction was employed to demonstrate the effect of blocking the PD-1 pathway to lymphocyte effector cells. T cells in the assay were tested for proliferation, IFN-gamma secretion and IL-2 secretion in the presence or absence of an anti-PD-1 HuMAb antibody.

Figure 16A:
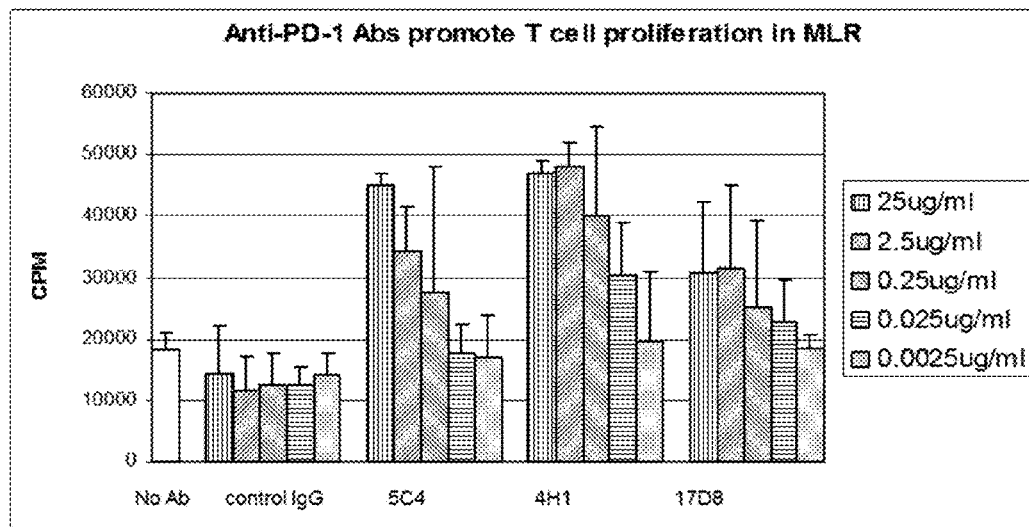
FIGS. 16A-16C show the results of experiments demonstrating that human monoclonal antibodies against human PD-1 promote T-cell proliferation, IFN-gamma secretion and IL-2 secretion in a mixed lymphocyte reaction assay.
Figure 16B:
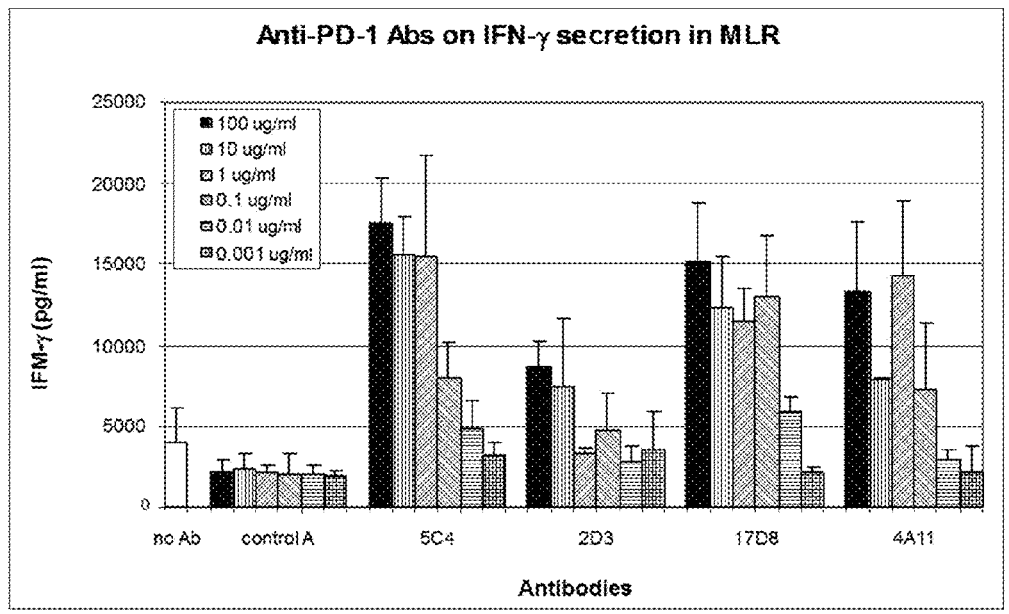
Figure 16C:
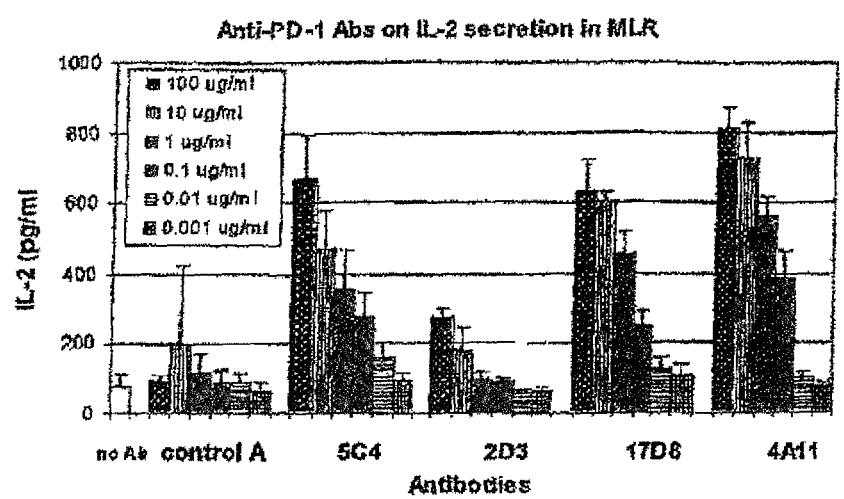

Human T-cells were purified from PBMC using a human CD4+ T cell enrichment column (R&D systems). Each culture contained $10^5$ purified T-cells and $10^4$ allogeneic dendritic cells in a total volume of 200 d. Anti-PD-1 monoclonal antibody 5C4, 4H1, 17D8, 2D3 or a Fab fragment portion of 5C4 was added to each culture at different antibody concentrations. Either no antibody or an isotype control antibody was used as a negative control. The cells were cultured for 5 days at 37° C. After day 5, 100 µl of medium was taken from each culture for cytokine measurement. The levels of IFN-gamma and other cytokines were measured using OptEIA ELISA kits (BD Biosciences). The cells were labeled with $^3$H-thymidine, cultured for another 18 hours, and analyzed for cell proliferation. The results are shown in FIGS. 16A (T cell proliferation), 16B (IFN-γ secretion) and 16C (IL-2 secretion). The anti-PD-1 human monoclonal antibodies promoted T-cell proliferation, IFN-gamma secretion and IL-2 secretion in a concentration dependent manner. The 5C4-Fab fragment also promoted T-cell proliferation, IFN-gamma secretion and IL-2 secretion in a concentration dependent manner. In contrast, cultures containing the isotype control antibody did not show an increase in T cell proliferation, IFN-gamma or IL-2 secretion.

Example 6

Blocking of Ligand Binding to PD-1 by Human Anti-PD4 Antibodies

Anti-PD-1 HuMAbs were tested for the ability to block binding of the ligands PD-L1 and PD-L2 to PD-1 expressed on transfected CHO cells by using a flow cytometry assay.

Figure 17A:
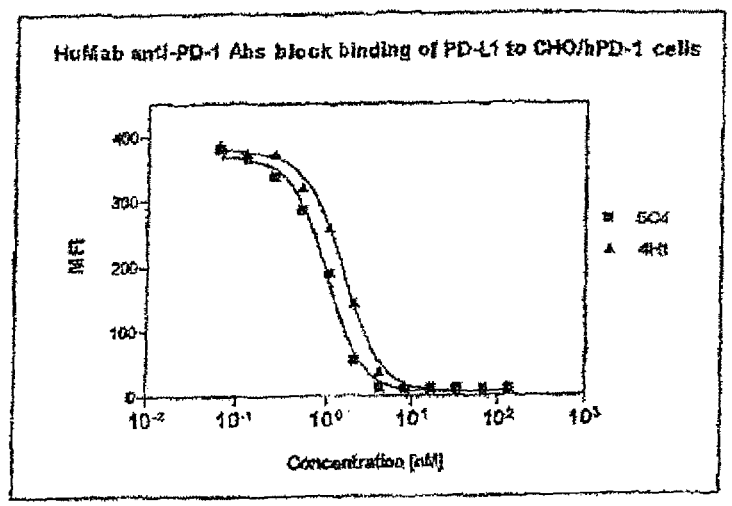
FIGS. 17A-17B show the results of flow cytometry experiments demonstrating that human monoclonal antibodies against human PD-1 block the binding of PD-L1 and PD-L2 to CHO transfected cells expressing PD-1.
Figure 17B:
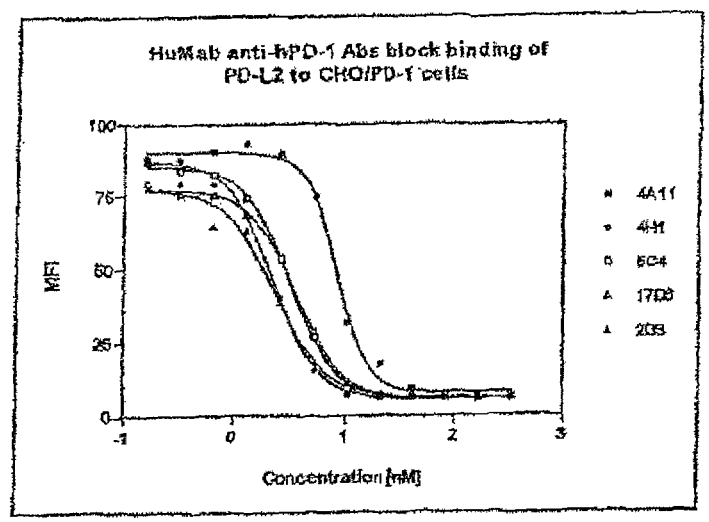

PD-1 expressing CHO cells were suspended in FACS buffer (PBS with 4% fetal calf serum). Various concentrations of the anti-PD-1 HuMAbs 5C4 and 4H1 were added to the cell suspension and incubated at 4° C. for 30 minutes. Unbound antibody was washed off and either FITC-labeled PD-L1 fusion protein or FITC-labeled PD-L2 fusion protein was added into the tubes and incubated at 4° C. for 30 minutes. Flow cytometric analyses were performed using a FACScan flow cytometer (Becton Dickinson, San Jose, Calif.). The results are depicted in FIGS. 17A (blocking of PD-L1) and 17B (blocking of PD-L2). The anti-PD-1 monoclonal antibodies 5C4 and 4H1 blocked binding of PD-L1 and PD-L2 to CHO cells transfected with human PD-1, as measured by the mean fluorescent intensity (MFI) of staining. These data demonstrate that the anti-PD-1 HuMAbs block binding of ligand (both PD-L1 and PD-L2) to cell surface PD-1.

Example 7

Effect of Human Anti-PD-1 Antibodies on the Release of Cytokines in Human Blood

The anti-PD-1 HuMAbs were mixed with fresh human whole blood in order to determine whether the anti-PD-1 HuMAbs alone stimulated the release of certain cytokines from human blood cells.

500 µl of heparinized-fresh human whole blood, was added into each well. Either 10 µg or 100 µg of an anti-PD-1 HuMAb (4H1 or 5C4, the latter either as an IgG1 or IgG4 isotype) was added to each well. Some wells were incubated with anti-CD3 antibody as a positive control, or a human IgG1 or human IgG4 antibody as isotype-matched negative controls. The cells were incubated at 37° C. for either 6 or 24 hours. The cells were spun down and the plasma was collected for measurement of the cytokines IFN-gamma, TNF-alpha, IL-2, IL-4, IL-6, IL-10 and IL-12 using a cytokine cytometric bead array assay (BD Biosciences). The concentration of each cytokine (pg/ml) is shown in Tables 3a, with a 6 hour incubation, and 3b, with a 24 hour incubation, below. The results show that treatment with the human anti-PD-1 antibodies 5C4 and 4H1 alone did not stimulate human blood cells to release any of the cytokines IFN-gamma, TNF-alpha, IL-2, IL-4, IL-6, IL-10 and IL-12.

TABLE 3a

Cytokine production following 6 hour incubation

| Ab | IFN-gamma (pg/ml) | TNF-alpha (pg/ml) | IL-10 (pg/ml) | IL-6 (pg/ml) | IL-4 (pg/ml) | IL-2 (pg/ml) |
|---|---|---|---|---|---|---|
| No Ab | 12.3 | 2 | 3 | 5 | 3.6 | 1.9 |
| 10 mg/ml anti-CD3 | 5000 | 530 | 82.6 | 510.4 | 37.2 | 467.9 |
| 100 mg/ml anti-CD3 | 5000 | 571 | 91.3 | 530 | 43.9 | 551.5 |
| 10 mg/ml hIgG1 | 7 | 1.8 | 2.8 | 4.4 | 2.6 | 1.5 |
| 100 mg/ml hIgG1 | 0 | 2.2 | 2.7 | 6 | 2.6 | 1.4 |
| 10 mg/ml hIgG4 | 5.4 | 1.4 | 2.5 | 4.5 | 2.1 | 1.3 |
| 100 mg/ml hIgG4 | 6.4 | 2.3 | 3 | 32.6 | 2.9 | 1.4 |
| 10 mg/ml 4H1 | 6.2 | 1.8 | 2.4 | 4.1 | 2.8 | 1.6 |
| 100 mg/ml 4H1 | 11.8 | 2 | 2.6 | 3.5 | 2.6 | 1.7 |
| 10 mg/ml 5C4 IgG1 | 4.2 | 1.6 | 2.3 | 3.9 | 2.5 | 1.3 |
| 100 mg/ml 5C4 IgG1 | 0 | 1.4 | 2.2 | 3.6 | 2.1 | 1.2 |
| 10 mg/ml 5C4 IgG4 | 8.3 | 2.5 | 1.9 | 4.8 | 1.6 | 1.5 |
| 100 mg/ml 5C4 IgG4 | 3.6 | 1.7 | 2.4 | 3.9 | 2.3 | 1.5 |

TABLE 3b

Cytokine production following 24 hour incubation

| Ab | IFN-gamma (pg/ml) | TNF-alpha (pg/ml) | IL-10 (pg/ml) | IL-6 (pg/ml) | IL-4 (pg/ml) | IL-2 (pg/ml) |
|---|---|---|---|---|---|---|
| No Ab | 11.2 | 2 | 6.1 | 5.9 | 2.6 | 1.7 |
| 10 mg/ml anti-CD3 | 5000 | 565.9 | 432 | 5000 | 64.5 | 1265.3 |
| 100 mg/ml anti-CD3 | 5000 | 535 | 461 | 5000 | 73.8 | 1334.9 |
| 10 mg/ml hIgG1 | 0 | 0 | 0 | 0 | 0 | 0 |
| 100 mg/ml hIgG1 | 11.5 | 1.7 | 7.9 | 60.8 | 2.9 | 1.5 |
| 10 mg/ml hIgG4 | 24.6 | 3.1 | 8.3 | 63.4 | 3.1 | 2.3 |
| 100 mg/ml hIgG4 | 11.2 | 1.8 | 8 | 27.7 | 3.1 | 2.4 |
| 10 mg/ml 4H1 | 27.3 | 2.9 | 8 | 13.9 | 5.3 | 2.6 |
| 100 mg/ml 4H1 | 17.5 | 2.5 | 4.4 | 7 | 4 | 2.1 |
| 10 mg/ml 5C4 IgG1 | 9.1 | 2 | 7.6 | 68.5 | 3.5 | 1.8 |
| 100 mg/ml 5C4 IgG1 | 12.9 | 1.9 | 6.1 | 25.3 | 2.9 | 1.7 |
| 10 mg/ml 5C4 IgG4 | 14 | 1.9 | 4.4 | 3.3 | 2.6 | 1.9 |
| 100 mg/ml 5C4 IgG4 | 0 | 0 | 0 | 0 | 0 | 0 |

Example 8

Effect of Anti-PD-1 Antibodies on the Apoptosis of T-Cells

Figure 18:
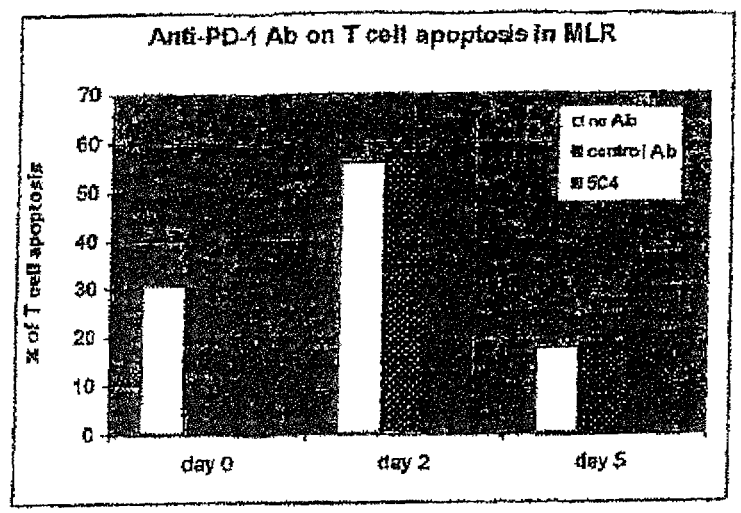
FIG. 18 shows the results of flow cytometry experiments demonstrating that human monoclonal antibodies against human PD-1 do not promote T-cell apoptosis.

The effect of anti-PD-1 antibodies on the induction of apoptosis of T-cells was measured using an annexin V staining test. T cells were cultured in a mixed lymphocyte reaction, as described above in Example 5. The anti-PD-1 antibody 5C4 was added to the tube at a concentration of 25 µg/ml. A non-specific antibody was used as a control. Annexin V and propidium iodide were added according to standard protocol (BD Biosciences). The mixture was incubated for 15 minutes in the dark at room temperature and then analyzed using a FACScan flow cytometer (Becton Dickinson, San Jose, Calif.). The results are shown in FIG. 18. The anti-PD-1 antibody 5C4 did not have an effect on T-cell apoptosis.

Example 9

Effect of Anti-PD-1 Antibodies on Cytokine Secretion by Viral-Stimulated PBMC Cells from a Virus Positive Donor In this example, peripheral blood mononuclear cells (PBMC) from a donor positive for CMV were isolated and exposed to a CMV lysate in the presence or absence of anti-PD-1 antibodies to examine the effect of the antibodies on cytokine secretion simulated by antigen.

Figure 19:
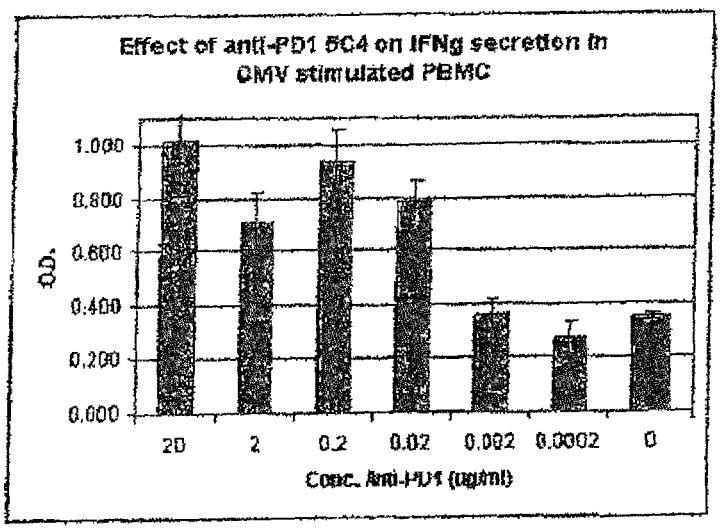
FIG. 19 shows the results of experiments demonstrating that anti-PD-1 HuMabs have a concentration dependent effect on IFN gamma secretion by PBMCs from CMV-positive donors when PBMCs were stimulated with a CMV lysate and anti-PD-1.

$2 \times 10^5$ human PMBCs from a CMV positive donor were cultured in a total volume of 200 µl and added into each well along with a lysate of CMV-infected cells. The anti-PD-1 HuMAb 5C4 was added to each well in various concentrations for 4 days. After day 4, 100 µl of medium was taken from each culture for cytokine measurement. The level of IFN-gamma was measured using OptEIA ELISA kits (BD Biosciences). The cells were labeled with $^3$H-thymidine, cultured for another 18 hours, and analyzed for cell proliferation. The cell proliferation was analyzed using the Cell Titer-Glo reagent (Promega). The results are shown in FIG. 19. The anti-PD-1 HuMab 5C4 increased IFN gamma secretion in a concentration dependent manner. These results shows that anti-PD-1 HuMAbs can stimulate IFN-gamma release in a memory T cell response from PBMC cells previously stimulated against an antigen.

Example 10

Effect of Anti-PD-1 Antibody on Secondary Antibody Response to Antigen

Mice were immunized and rechallenged with a T1-antigen (DNP-Ficoll) and also treated with a rat anti-mouse-PD-1 antibody, or a control antibody to examine the effect of the anti-PD-1 antibody on antibody titers.

Female C57BL6 mice were divided into two groups, with 6 mice/group. One group was treated with a control rat IgG and the other with a rat anti-mouse PD-1 antibody. The mice were immunized with 5 µg of DNP-Ficoll (a T1-antigen) in 50 µl CFA by i.p. at day 0. Either the control rat IgG antibody or the rat-mPD-1 antibody (200 µg/mouse) was given by i.p. at days −1, 0 and 2. Four weeks later, mice were rechallenged with 5 µg of DNP-Ficoll in 50 µl IFA by i.p. at day 0. Rat anti-mPD-1 antibody or control antibody (200 µg/mouse) was given by i.p. at days 0 and 1. Antibody titers were measured by standard ELISA assay at day 7 following the boost. The results are shown in Table 4 below. In the mice treated with the anti-mPD-1 antibody, both IgM and IgG3 isotypes showed the greatest increase in titer following challenge with the T1-antigen, as compared to mice treated with a control antibody. These results demonstrate that anti-PD-1 treatment can increase antibody titers in response to T1-antigen.

TABLE 4

Murine secondary response following treatment with anti-PD-1 antibody

| Antibody Isotype | Control group | Rat anti-mouse PD-1 antibody | P value |
|---|---|---|---|
| IgM | 606 | 1200 | 0.026 |
| IgG | 9 | 15.55 | 0.18 |
| IgG1 | 1.2 | 1.1 | 0.83 |
| IgG2b | 5.05 | 9.26 | 0.18 |
| IgG3 | 21.9 | 81.2 | 0.03 |

*Results shown are average concentration of antibody isotype (μg/ml)

Example 11

Treatment of In Vivo Tumor Model Using Anti-PD-1 Antibodies

Mice implanted with a cancerous tumor were treated in vivo with anti-PD-1 antibodies to examine the in vivo effect of the antibodies on tumor growth. As a positive control, an anti-CTLA-4 antibody was used, since such antibodies have been shown to inhibit tumor growth in vivo.

In this experiment, the anti-PD-1 antibody used was a chimeric rat anti-mouse-PD-1 antibody generated using well known laboratory techniques. To generate the rat anti-mouse PD-1 antibody, rats were immunized with mouse cells transfected to express a recombinant mouse PD-1 fusion protein (R&D Systems Catalog No. 1021-PD) and monoclonal antibodies were screened for binding to mouse PD-1 antigen by ELISA assay. The rat anti-PD-1 antibody V regions were then recombinantly linked to a murine IgG1 constant region using standard molecular biology techniques and rescreened for binding to mouse PD-1 by ELISA and FACS. The chimeric rat anti-mouse-PD-1 antibody used herein is referred to as 4H2.

Figure 20:
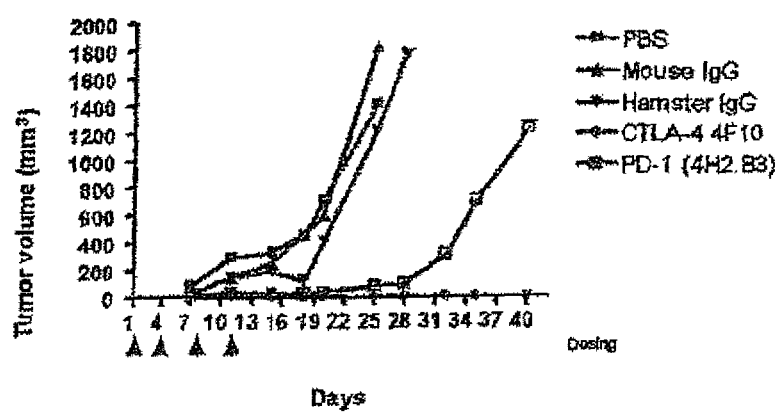
FIG. 20 shows the results of tumor growth experiments in a mouse model system demonstrating that treatment in vivo of mouse tumors with anti-PD-1 antibodies inhibits the growth of tumors.

For the tumor studies, female AJ mice between 6-8 weeks of age (Harlan Laboratories) were randomized by weight into 6 groups. The mice were implanted subcutaneously in the right flank with $2\times10^6$ SA1/N fibrosarcoma cells dissolved in 200 μl of DMEM media on day 0. The mice were treated with PBS vehicle, or antibodies at 10 mg/kg. The animals were dosed by intraperitoneal injection with approximately 200 μl of PBS containing antibody or vehicle on days 1, 4, 8 and 11. Each group contained 10 animals and the groups consisted of: (i) a vehicle group, (ii) control IgG, (iii) control hamster IgG, (iv) hamster anti-mouse CTLA-4 antibody and (v) the chimeric anti-PD-1 antibody 4H2. The mice were monitored twice weekly for tumor growth for approximately 6 weeks. Using an electronic caliper, the tumors were measured three dimensionally (height×width×length) and tumor volume was calculated. Mice were euthanized when the tumors reached tumor end point (1500 mm³) or show greater than 15% weight loss. The results are shown in FIG. 20. The anti-PD-1 antibody extended the mean time to reaching the tumor end point volume (1500 mm³) from ~25 days in the control groups to ~40 days. Thus, treatment with an anti-PD-1 antibody has a direct in vivo inhibitory effect on tumor growth.

Example 12

Generation of Chimeric (Rat-Mouse) Anti-PD-1 Antibody 4H2

Figure 41:
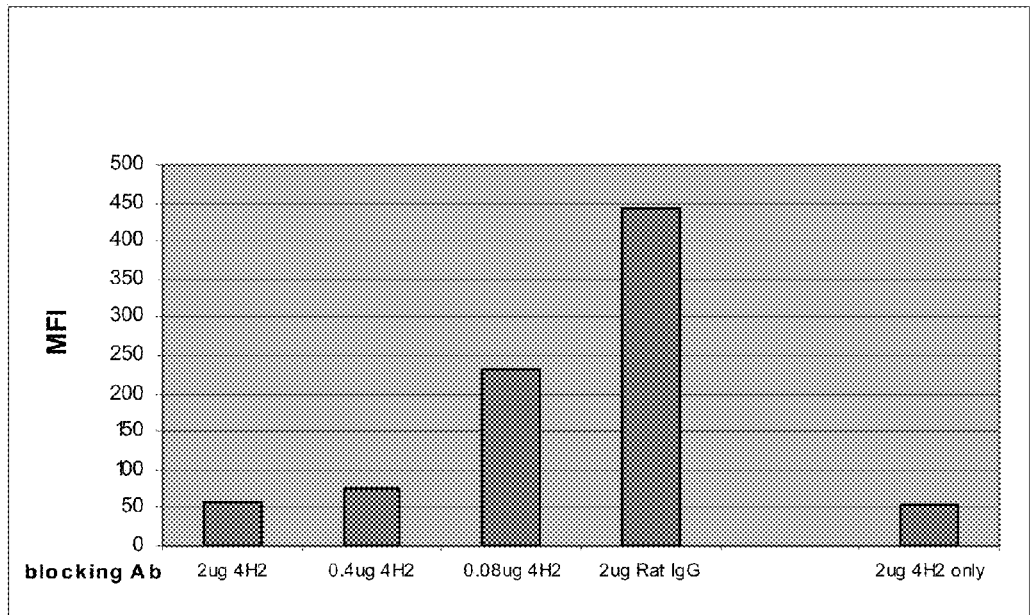
FIG. 41 shows binding of mouse PD-L2-Fc fusion protein to mouse PD-1 (mPD-1) is blocked by anti-mPD-1 antibody 4H2 in a dose dependent manner. The binding is detected by measuring fluorescence of FITC-labeled donkey-anti-rat IgG by ELISA. The greater the MFI (mean fluorescence intensity) the greater the binding.
Figure 42:
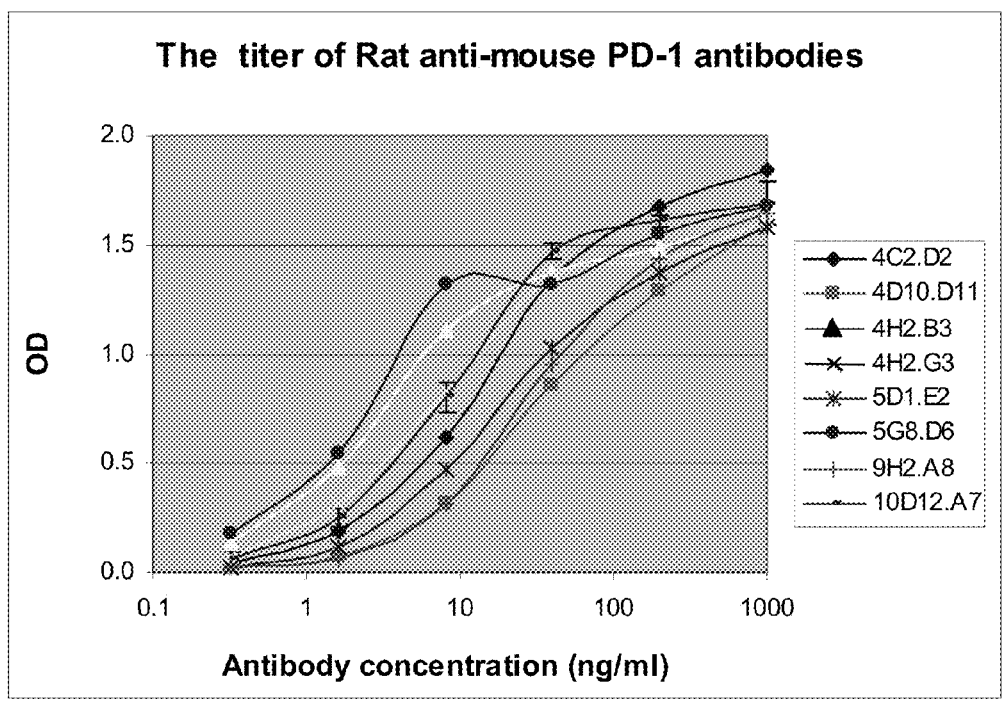
FIG. 42 shows binding curves of anti-mPD-1 antibodies to immobilized mPD-1-Fc fusion protein by ELISA.

Rat monoclonal antibody against mouse PD-1 antibodies (rat anti-mPD-1) were generated from rats immunized with inPD-1-hFc fusion protein using standard hybridoma production methods (see Kohler and Milstein (1975) *Nature* 256:495; and Harlow and Lane (1988) *Antibodies, A Laboratory Manual*, Cold Spring Harbor Laboratory Press, Cold Spring Harbor N.Y.). Eight hybridomas were subcloned, and antibodies were isolated and screened for their ability to block mouse PD-L2 (mPD-L2) binding to mPD-1. Several anti-mPD-1 antibodies capable of blocking mPD-L2 binding to mPD-1 were identified (see, e.g., activity of 4H2, FIG. 41) and the binding affinity of several of these antibodies to mPD-1-Fc fusion protein was determined by ELISA (FIG. 42).

Figure 43:
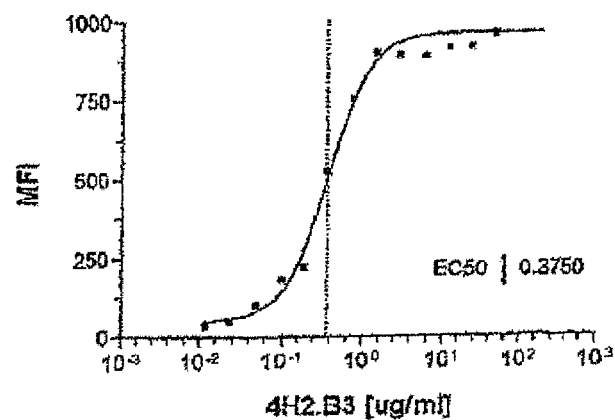
FIG. 43 shows the binding curve of rat anti-mPD-1 antibody 4H2.B3 to mPD-1-expressing CHO cells. Binding was detected with donkey-anti-rat IgG, FITC conjugated and measured by FACS (MFI).
Figure 44:
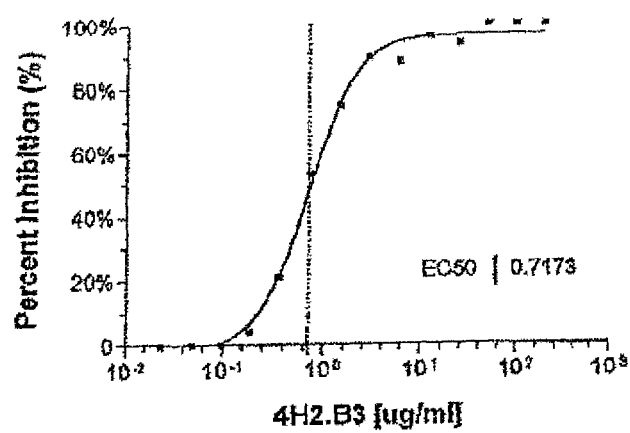
FIG. 44 shows the binding curve of mPD-L1-hFc fusion protein to mPD-1-expressing CHO cells in the presence of increasing concentrations of anti-mPD-1 antibody 4H2.B3. Binding was detected with goat-anti-human IgG, FITC conjugated and measured by FACS (MFI).

Antibody 4H2.B3 was further characterized, which is referred to interchangeably herein as "4H2." CHO cells expressing mouse PD-1 were constructed and incubated with 4H2 anti-mPD-1 antibody at a concentration ranging from 200 μg/ml to 0.012 μg/ml to determine the binding affinity of 4H2 to PD-1. Binding of anti-mPD-1 antibody to the PD-1 expressing CHO cells was detected by incubating with donkey-anti-rat IgG, FITC conjugated and measured by FACS. The anti-mPD-1 antibody had an $EC_{50}$ (50% effective concentration) of about 0.38 μg (FIG. 43) and a $K_D$ of $4.7\times10^{-9}$ M. To examine the inhibition of PD-L1 binding to PD-1, the same assay was performed except that the cells were also incubated with 0.16 μg mPD-L1-hFc fusion protein, then binding of PD-L1 to the PD-1 expressing CHO cells was detected by incubating with goat-anti-human IgG (Fc specific), FITC conjugated and measuring binding signal by FACS (MFT, mean fluorescence intensity). The anti-mPD-1 antibody had an $EC_{50}$ of about 0.72 μg (FIG. 44).

Figure 45:
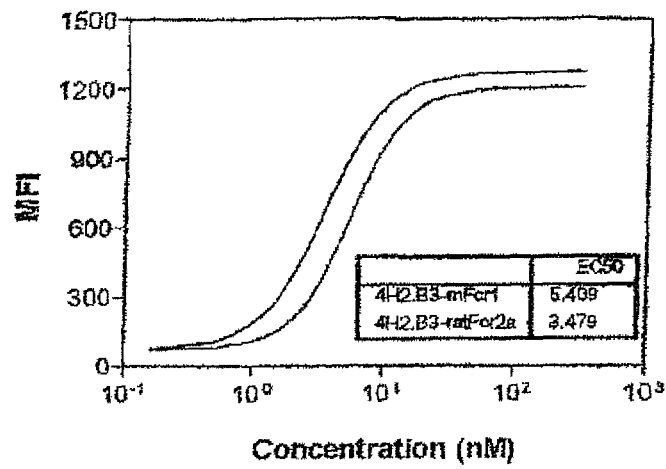
FIG. 45 shows the binding curves of rat anti-mPD-1 antibody 4H2.B3 to mPD-1-expressing CHO cells as compared to chimeric rat:mouse anti-mPD-1 antibody 4H2.
Figure 46:
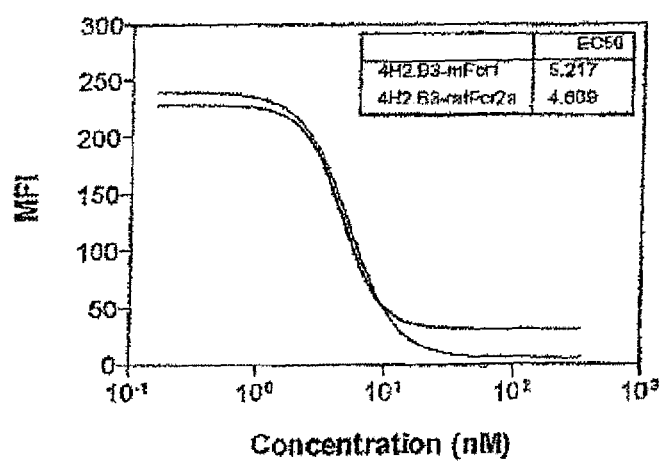
FIG. 46 shows the binding curves of mPD-L1-hFc fusion protein to mPD-1-expressing CHO cells in the presence of increasing concentrations of either rat anti-mPD-1 antibody 4H2.B3 or chimeric rat:mouse anti-mPD-1 antibody 4H2.

For use in the mouse tumor models, the 4H2 rat anti-mPD-1 needed to be modified so the mouse immune system would not neutralize the immunotherapeutic antibody (i.e., so the antibody would have better pharmacokinetics) and to avoid antibody-dependent cellular cytotoxicity (ADCC) by reducing Fc receptor interactions (i.e., so blockade by anti-PD-1 could be evaluated with being compromised by ADCC effects). The original rat anti-mPD-1 antibody, 4H2, was determined to be a rat IgG2a isotype. Hence, the Fc-portion of the 4H2 antibody was replaced with an Fc-portion from a mouse IgG1 isotype. Using the assay described above, the binding affinity of the rat-mouse chimeric 4H2 to mPD-1 was found to be comparable to the rat 4H2.B3 anti-mPD-1 antibody (FIG. 45). Similarly, inhibition of PD-L1 binding to PD-1 was comparable for both antibodies (FIG. 46). Thus, the rat-mouse chimeric 4H2 anti-mPD-1 antibody was used to examine the therapeutic efficacy of anti-PD-1 in combination with anti-CTLA-4.

Example 13

In Vivo Efficacy of Combination Therapy (Anti-CTLA-4 and Anti-PD-1 Antibodies) on Tumor Establishment and Growth MC38 colorectal cancer cells (PD-L1⁻) (available from Dr. N. Restifo, National Cancer Institute, Bethesda, Md.; or Jeffrey Schlom, National Institutes of Health, Bethesda, Md.) were implanted in C57BL/6 mice ($2\times10^6$ cells/mouse). On day 0 (i.e., the day the MC38 cells were implanted in the mice), each of four groups of 10 mice each was injected intraperitoneally (IP) with one of the following: (1) mouse IgG (control), (2) anti-CTLA-4 monoclonal antibody 9D9 (mouse anti-mouse CTLA-4, obtained from J. Allison, Memorial Sloan-Kettering Cancer Center, New York, N.Y.), (3) anti-PD-1 monoclonal antibody 4H2 (chimeric antibody in which a rat anti-mouse PD-1 was modified with a mouse Fc region, as described in Example 6), or (4) anti-CTLA-4 antibody 9D9 and anti-PD-1 antibody 4H2. Antibody injections were then further administered on days 3, 6 and 10. The single antibody treatments were dosed at 10 mg/kg, and the combination of anti-CTLA-4 antibody and anti-PD-1 antibody was dosed at 5 mg/kg of each antibody (i.e., 10 mg/kg of total antibody). Using an electronic caliper, the tumors were measured three dimensionally (height×width×length) and tumor volume was calculated. Mice were euthanized when the tumors reached a designated tumor end-point. The results are shown in Table 5 and FIG. 21.

TABLE 5

Percentage of Tumor-Free Mice Following Anti-PD-1 and/or Anti-CTLA-4 Treatment

| Treatment | Total mice studied | Tumor-free mice (%) |
| --- | --- | --- |
| mIgG1 | 10 | 0 |
| anti-CTLA-4 | 10 | 1 (10) |
| anti-PD-1 | 10 | 3 (30) |
| anti-CTLA-4 + anti-PD-1 | 10 | 6 (60) |

Figure 21A:
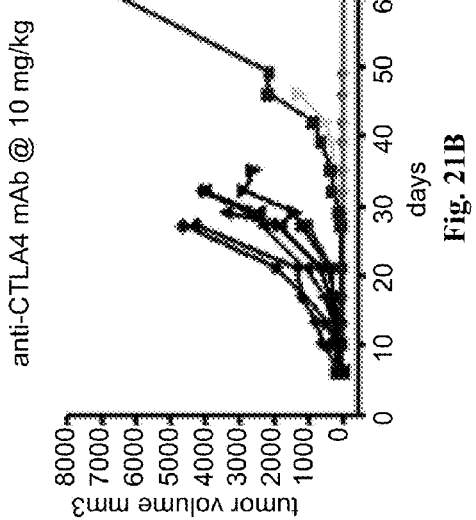
FIGS. 21A to 21D show the tumor volume over time in individual mice that were implanted with MC38 colon tumor cells (PD-L1⁻) and on the same day treated with one of the following therapies: (A) mouse IgG (control), (B) anti-CTLA-4 antibody, (C) anti-PD-1 antibody, and (D) anti-CTLA-4 antibody and anti-PD-1 antibody. The mice received subsequent antibody treatments on days 3, 6 and 10 as described in Example 13 and tumor volume was monitored over 60 days.
Figure 21B:
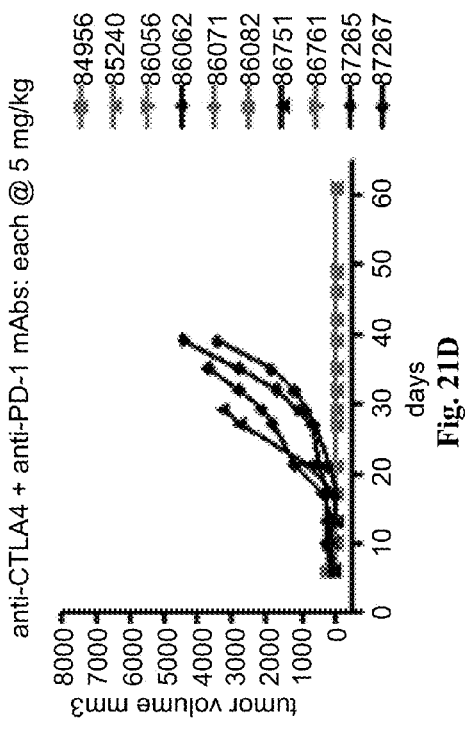
Figure 21C:
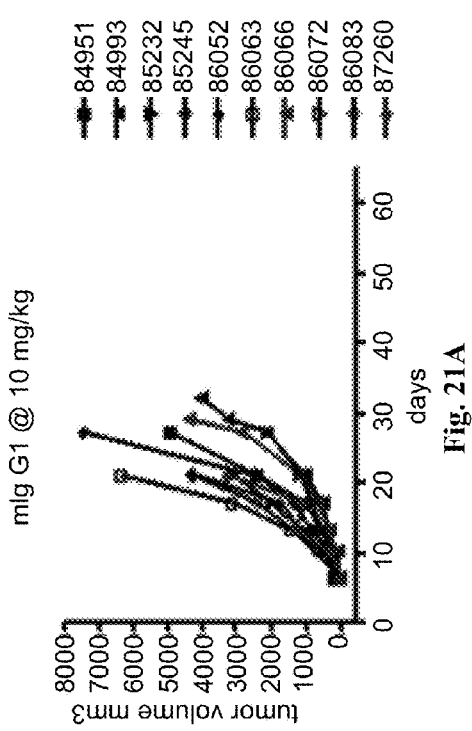
Figure 21D:
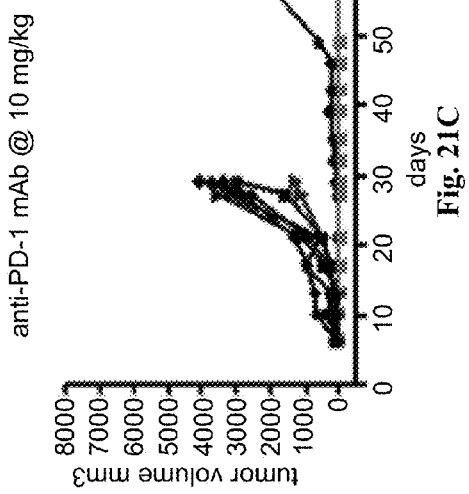

Eight mice in the IgG group reached the tumor end-point by about day 30 and two mice (86066 and 87260) in the IgG group had ulcerated tumors (FIG. 21A). In the anti-CTLA-4 antibody alone group, seven mice reached the tumor end-point by about day 60, one mouse had an ulcerated tumor (84952), one mouse had a tumor with a volume of less than 1500 mm$^3$ (85246), and one mouse was tumor-free (86057) (FIG. 21B). In the anti-PD-1 antibody alone group, six mice reached the tumor end-point by about day 60, one mouse had an ulcerated tumor (86055), and three mice were tumor-free (84955, 85239 and 86750) (FIG. 21C). In the anti-CTLA-4 antibody and anti-PD-1 antibody combination group, four mice reached the tumor end-point by about Day 40, and six mice were tumor-free (84596, 85240, 86056, 86071, 86082 and 86761) (FIG. 21D).

Figure 22:
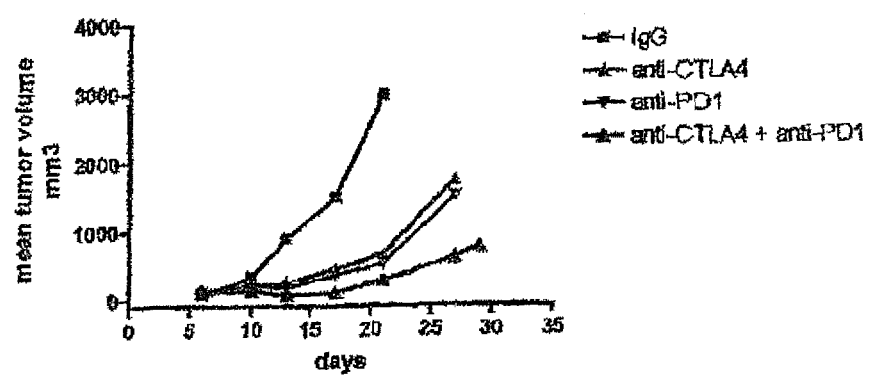
FIG. 22 shows the mean tumor volume of the mice shown in FIG. 21.
Figure 23:
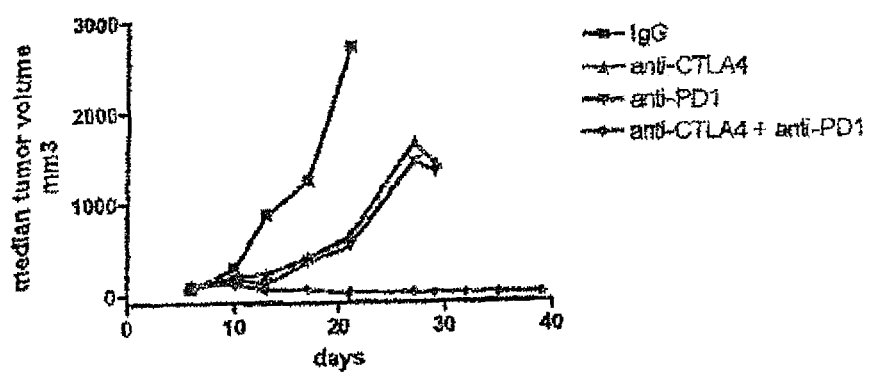
FIG. 23 shows the median tumor volume of the mice shown in FIG. 21.

FIG. 22 shows that the mean tumor volume measured at day 21 was about 2955 mm$^3$ for the IgG control group; about 655 mm$^3$ for the CTLA-4 antibody alone group, about 510 mm$^3$ for the PD-1 antibody alone group, and about 280 mm$^3$ for the anti-CTLA-4 antibody and anti-PD-1 antibody combination group. FIG. 23 shows that the median tumor volume measured at day 21 was about 2715 mm$^3$ for the IgG group; about 625 mm$^3$ for the CTLA-4 antibody alone group; about 525 mm$^3$ for the PD-1 antibody alone group; and about 10 mm$^3$ for the CTLA-4 antibody and PD-1 antibody combination group (and down to 0 mm$^3$ by day 32).

This study indicates that, in a murine tumor model, CTLA-4 antibody treatment alone and PD-1 antibody treatment alone have a modest effect on tumor growth, and that the combination treatment of CTLA-4 antibody and PD-1 antibody has a significantly greater effect on tumor growth. It is interesting to note that the combination treatment with CTLA-4 antibody and PD-1 antibody had a more significant effect on tumor growth at a dose of 5 mg/kg of each antibody as compared to the effect of either antibody alone when each is administered at a higher dose of 10 mg/kg.

Example 14

In Vivo Efficacy of Combination Therapy (Anti-CTLA-4 and Anti-PD-1 Antibodies) on Established Tumor Growth MC38 colorectal cancer cells (PD-L1$^-$) were implanted in C57BL/6 mice (2×10$^6$ cells/mouse) for a time sufficient (about 6 to 7 days) to permit the formation of tumors. On day 6 post-implantation (day −1), tumor measurements were taken and mice were randomized based on mean tumor volume (about 250 mm$^3$) into 11 groups for subsequent antibody therapy. At day 0 (i.e., one week after the MC38 cells were implanted), mice were injected IP with (1) mouse IgG (control), (2) anti-CTLA-4 monoclonal antibody 9D9, (3) anti-PD-1 monoclonal antibody 4H2, or (4) anti-CTLA-4 monoclonal antibody 9D9 and anti-PD-1 antibody monoclonal antibody 4H2, at a concentration of 10 mg/kg per mouse. Antibody injections were also administered on days 3, 6 and 10. The monoclonal antibody compositions used had low levels of endotoxin and did not significantly aggregate. Using an electronic caliper, the tumors were measured three dimensionally (height×width×length) and tumor volume was calculated. Tumor measurements were taken on day 0 (tumors at the beginning of treatment had a volume of about 125 mm$^3$), and on days 3, 6, 10, 13, 17 and 20 post-antibody injection. Mice were euthanized when the tumors reached a designated tumor end-point (a particular tumor volume such as 1500 mm$^3$ and/or when the mice showed greater than about 15% weight loss).

Figures 24A, 24B, 24C, 24D:
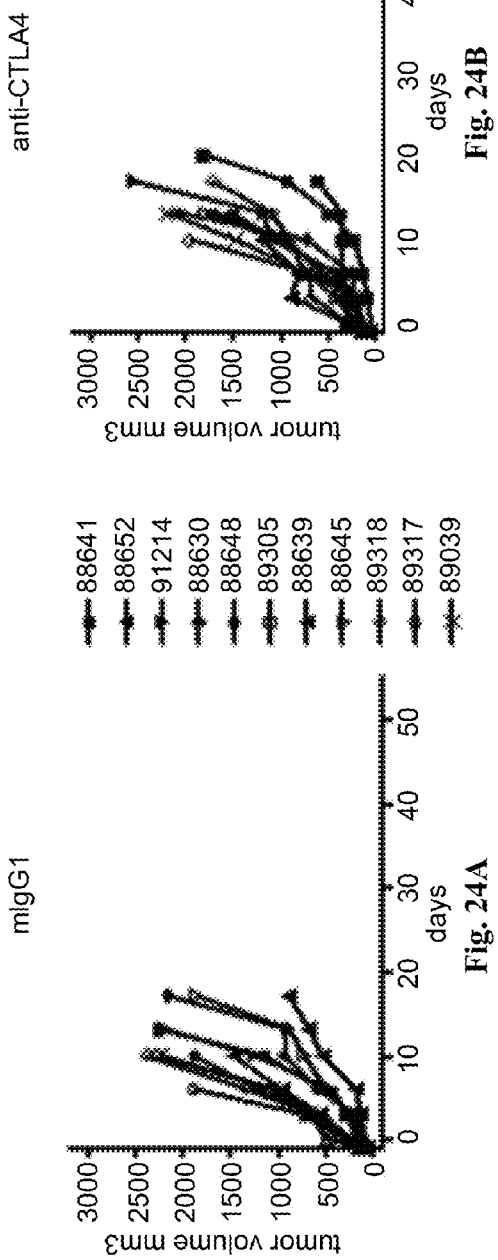
FIGS. 24A to 24D show the tumor volume over time in individual mice that were implanted with MC38 colon tumor cells (PD-L1⁻) and one week later treated with one of the following therapies: (A) mouse IgG (control), (B) anti-CTLA-4 antibody, (C) anti-PD-1 antibody, and (D) anti-CTLA-4 antibody and anti-PD-1 antibody. The tumor volume on the first day of treatment was about 315 mm³. The mice received subsequent antibody treatments on days 3, 6 and 10 as described in Example 14.

All eleven mice in the IgG group reached the tumor end-point by about day 17 (FIG. 24A). In the anti-CTLA-4 antibody alone group, seven of eleven mice reached the tumor end-point by about day 12 (FIG. 24B). In the anti-PD-1 antibody alone group, four mice reached the tumor end-point by about day 13 and two mice were tumor-free (FIG. 24C). In the anti-CTLA-4 antibody and anti-PD-1 antibody combination group, one mouse reached the tumor end-point by about day 17, one mouse reached the tumor end-point by about day 45 and nine mice were tumor-free on day 45 (FIG. 24D).

Figure 25:
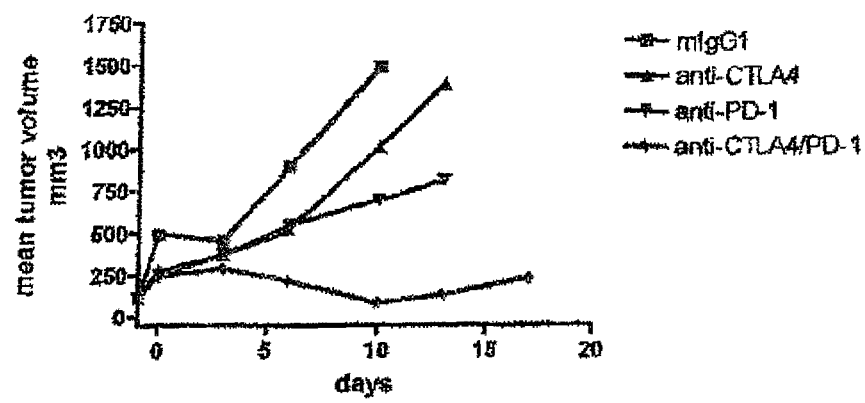
FIG. 25 shows the mean tumor volume of the mice shown in FIG. 24.
Figure 26:
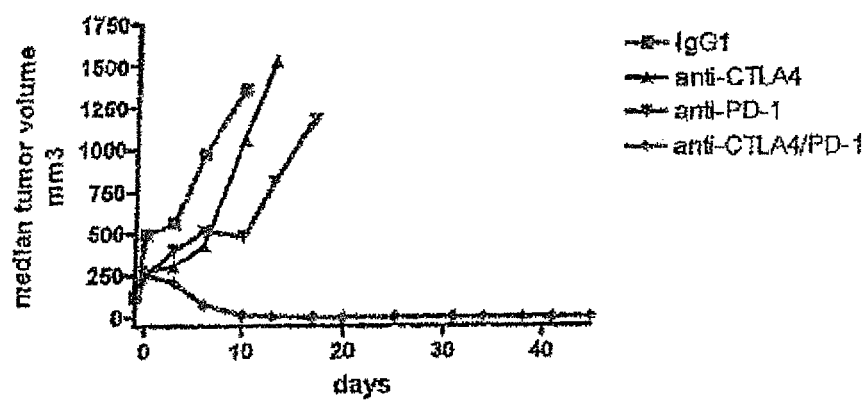
FIG. 26 shows the median tumor volume of the mice shown in FIG. 24.

FIG. 25 shows that the mean tumor volume measured at day 10 was about 1485 mm$^3$ for the IgG control group; about 1010 mm$^3$ for the CTLA-4 antibody alone group; about 695 mm$^3$ for the PD-1 antibody alone group; and about 80 mm$^3$ for the anti-CTLA-4 antibody and anti-PD-1 antibody combination group. FIG. 26 shows that the median tumor volume measured at day 10 was about 1365 mm$^3$ for the IgG group; about 1060 mm$^3$ for the anti-CTLA-4 antibody alone group; about 480 mm$^3$ for the anti-PD-1 antibody alone group; and about 15 mm$^3$ for the anti-CTLA-4 antibody and anti-PD-1 antibody combination group (which was down to 0 mm$^3$ by day 17).

This study indicates that, in a murine tumor model, treatment with the combination of CTLA-4 antibody and PD-1 antibody has a significantly greater effect on tumor growth than either antibody alone, even when a tumor is already well established.

Example 15

Dose Titration of Combination Therapy (Anti-CTLA-4 and Anti-PD-1 Antibodies) on Established Tumor Growth MC38 colorectal cancer cells (PD-L1$^-$) were implanted in C57BL/6 mice (2×10$^6$ cells/mouse) for a time sufficient (about 6 to 7 days) to permit the formation of tumors as described in Example 3. Groups of 10 mice were injected IP at days 0, 3, 6 and 10 as follows: Group (A) mouse IgG (control, 20 mg/kg), Group (B) anti-PD-1 monoclonal antibody 4H2 (10 mg/kg) and mouse IgG (10 mg/kg), Group (C) anti-CTLA-4 monoclonal antibody 9D9 (10 mg/kg) and mouse IgG (10 mg/kg), Group (D) anti-CTLA-4 monoclonal antibody 9D9 (10 mg/kg) and anti-PD-1 antibody monoclonal antibody 4H2 (10 mg/kg), Group (E) anti-CTLA-4 monoclonal antibody 9D9 (3 mg/kg) and anti-PD-1 antibody monoclonal antibody 4H2 (3 mg/kg), or Group (F) anti-CTLA-4 monoclonal antibody 9D9 (1 mg/kg) and anti-PD-1 antibody monoclonal antibody 4H2 (1 mg/kg). Using an electronic caliper, the tumors were measured three dimensionally (height×width×length) and tumor volume was calculated. Tumor measurements were taken at the beginning of treatment (i.e., on day 0 tumors had an average volume of about 90 mm$^3$), and on days 3, 6, 10, 13, 17 and 20 post-antibody treatment. Mice were euthanized when the tumors reached a designated tumor end-point (a particular tumor volume such as 1500 mm$^3$ and/or when the mice showed greater than about 15% weight loss).

Figure 27A:
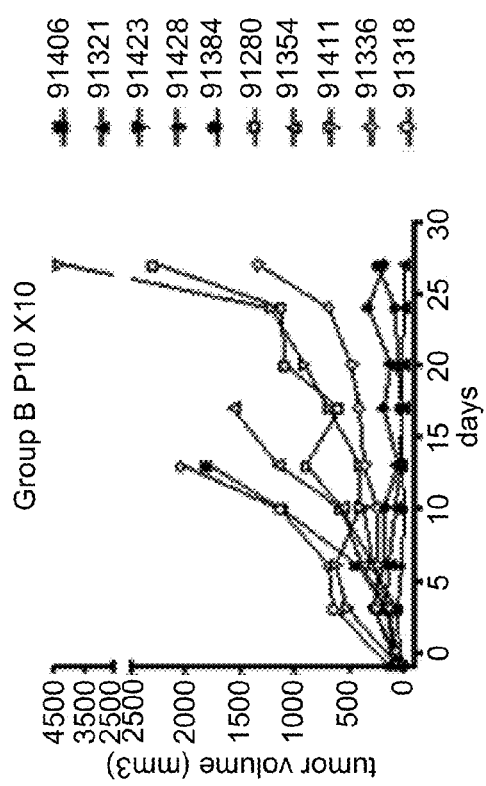
FIG. 27 shows the mean tumor volume over time in individual mice that were implanted with MC38 colon tumor cells (PD-L1⁻) (day −7) and then treated on days 0, 3, 6 and 10 post-implantation (as described in Example 15) with one of the following therapies: (A) mouse IgG as a control (20 mg/kg, $X_{20}$) (B) anti-PD-1 antibody (10 mg/kg) and mouse IgG (10 mg/kg) ($P_{10}X_{10}$), (C) anti-CTLA-4 antibody (10 mg/kg) and mouse IgG (10 mg/kg) ($C_{10}X_{10}$), (D) anti-CTLA-4 antibody and anti-PD-1 antibody (10 mg/kg each) ($C_{10}P_{10}$), (E) anti-CTLA-4 antibody and anti-PD-1 antibody (3 mg/kg each) ($C_3P_3$), and (F) anti-CTLA-4 antibody and anti-PD-1 antibody (1 mg/kg each) ($C_1P_1$). Two groups of mice were treated with each antibody sequentially as follows: (G) anti-CTLA-4 antibody (10 mg/kg, day 0), anti-CTLA-4 antibody (10 mg/kg, day 3), anti-PD-1 antibody (10 mg/kg, day 6), and anti-PD-1 antibody (10 mg/kg, day 10) ($C_{10}C_{10}P_{10}P_{10}$); and (H) anti-PD-1 antibody (10 mg/kg, day 0), anti-PD-1 antibody (10 mg/kg, day 3), anti-CTLA-4 antibody (10 mg/kg, day 6), and anti-CTLA-4 antibody (10 ing/kg, day 10) (10 mg/kg, day 10) ($P_{10}P_{10}C_{10}C_{10}$).
Figure 27B:
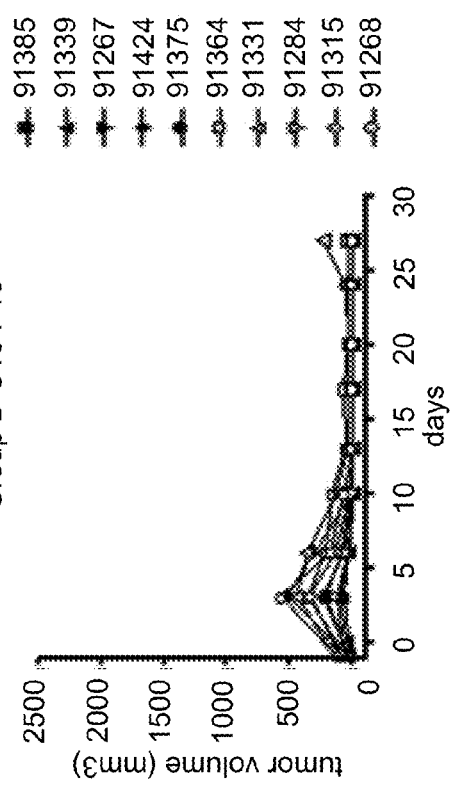
Figure 27C:
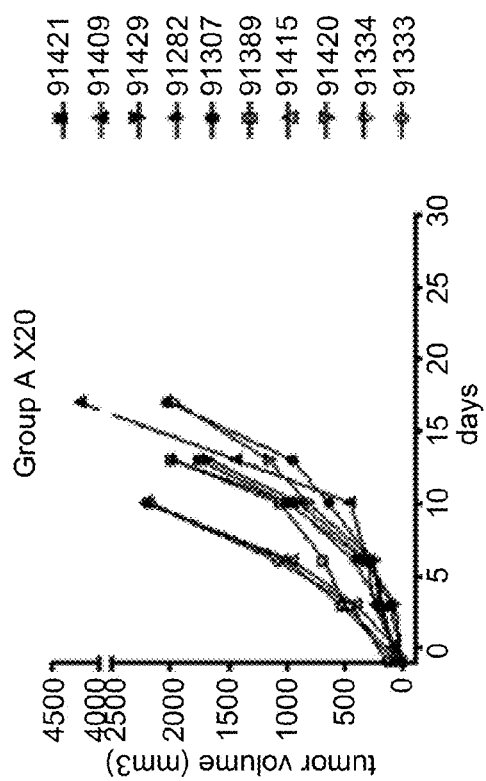
Figure 27D:
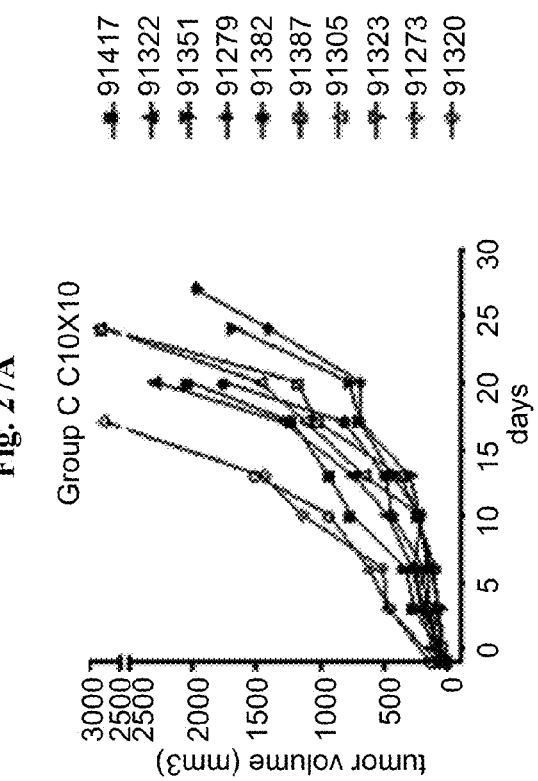
Figure 27E:
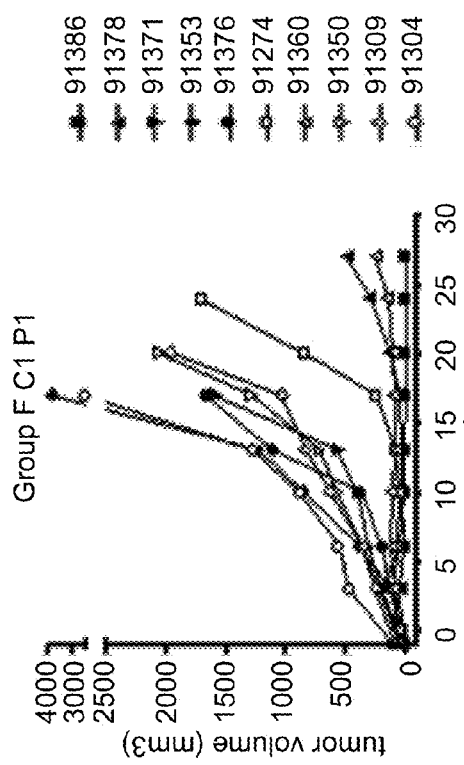
Figure 27F:
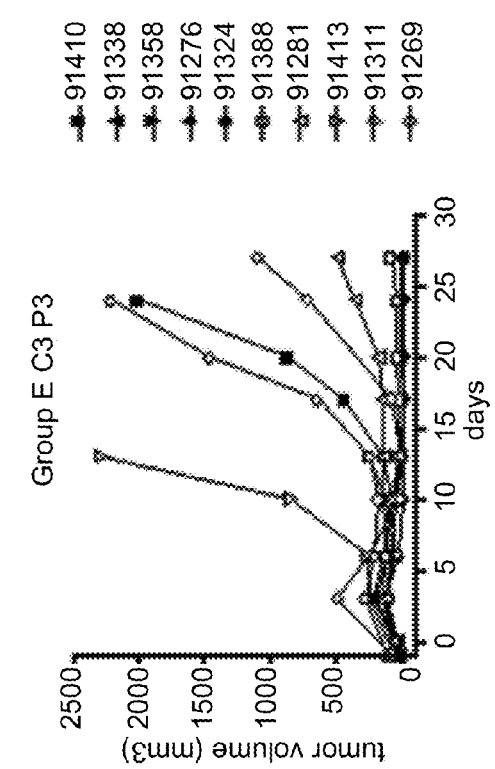

FIG. 27A shows that all 10 control mice had reached a tumor end-point. FIG. 27B shows that the group treated with 10 mg/kg anti-PD-1 antibody (Group B) had 6 mice that reached the tumor end-point and 4 mice with tumors having a volume of about 750 mm$^3$ or less. FIG. 27C shows that the group treated with 10 mg/kg anti-CTLA-4 antibody (Group C) had 3 mice that reached the tumor end-point and 7 mice with tumors having a volume of about 1000 mm$^3$ or less. FIG. 27D shows that the group treated with a combination of 10 mg/kg anti-PD-1 antibody with 10 mg/kg anti-CTLA-4 antibody (Group D) had 2 mice with tumors having a volume of about 1000 mm$^3$ or less, and 8 mice that were tumor free. FIG. 27E shows that the group treated with a combination of 3 mg/kg anti-PD-1 antibody with 3 mg/kg anti-CTLA-4 antibody (Group E) had one mouse that had reached the tumor end-point, 7 mice with tumors having a volume of about 500 mm$^3$ or less, and 2 mice that were tumor free. FIG. 27F shows that the group treated with a combination of 1 mg/kg anti-PD-1 antibody with 1 mg/kg anti-CTLA-4 antibody (Group F) had 4 mice that had reached the tumor end-point, 5 mice with tumors having a volume of about 1100 mm$^3$ or less, and one mouse that was tumor free.

Figure 27G:
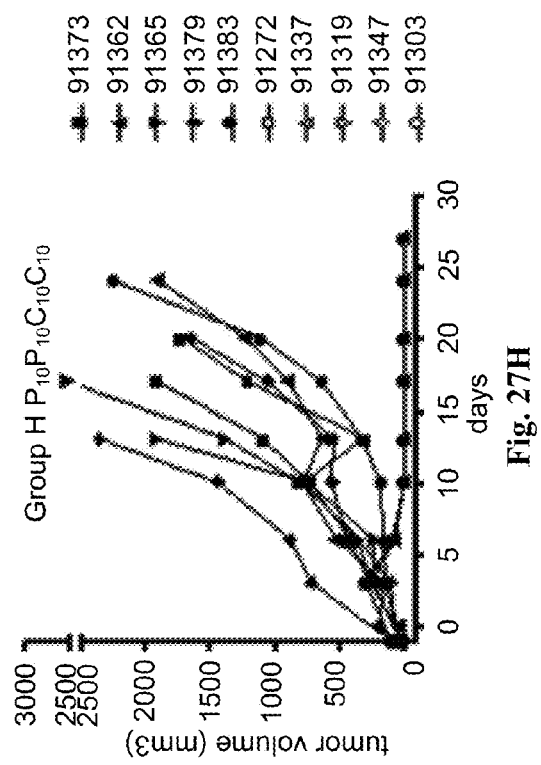
Figure 27H:
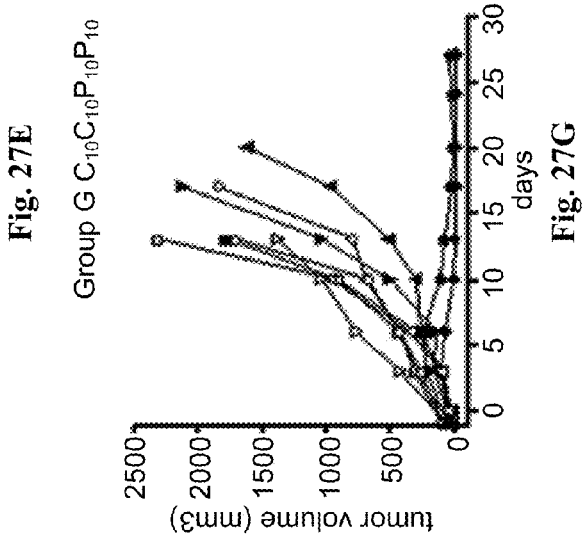

FIGS. 27G and 27H show the tumor volumes in mice treated sequentially with anti-PD-1 antibody first and anti-CTLA-4 antibody second, and vice versa. The mice of FIG. 27G first received 10 mg/kg anti-CTLA-4 on each of days 0 and 3, and then received 10 mg/kg anti-PD-1 antibody on each of days 6 and 10. The mice of FIG. 27H first received 10 mg/kg anti-PD-1 antibody on each of days 0 and 3, and then received 10 mg/kg anti-CTLA-4 antibody on each of days 6 and 10. For group G at day 27, 8 mice reached the tumor end-point, one mouse had a very small tumor (which, after a significant delay, eventually grew out) and one mouse was tumor free. For group H at day 27, 8 mice reached the tumor end-point and 2 were tumor free.

Figure 28:
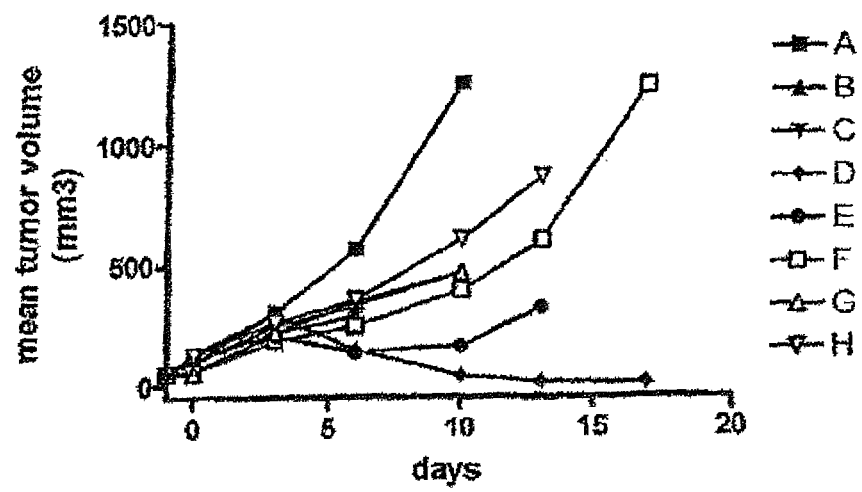
FIG. 28 shows the mean tumor volume of the mice shown in FIG. 27.
Figure 29:
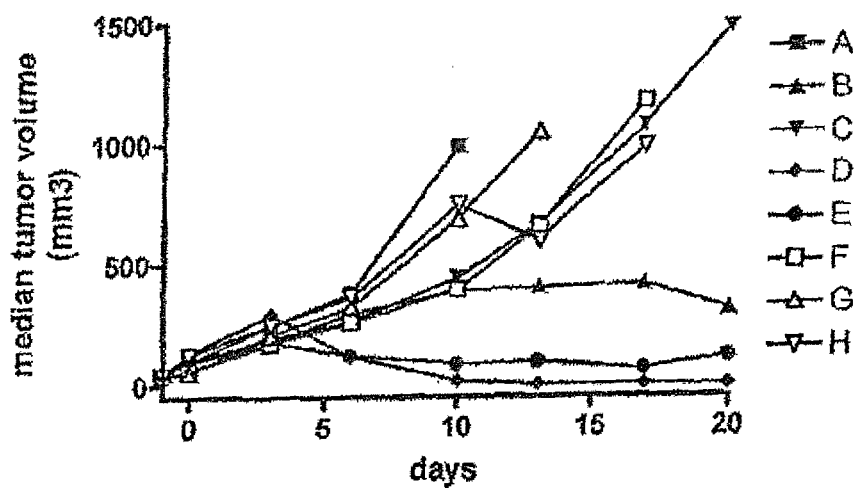
FIG. 29 shows the median tumor volume of the mice shown in FIG. 27.

FIG. 28 shows that the mean tumor volume measured at day 10 was about 1250 mm$^3$ for the IgG control group; about 470 mm$^3$ for the PD-1 antibody with the IgG control; about 290 mm$^3$ for the CTLA-4 antibody with the IgG control (measured at day 6); about 40 mm$^3$ for the anti-CTLA-4 antibody (10 mg/kg) and anti-PD-1 antibody (10 mg/kg) combination group; about 165 mm$^3$ for the anti-CTLA-4 antibody (3 mg/kg) and anti-PD-1 antibody (3 mg/kg) combination group; and about 400 mm$^3$ for the anti-CTLA-4 antibody (1 mg/kg) and anti-PD-1 antibody (1 mg/kg) combination group. FIG. 29 shows that the median tumor volume measured at day 13 was about 1680 mm$^3$ for the IgG control group; about 400 mm$^3$ for the PD-1 antibody with the IgG control; about 660 mm$^3$ for the CTLA-4 antibody with the IgG control; 0 mm$^3$ for the anti-CTLA-4 antibody (10 mg/kg) and anti-PD-1 antibody (10 mg/kg) combination group; about 90 mm$^3$ for the anti-CTLA-4 antibody (3 mg/kg) and anti-PD-1 antibody (3 mg/kg) combination group; and about 650 mm$^3$ for the anti-CTLA-4 antibody (1 mg/kg) and anti-PD-1 antibody (1 mg/kg) combination group. For the combination treatment of the anti-PD-1 antibody with the anti-CTLA-4 antibody, the number of mice per group that were tumor free at day 27 of the study was 8/10 (10 mg/kg), 2/10 (3 mg/kg) and 1/10 (1 mg/kg) (data not shown).

This study indicates that, in a murine tumor model, treatment with the combination of CTLA-4 antibody and PD-1 antibody functions in a dose dependent manner and has a significantly greater effect on tumor growth than both antibodies alone, even at a lower dose and even when a tumor is already well established. Moreover, the antibodies may be administered sequentially (anti-CTLA-4 antibody first and anti-PD-1 antibody second, or vice versa) and the combination is still superior to the antibody monotherapies.

Example 16

In Vivo Efficacy of Combination Therapy (Anti-CTLA-4 and Anti-PD-1 Antibodies) on Fibrosarcoma Establishment and Growth SA1/N fibrosarcoma cells (PD-L1$^-$) (Leach et al. (1996) *Science* 271:1734-1736) were implanted subcutaneously in A/J mice (2×10$^6$ cells/mouse) on day 0. On days 1, 4, 7 and 11 post-implantation, mice were injected IP as follows: Group (A) PBS alone (referred to as the "vehicle"); Group (B) mouse IgG (control, 10 mg/kg per mouse), Group (C) anti-PD-1 monoclonal antibody 4H2 (10 mg/kg per mouse), Group (D) anti-CTLA-4 monoclonal antibody 9D9 (10 mg/kg or 0.2 mg/kg per mouse), and Group (E) anti-PD-1 monoclonal antibody 4H2 (10 mg/kg per mouse) in combination with anti-CTLA-4 monoclonal antibody 9D9 (0.2 mg/kg per mouse). The study lasted 41 days and tumor measurements were taken on various days throughout the course of the study (see FIG. 29). Tumor volume was calculated by measuring tumors in three dimensions (height×width×length) using an electronic caliper. Mice were euthanized when the tumors reached a designated tumor end-point-a volume of 1500 mm$^3$ and/or an ulcerated tumor.

Figure 30A:
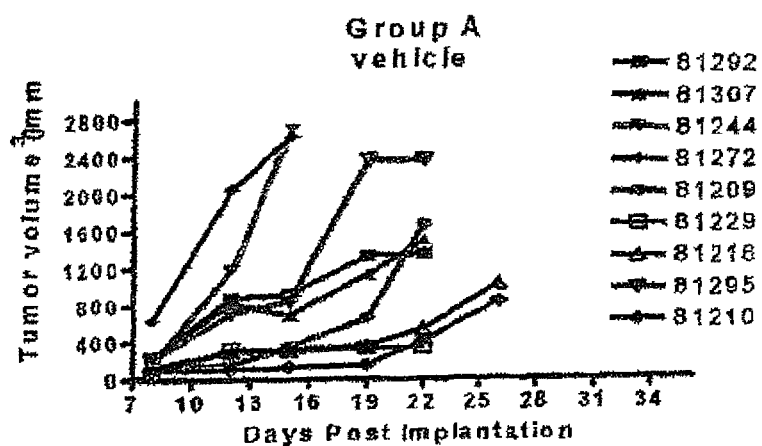
FIGS. 30A to 30F show the tumor volume over time in individual mice that were implanted with SA1/N fibrosarcoma cells (PD-L1⁻) and one day later treated with one of the following therapies: (A) PBS (vehicle control), (B) mouse IgG (antibody control, 10 mg/kg), (C) anti-PD-1 antibody (10 mg/kg), (D) anti-CTLA-4 antibody (10 mg/kg), (E) anti-CTLA-4 antibody (0.2 mg/kg), and (F) anti-PD-1 antibody (10 mg/kg) and anti-CTLA-4 antibody (0.2 mg/kg). The mice received subsequent antibody treatments on days 4, 7 and 11 as described in Example 16 and tumor volume was monitored over 41 days.
Figure 30B:
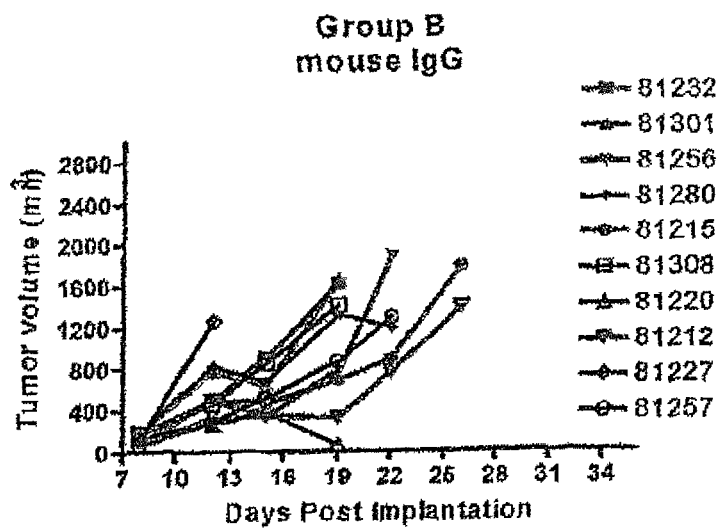
Figure 30C:
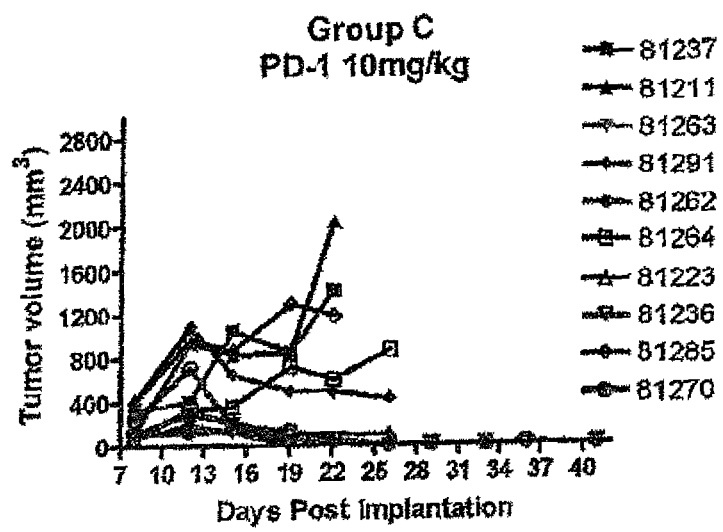
Figure 30D:
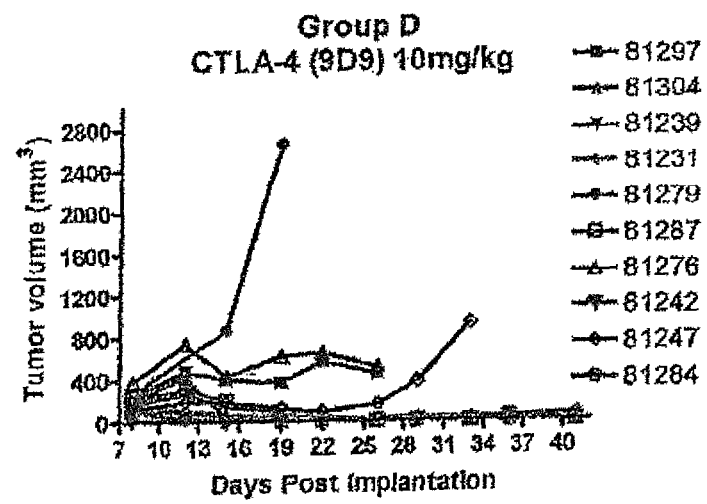
Figure 30E:
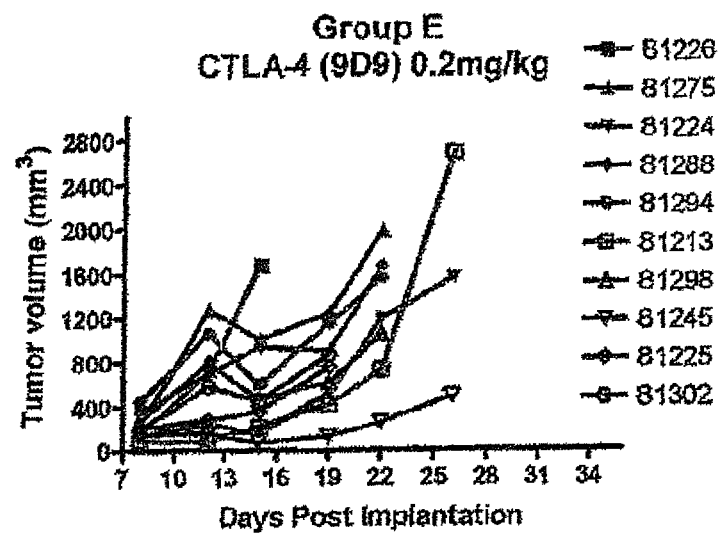
Figure 30F:
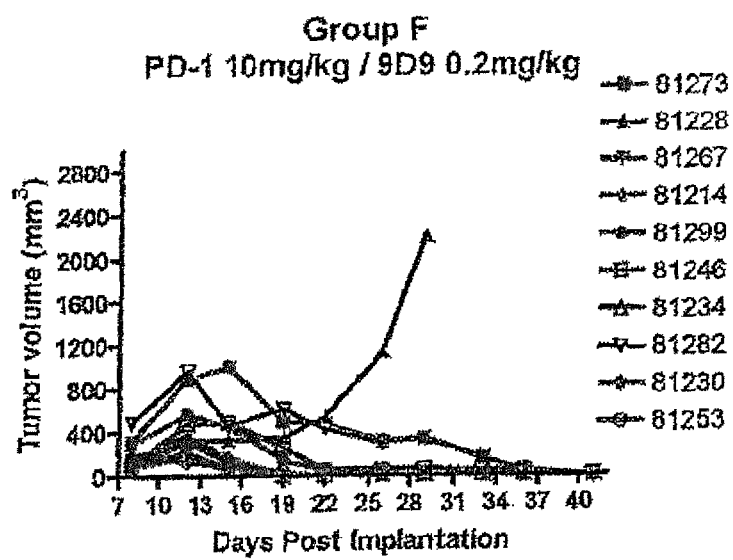

FIGS. 30A and 30B show that 19 out of the 20 control (9/10 in Group A and 10/10 in Group B) mice had either reached a tumor end-point or had developed ulcerated tumors. FIG. 30C shows that the group treated with 10 mg/kg anti-PD-1 antibody (Group C) had 6 mice that reached a tumor end-point (2 with a volume greater than 1500 mm$^3$ and 4 with an ulcerated tumor) and 4 mice that were tumor free. FIG. 30D shows that the group treated with 10 mg/kg anti-CTLA-4 antibody (Group D) had 5 mice that reached a tumor end-point (2 with a volume greater than 1500 mm$^3$ and 3 with an ulcerated tumor), one mouse with a small tumor (volume of about 70 mm$^3$) and 4 mice that were tumor free. FIG. 30E shows that the group treated with 0.2 mg/kg anti-CTLA-4 antibody (Group E) had 10 mice that reached a tumor end-point (6 with a volume greater than 1500 mm$^3$ and 4 with an ulcerated tumor). FIG. 30F shows that the group treated with a combination of 10 mg/kg anti-PD-1 antibody with 0.2 mg/kg anti-CTLA-4 antibody (Group F) had 2 mice that reached a tumor end-point (one with a volume greater than 1500 mm$^3$ and one with an ulcerated tumor) and 8 mice that were tumor free.

Figure 31:
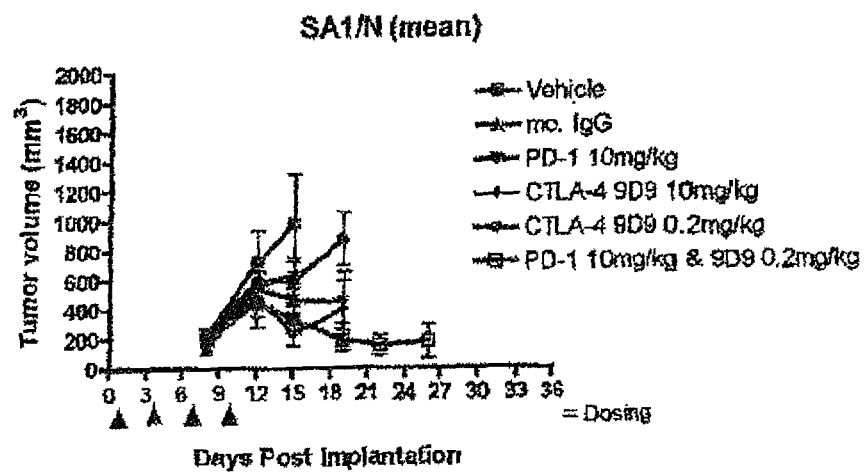
FIG. 31 shows the mean tumor volume of the mice shown in FIG. 29.
Figure 32:
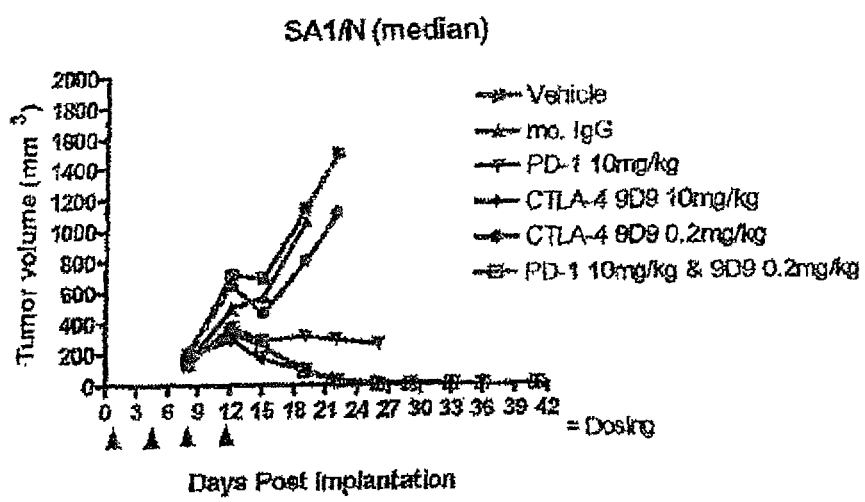
FIG. 32 shows the median tumor volume of the mice shown in FIG. 29.
Figure 33A:
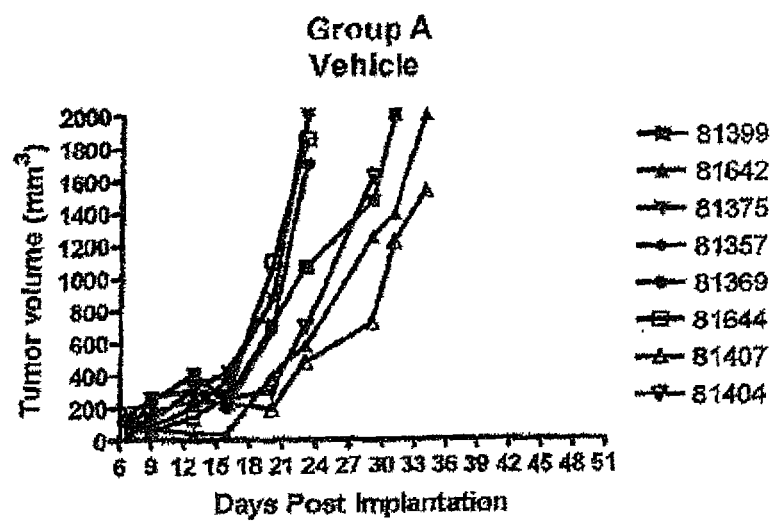
FIGS. 33A to 33J show the tumor volume over time in individual mice that were implanted with SA1/N fibrosarcoma cells (PD-L1⁻) and then treated on days 7, 10, 13 and 17 post-implantation (as described in Example 17) with one of the following therapies: (A) PBS (vehicle control), (B) mouse IgG (antibody control, 10 mg/kg), (C) anti-CTLA-4 antibody (0.25 mg/kg), (D) anti-CTLA-4 antibody (0.5 mg/kg), (E) anti-CTLA-4 antibody (5 mg/kg), (F) anti-PD-1 antibody (3 mg/kg), (G) anti-PD-1 antibody (10 mg/kg), (H) anti-PD-1 antibody (10 mg/kg) and anti-CTLA-4 antibody (0.25 mg/kg), (I) anti-PD-1 antibody (10 mg/kg) and anti-CTLA-4 antibody (0.5 mg/kg), and (F) anti-PD-1 antibody (3 mg/kg) and anti-CTLA-4 antibody (0.5 mg/kg). The tumor volume on the first day of treatment was about 110 mm³.
Figure 33B:
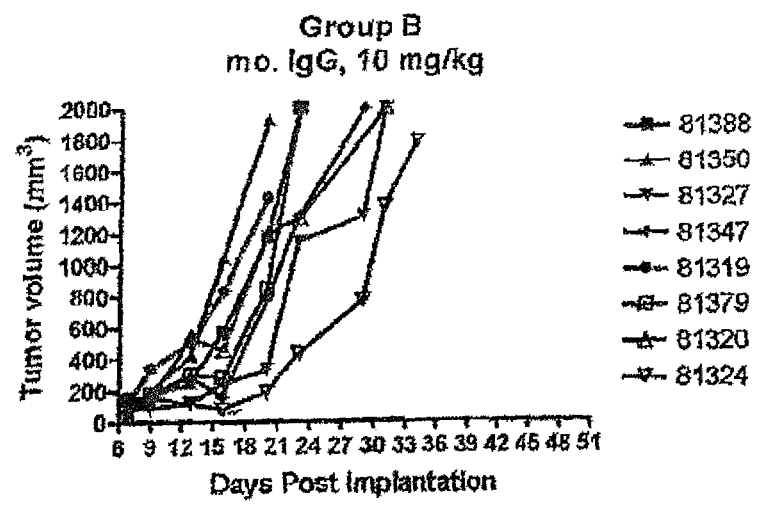
Figure 33C:
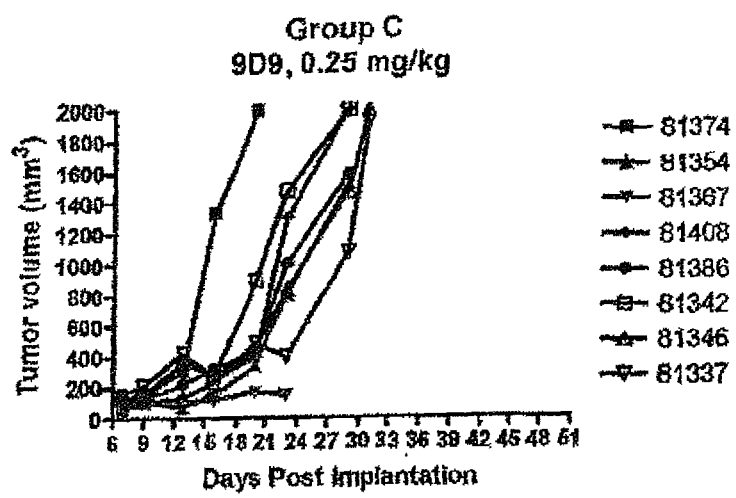
Figure 33D:
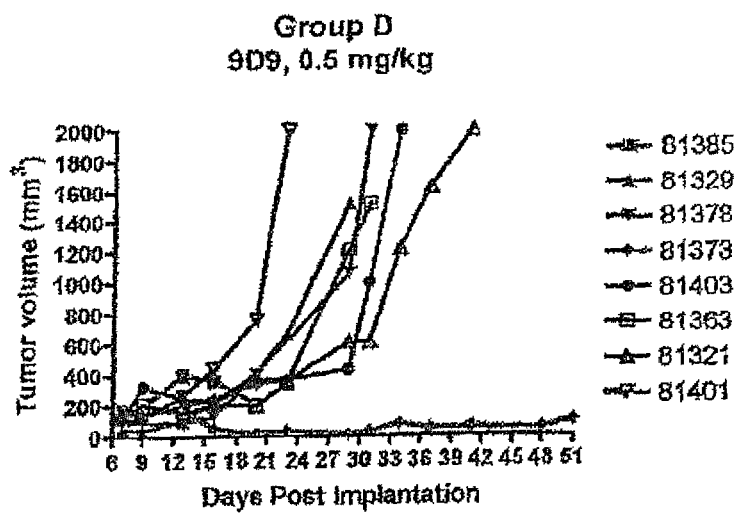
Figure 33E:
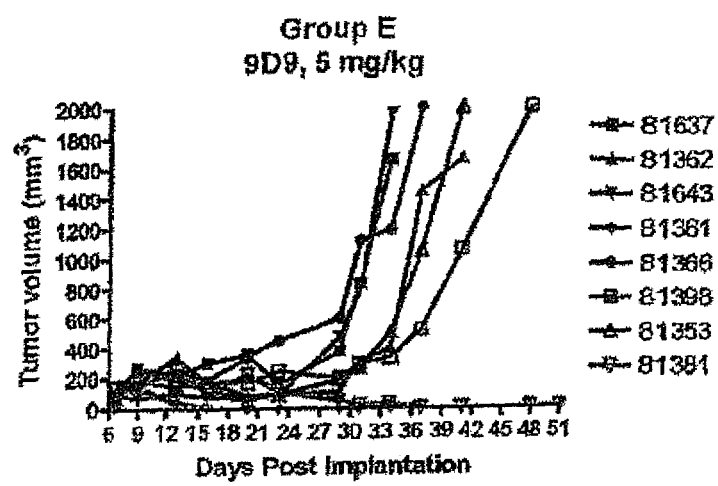
Figure 33F:
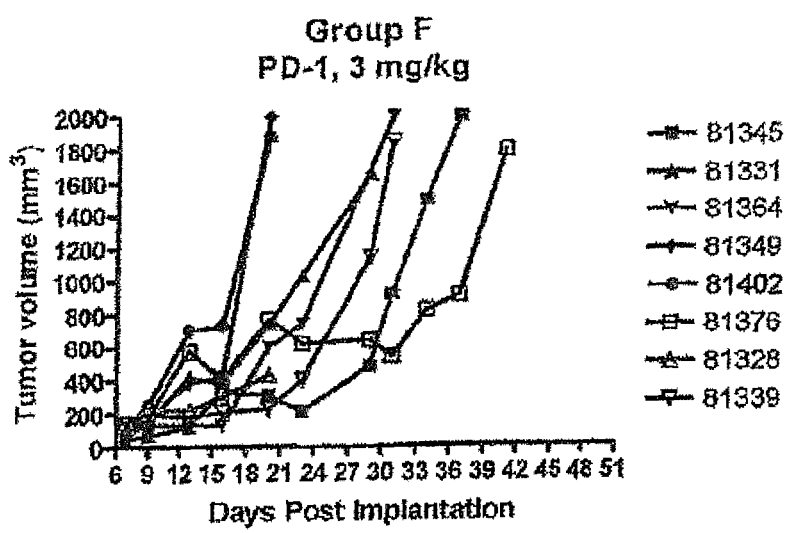
Figure 33G:
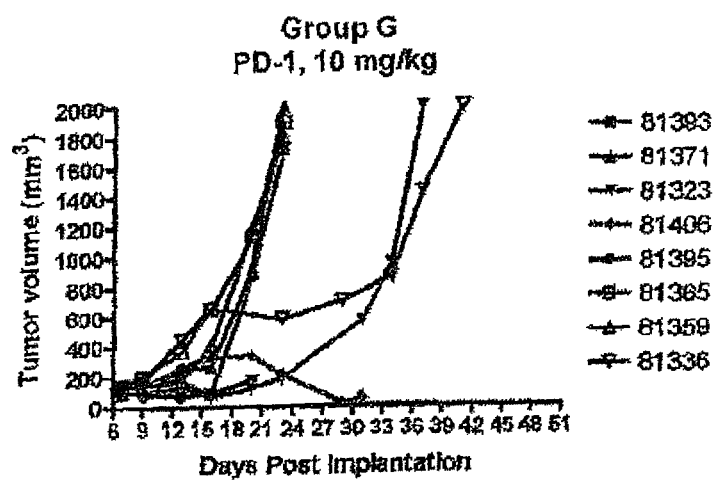
Figure 33H:
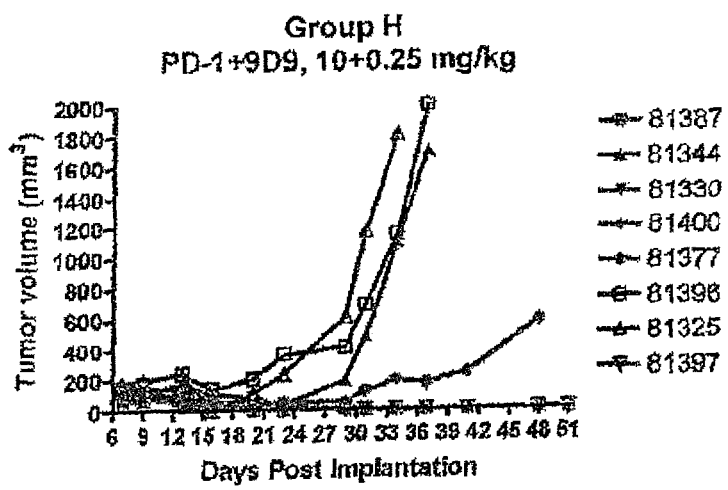
Figure 33I:
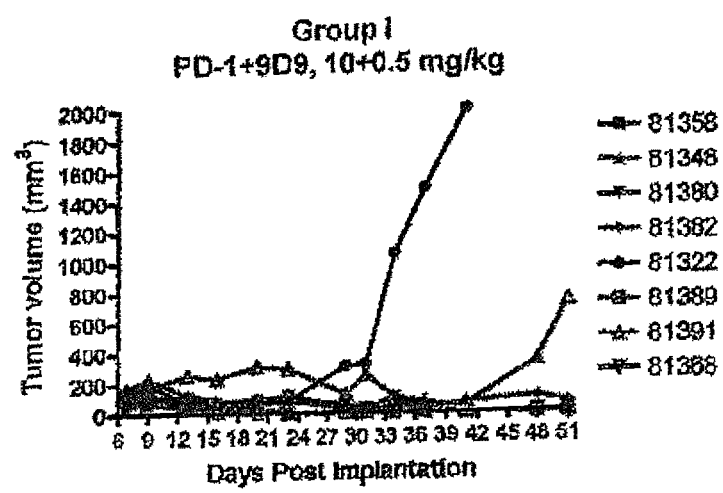
Figure 33J:
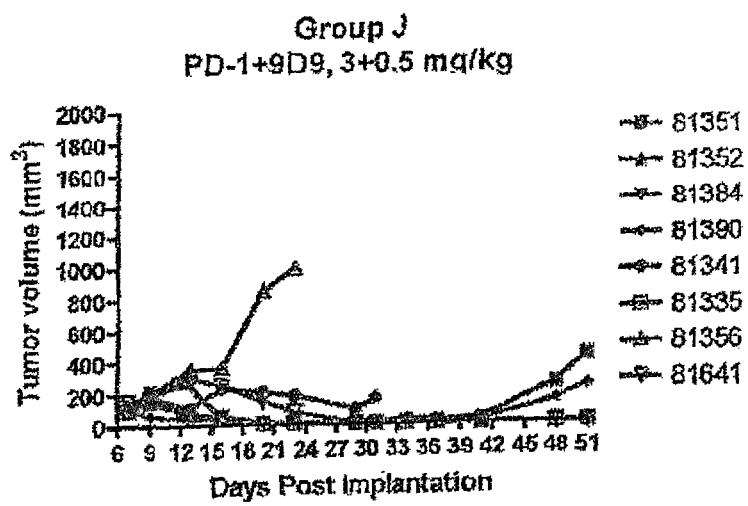

FIGS. 31 and 32 show the mean and median tumor volume, respectively, that developed in treated and untreated mice over the course of this study. The tumor growth inhibition in mice treated with these antibodies, as compared to mice treated with the control antibody mouse IgG, is summarized in Table 6.

TABLE 6

Tumor Growth Inhibition and Tumor Free Mice Following Anti-PD-1 and/or Anti-CTLA-4 Treatment

| Group[†] | Median Tumor Volume - mm³ (Day 15) | TGI* (%) (Day 15) | Median Tumor Volume - mm³ (Day 19) | TGI (%) (Day 19) | No. of Tumor Free Mice (Day 41) |
|---|---|---|---|---|---|
| A | 985 | — | 1140 | — | 0/10 |
| B | 635 | — | 1060 | — | 0/10 |
| C | 465 | 27 | 310 | 71 | 4/10 |
| D | 235 | 63 | 90 | 91 | 4/10 |
| E | 600 | 6 | 805 | 24 | 0/10 |
| F | 330 | 48 | 90 | 92 | 8/10 |

*TGI = tumor growth inhibition; the median could be calculated only when fewer than 50% of the mice reached the tumor end point.
[†]Groups are as defined in FIG. 30. A = vehicle (PBS); B = mouse IgG; C = anti-PD-1, 10 mg/kg; D = anti-CTLA-4, 10 mg/kg; E = anti-CTLA-4, 0.2 mg/kg; and F = anti-PD-1, 10 mg/kg with anti-CTLA-4, 0.2 mg/kg.

These data further indicate that the combination therapy comprising anti-PD-1 and anti-CTLA-4 antibodies is substantially more effective than treatment with either antibody alone, Indeed, the combination is still more effective than single antibody treatments even when the combination therapy contains a subtherapeutic dose of anti-CTLA-4 antibody. These data also indicate that surprisingly the presence or absence of PD-L1 on the tumor may have no effect on the efficacy of treatment with this antibody combination, although the presence of PD-L1 may influence the effect of the antibody monotherapies in that expression of PD-L1 on the tumor may also lead to inhibition of anti-tumor T cell responses (see FIG. 40).

Example 17

In Vivo Efficacy and Dose Titration of Combination Therapy (Anti-CTLA-4 and Anti-PD-1 Antibodies) on PD-L1⁻ Fibrosarcoma Growth SA1/N fibrosarcoma cells (PD-L1⁻) were implanted subcutaneously in ALI mice (2×10⁶ cells/mouse) on day 0 for a time sufficient (about 7 days) to permit the establishment of a tumor. On days 7, 10, 13 and 16 post-implantation, ten groups of 8 mice having an average tumor volume of 110 mm³ were injected IP as follows: Group (A) PBS alone (referred to as the "vehicle"); Group (B) mouse IgG (control, 10 mg/kg per mouse); Group (C) anti-CTLA-4 monoclonal antibody 9D9 (0.25 mg/kg); Group (D) anti-CTLA-4 monoclonal antibody 9D9 (0.5 mg/kg per mouse); Group (E) anti-CTLA-4 monoclonal antibody 9D9 (5 mg/kg); Group (F) anti-PD-1 monoclonal antibody 4H2 (3 mg/kg per mouse); Group (G) anti-PD-1 monoclonal antibody 4H2 (10 mg/kg per mouse); Group (H) anti-PD-1 monoclonal antibody 4H2 (10 mg/kg per mouse) in combination with anti-CTLA-4 monoclonal antibody 9D9 (0.25 mg/kg per mouse); Group (I) anti-PD-1 monoclonal antibody 4112 (10 mg/kg per mouse) in combination with anti-CTLA-4 monoclonal antibody 9D9 (0.5 mg/kg per mouse); and Group (I) anti-PD-1 monoclonal antibody 4H2 (3 mg/kg per mouse) in combination with anti-CTLA-4 monoclonal antibody 9D9 (0.5 mg/kg per mouse).

On days 10, 13, 16 and 19 post-implantation, two groups of 6 mice having an average tumor volume of 255 mm³ were injected IP as follows: Group (K) mouse IgG (control, 10 mg/kg per mouse); and Group (L) anti-PD-1 monoclonal antibody 4112 (10 mg/kg per mouse) in combination with anti-CTLA-4 monoclonal antibody 9D9 (1 mg/kg per mouse). The study lasted 51 days and tumor measurements were taken on various days throughout the course of the study (see FIGS. 33-38). Tumor volume was calculated by measuring tumors in three dimensions (height×width×length) using an electronic caliper. Mice were euthanized when the tumors reached a designated tumor end-point-a volume of 1500 mm³ and/or an ulcerated tumor.

Figure 34:
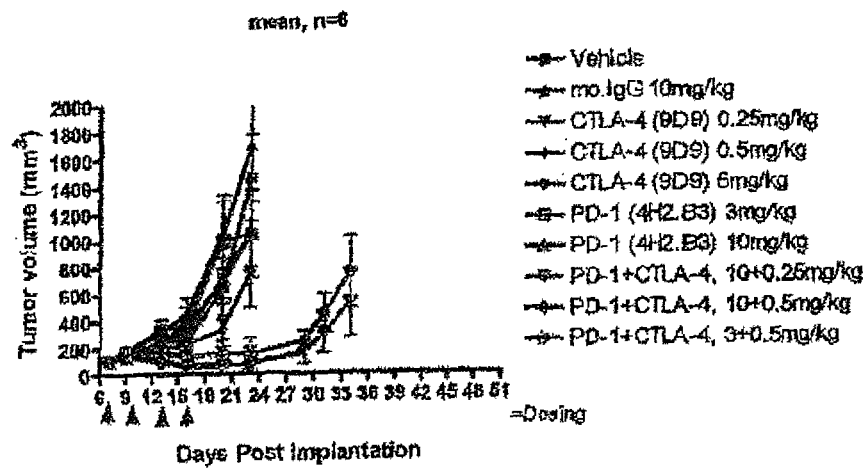
FIG. 34 shows the mean tumor volume of the mice shown in FIG. 33.
Figure 35:
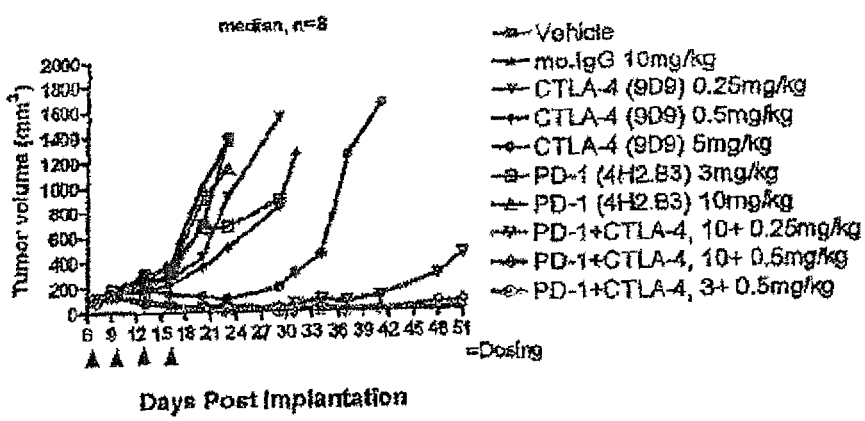
FIG. 35 shows the median tumor volume of the mice shown in FIG. 33.

FIG. 33 shows the response to immunostimulatory antibody treatment in mice with tumors having an initial volume of about 110 mm³ (i.e., at the time of the first antibody treatment. FIGS. 33A and 33B show that all 16 control mice (Groups A and B) reached a tumor end-point (15 with a tumor volume greater than 1500 mm³ and 1 with an ulcerated tumor). FIGS. 33C-33E show that tumor bearing mice respond to treatment with anti-CTLA-4 antibody in a dose-dependent manner (e.g., Group C receiving 0.25 mg/kg had 7/8 mice reach the tumor end-point and one mouse with a tumor volume less than 200 mm³, whereas Group E receiving 5 mg/kg had 6/8 mice reach the tumor end-point and two mice were tumor free). FIGS. 33F and 33G show that mice responded about the same regardless of the anti-PD-1 antibody dose (Group F received 3 mg/kg and Group G received 10 mg/kg). In contrast, the mice receiving a combination treatment of 10 or 3 mg/kg anti-PD-1 antibody with 0.25 or 0.5 mg/kg anti-CTLA-4 antibody (Groups H, I and J) showed a significant reduction in tumor growth. For example, FIG. 33S shows that the group treated with a combination of 3 mg/kg anti-PD-1 antibody with 0.5 mg/kg anti-CTLA-4 antibody (Group J) had 2 mice that had ulcerated tumors, 2 mice with a tumor volume less than 500 mm³, and 4 mice that were tumor free. The unexpected synergistic effect of an anti-PD-1 antibody combined with an anti-CTLA-4 antibody, along with the surprising effectiveness of subtherapeutic levels of anti-CTLA-4 antibody in the combination, are shown in FIGS. 34 (mean tumor volume) and 35 (median tumor volume).

Figure 36A:
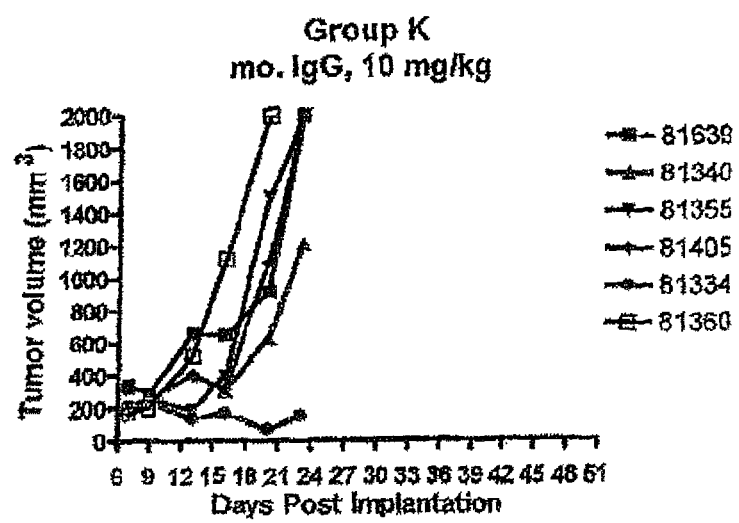
FIGS. 36A and 36B show the tumor volume over time in individual mice that were implanted with SA1/N fibrosarcoma cells (PD-L1⁻) and then treated on days 10, 13, 16 and 19 post-implantation (as described in Example 17) with one of the following therapies: (A) mouse IgG (antibody control, 10 mg/kg) or (B) anti-PD-1 antibody (10 mg/kg) and anti-CTLA-4 antibody (1 mg/kg). The tumor volume on the first day of treatment was about 250 mm³.
Figure 36B:
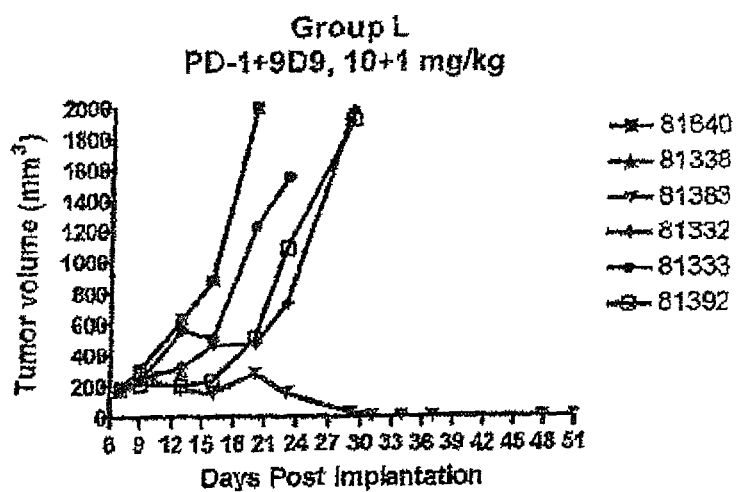
Figure 37:
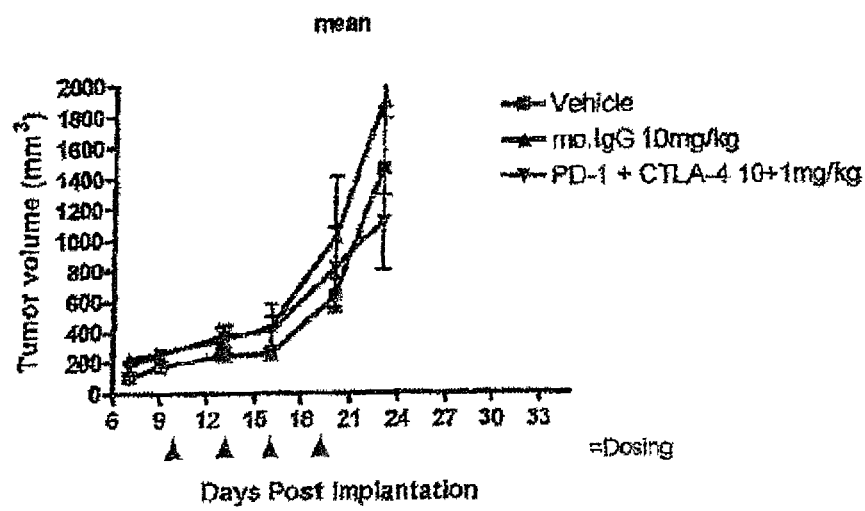
FIG. 37 shows the mean tumor volume of the mice shown in FIG. 36.
Figure 38:
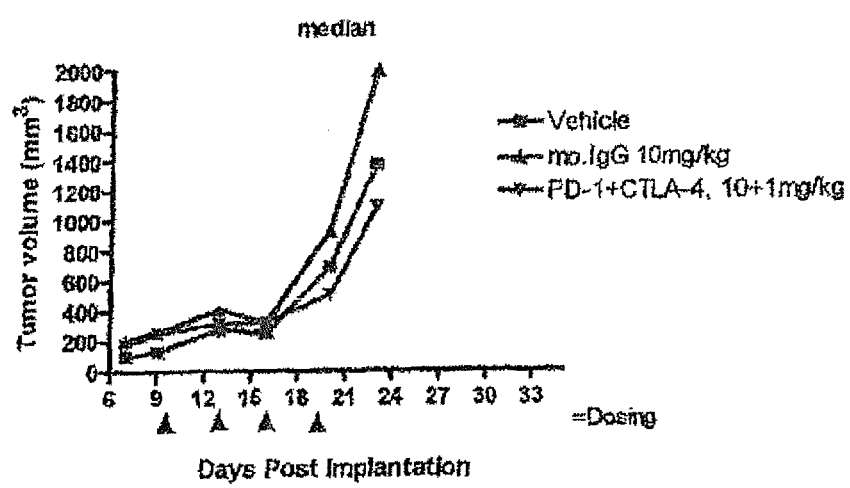
FIG. 38 shows the median tumor volume of the mice shown in FIG. 36.

FIG. 36 shows the response to immunostimulatory antibody treatment in mice with larger tumors, those having an initial volume of about 250 mm³ (i.e., at the time of the first antibody treatment). FIG. 36A shows that all 6 control mice (Group K) reached a tumor end-point (4 with a tumor volume greater than 1500 mm³ and 2 with an ulcerated tumor). FIG. 36B shows that the group treated with a combination of 10 mg/kg anti-PD-1 antibody with 1 mg/kg anti-CTLA-4 antibody (Group L) had one mouse with an ulcerated tumor, 4 mice with a tumor volume greater than 1500 mm³, and one mouse that was tumor free. The mean and median tumor volumes are shown in FIGS. 37 and 38.

Figure 39:
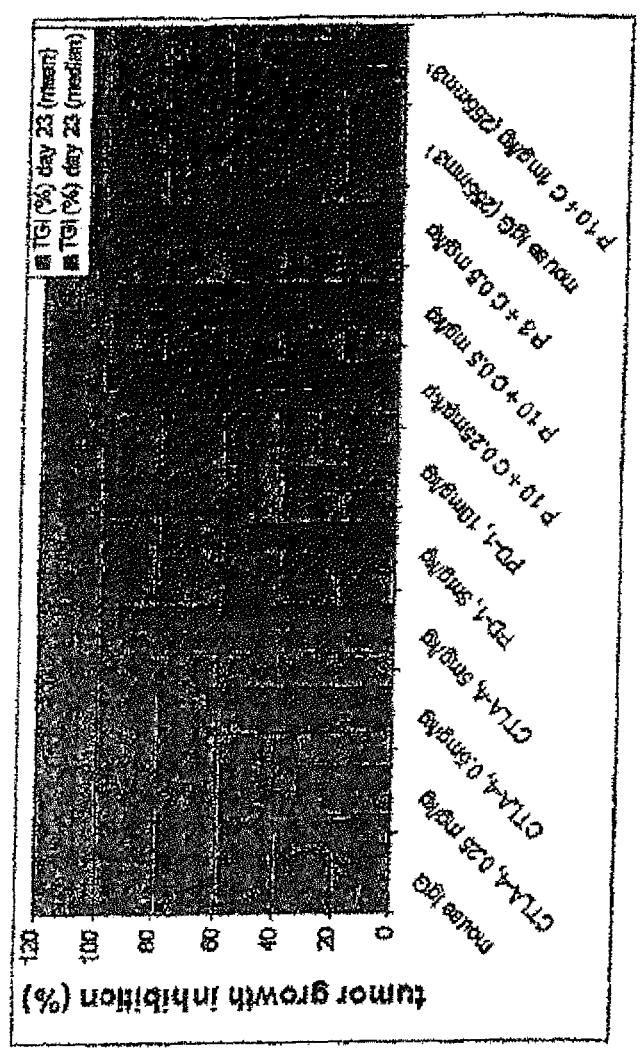
FIG. 39 shows the mean and median percent tumor inhibition calculated from the tumor volumes shown in FIGS. 33 and 36.
Figure 40A:
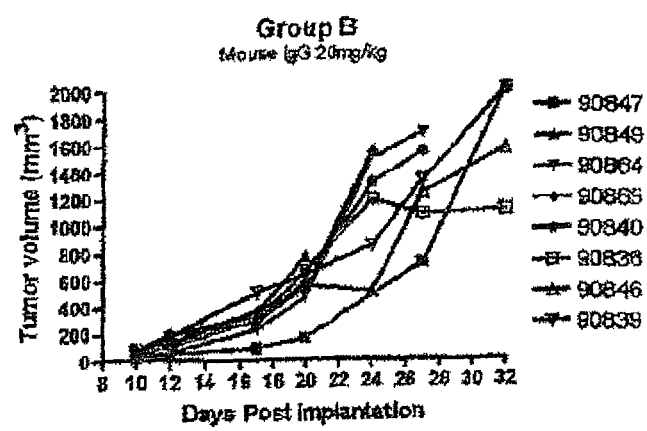
FIGS. 40A to 40D show the tumor volume in BALB/c mice that were implanted subcutaneously with RENCA renal adenocarcinoma cells (PD-L1$^+$) (Murphy and Hrushesky (1973) *J. Nat'l. Cancer Res.* 50:1013-1025) (day −12) and then treated intraperitoneally on days 0, 3, 6 and 9 post-implantation with one of the following therapies: (A) mouse IgG (antibody control, 20 mg/kg), (B) anti-PD-1 antibody (10 mg/kg), (C) anti-CTLA-4 antibody (10 mg/kg), and (D) anti-PD-1 antibody (10 mg/kg) in combination with anti-CTLA-4 antibody (10 mg/kg). The tumor volume on the first day of treatment was about 115 mm$^3$.
Figure 40B:
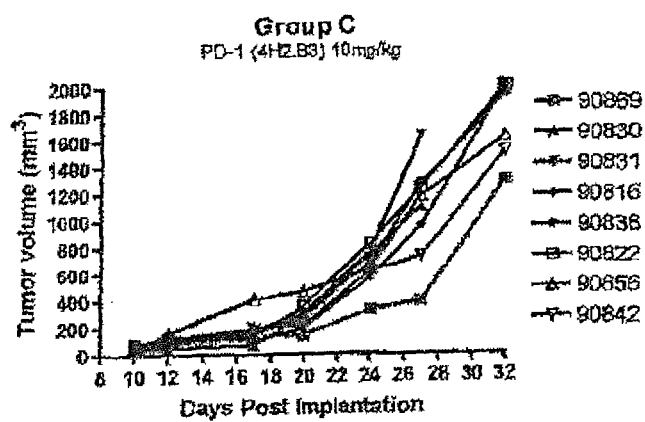
Figure 40C:
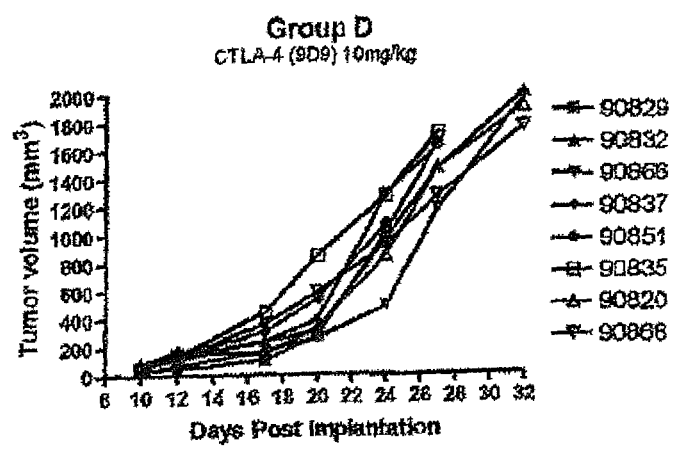
Figure 40D:
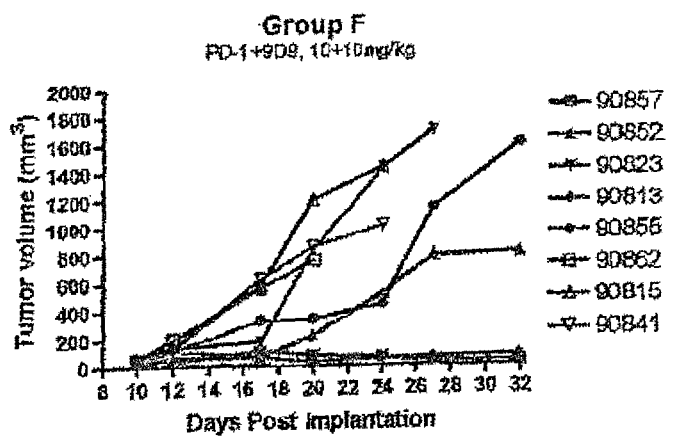

The tumor growth inhibition in mice treated with these antibodies, as compared to mice treated with the control antibody mouse IgG, is summarized in Table 7 and FIG. 39.

TABLE 7

Tumor Growth Inhibition Following Anti-PD-1 and/or Anti-CTLA-4 Treatment

| Group | Mean Tumor Volume - mm³ (Day 23) | TGI* (Mean) | Median Tumor Volume - mm³ (Day 23) | TGI (Median) | Tumor Free Mice (Day 51) | No. Mice at Tumor End Point |
|---|---|---|---|---|---|---|
| A | 700 | — | 1,380 | — | — | — |
| B | 1,710 | — | 1,360 | — | — | — |
| C | 1,050 | 39% | 925 | 32 | — | — |
| D | 770 | 55% | 505 | 63 | — | — |
| E | 155 | 91% | 100 | 93 | 2/8 | 6/8 |
| F | 1,050 | 39% | 675 | 50 | — | 7/8 |
| G | 1,070 | 37% | 1,145 | 16 | — | 6/8 |
| H | 85 | 95% | 25 | 98 | 4/8 | 3/8 |
| I | 75 | 96% | 60 | 95 | 4/8 | 1/8 |
| J | 80 | 95% | 5 | 99 | 4/8 | 0/8 |
| K | 1,900 | — | 2,125 | — | — | — |
| L | 1,115 | 41 | 1,090 | 49 | 1/6 | — |

*TGI = tumor growth inhibition; the median could only be calculated when fewer than 50% of the mice reached the tumor end point.
† Groups are as defined in FIGS. 33 and 36. For smaller initial tumor: A = vehicle (PBS); B = mouse IgG, 10 mg/kg; C = anti-CTLA-4, 0.25 mg/kg; D = anti-CTLA-4, 0.5 mg/kg; E = anti-CTLA-4, 5 mg/kg; F = anti-PD-1, 3 mg/kg; G = anti-PD-1, 10 mg/kg; H = anti-PD-1, 10 mg/kg with anti-CTLA-4, 0.25 mg/kg; I = anti-PD-1, 10 mg/kg with anti-CTLA-4, 0.5 mg/kg; and J = anti-PD-1, 3 mg/kg with anti-CTLA-4, 0.5 mg/kg. For larger initial tumor: K = mouse IgG, 10 mg/kg; and L = anti-PD-1, 10 mg/kg with anti-CTLA-4, 0.25 mg/kg.

Together these data indicate that the combination therapy comprising anti-PD-1 and anti-CTLA-4 antibodies is substantially more effective than treatment with either antibody alone. In addition, surprisingly the dose of each antibody can be reduced without affecting the synergistic efficacy of this combination of immunostimulatory therapeutic antibodies. The combination therapy still seems to be effective even when the tumor mass is more mature (i.e., larger).

Example 18

Tumor Immunity in Mice Following Anti-PD-1 Antibody Treatment and Re-Challenge with PD-L1⁻ Fibrosarcoma Cells Mice that survived tumor-free from a challenge with tumor cells and treatment with anti-PD-1 antibody (i.e., treatment similar to the efficacy studies described in Examples 5 and 6) were then re-challenged with tumor cells to investigate immunity to tumor formation after such a treatment. Briefly, in the initial challenge, SA1/N fibrosarcoma cells (PD-L1⁻) were implanted subcutaneously in A/J mice ($1\times10^6$ cells/mouse) on day 0. On days 1, 4, 7, 10, 14, 17 and 20 post-implantation, groups of mice were injected IP with either mouse IgG (control, 10 mg/kg per mouse) or with one of various doses of anti-PD-1 monoclonal antibody 4H2 (30, 10, 3, 1 and 0.3 mg/kg per mouse). Tumor formation and volume was monitored with a precision electronic caliper twice a week until the study was complete. A group of 8 mice were tumor-free after the anti-PD1 antibody treatment (4 that were treated with 30 mg/kg, 2 with 3 mg/kg, one with 1 mg/kg, and one with 0.3 mg/kg).

Figure 47:
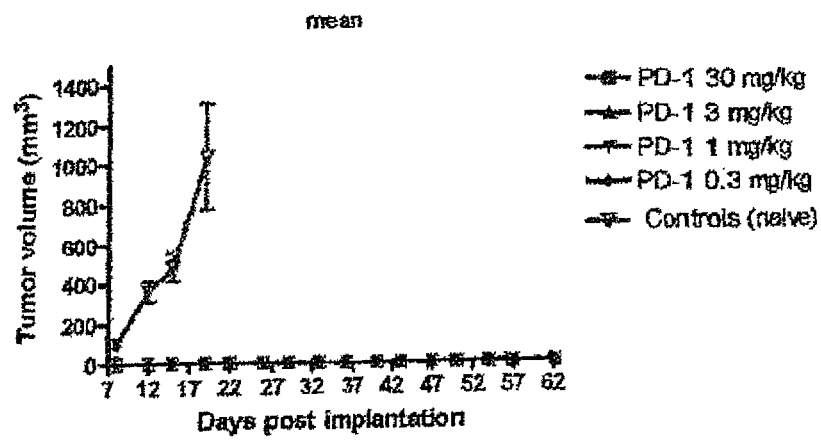
FIG. 47 shows the mean tumor volume of tumor-free mice previously treated with anti-PD1 antibody and re-challenged with SA1/N fibrosarcoma cells (PD-L1$^-$). Also shown is the mean tumor volume of naïve mice (control, not previously challenged or treated) implanted with SA1/N fibrosarcoma cells.

The eight treated, tumor-free A/J mice were re-challenged by subcutaneously implanting $1\times10^6$ SA1/N fibrosarcoma cells/mouse. As a control, nine naïve mice were subcutaneously implanted with $1\times10^6$ SA1/N fibrosarcoma cells/mouse. Tumor formation and volume was monitored with a precision electronic caliper twice a week until day 62 post-implantation. All nine naïve (control) mice reached the tumor end-point by day 22 post-implantation of the fibrosarcoma cells. In contrast, the eight tumor-free mice re-challenged with fibrosarcoma cells did not develop tumors up to 62 days post-implantation. FIG. 47 shows the mean tumor volume for the naïve and re-challenged mice. These results demonstrate that treatment with an immunostimulatory antibody, such as anti-PD-1, provides the treated subject with immunity to further tumor formation, even in the presence of cells capable of forming a tumor.

Example 19

Tumor Immunity in Mice Following Single Antibody Therapy (Anti-PD-1) or Combination Antibody Therapy (Anti-CTLA-4 and Anti-PD-1 Re-Challenged with PD-L1⁻ Colorectal Cancer Cells Mice that survived tumor-free from a challenge with tumor cells and treatment with either anti-PD-1 antibody alone or anti-PD-1 antibody combined with anti-CTLA-4 antibody (i.e., treatment similar to the efficacy studies described in Examples 2-4) were then re-challenged with tumor cells to investigate immunity to tumor formation after such treatments. Briefly, in the initial challenge, MC38 colorectal cancer cells (PD-L1⁻) were implanted in C57BL/6 mice ($2\times10^6$ cells/mouse) on day 0. On days 0, 3, 6 and 10 post-implantation, groups of mice were injected IP with one of the following treatments: (1) mouse IgG (control, 10 mg/kg per mouse), anti-PD-1 monoclonal antibody 4H2, or (3) anti-PD-1 monoclonal antibody 4H2 in combination with anti-CTLA-4 monoclonal antibody 9D9. Tumor growth was monitored with a precision electronic caliper as described in Example 15. A group of 11 mice were tumor-free after the anti-PD1 antibody treatment (2 total) or the combination anti-PD-1/anti-CTLA-4 antibody treatment (9 total).

Figure 48:
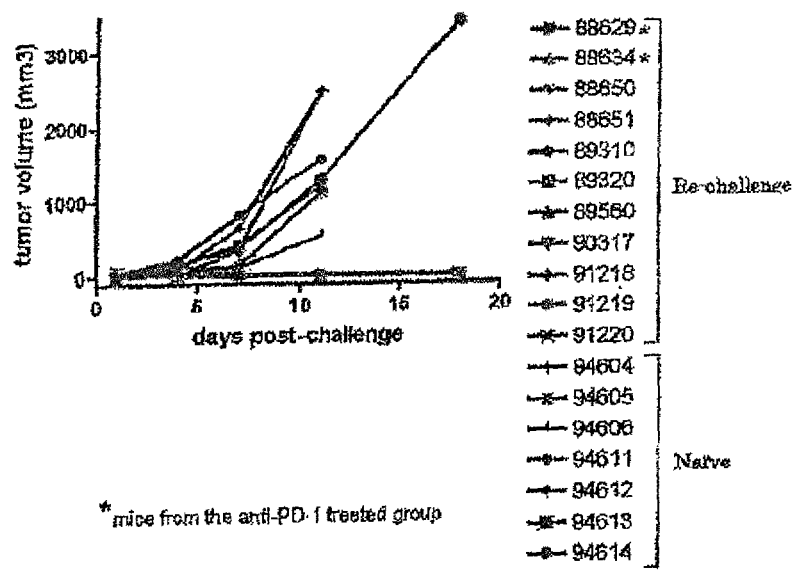
FIG. 48 shows the tumor volume over time in individual mice, which survived tumor-free following implantation of MC38 colon tumor cells (PD-L1$^-$) and treatment with anti-PD1 antibody or a combination of anti-PD1 antibody with anti-CTLA-4 antibody), re-challenged with 10× more MC38 colon tumor cells than the initial treatment. Also shown is the mean tumor volume of naïve mice (control, not previously challenged or treated) implanted with MC38 colon tumor cells.
Figure 49:
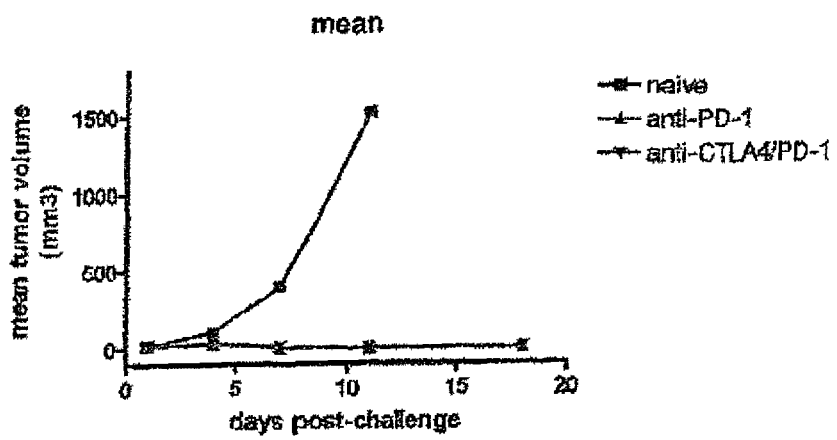
FIG. 49 shows the mean tumor volume of the mice shown in FIG. 48.

The 11 treated, tumor-free C57BL/6 mice were re-challenged by implantation of $2\times10^7$ MC38 colorectal cancer cells/mouse (i.e., a dose of cells 10× greater than the initial challenge). As a control, seven naïve mice were implanted with $2\times10^7$ MC38 colorectal cancer cells/mouse. Tumor formation and volume was monitored with a precision electronic caliper for the duration of the re-challenge experiment (at least 20 days). FIG. 48 shows that all seven naïve (control) mice developed a tumor and reached the tumor end-point by day 18 post-implantation of the colorectal cancer cells. In contrast, all 11 tumor-free mice re-challenged with colorectal cancer cells did not develop tumors up to 18 days post-implantation. FIG. 49 shows the mean tumor volume for the naïve and re-challenged mice. These data indicate that, similar to the antibody monotherapy, the combination antibody therapy resulting in PD-1 and CTLA-4 blockade produces a persistent immunity to tumor relapse.

Example 20

Figure 50:
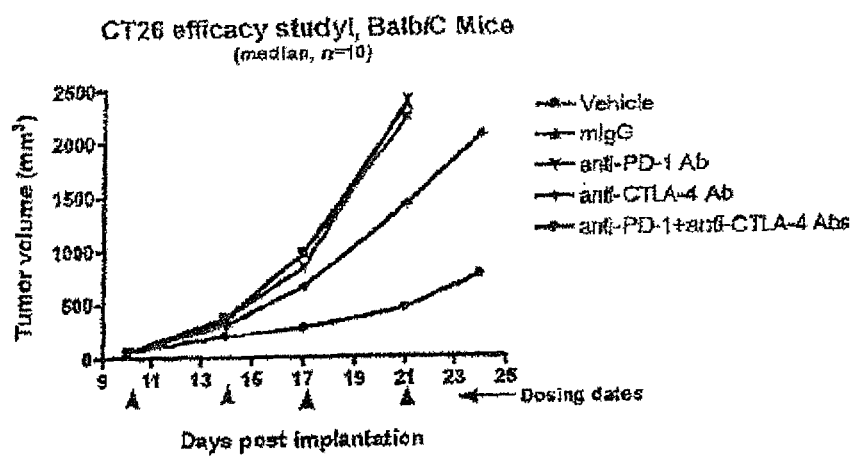
FIG. 50 shows the mean tumor volume over time in individual mice that were implanted with CT26 colon tumor cells.

In Vivo Efficacy of Combination Therapy (Anti-CTLA-4 and Anti-PD-1 Antibodies) on Established Tumor Growth CT26 colorectal cancer cells were implanted in BALB/Cmice ($2\times10^6$ cells/mouse) for a time sufficient (about 10 days) to permit the formation of tumors. On day 10 post-implantation, tumor measurements were taken and mice were randomized based on mean tumor volume (about 250 mm$^3$) into 5 groups for subsequent antibody therapy. At day 0 (i.e., 10 days after the CT26 cells were implanted), mice were injected IP with (1) mouse IgG (control), (2) anti-CTLA-4 monoclonal antibody 9D9, (3) anti-PD-1 monoclonal antibody 4H2, or (4) anti-CTLA-4 monoclonal antibody 9D9 and anti-PD-1 antibody monoclonal antibody 4H2, at a concentration of 10 mg/kg per mouse. Antibody injections were also administered on days 3, 6 and 10. The monoclonal antibody compositions used had low levels of endotoxin and did not significantly aggregate. Using an electronic caliper, the tumors were measured three dimensionally (height× width×length) and tumor volume was calculated. Tumor measurements were taken on day 0 (tumors at the beginning of treatment had a volume of about 125 mm$^3$), and on days 3, 6, 10, 13, 17 and 20 post-antibody injection. Mice were euthanized when the tumors reached a designated tumor end-point (a particular tumor volume such as 1500 mm$^3$ and/or when the mice showed greater than about 15% weight loss). The results are shown in FIG. 50. This study indicates that, in a murine tumor model, treatment with the combination of CTLA-4 antibody and PD-1 antibody has a significantly greater effect on tumor growth than either antibody alone, even when a tumor is already well established.

Example 21

Effect of Human Anti-PD-1 Antibody on Function of T Regulatory Cells

T regulatory cells are lymphocytes that suppress the immune response. In this example, T regulatory cells were tested for its inhibitory function on proliferation and IFN-gamma secretion of CD4+CD25− T cells in the presence or absence of an anti-PD-1 human monoclonal antibody.

Figure 51A:
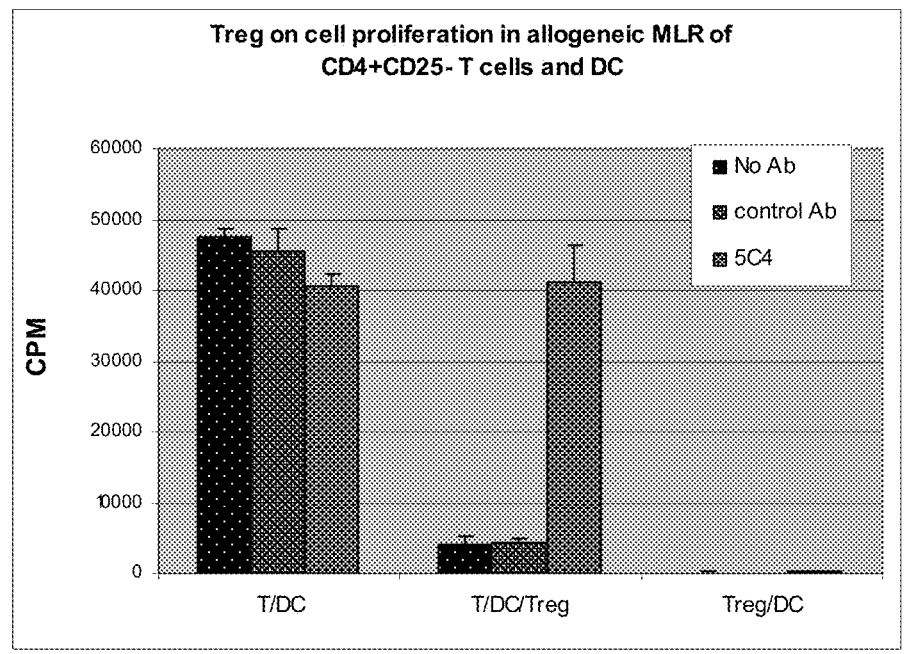
FIGS. 51A-B shows the results of experiments demonstrating that human monoclonal antibodies against human PD-1 promote T-cell proliferation and IFN-gamma secretion in cultures containing T regulatory cells.
Figure 51B:
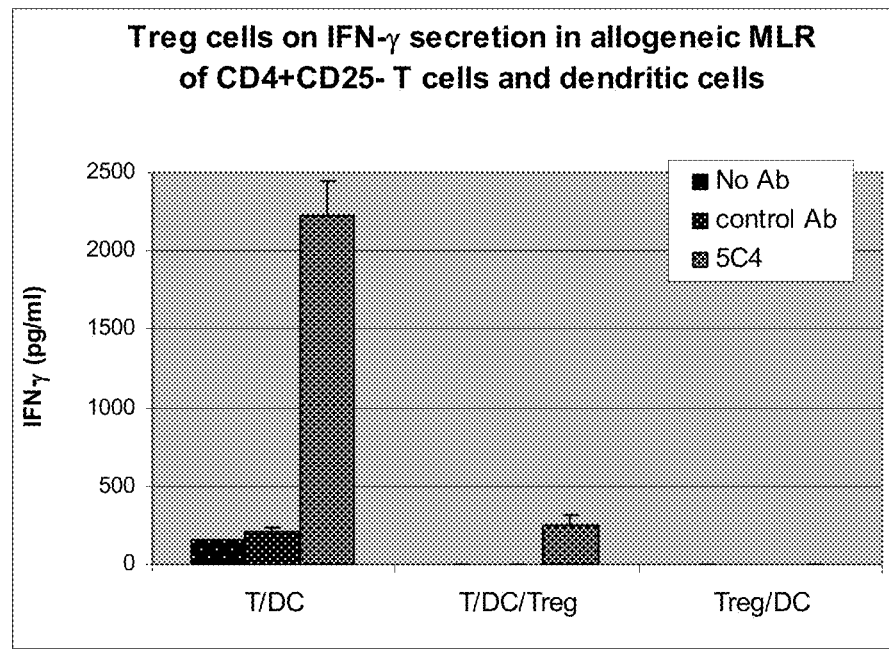

T regulatory cells were purified from PBMC using a CD4+CD25+ regulatory T cell isolation kit (Miltenyi Biotec). T regulatory cells were added into a mixed lymphocyte reaction (see above) containing purified CD4+CD25− T cells and allogeneic dendritic cells in a 2:1 ratio of CD4+ CD25− to T regulatory cells. Anti-PD-1 monoclonal antibody 5C4 was added at a concentration of 10 μg/ml. Either no antibody or an isotype control antibody was used as a negative control. Culture supernatants were harvested on Day 5 for cytokine measurement using a Beadlyte cytokine detection system (Upstate). The cells were labeled with $^3$H-thymidine, cultured for another 18 hours, and analyzed for cell proliferation. The results are shown in FIGS. 51A (T cell proliferation) and 51B (IFN-gamma secretion). The addition of anti-PD-1 human monoclonal antibody 5C4 partially released inhibition imposed by Treg cells on proliferation and IFN-gamma secretion of CD4+CD25− T cells, indicating that anti-PD-1 antibodies have an effect on T regulatory cells.

Example 22

Effect of Human Anti-PD4 Antibody on T Cell Activation

Figure 52A:
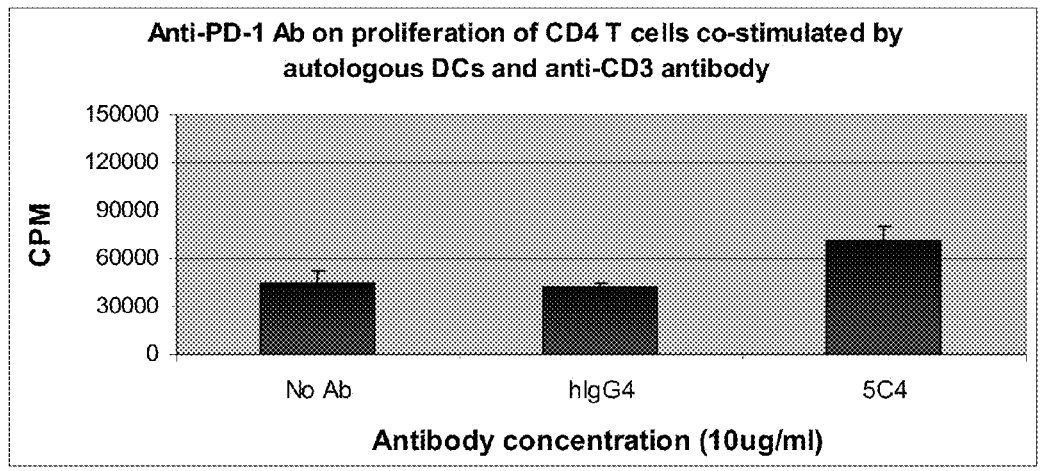
FIGS. 52A-B shows the results of experiments demonstrating that human monoclonal antibodies against human PD-1 promote T-cell proliferation and IFN-gamma secretion in cultures containing activated T cells.
Figure 52B:
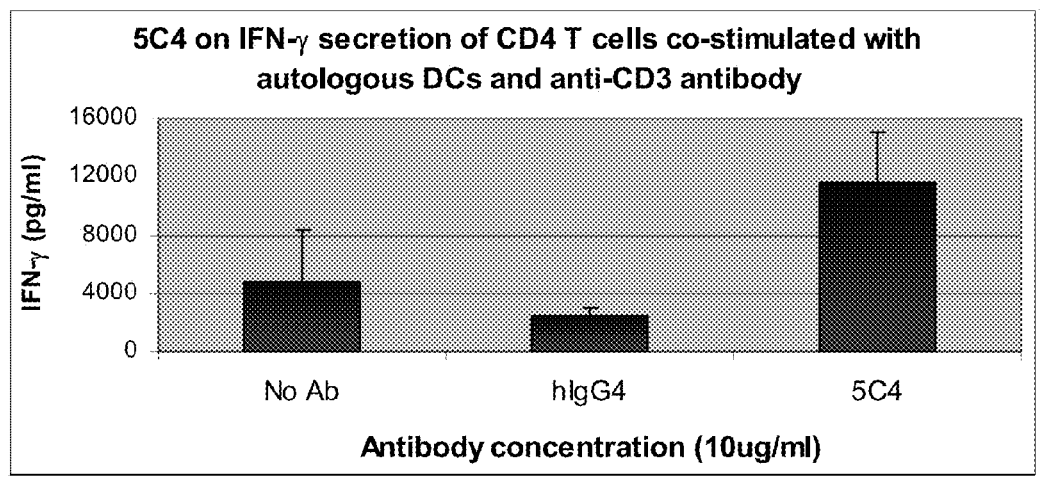

In this example, effect of blockade of PD-1 pathway by anti-PD-1 antibody 5C4 on T cell activation was examined. Purified human CD4+ T cells (Dynal CD4 T cell purification kit) were activated with 1 μg/ml soluble anti-CD3 antibody (BD) in the presence of autologous monocytes or monocyte-derived dendritic cells (DCs). Monocytes were purified using Miltenyi CD14 monocyte purification kit, and DCs was generated in vitro after culture of monocytes with GM-CSF and IL-4 (PeproTech) for 7 days. After three days of activation in the presence or absence of titrated anti-PD-1 antibody or irrelevant isotype control mAb, culture supernatants were harvested for ELISA analysis of IFNγ secretion while tritiated thymidine was added during the final 18 hours of the assay in order to measure T cell proliferation. The results shown in FIGS. 52A and 52B demonstrate that PD-1 blockade by anti-PD-1 antibody resulted in enhanced T cell proliferation and IFN-γ secretion. Synergic effect by anti-PD-1 antibody and anti-CTLA-4 antibody on T cell activation (specifically on IFN-γ secretion) in the presence of monocytes was also observed.

Example 23

Assessment of ADCC Activity of Anti-PD-1 Antibody

Figure 53:
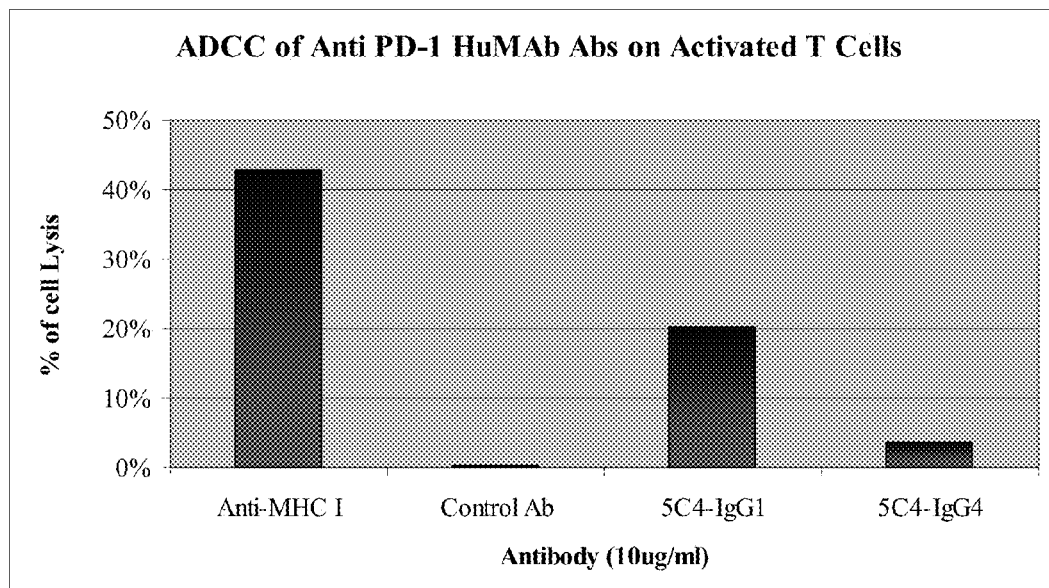
FIG. 53 shows the results of an antibody dependent cellular cytotoxicity (ADCC) assay demonstrating that human monoclonal anti-PD-1 antibodies kill human activated T cells in an ADCC concentration-dependent manner in relation to the Fc region of the anti-PD-1 antibody.

In this example, an antibody-dependent cellular cytotoxicity (ADCC) assay was performed to evaluate whether anti-PD-1 antibody could induce ADCC to target cells. Two versions of 5C4, one with an Fc region of human IgG1 (5C4-IgG1) and the other with an Fc region of human IgG4 (5C4-IgG4), were tested in the assay. The Delfia Cell Cytotoxicity Kit from Perkin Elmer was used for the assay. Briefly, purified human CD4 T cells (Dynal CD4 T cell purification kit) were activated by plate-bound anti-CD3 antibody (BD) to induce PD-1 expression. Target activated CD4 T cells were then labeled with BATDA reagent. Labeled CD4 T cells were added to a V-bottom 96-well plate, followed by the addition of human PBMC (an effector to target (E/T) cell ratio of 50:1) and designed antibody. After incubation for 1 hour at 37° C., the plate was spun down. Supernatant was transferred into a flat bottom 96-well plate and the plate was read using a RubyStar plate reader. Results showed that 5C4-IgG4 did not mediate ADCC on activated CD4 T cells, while 5C4-IgG1 did mediate ADCC on activated CD4 T cells (FIG. 53), indicating that ADCC activity is related to its Fc region of the anti-PD-1 antibody.

Example 24

Assessment of Complement-Dependent Cytotoxicity of Anti-PD-1 Antibody

Figure 54:
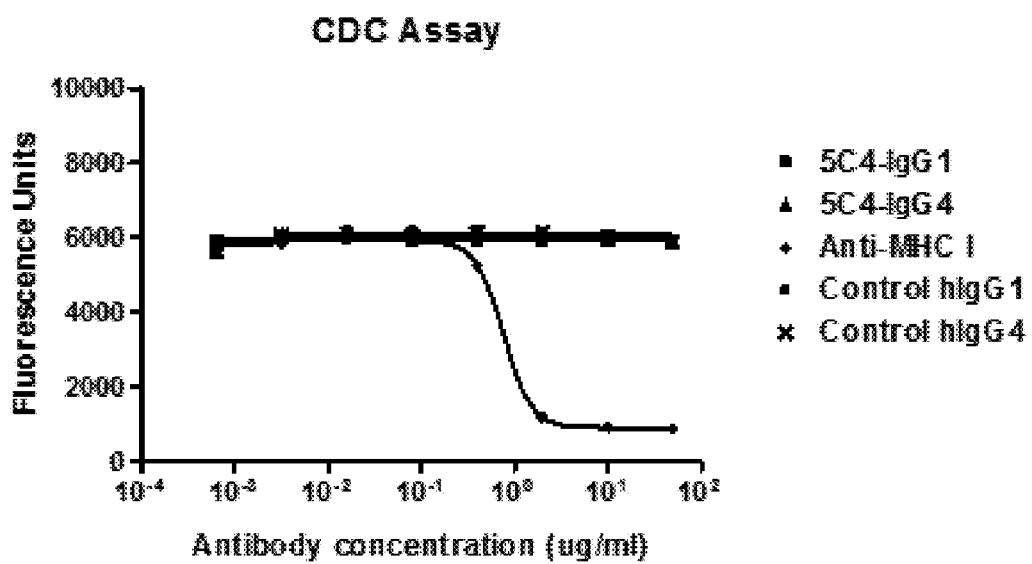
FIG. 54 shows the results of a complement dependent cytotoxicity (CDC) assay demonstrating that human monoclonal anti-PD-1 antibodies do not kill human activated T cells in a CDC concentration-dependent manner.

In this example, complement dependant cytotoxicity (CDC) of anti-PD-1 antibody was examined. Two versions of 5C4, one with Fc region of human IgG1 (5C4-IgG1) and the other with Fc region of human IgG4 (5C4-IgG4), were tested in the assay. Briefly, purified human CD4 T cells (Dynal CD4 T cell purification kit) were activated by plate-bound anti-CD3 antibody (BD) to induce PD-1 expression. Serial dilutions of anti-PD-1 antibody (5C4) and control antibodies from 50 μg/mL to 640 pg/mL were tested for CDC in the presence of human complement (Quidel-A113). Alamar blue (Biosource International) was used to measure cytotoxicity. The plate was read on a fluorescent plate reader (EX530 EM590). Viable cell counts are proportional to fluorescence units. Results showed that neither 5C4-IgG1 or 5C4-IgG4 mediated CDC on activated CD4 T cells, while the positive control antibody (anti-HLA-ABC antibody) did (FIG. 54).

Example 25

Assessment of PD-1 Expression on Human T Cells

In this example, human PBMCs from different donors were examined for PD-1 expression on various cell subsets by FACS. Biotinylated anti-PD-1 antibody, which has displayed a much higher sensitivity than commercially available anti-PD-1 antibody on detection of PD-1 molecules on cell surface, was used in the assay. Bound antibody was detected using an PE-conjugated streptavidin. Flow cytometric analyses were performed using a FACScan flow cytometry (Becton Dickinson) and Flowjo software (Tree Star). PD-1 expression was detected on some peripheral human T cells, but not on B cells or monocytes. Further examination of T cell subsets indicates that PD-1 is expressed on CD4 and CD8 memory and effector T cells, but absent on naïve CD4 or CD8 T cells.

The present invention is not to be limited in scope by the specific embodiments described herein. Indeed, various modifications of the invention, in addition to those described herein, will become apparent to those skilled in the art from the foregoing description and the accompanying figures. Such modifications are intended to fall within the scope of the appended claims. The invention is, therefore, to be limited only by the terms of the appended claims along with the full scope of equivalents to which the claims are entitled.

---

What is claimed is:

1. A method for treating a cancer in a subject comprising administering to the subject an anti-PD-1 monoclonal antibody, or an antigen-binding portion thereof, which cross-competes for binding to PD-1 with a reference antibody, or antigen-binding portion thereof, comprising:
   (a) a heavy chain CDR1 comprising amino acids having the sequence set forth in SEQ ID NO: 15; a heavy chain CDR2 comprising amino acids having the sequence set forth in SEQ ID NO: 22; a heavy chain CDR3 comprising amino acids having the sequence set forth in SEQ ID NO: 29; a light chain CDR1 comprising amino acids having the sequence set forth in SEQ ID NO: 36; a light chain CDR2 comprising amino acids having the sequence set forth in SEQ ID NO: 43; and a light chain CDR3 comprising amino acids having the sequence set forth in SEQ ID NO: 50;
   (b) a heavy chain CDR1 comprising amino acids having the sequence set forth in SEQ ID NO: 16; a heavy chain CDR2 comprising amino acids having the sequence set forth in SEQ ID NO: 23; a heavy chain CDR3 comprising amino acids having the sequence set forth in SEQ ID NO: 30; a light chain CDR1 comprising amino acids having the sequence set forth in SEQ ID NO: 37; a light chain CDR2 comprising amino acids having the sequence set forth in SEQ ID NO: 44; and a light chain CDR3 comprising amino acids having the sequence set forth in SEQ ID NO: 51;
   (c) a heavy chain CDR1 comprising amino acids having the sequence set forth in SEQ ID NO: 17; a heavy chain CDR2 comprising amino acids having the sequence set forth in SEQ ID NO: 24; a heavy chain CDR3 comprising amino acids having the sequence set forth in SEQ ID NO: 31; a light chain CDR1 comprising amino acids having the sequence set forth in SEQ ID NO: 38; a light chain CDR2 comprising amino acids having the sequence set forth in SEQ ID NO: 45; and a light chain CDR3 comprising amino acids having the sequence set forth in SEQ ID NO: 52;
   (d) a heavy chain CDR1 comprising amino acids having the sequence set forth in SEQ ID NO: 18; a heavy chain CDR2 comprising amino acids having the sequence set forth in SEQ ID NO: 25; a heavy chain CDR3 comprising amino acids having the sequence set forth in SEQ ID NO: 32; a light chain CDR1 comprising amino acids having the sequence set forth in SEQ ID NO: 39; a light chain CDR2 comprising amino acids having the sequence set forth in SEQ ID NO: 46; and a light chain CDR3 comprising amino acids having the sequence set forth in SEQ ID NO: 53;
   (e) a heavy chain CDR1 comprising amino acids having the sequence set forth in SEQ ID NO: 19; a heavy chain CDR2 comprising amino acids having the sequence set forth in SEQ ID NO: 26; a heavy chain CDR3 comprising amino acids having the sequence set forth in SEQ ID NO: 33; a light chain CDR1 comprising amino acids having the sequence set forth in SEQ ID NO: 40; a light chain CDR2 comprising amino acids having the sequence set forth in SEQ ID NO: 47; and a light chain CDR3 comprising amino acids having the sequence set forth in SEQ ID NO: 54;
   (f) a heavy chain CDR1 comprising amino acids having the sequence set forth in SEQ ID NO: 20; a heavy chain CDR2 comprising amino acids having the sequence set forth in SEQ ID NO: 27; a heavy chain CDR3 comprising amino acids having the sequence set forth in SEQ ID NO: 34; a light chain CDR1 comprising amino acids having the sequence set forth in SEQ ID NO: 41; a light chain CDR2 comprising amino acids having the sequence set forth in SEQ ID NO: 48; and a light chain CDR3 comprising amino acids having the sequence set forth in SEQ ID NO: 55; or
   (g) a heavy chain CDR1 comprising amino acids having the sequence set forth in SEQ ID NO: 21; a heavy chain CDR2 comprising amino acids having the sequence set forth in SEQ ID NO: 28; a heavy chain CDR3 comprising amino acids having the sequence set forth in SEQ ID NO: 35; a light chain CDR1 comprising amino acids having the sequence set forth in SEQ ID NO: 42; a light chain CDR2 comprising amino acids having the sequence set forth in SEQ ID NO: 49; and a light chain CDR3 comprising amino acids having the sequence set forth in SEQ ID NO: 56, wherein the anti-PD-1 monoclonal antibody or antigen-binding portion thereof exhibits at least one of the following properties:

(i) binds to human PD-1 with a $K_D$ of $1\times10^{-7}$ M or less, wherein the $K_D$ is measured by surface plasmon resonance (Biacore) analysis;

(ii) binds to human PD-1 with an on rate ($k_{on}$) of about $0.76\times10^5$ l/Ms or more, wherein the on rate ($k_{on}$) is measured by surface plasmon resonance (Biacore) analysis; and (iii) binds to human PD-1 with an off rate ($k_{off}$) of about $4.5\times10$ l/s or less, wherein the off rate ($k_{off}$) is measured by surface plasmon resonance (Biacore) analysis.

2. The method of claim 1, wherein the reference antibody or antigen-binding portion thereof comprises a heavy chain CDR1 comprising amino acids having the sequence set forth in SEQ ID NO: 18; a heavy chain CDR2 comprising amino acids having the sequence set forth in SEQ ID NO: 25; a heavy chain CDR3 comprising amino acids having the sequence set forth in SEQ ID NO: 32; a light chain CDR1 comprising amino acids having the sequence set forth in SEQ ID NO: 39; a light chain CDR2 comprising amino acids having the sequence set forth in SEQ ID NO: 46; and a light chain CDR3 comprising amino acids having the sequence set forth in SEQ ID NO: 53.

3. The method of claim 1, wherein the reference antibody or antigen-binding portion thereof comprises:

(a) a heavy chain variable region comprising amino acids having the sequence set forth in SEQ ID NO: 1 and a light chain variable region comprising amino acids having the sequence set forth in SEQ ID NO: 8;

(b) a heavy chain variable region comprising amino acids having the sequence set forth in SEQ ID NO: 2 and a light chain variable region comprising amino acids having the sequence set forth in SEQ ID NO: 9;

(c) a heavy chain variable region comprising amino acids having the sequence set forth in SEQ ID NO: 3 and a light chain variable region comprising amino acids having the sequence set forth in SEQ ID NO: 10;

(d) a heavy chain variable region comprising amino acids having the sequence set forth in SEQ ID NO: 4 and a light chain variable region comprising amino acids having the sequence set forth in SEQ ID NO: 11;

(e) a heavy chain variable region comprising amino acids having the sequence set forth in SEQ ID NO: 5 and a light chain variable region comprising amino acids having the sequence set forth in SEQ ID NO: 12;

(f) a heavy chain variable region comprising amino acids having the sequence set forth in SEQ ID NO: 6 and a light chain variable region comprising amino acids having the sequence set forth in SEQ ID NO: 13; or (g) a heavy chain variable region comprising amino acids having the sequence set forth in SEQ ID NO: 7 and a light chain variable region comprising amino acids having the sequence set forth in SEQ ID NO: 14.

4. The method of claim 3, wherein the reference antibody or antigen-binding portion thereof comprises a heavy chain variable region comprising amino acids having the sequence set forth in SEQ ID NO: 4 and a light chain variable region comprising amino acids having the sequence set forth in SEQ ID NO: 11.

5. A method for treating a cancer in a subject comprising administering to the subject an anti-PD-1 monoclonal antibody, or an antigen-binding portion thereof, which binds to the same epitope on human PD-1 as does a reference antibody, or antigen-binding portion thereof, comprising:

(a) a heavy chain variable region comprising amino acids having the sequence set forth in SEQ ID NO: 1 and a light chain variable region comprising amino acids having the sequence set forth in SEQ ID NO: 8;

(b) a heavy chain variable region comprising amino acids having the sequence set forth in SEQ ID NO: 2 and a light chain variable region comprising amino acids having the sequence set forth in SEQ ID NO: 9;

(c) a heavy chain variable region comprising amino acids having the sequence set forth in SEQ ID NO: 3 and a light chain variable region comprising amino acids having the sequence set forth in SEQ ID NO: 10;

(d) a heavy chain variable region comprising amino acids having the sequence set forth in SEQ ID NO: 4 and a light chain variable region comprising amino acids having the sequence set forth in SEQ ID NO: 11;

(e) a heavy chain variable region comprising amino acids having the sequence set forth in SEQ ID NO: 5 and a light chain variable region comprising amino acids having the sequence set forth in SEQ ID NO: 12;

(f) a heavy chain variable region comprising amino acids having the sequence set forth in SEQ ID NO: 6 and a light chain variable region comprising amino acids having the sequence set forth in SEQ ID NO: 13; or (g) a heavy chain variable region comprising amino acids having the sequence set forth in SEQ ID NO: 7 and a light chain variable region comprising amino acids having the sequence set forth in SEQ ID NO: 14.

6. The method of claim 5, wherein the reference antibody or antigen-binding portion thereof comprises a heavy chain variable region comprising amino acids having the sequence set forth in SEQ ID NO: 4 and a light chain variable region comprising amino acids having the sequence set forth in SEQ ID NO: 11.

7. The method of claim 1, wherein the anti-PD-1 monoclonal antibody, or an antigen-binding portion thereof, comprises a heavy chain variable region that comprises CDR1, CDR2, and CDR3 domains; and a light chain variable region that comprises CDR1, CDR2, and CDR3 domains, wherein the heavy chain variable region and light chain variable region CDR3 domains are selected from the group consisting of:

a) a heavy chain variable region CDR3 comprising amino acids having the sequence set forth in SEQ ID NO: 29; and a light chain variable region CDR3 comprising amino acids having the sequence set forth in SEQ ID NO: 50 and or a conservative modification thereof;

b) a heavy chain variable region CDR3 comprising amino acids having the sequence set forth in SEQ ID NO: 30; and a light chain variable region CDR3 comprising amino acids having the sequence set forth in SEQ ID NO: 51 and or a conservative modification thereof;

c) a heavy chain variable region CDR3 comprising amino acids having the sequence set forth in SEQ ID NO: 31; and a light chain variable region CDR3 comprising amino acids having the sequence set forth in SEQ ID NO: 52 and or a conservative modification thereof;

d) a heavy chain variable region CDR3 comprising amino acids having the sequence set forth in SEQ ID NO: 32;

and a light chain variable region CDR3 comprising amino acids having the sequence set forth in SEQ ID NO: 53 and or a conservative modification thereof;
- e) a heavy chain variable region CDR3 comprising amino acids having the sequence set forth in SEQ ID NO: 33; and a light chain variable region CDR3 comprising amino acids having the sequence set forth in SEQ ID NO: 54 and or a conservative modification thereof;
- f) a heavy chain variable region CDR3 comprising amino acids having the sequence set forth in SEQ ID NO: 34; and a light chain variable region CDR3 comprising amino acids having the sequence set forth in SEQ ID NO: 55 and or a conservative modification thereof; and
- g) a heavy chain variable region CDR3 comprising amino acids having the sequence set forth in SEQ ID NO: 35; and a light chain variable region CDR3 comprising amino acids having the sequence set forth in SEQ ID NO: 56 or a conservative modification thereof.

8. The method of claim 7, wherein the heavy chain variable region and light chain variable region CDR2 domains of the anti-PD-1 monoclonal antibody or antigen-binding portion thereof are selected from the group consisting of:
- a) a heavy chain variable region CDR2 comprising amino acids having the sequence set forth in SEQ ID NO: 22 and or a conservative modification thereof; and a light chain variable region CDR2 comprising amino acids having the sequence set forth in SEQ ID NO: 43 and or a conservative modification thereof;
- b) a heavy chain variable region CDR2 comprising amino acids having the sequence set forth in SEQ ID NO: 23 and or a conservative modification thereof; and a light chain variable region CDR2 comprising amino acids having the sequence set forth in SEQ ID NO: 44 and or a conservative modification thereof;
- c) a heavy chain variable region CDR2 comprising amino acids having the sequence set forth in SEQ ID NO: 24 and or a conservative modification thereof; and a light chain variable region CDR2 comprising amino acids having the sequence set forth in SEQ ID NO: 45 and or a conservative modification thereof;
- d) a heavy chain variable region CDR2 comprising amino acids having the sequence set forth in SEQ ID NO: 25 and or a conservative modification thereof; and a light chain variable region CDR2 comprising amino acids having the sequence set forth in SEQ ID NO: 46 and or a conservative modification thereof;
- e) a heavy chain variable region CDR2 comprising amino acids having the sequence set forth in SEQ ID NO: 26 and or a conservative modification thereof; and a light chain variable region CDR2 comprising amino acids having the sequence set forth in SEQ ID NO: 47 and or a conservative modification thereof;
- f) a heavy chain variable region CDR2 comprising amino acids having the sequence set forth in SEQ ID NO: 27 and or a conservative modification thereof; and a light chain variable region CDR2 comprising amino acids having the sequence set forth in SEQ ID NO: 48 and or a conservative modification thereof; and
- g) a heavy chain variable region CDR2 comprising amino acids having the sequence set forth in SEQ ID NO: 28 and or a conservative modification thereof; and a light chain variable region CDR2 comprising amino acids having the sequence set forth in SEQ ID NO: 49 and or a conservative modification thereof.

9. The method of claim 8, wherein the heavy chain variable region and light chain variable region CDR1 domains of the anti-PD-1 monoclonal antibody or antigen-binding portion thereof are selected from the group consisting of:
- a) a heavy chain variable region CDR1 comprising amino acids having the sequence set forth in SEQ ID NO: 15 and or a conservative modification thereof; and a light chain variable region CDR1 comprising amino acids having the sequence set forth in SEQ ID NO: 36 and or a conservative modification thereof;
- b) a heavy chain variable region CDR1 comprising amino acids having the sequence set forth in SEQ ID NO: 16 and or a conservative modification thereof; and a light chain variable region CDR1 comprising amino acids having the sequence set forth in SEQ ID NO: 37 and or a conservative modification thereof;
- c) a heavy chain variable region CDR1 comprising amino acids having the sequence set forth in SEQ ID NO: 17 and or a conservative modification thereof; and a light chain variable region CDR1 comprising amino acids having the sequence set forth in SEQ ID NO: 38 and or a conservative modification thereof;
- d) a heavy chain variable region CDR1 comprising amino acids having the sequence set forth in SEQ ID NO: 18 and or a conservative modification thereof; and a light chain variable region CDR1 comprising amino acids having the sequence set forth in SEQ ID NO: 39 and or a conservative modification thereof;
- e) a heavy chain variable region CDR1 comprising amino acids having the sequence set forth in SEQ ID NO: 19 and or a conservative modification thereof; and a light chain variable region CDR1 comprising amino acids having the sequence set forth in SEQ ID NO: 40 and or a conservative modification thereof;
- f) a heavy chain variable region CDR1 comprising amino acids having the sequence set forth in SEQ ID NO: 20 and or a conservative modification thereof; and a light chain variable region CDR1 comprising amino acids having the sequence set forth in SEQ ID NO: 41 and or a conservative modification thereof; and
- g) a heavy chain variable region CDR1 comprising amino acids having the sequence set forth in SEQ ID NO: 21 and or a conservative modification thereof; and a light chain variable region CDR1 comprising amino acids having the sequence set forth in SEQ ID NO: 42 and or a conservative modification thereof.

10. A method for treating a cancer in a subject comprising administering to the subject an anti-PD-1 monoclonal antibody, or an antigen-binding portion thereof, comprising:
- (a) a heavy chain CDR1 comprising amino acids having the sequence set forth in SEQ ID NO: 15; a heavy chain CDR2 comprising amino acids having the sequence set forth in SEQ ID NO: 22; a heavy chain CDR3 comprising amino acids having the sequence set forth in SEQ ID NO: 29; a light chain CDR1 comprising amino acids having the sequence set forth in SEQ ID NO: 36; a light chain CDR2 comprising amino acids having the sequence set forth in SEQ ID NO: 43; and a light chain CDR3 comprising amino acids having the sequence set forth in SEQ ID NO: 50;
- (b) a heavy chain CDR1 comprising amino acids having the sequence set forth in SEQ ID NO: 16; a heavy chain CDR2 comprising amino acids having the sequence set forth in SEQ ID NO: 23; a heavy chain CDR3 comprising amino acids having the sequence set forth in SEQ ID NO: 30; a light chain CDR1 comprising amino acids having the sequence set forth in SEQ ID NO: 37; a light chain CDR2 comprising amino acids having the sequence set forth in SEQ ID NO: 44; and a light chain CDR3 comprising amino acids having the sequence set forth in SEQ ID NO: 51;
(c) a heavy chain CDR1 comprising amino acids having the sequence set forth in SEQ ID NO: 17; a heavy chain CDR2 comprising amino acids having the sequence set forth in SEQ ID NO: 24; a heavy chain CDR3 comprising amino acids having the sequence set forth in SEQ ID NO: 31; a light chain CDR1 comprising amino acids having the sequence set forth in SEQ ID NO: 38; a light chain CDR2 comprising amino acids having the sequence set forth in SEQ ID NO: 45; and a light chain CDR3 comprising amino acids having the sequence set forth in SEQ ID NO: 52;
(d) a heavy chain CDR1 comprising amino acids having the sequence set forth in SEQ ID NO: 18; a heavy chain CDR2 comprising amino acids having the sequence set forth in SEQ ID NO: 25; a heavy chain CDR3 comprising amino acids having the sequence set forth in SEQ ID NO: 32; a light chain CDR1 comprising amino acids having the sequence set forth in SEQ ID NO: 39; a light chain CDR2 comprising amino acids having the sequence set forth in SEQ ID NO: 46; and a light chain CDR3 comprising amino acids having the sequence set forth in SEQ ID NO: 53;
(e) a heavy chain CDR1 comprising amino acids having the sequence set forth in SEQ ID NO: 19; a heavy chain CDR2 comprising amino acids having the sequence set forth in SEQ ID NO: 26; a heavy chain CDR3 comprising amino acids having the sequence set forth in SEQ ID NO: 33; a light chain CDR1 comprising amino acids having the sequence set forth in SEQ ID NO: 40; a light chain CDR2 comprising amino acids having the sequence set forth in SEQ ID NO: 47; and a light chain CDR3 comprising amino acids having the sequence set forth in SEQ ID NO: 54;
(f) a heavy chain CDR1 comprising amino acids having the sequence set forth in SEQ ID NO: 20; a heavy chain CDR2 comprising amino acids having the sequence set forth in SEQ ID NO: 27; a heavy chain CDR3 comprising amino acids having the sequence set forth in SEQ ID NO: 34; a light chain CDR1 comprising amino acids having the sequence set forth in SEQ ID NO: 41; a light chain CDR2 comprising amino acids having the sequence set forth in SEQ ID NO: 48; and a light chain CDR3 comprising amino acids having the sequence set forth in SEQ ID NO: 55; or
(g) a heavy chain CDR1 comprising amino acids having the sequence set forth in SEQ ID NO: 21; a heavy chain CDR2 comprising amino acids having the sequence set forth in SEQ ID NO: 28; a heavy chain CDR3 comprising amino acids having the sequence set forth in SEQ ID NO: 35; a light chain CDR1 comprising amino acids having the sequence set forth in SEQ ID NO: 42; a light chain CDR2 comprising amino acids having the sequence set forth in SEQ ID NO: 49; and a light chain CDR3 comprising amino acids having the sequence set forth in SEQ ID NO: 56.

11. The method of claim 10, wherein the anti-PD-1 monoclonal antibody or antigen-binding portion thereof comprises a heavy chain CDR1 comprising amino acids having the sequence set forth in SEQ ID NO: 18; a heavy chain CDR2 comprising amino acids having the sequence set forth in SEQ ID NO: 25; a heavy chain CDR3 comprising amino acids having the sequence set forth in SEQ ID NO: 32; a light chain CDR1 comprising amino acids having the sequence set forth in SEQ ID NO: 39; a light chain CDR2 comprising amino acids having the sequence set forth in SEQ ID NO: 46; and a light chain CDR3 comprising amino acids having the sequence set forth in SEQ ID NO: 53.

12. The method of claim 10, wherein the anti-PD-1 monoclonal antibody or antigen-binding portion thereof comprises:
(a) a heavy chain variable region comprising amino acids having the sequence set forth in SEQ ID NO: 1 and a light chain variable region comprising amino acids having the sequence set forth in SEQ ID NO: 8;
(b) a heavy chain variable region comprising amino acids having the sequence set forth in SEQ ID NO: 2 and a light chain variable region comprising amino acids having the sequence set forth in SEQ ID NO: 9;
(c) a heavy chain variable region comprising amino acids having the sequence set forth in SEQ ID NO: 3 and a light chain variable region comprising amino acids having the sequence set forth in SEQ ID NO: 10;
(d) a heavy chain variable region comprising amino acids having the sequence set forth in SEQ ID NO: 4 and a light chain variable region comprising amino acids having the sequence set forth in SEQ ID NO: 11;
(e) a heavy chain variable region comprising amino acids having the sequence set forth in SEQ ID NO: 5 and a light chain variable region comprising amino acids having the sequence set forth in SEQ ID NO: 12;
(f) a heavy chain variable region comprising amino acids having the sequence set forth in SEQ ID NO: 6 and a light chain variable region comprising amino acids having the sequence set forth in SEQ ID NO: 13; or
(g) a heavy chain variable region comprising amino acids having the sequence set forth in SEQ ID NO: 7 and a light chain variable region comprising amino acids having the sequence set forth in SEQ ID NO: 14.

13. The method of claim 12, wherein the anti-PD-1 monoclonal antibody or antigen-binding portion thereof comprises a heavy chain variable region comprising amino acids having the sequence set forth in SEQ ID NO: 4 and a light chain variable region comprising amino acids having the sequence set forth in SEQ ID NO: 11.

14. The method of any one of claims 1, 5, 7 and 10, wherein the anti-PD-1 antibody or antigen-binding portion thereof is a humanized or human monoclonal antibody or an antigen-binding portion thereof.

15. The method of any one of claims 1, 5, 7 and 10, wherein the anti-PD-1 antibody or antigen-binding portion thereof further comprises a heavy chain constant region which is of a human IgG1 or IgG4 isotype.

16. The method of claim 13, wherein the anti-PD-1 antibody or antigen-binding portion thereof comprises a heavy chain constant region which is of a human IgG1 or IgG4 isotype.

17. The method of any one of claims 1, 5, 7 and 10, wherein the anti-PD-1 antibody or antigen-binding portion thereof comprises a light chain constant region which is a human kappa or lambda constant region.

18. The method of claim 13, wherein the anti-PD-1 antibody or antigen-binding portion thereof comprises a light chain constant region which is a human kappa or lambda constant region.

19. The method of any one of claims 1, 5, 7 and 10, wherein the antigen-binding portion is a Fab, Fab', F(ab')$_2$, Fv, or a single chain Fv fragment.

20. The method of claim 13, wherein the antigen-binding portion is a Fab, Fab', F(ab')$_2$, Fv, or a single chain Fv fragment.

21. The method of any one of claims 1, 5, 7 and 10, wherein the cancer is selected from the group consisting of melanoma, lung cancer, renal cancer, prostate cancer, breast cancer, colorectal cancer, fibrosarcoma, and any combination thereof.

22. The method of any one of claims 1, 5, 7 and 10, wherein the cancer is selected from the group consisting of bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

23. The method of any one of claims 3, 5, and 12, wherein the anti-PD-1 monoclonal antibody or antigen-binding portion thereof comprises a light chain variable region comprising amino acids EIVLTQSPATLSLSPGERATLSC (SEQ ID NO: 75).

24. The method of any one of claims 3, 5, and 12, wherein the $V_H$ of the anti-PD-1 monoclonal antibody or antigen-binding portion thereof comprises $V_H$-FR1, $V_H$-CDR1, $V_H$-FR2, $V_H$-CDR2, $V_H$-FR3, $V_H$-CDR3, and $V_H$-FR4, and the $V_L$ comprises $V_L$-FR1, $V_L$-CDR1, $V_L$-FR2, $V_L$-CDR2, $V_L$-FR3, $V_L$-CDR3, and $V_L$-FR4, and wherein the $V_L$-FR1, $V_L$-FR2, and $V_L$-FR3 comprise amino acid sequences derived from a human $V_K$ L6 germline sequence and the $V_L$-FR4 comprises an amino acid sequence derived from a human $V_K$ JK1 or $V_K$ JK4 germline sequence.

25. A method for treating a cancer in a subject comprising administering to the subject an anti-PD-1 monoclonal antibody or an antigen-binding portion thereof, which cross-competes for binding to human PD-1 with a reference antibody that comprises:
(a) a heavy chain variable region comprising the amino acid sequence set forth in SEQ ID NO: 1 and a light chain variable region comprising the amino acid sequence set forth in SEQ ID NO: 8;
(b) a heavy chain variable region comprising the amino acid sequence set forth in SEQ ID NO: 2 and a light chain variable region comprising the amino acid sequence set forth in SEQ ID NO: 9;
(c) a heavy chain variable region comprising the amino acid sequence set forth in SEQ ID NO: 4 and a light chain variable region comprising the amino acid sequence set forth in SEQ ID NO: 11; or
(d) a heavy chain variable region comprising the amino acid sequence set forth in SEQ ID NO: 6 and a light chain variable region comprising the amino acid sequence set forth in SEQ ID NO: 13;
wherein the anti-PD-1 monoclonal antibody or antigen-binding portion thereof binds to human PD-1 with a $K_D$ of $1 \times 10^{-8}$ M or less, wherein the $K_D$ is measured by surface plasmon resonance (Biacore) analysis and
wherein the anti-PD-1 monoclonal antibody or antigen-binding portion thereof comprises (i) a light chain variable region, which comprises the amino acid sequence of EIVLTQSPATLSLSPGERATLSC (SEQ ID NO: 75) or EIVLTQSPATLSLSPGERATLSC (SEQ ID NO: 75) containing one amino acid modification and (ii) a heavy chain variable region.

26. The method of claim 25, wherein the light chain variable region of the anti-PD-1 monoclonal antibody or the antigen-binding portion thereof further comprises the amino acid sequence of WYQQKPGQAPRLLIY (SEQ ID NO: 76) or WYQQKPGQAPRLLIY (SEQ ID NO: 76) containing one amino acid modification.

27. The method of claim 25, wherein the light chain variable region of the anti-PD-1 monoclonal antibody or the antigen-binding portion thereof comprises the amino acid sequence of GIPARFSGSGSGTDFTLTISSLEPEDFAVYYC (SEQ ID NO: 77) or GIPARFSGSGSGTDFTLTISSLEPEDFAVYYC (SEQ ID NO: 77) containing one amino acid modification.

28. The method of claim 25, wherein the light chain variable region of the anti-PD-1 monoclonal antibody or the antigen-binding portion thereof comprises the amino acid sequence of FGGGTKVEIK (SEQ ID NO: 78) or FGGGTKVEIK (SEQ ID NO: 78) containing one amino acid modification.

29. The method of claim 25, wherein the light chain variable region of the anti-PD-1 monoclonal antibody or the antigen-binding portion thereof further comprises the amino acid sequences of WYQQKPGQAPRLLIY (SEQ ID NO: 76) and FGGGTKVEIK (SEQ ID NO: 78).

30. The method of claim 29, wherein the anti-PD-1 monoclonal antibody or the antigen-binding portion thereof further comprises a heavy chain comprising the amino acid sequence of WGQGTLVTVSS (SEQ ID NO: 82) or WGQGTLVTVSS (SEQ ID NO: 82) containing one amino acid modification.

31. The method of claim 30, wherein the $K_D$ is $1 \times 10^{-8}$ M or less and wherein the $K_D$ is measured by surface plasmon resonance (Biacore) analysis.

32. The method of claim 31, wherein the $K_D$ is $5 \times 10^{-9}$ M or less and wherein the $K_D$ is measured by surface plasmon resonance (Biacore) analysis.

33. The method of claim 32, wherein the $K_D$ is $1 \times 10^{-9}$ M or less and wherein the $K_D$ is measured by surface plasmon resonance (Biacore) analysis.

34. The method of claim 25, which mediates neither ADCC activity nor CDC activity.

35. The method of claim 25, further comprising a heavy chain constant region which is of a human IgG1, IgG2, IgG3, or IgG4 isotype.

36. The method of claim 25, wherein the heavy chain constant region is of a human IgG4 isotype.

37. A method for treating a cancer in a subject comprising administering to the subject an anti-PD-1 monoclonal antibody or an antigen-binding portion thereof, which cross-competes for binding to human PD-1 with a reference antibody that comprises:
(a) a heavy chain variable region comprising the amino acid sequence set forth in SEQ ID NO: 1 and a light chain variable region comprising the amino acid sequence set forth in SEQ ID NO: 8;
(b) a heavy chain variable region comprising the amino acid sequence set forth in SEQ ID NO: 2 and a light chain variable region comprising the amino acid sequence set forth in SEQ ID NO: 9;

(c) a heavy chain variable region comprising the amino acid sequence set forth in SEQ ID NO: 4 and a light chain variable region comprising the amino acid sequence set forth in SEQ ID NO: 11; or (d) a heavy chain variable region comprising the amino acid sequence set forth in SEQ ID NO: 6 and a light chain variable region comprising the amino acid sequence set forth in SEQ ID NO: 13;

wherein the anti-PD-1 monoclonal antibody or the antigen-binding portion thereof comprises a light chain variable region that has at least about 80% sequence identity to an amino acid sequence selected from SEQ ID NO: 8, SEQ ID NO: 9, and SEQ ID NO: 11.

38. The method of claim 37, wherein the light chain variable region of the anti-PD-1 monoclonal antibody or the antigen-binding portion thereof has at least about 85% sequence identity to an amino acid sequence selected from SEQ ID NO: 8, SEQ ID NO: 9, and SEQ ID NO: 11.

39. The method of claim 37, wherein the heavy chain variable region of the reference antibody comprises the amino acid sequence set forth in SEQ ID NO: 4 and the light chain variable region of the reference antibody comprises the amino acid sequence set forth in SEQ ID NO: 11 and wherein the light chain variable region of the monoclonal antibody or the antigen-binding portion thereof has at least about 80% sequence identity to SEQ ID NO: 11.

40. The method of claim 39, wherein the light chain variable region of the anti-PD-1 monoclonal antibody or the antigen-binding portion thereof has at least about 85% sequence identity to SEQ ID NO: 11.

41. A method for treating a cancer in a subject comprising administering to the subject an anti-PD-1 monoclonal antibody or an antigen-binding portion thereof, which cross-competes for binding to human PD-1 with a reference antibody that comprises a heavy chain variable region comprising the amino acid sequence set forth in SEQ ID NO: 6 and a light chain variable region comprising the amino acid sequence set forth in SEQ ID NO: 13; wherein the anti-PD-1 monoclonal antibody or the antigen-binding portion thereof comprises a light chain variable region encoded by a nucleic acid sequence that has at least about 80% sequence identity to the nucleotide sequence set forth in SEQ ID NO: 69.

42. The method of claim 41, wherein the anti-PD-1 monoclonal antibody or the antigen-binding portion thereof comprises a light chain variable region encoded by a nucleic acid sequence that has at least about 85% sequence identity to the nucleotide sequence set forth in SEQ ID NO: 69.

43. The method of claim 41, wherein the anti-PD-1 monoclonal antibody or the antigen-binding portion thereof comprises a light chain variable region encoded by a nucleic acid sequence that has at least about 90% sequence identity to the nucleotide sequence set forth in SEQ ID NO: 69.

44. A method for treating a cancer in a subject comprising administering to the subject an anti-PD-1 monoclonal antibody or an antigen-binding portion thereof, which cross-competes for binding to human PD-1 with a reference antibody comprising a heavy chain variable region that comprises CDR1, CDR2, and CDR3 domains and a light chain variable region that comprises CDR1, CDR2, and CDR3 domains selected from the group consisting of:

(a) a heavy chain CDR1 comprising the amino acid sequence set forth in SEQ ID NO: 15; a heavy chain CDR2 comprising the amino acid sequence set forth in SEQ ID NO: 22; a heavy chain CDR3 comprising the amino acid sequence set forth in SEQ ID NO: 29; a light chain CDR1 comprising the amino acid sequence set forth in SEQ ID NO: 36; a light chain CDR2 comprising the amino acid sequence set forth in SEQ ID NO: 43; and a light chain CDR3 comprising the amino acid sequence set forth in SEQ ID NO: 50;

(b) a heavy chain CDR1 comprising the amino acid sequence set forth in SEQ ID NO: 16; a heavy chain CDR2 comprising the amino acid sequence set forth in SEQ ID NO: 23; a heavy chain CDR3 comprising the amino acid sequence set forth in SEQ ID NO: 30; a light chain CDR1 comprising the amino acid sequence set forth in SEQ ID NO: 37; a light chain CDR2 comprising the amino acid sequence set forth in SEQ ID NO: 44; and a light chain CDR3 comprising the amino acid sequence set forth in SEQ ID NO: 51;

(c) a heavy chain CDR1 comprising the amino acid sequence set forth in SEQ ID NO: 18; a heavy chain CDR2 comprising the amino acid sequence set forth in SEQ ID NO: 25; a heavy chain CDR3 comprising the amino acid sequence set forth in SEQ ID NO: 32; a light chain CDR1 comprising the amino acid sequence set forth in SEQ ID NO: 39; a light chain CDR2 comprising the amino acid sequence set forth in SEQ ID NO: 46; and a light chain CDR3 comprising the amino acid sequence set forth in SEQ ID NO: 53; and (d) a heavy chain CDR1 comprising the amino acid sequence set forth in SEQ ID NO: 20; a heavy chain CDR2 comprising the amino acid sequence set forth in SEQ ID NO: 27; a heavy chain CDR3 comprising the amino acid sequence set forth in SEQ ID NO: 34; a light chain CDR1 comprising the amino acid sequence set forth in SEQ ID NO: 41; a light chain CDR2 comprising the amino acid sequence set forth in SEQ ID NO: 48; and a light chain CDR3 comprising the amino acid sequence set forth in SEQ ID NO: 55; and wherein the anti-PD-1 monoclonal antibody or antigen-binding portion thereof comprises a heavy chain, which comprises CDR1, CDR2, CDR3, and framework regions, and a light chain, which comprises CDR1, CDR2, CDR3, and framework regions, wherein the light chain framework regions of the anti-PD-1 monoclonal antibody or antigen-binding portion thereof comprise amino acids that have at least about 90% sequence identity to the framework regions of a light chain variable region selected from the group consisting of SEQ ID NO: 8, SEQ ID NO: 9, and SEQ ID NO: 11; and wherein the anti-PD-1 monoclonal antibody or antigen-binding portion thereof exhibits at least one property selected from:

(i) binding to human PD-1 with a $K_D$ of $1\times10^{-7}$ M or less, wherein the $K_D$ is measured by surface plasmon resonance (Biacore) analysis;

(ii) binding to human PD-1 with an on rate ($k_{on}$) of about $0.76\times10^5$ 1/Ms or more, wherein the on rate ($k_{on}$) is measured by surface plasmon resonance (Biacore) analysis; and (iii) binding to human PD-1 with an off rate ($k_{off}$) of about $4.5\times10^{-4}$ 1/s or less, wherein the off rate ($k_{on}$) is measured by surface plasmon resonance (Biacore) analysis.

45. The method of claim 44, wherein the light chain framework regions of the anti-PD-1 antibody or antigen-binding portion thereof comprise amino acids that have at least about 95% sequence identity to the framework regions of a light chain variable region selected from the group consisting of SEQ ID NO: 8, SEQ ID NO: 9, and SEQ ID NO: 11.

46. The method of claim 44, wherein the light chain framework regions of the anti-PD-1 monoclonal antibody or antigen-binding portion thereof comprise amino acids that have at least about 96% sequence identity to the framework regions of a light chain variable region selected from the group consisting of SEQ ID NO: 8, SEQ ID NO: 9, and SEQ ID NO: 11.

47. The method of claim 44, wherein the light chain framework regions of the anti-PD-1 monoclonal antibody or antigen-binding portion thereof comprise amino acids that have at least about 97% sequence identity to the framework regions of a light chain variable region selected from the group consisting of SEQ ID NO: 8, SEQ ID NO: 9, and SEQ ID NO: 11.

48. The method of claim 44, wherein the light chain framework regions of the anti-PD-1 monoclonal antibody or antigen-binding portion thereof comprise amino acids that have at least about 98% sequence identity to the framework regions of a light chain variable region selected from the group consisting of SEQ ID NO: 8, SEQ ID NO: 9, and SEQ ID NO: 11.

49. A method for treating a cancer in a subject comprising administering to the subject an anti-PD-1 monoclonal antibody or an antigen-binding portion thereof, which cross-competes for binding to PD-1 with a reference antibody comprising a heavy chain variable region that comprises CDR1, CDR2, and CDR3 domains and a light chain variable region that comprises CDR1, CDR2, and CDR3 domains selected from the group consisting of:
  (a) a heavy chain CDR1 comprising the amino acid sequence set forth in SEQ ID NO: 15; a heavy chain CDR2 comprising the amino acid sequence set forth in SEQ ID NO: 22; a heavy chain CDR3 comprising the amino acid sequence set forth in SEQ ID NO: 29; a light chain CDR1 comprising the amino acid sequence set forth in SEQ ID NO: 36; a light chain CDR2 comprising the amino acid sequence set forth in SEQ ID NO: 43; and a light chain CDR3 comprising the amino acid sequence set forth in SEQ ID NO: 50;
  (b) a heavy chain CDR1 comprising the amino acid sequence set forth in SEQ ID NO: 16; a heavy chain CDR2 comprising the amino acid sequence set forth in SEQ ID NO: 23; a heavy chain CDR3 comprising the amino acid sequence set forth in SEQ ID NO: 30; a light chain CDR1 comprising the amino acid sequence set forth in SEQ ID NO: 37; a light chain CDR2 comprising the amino acid sequence set forth in SEQ ID NO: 44; and a light chain CDR3 comprising the amino acid sequence set forth in SEQ ID NO: 51;
  (c) a heavy chain CDR1 comprising the amino acid sequence set forth in SEQ ID NO: 18; a heavy chain CDR2 comprising the amino acid sequence set forth in SEQ ID NO: 25; a heavy chain CDR3 comprising the amino acid sequence set forth in SEQ ID NO: 32; a light chain CDR1 comprising the amino acid sequence set forth in SEQ ID NO: 39; a light chain CDR2 comprising the amino acid sequence set forth in SEQ ID NO: 46; and a light chain CDR3 comprising the amino acid sequence set forth in SEQ ID NO: 53; and
  (d) a heavy chain CDR1 comprising the amino acid sequence set forth in SEQ ID NO: 20; a heavy chain CDR2 comprising the amino acid sequence set forth in SEQ ID NO: 27; a heavy chain CDR3 comprising the amino acid sequence set forth in SEQ ID NO: 34; a light chain CDR1 comprising the amino acid sequence set forth in SEQ ID NO: 41; a light chain CDR2 comprising the amino acid sequence set forth in SEQ ID NO: 48; and a light chain CDR3 comprising the amino acid sequence set forth in SEQ ID NO: 55; and
  wherein the anti-PD-1 monoclonal antibody or antigen-binding portion thereof comprises a heavy chain, which comprises CDR1, CDR2, CDR3, framework region (FR) 1, FR2, FR3, and FR4, and a light chain, which comprises CDR1, CDR2, CDR3, FR1, FR2, FR3, and FR4,
  wherein the light chains FR1, FR2, and FR3 of the anti-PD-1 monoclonal antibody or antigen-binding portion thereof comprise amino acids derived from the human $V_K$ L6 germline sequence and the light chain FR4 of the anti-PD-1 monoclonal antibody or antigen-binding portion thereof comprises an amino acid sequence derived from the human $V_K$ JK1 or JK4 germline sequence; and
  wherein the anti-PD-1 monoclonal antibody or antigen-binding portion thereof exhibits at least one property selected from:
  (i) binding to human PD-1 with a $K_D$ of $1 \times 10^{-7}$ M or less, wherein the $K_D$ is measured by surface plasmon resonance (Biacore) analysis;
  (ii) binding to human PD-1 with an on rate ($k_{on}$) of about $0.76 \times 10^5$ 1/Ms or more, wherein the on rate ($k_{on}$) is measured by surface plasmon resonance (Biacore) analysis; and
  (iii) binding to human PD-1 with an off rate ($k_{off}$) of about $4.5 \times 10^{-4}$ 1/s or less, wherein the off rate ($k_{off}$) is measured by surface plasmon resonance (Biacore) analysis.

50. The method of claim 49, wherein the light chain FR4 of the anti-PD-1 monoclonal antibody or antigen-binding portion thereof comprises an amino acid sequence derived from the human $V_K$ JK4 germline sequence.

51. The method of claim 49, wherein the light chain FR1 of the anti-PD-1 monoclonal antibody or the antigen-binding portion thereof comprises the amino acid sequence of EIVLTQSPATLSLSPGERATLSC (SEQ ID NO: 75).

52. The method of claim 50, wherein the light chain FR4 of the anti-PD-1 monoclonal antibody or the antigen-binding portion thereof comprises the amino acid sequence of FGGGTKVEIK (SEQ ID NO: 78).

53. The method of claim 44 or 47, wherein the $K_D$ is $1 \times 10^{-8}$ M or less and wherein the $K_D$ is measured by surface plasmon resonance (Biacore) analysis.

54. The method of claim 53, wherein the anti-PD-1 monoclonal antibody or the antigen-binding portion thereof binds to human PD-1 with a $K_D$ of $5 \times 10^{-9}$ M or less and wherein the $K_D$ is measured by surface plasmon resonance (Biacore) analysis.

55. The method of claim 54, wherein the $K_D$ is $1 \times 10^{-9}$ M or less, wherein the $K_D$ is measured by surface plasmon resonance (Biacore) analysis.

56. The method of claim 47, wherein the anti-PD-1 monoclonal antibody or the antigen-binding portion thereof binds to human PD-1 with an on rate ($k_{on}$) of about $2.56 \times 10^5$ 1/Ms or more and wherein the on rate ($k_{on}$) is measured by surface plasmon resonance (Biacore) analysis.

57. The method of claim 47, wherein the anti-PD-1 monoclonal antibody or the antigen-binding portion thereof binds to human PD-1 with an off rate ($k_{off}$) of about $4.5 \times 10^{-4}$ 1/s or less and wherein the off rate ($k_{off}$) is measured by surface plasmon resonance (Biacore) analysis.

58. The method of claim 1, wherein the anti-PD-1 monoclonal antibody or antigen-binding portion thereof comprises a heavy chain variable region, which comprises framework region (FR) 1, FR2, FR3, and FR4, and a light chain variable region, which comprises FR1, FR2, FR3, and FR4,
- wherein the light chain FR1 of the anti-PD-1 monoclonal antibody or antigen-binding portion thereof comprises the amino acid sequence of EIVLTQSPATLSLSPGERATLSC (SEQ ID NO: 75) or EIVLTQSPATLSLSPGERATLSC (SEQ ID NO: 75) containing one amino acid modification;
- wherein the light chain FR2 of the anti-PD-1 monoclonal antibody or the antigen-binding portion thereof comprises the amino acid sequence of WYQQKPGQAPRLLIY (SEQ ID NO: 76) or WYQQKPGQAPRLLIY (SEQ ID NO: 76) containing one amino acid modification;
- wherein the light chain FR3 of the anti-PD-1 monoclonal antibody or the antigen-binding portion thereof comprises the amino acid sequence of GIPARFSGSGSGTDFTLTISSLEPEDFAVYYC (SEQ ID NO: 77) or GIPARFSGSGSGTDFTLTISSLEPEDFAVYYC (SEQ ID NO: 77) containing one amino acid modification;
- wherein the light chain FR4 of the anti-PD-1 monoclonal antibody or the antigen-binding portion thereof comprises the amino acid sequence of FGGGTKVEIK (SEQ ID NO: 78) or FGGGTKVEIK (SEQ ID NO: 78) containing one amino acid modification;
- wherein the anti-PD-1 monoclonal antibody or antigen-binding portion thereof binds to human PD-1 with a $K_D$ of $1 \times 10^{-8}$ M or less, wherein the $K_D$ is measured by surface plasmon resonance (Biacore) analysis; and
- wherein the administration of the anti-PD-1 monoclonal antibody or antigen-binding portion thereof inhibits tumor growth in the subject.

59. The method of claim 58, wherein the anti-PD-1 monoclonal antibody or antigen-binding portion thereof binds to human PD-1 with a $K_D$ of $5 \times 10^{-8}$ M or less and wherein the $K_D$ is measured by surface plasmon resonance (Biacore) analysis.

60. The method of claim 58, wherein the anti-PD-1 monoclonal antibody or an antigen-binding portion thereof binds to human PD-1 with a $K_D$ of $5 \times 10^{-9}$ M or less and wherein the $K_D$ is measured by surface plasmon resonance (Biacore) analysis.

61. The method of claim 58, wherein the anti-PD-1 monoclonal antibody or an antigen-binding portion thereof binds to human PD-1 with a $K_D$ of $1 \times 10^{-9}$ M or less and wherein the $K_D$ is measured by surface plasmon resonance (Biacore) analysis.

62. The method of claim 58, wherein the anti-PD-1 monoclonal antibody or an antigen-binding portion thereof binds to human PD-1 with an on rate ($k_{on}$) of about $4.32 \times 10^5$ l/Ms or more and wherein the on rate ($k_{on}$) is measured by surface plasmon resonance (Biacore) analysis.

63. The method of claim 58, wherein the anti-PD-1 monoclonal antibody or an antigen-binding portion thereof binds to human PD-1 with an off rate ($k_{off}$) of about $3.15 \times 10^{-4}$ l/s or less and wherein the off rate ($k_{off}$) is measured by surface plasmon resonance (Biacore) analysis.

64. The method of claim 58, wherein the anti-PD-1 monoclonal antibody or an antigen-binding portion thereof inhibits the suppression of $CD4^+CD25^-$ T cells by regulatory T cells.

65. The method of claim 58, wherein the anti-PD-1 monoclonal antibody or an antigen-binding portion thereof enhances the antigen specific-memory response to a tumor or a pathogen.

66. The method of claim 58, wherein the anti-PD-1 monoclonal antibody or an antigen-binding portion thereof confers a persistent immunity to tumor relapse.

67. The method of claim 58, wherein the anti-PD-1 monoclonal antibody or an antigen-binding portion thereof increases activation of T cells.

68. The method of claim 58, wherein the anti-PD-1 monoclonal antibody or an antigen-binding portion thereof further comprises a heavy chain constant region which is of a human IgG1, IgG2, IgG3, or IgG4 isotype.

69. The method of claim 58, wherein the anti-PD-1 monoclonal antibody or an antigen-binding portion thereof wherein the heavy chain constant region is of a human IgG4 isotype.

70. The method of claim 58, wherein the anti-PD-1 monoclonal antibody or an antigen-binding portion thereof mediates neither ADCC activity nor CDC activity.

71. The method of claim 58, wherein the anti-PD-1 monoclonal antibody or an antigen-binding portion thereof comprises a light chain constant region which is a human kappa or lambda constant region.

72. The method of claim 58, wherein the anti-PD-1 monoclonal antibody or an antigen-binding portion thereof comprises a light chain constant region which is a human kappa constant region.

73. The method of claim 58, wherein the heavy chain FR1 of the anti-PD-1 monoclonal antibody or the antigen-binding portion thereof comprises the amino acid sequence of QVQLVESGGDVVQPGRSLRLSCAASGLTFT (SEQ ID NO: 79) or QVQLVESGGDVVQPGRSLRLSCAASGLTFT (SEQ ID NO: 79) containing one amino acid modification.

74. The method of claim 58 wherein the heavy chain FR2 of the anti-PD-1 monoclonal antibody or the antigen-binding portion thereof comprises the amino acid sequence of WVRQAPGKGLEWVA (SEQ ID NO: 80) or WVRQAPGKGLEWVA (SEQ ID NO: 80) containing one amino acid modification.

75. The method of claim 58, wherein the heavy chain FR3 of the anti-PD-1 monoclonal antibody or the antigen-binding portion thereof comprises the amino acid sequence of RFTISRDNSKNTLYLQMNNLRAEDTAVYYCAT (SEQ ID NO: 81) or RFTISRDNSKNTLYLQMNNLRAEDTAVYYCAT (SEQ ID NO: 81) containing one amino acid modification.

76. The method of claim 58, wherein the heavy chain FR4 of the anti-PD-1 monoclonal antibody or the antigen-binding portion thereof comprises the amino acid sequence of WGQGTLVTVSS (SEQ ID NO: 82) or WGQGTLVTVSS (SEQ ID NO: 82) containing one amino acid modification.

77. The method of claim 58, wherein the anti-PD-1 monoclonal antibody or the antigen-binding portion thereof is a humanized antibody.

78. The method of claim 58, wherein the anti-PD-1 monoclonal antibody or the antigen-binding-portion thereof does not substantially bind to human CD28, CTLA-4, or ICOS.

79. The method of claim 1, wherein the anti-PD-1 monoclonal antibody or the antigen-binding-portion thereof does not substantially bind to human CD28, CTLA-4, or ICOS.

* * * * *

SEQUENCE LISTING

<160> NUMBER OF SEQ ID NOS: 82

<210> SEQ ID NO 1
<211> LENGTH: 113
<212> TYPE: PRT
<213> ORGANISM: Homo sapiens

<400> SEQUENCE: 1

```
Gln Val Gln Leu Val Glu Ser Gly Gly Asp Val Val Gln Pro Gly Gly
1               5                   10                  15

Ser Leu Arg Leu Ser Cys Ala Ala Ser Gly Val Ala Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Met Tyr Tyr Cys
                85                  90                  95

Ala Arg Asn Asp Asp Tyr Trp Gly Gln Gly Thr Leu Val Thr Val Ser
                100                 105                 110

Ser
```

<210> SEQ ID NO 2
<211> LENGTH: 113
<212> TYPE: PRT
<213> ORGANISM: Homo sapiens

<400> SEQUENCE: 2

```
Gln Val Gln Leu Val Glu Ser Gly Gly Asp Val Val Gln Pro Gly Arg
1               5                   10                  15

Ser Leu Arg Leu Ser Cys Ala Ala Ser Gly Leu Thr Phe Thr Asn Tyr
            20                  25                  30

Gly Phe His Trp Val Arg Gln Ala Pro Gly Lys Gly Leu Glu Trp Val
        35                  40                  45

Ala Val Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Thr Gly Asp Asp Tyr Trp Gly Gln Gly Thr Leu Val Thr Val Ser
                100                 105                 110
```

Ser

<210> SEQ ID NO 3
<211> LENGTH: 113
<212> TYPE: PRT
<213> ORGANISM: Homo sapiens

<400> SEQUENCE: 3

Gln Val Tyr Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Leu Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Thr Ser Leu Arg Val Glu Asp Thr Ala Val Tyr Tyr Cys
                85                  90                  95

Ala Ser Asn Val Asp His Trp Gly Gln Gly Thr Leu Val Thr Val Ser
            100                 105                 110

Ser

<210> SEQ ID NO 4
<211> LENGTH: 113
<212> TYPE: PRT
<213> ORGANISM: Homo sapiens

<400> SEQUENCE: 4

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 5
<211> LENGTH: 121
<212> TYPE: PRT
<213> ORGANISM: Homo sapiens

<400> SEQUENCE: 5

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Arg Ser
                20                  25                  30

```
Ser Phe Phe Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Val Arg Asp Tyr Asp Ile Leu Thr Gly Asp Glu Asp Tyr Trp Gly
                100                 105                 110

Gln Gly Thr Leu Val Thr Val Ser Ser
            115                 120

<210> SEQ ID NO 6
<211> LENGTH: 113
<212> TYPE: PRT
<213> ORGANISM: Homo sapiens

<400> SEQUENCE: 6

Gln Val Gln Leu Val Glu Ser Gly Gly Val Val Gln Pro Gly Arg
 1               5                  10                  15

Ser Leu Arg Leu Ser Cys Thr Thr Ser Gly Ile Thr Phe Ser Ser Tyr
                 20                  25                  30

Gly Phe His Trp Val Arg Gln Ala Pro Gly Lys Gly Leu Glu Trp Val
             35                  40                  45

Ala Val Ile Trp Tyr Asp Gly Ser Lys Lys Tyr Tyr Ala Asp Ser Val
 50                  55                  60

Lys Gly Arg Phe Thr Leu Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Thr Gly Asp Asp Tyr Trp Gly Gln Gly Thr Leu Val Thr Val Ser
                100                 105                 110

Ser

<210> SEQ ID NO 7
<211> LENGTH: 121
<212> TYPE: PRT
<213> ORGANISM: Homo sapiens

<400> SEQUENCE: 7

Gln Leu Gln Leu Gln Glu Ser Gly Pro Gly Leu Val Lys Pro Ser Glu
 1               5                  10                  15

Thr Leu Ser Leu Thr Cys Ser Val Ser Gly Gly Ser Leu Ser Arg Ser
                 20                  25                  30

Ser Tyr Phe Trp Gly Trp Ile Arg Gln Pro Pro Gly Lys Gly Leu Glu
             35                  40                  45

Trp Ile Ala Ser Ile Phe Tyr Ser Gly Glu Thr Tyr Phe Asn Pro Ser
 50                  55                  60

Leu Lys Ser Arg Val Thr Ile Ser Val Asp Thr Ser Arg Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Tyr Asp Ile Leu Thr Gly Asp Glu Asp Tyr Trp Gly
                100                 105                 110

Gln Gly Thr Leu Val Thr Val Ser Ser
```

```
                115                 120

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Ile Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 9
<211> LENGTH: 107
<212> TYPE: PRT
<213> ORGANISM: Homo sapiens

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 10
<211> LENGTH: 107
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 11
<211> LENGTH: 107
<212> TYPE: PRT
<213> ORGANISM: Homo sapiens

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Asn Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Arg
                85                  90                  95

Thr Phe Gly Gln Gly Thr Lys Val Glu Ile Lys
            100                 105

<210> SEQ ID NO 13
<211> LENGTH: 107
<212> TYPE: PRT
<213> ORGANISM: Homo sapiens

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 14
<211> LENGTH: 107
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Arg
                85                  90                  95

Thr Phe Gly Gln Gly Thr Lys Val Glu Ile Lys
            100                 105

<210> SEQ ID NO 15
<211> LENGTH: 5
<212> TYPE: PRT
<213> ORGANISM: Homo sapiens

<400> SEQUENCE: 15

Asn Tyr Gly Met His
1               5

<210> SEQ ID NO 16
<211> LENGTH: 5
<212> TYPE: PRT
<213> ORGANISM: Homo sapiens

<400> SEQUENCE: 16

Asn Tyr Gly Phe His
1               5

<210> SEQ ID NO 17
<211> LENGTH: 5
<212> TYPE: PRT
<213> ORGANISM: Homo sapiens

<400> SEQUENCE: 17

Asn Tyr Gly Met His
1               5

<210> SEQ ID NO 18
<211> LENGTH: 5
<212> TYPE: PRT
<213> ORGANISM: Homo sapiens

<400> SEQUENCE: 18

Asn Ser Gly Met His
1               5

<210> SEQ ID NO 19
<211> LENGTH: 7
<212> TYPE: PRT
<213> ORGANISM: Homo sapiens

<400> SEQUENCE: 19

Arg Ser Ser Phe Phe Trp Gly
1               5

<210> SEQ ID NO 20
<211> LENGTH: 5
<212> TYPE: PRT
<213> ORGANISM: Homo sapiens

<400> SEQUENCE: 20

Ser Tyr Gly Phe His
1               5

<210> SEQ ID NO 21
<211> LENGTH: 7
<212> TYPE: PRT
<213> ORGANISM: Homo sapiens

<400> SEQUENCE: 21

Arg Ser Ser Tyr Phe Trp Gly
1               5

<210> SEQ ID NO 22
<211> LENGTH: 17
<212> TYPE: PRT
<213> ORGANISM: Homo sapiens

<400> SEQUENCE: 22

Val Ile Trp Tyr Asp Gly Ser Asn Lys Tyr Tyr Ala Asp Ser Val Lys
1               5                   10                  15

Gly

<210> SEQ ID NO 23
<211> LENGTH: 17
<212> TYPE: PRT
<213> ORGANISM: Homo sapiens

<400> SEQUENCE: 23

Val Ile Trp Tyr Asp Gly Ser Lys Lys Tyr Tyr Ala Asp Ser Val Lys
1               5                   10                  15

Gly

<210> SEQ ID NO 24
<211> LENGTH: 17
<212> TYPE: PRT
<213> ORGANISM: Homo sapiens

<400> SEQUENCE: 24

Leu Ile Trp Tyr Asp Gly Ser Asn Lys Tyr Tyr Ala Asp Ser Val Lys
1               5                   10                  15
Gly

<210> SEQ ID NO 25
<211> LENGTH: 17
<212> TYPE: PRT
<213> ORGANISM: Homo sapiens

<400> SEQUENCE: 25

Val Ile Trp Tyr Asp Gly Ser Lys Arg Tyr Tyr Ala Asp Ser Val Lys
1               5                   10                  15
Gly

<210> SEQ ID NO 26
<211> LENGTH: 16
<212> TYPE: PRT
<213> ORGANISM: Homo sapiens

<400> SEQUENCE: 26

Ser Ile Tyr Tyr Ser Gly Ser Thr Tyr Tyr Asn Pro Ser Leu Lys Ser
1               5                   10                  15

<210> SEQ ID NO 27
<211> LENGTH: 17
<212> TYPE: PRT
<213> ORGANISM: Homo sapiens

<400> SEQUENCE: 27

Val Ile Trp Tyr Asp Gly Ser Lys Lys Tyr Tyr Ala Asp Ser Val Lys
1               5                   10                  15
Gly

<210> SEQ ID NO 28
<211> LENGTH: 16
<212> TYPE: PRT
<213> ORGANISM: Homo sapiens

<400> SEQUENCE: 28

Ser Ile Phe Tyr Ser Gly Glu Thr Tyr Phe Asn Pro Ser Leu Lys Ser
1               5                   10                  15

<210> SEQ ID NO 29
<211> LENGTH: 4
<212> TYPE: PRT
<213> ORGANISM: Homo sapiens

<400> SEQUENCE: 29

Asn Asp Asp Tyr
1

<210> SEQ ID NO 30
<211> LENGTH: 4
<212> TYPE: PRT
<213> ORGANISM: Homo sapiens

<400> SEQUENCE: 30

Gly Asp Asp Tyr
1

<210> SEQ ID NO 31
<211> LENGTH: 4
<212> TYPE: PRT

<213> ORGANISM: Homo sapiens

<400> SEQUENCE: 31

Asn Val Asp His
1

<210> SEQ ID NO 32
<211> LENGTH: 4
<212> TYPE: PRT
<213> ORGANISM: Homo sapiens

<400> SEQUENCE: 32

Asn Asp Asp Tyr
1

<210> SEQ ID NO 33
<211> LENGTH: 11
<212> TYPE: PRT
<213> ORGANISM: Homo sapiens

<400> SEQUENCE: 33

Asp Tyr Asp Ile Leu Thr Gly Asp Glu Asp Tyr
1               5                   10

<210> SEQ ID NO 34
<211> LENGTH: 4
<212> TYPE: PRT
<213> ORGANISM: Homo sapiens

<400> SEQUENCE: 34

Gly Asp Asp Tyr
1

<210> SEQ ID NO 35
<211> LENGTH: 11
<212> TYPE: PRT
<213> ORGANISM: Homo sapiens

<400> SEQUENCE: 35

Asp Tyr Asp Ile Leu Thr Gly Asp Glu Asp Tyr
1               5                   10

<210> SEQ ID NO 36
<211> LENGTH: 11
<212> TYPE: PRT
<213> ORGANISM: Homo sapiens

<400> SEQUENCE: 36

Arg Ala Ser Gln Ser Val Ser Ser Tyr Leu Ala
1               5                   10

<210> SEQ ID NO 37
<211> LENGTH: 11
<212> TYPE: PRT
<213> ORGANISM: Homo sapiens

<400> SEQUENCE: 37

Arg Ala Ser Gln Ser Val Ser Ser Tyr Leu Ala
1               5                   10

<210> SEQ ID NO 38
<211> LENGTH: 11
<212> TYPE: PRT
<213> ORGANISM: Homo sapiens

```
<400> SEQUENCE: 38

Arg Ala Ser Gln Ser Val Ser Ser Tyr Leu Ala
1               5                   10

<210> SEQ ID NO 39
<211> LENGTH: 11
<212> TYPE: PRT
<213> ORGANISM: Homo sapiens

<400> SEQUENCE: 39

Arg Ala Ser Gln Ser Val Ser Ser Tyr Leu Ala
1               5                   10

<210> SEQ ID NO 40
<211> LENGTH: 11
<212> TYPE: PRT
<213> ORGANISM: Homo sapiens

<400> SEQUENCE: 40

Arg Ala Ser Gln Gly Ile Ser Ser Trp Leu Ala
1               5                   10

<210> SEQ ID NO 41
<211> LENGTH: 11
<212> TYPE: PRT
<213> ORGANISM: Homo sapiens

<400> SEQUENCE: 41

Arg Ala Ser Gln Ser Val Ser Ser Tyr Leu Ala
1               5                   10

<210> SEQ ID NO 42
<211> LENGTH: 11
<212> TYPE: PRT
<213> ORGANISM: Homo sapiens

<400> SEQUENCE: 42

Arg Ala Ser Gln Gly Ile Ser Ser Trp Leu Ala
1               5                   10

<210> SEQ ID NO 43
<211> LENGTH: 7
<212> TYPE: PRT
<213> ORGANISM: Homo sapiens

<400> SEQUENCE: 43

Asp Ala Ser Asn Arg Ala Thr
1               5

<210> SEQ ID NO 44
<211> LENGTH: 7
<212> TYPE: PRT
<213> ORGANISM: Homo sapiens

<400> SEQUENCE: 44

Asp Thr Ser Asn Arg Ala Thr
1               5

<210> SEQ ID NO 45
<211> LENGTH: 7
<212> TYPE: PRT
<213> ORGANISM: Homo sapiens

<400> SEQUENCE: 45
```

Asp Ala Ser Asn Arg Ala Thr
1               5

<210> SEQ ID NO 46
<211> LENGTH: 7
<212> TYPE: PRT
<213> ORGANISM: Homo sapiens

<400> SEQUENCE: 46

Asp Ala Ser Asn Arg Ala Thr
1               5

<210> SEQ ID NO 47
<211> LENGTH: 7
<212> TYPE: PRT
<213> ORGANISM: Homo sapiens

<400> SEQUENCE: 47

Ala Ala Ser Asn Leu Arg Ser
1               5

<210> SEQ ID NO 48
<211> LENGTH: 7
<212> TYPE: PRT
<213> ORGANISM: Homo sapiens

<400> SEQUENCE: 48

Asp Ala Ser Asn Arg Ala Thr
1               5

<210> SEQ ID NO 49
<211> LENGTH: 7
<212> TYPE: PRT
<213> ORGANISM: Homo sapiens

<400> SEQUENCE: 49

Ala Ala Ser Ser Leu Gln Ser
1               5

<210> SEQ ID NO 50
<211> LENGTH: 9
<212> TYPE: PRT
<213> ORGANISM: Homo sapiens

<400> SEQUENCE: 50

Gln Gln Arg Ser Asn Trp Pro Leu Thr
1               5

<210> SEQ ID NO 51
<211> LENGTH: 9
<212> TYPE: PRT
<213> ORGANISM: Homo sapiens

<400> SEQUENCE: 51

Gln Gln Arg Ser Asn Trp Pro Leu Thr
1               5

<210> SEQ ID NO 52
<211> LENGTH: 9
<212> TYPE: PRT
<213> ORGANISM: Homo sapiens

<400> SEQUENCE: 52

Gln Gln Ser Ser Asn Trp Pro Arg Thr
1               5

<210> SEQ ID NO 53
<211> LENGTH: 9
<212> TYPE: PRT
<213> ORGANISM: Homo sapiens

<400> SEQUENCE: 53

Gln Gln Ser Ser Asn Trp Pro Arg Thr
1               5

<210> SEQ ID NO 54
<211> LENGTH: 9
<212> TYPE: PRT
<213> ORGANISM: Homo sapiens

<400> SEQUENCE: 54

Gln Gln Tyr Tyr Ser Tyr Pro Arg Thr
1               5

<210> SEQ ID NO 55
<211> LENGTH: 9
<212> TYPE: PRT
<213> ORGANISM: Homo sapiens

<400> SEQUENCE: 55

Gln Gln Arg Ser Asn Trp Pro Leu Thr
1               5

<210> SEQ ID NO 56
<211> LENGTH: 9
<212> TYPE: PRT
<213> ORGANISM: Homo sapiens

<400> SEQUENCE: 56

Gln Gln Tyr Tyr Ser Tyr Pro Arg Thr
1               5

<210> SEQ ID NO 57
<211> LENGTH: 339
<212> TYPE: DNA
<213> ORGANISM: Homo sapiens
<220> FEATURE:
<221> NAME/KEY: CDS
<222> LOCATION: (1)..(339)

<400> SEQUENCE: 57

| cag gtg cag ctg gtg gag tct ggg gga gac gtg gtc cag cct ggg ggg | 48 |
| Gln Val Gln Leu Val Glu Ser Gly Gly Asp Val Val Gln Pro Gly Gly | |
| 1               5                   10                  15      | |

| tcc ctg aga ctc tcc tgt gca gcg tct gga gtc gcc ttc agt aac tat | 96 |
| Ser Leu Arg Leu Ser Cys Ala Ala Ser Gly Val Ala Phe Ser Asn Tyr | |
|             20                  25                  30          | |

| ggc atg cac tgg gtc cgc cag gct ccc ggc aag ggg ctg gag tgg gtg | 144 |
| Gly Met His Trp Val Arg Gln Ala Pro Gly Lys Gly Leu Glu Trp Val | |
|         35                  40                  45              | |

| gca gtt atc tgg tat gat gga agt aat aaa tac tat gca gac tcc gtg | 192 |
| Ala Val Ile Trp Tyr Asp Gly Ser Asn Lys Tyr Tyr Ala Asp Ser Val | |
|     50                  55                  60                  | |

| aag ggc cgg ttc acc atc tcc aga gac aat tcc aag aac atg ctc tat | 240 |
| Lys Gly Arg Phe Thr Ile Ser Arg Asp Asn Ser Lys Asn Met Leu Tyr | |
| 65                  70                  75                  80  | |

| ctg caa atg aac agc ctg aga gcc gag gac acg gct atg tat tac tgt | 288 |
| Leu Gln Met Asn Ser Leu Arg Ala Glu Asp Thr Ala Met Tyr Tyr Cys | |
|                 85                  90                  95      | |

```
gcg agg aac gat gac tac tgg ggc cag gga acc ctg gtc acc gtc tcc        336
Ala Arg Asn Asp Asp Tyr Trp Gly Gln Gly Thr Leu Val Thr Val Ser
            100                 105                 110 tca                                                                    339
Ser

<210> SEQ ID NO 58
<211> LENGTH: 339
<212> TYPE: DNA
<213> ORGANISM: Homo sapiens
<220> FEATURE:
<221> NAME/KEY: CDS
<222> LOCATION: (1)..(339)

<400> SEQUENCE: 58 cag gtg cag ctg gtg gaa tct ggg gga gac gtg gtc cag cct ggg agg         48
Gln Val Gln Leu Val Glu Ser Gly Gly Asp Val Val Gln Pro Gly Arg
1               5                   10                  15 tcc ctg aga ctc tcc tgt gca gcg tct gga tta acc ttc act aac tat         96
Ser Leu Arg Leu Ser Cys Ala Ala Ser Gly Leu Thr Phe Thr Asn Tyr
                20                  25                  30 ggc ttc cac tgg gtc cgc cag gct cca ggc aag ggg ctg gag tgg gtg        144
Gly Phe His Trp Val Arg Gln Ala Pro Gly Lys Gly Leu Glu Trp Val
            35                  40                  45 gct gtt ata tgg tat gat gga agt aag aaa tat tat gca gac tcc gtg        192
Ala Val Ile Trp Tyr Asp Gly Ser Lys Lys Tyr Tyr Ala Asp Ser Val
50                  55                  60 aag ggc cga ttc acc atc tcc aga gac aat tcc aag aac acg ctg tat        240
Lys Gly Arg Phe Thr Ile Ser Arg Asp Asn Ser Lys Asn Thr Leu Tyr
65                  70                  75                  80 ctg caa atg aac aac ctg aga gcc gag gac acg gct gtg tat tac tgt        288
Leu Gln Met Asn Asn Leu Arg Ala Glu Asp Thr Ala Val Tyr Tyr Cys
                85                  90                  95 gcg act ggg gat gac tac tgg ggc cag gga acc ctg gtc acc gtc tcc        336
Ala Thr Gly Asp Asp Tyr Trp Gly Gln Gly Thr Leu Val Thr Val Ser
            100                 105                 110 tca                                                                    339
Ser

<210> SEQ ID NO 59
<211> LENGTH: 339
<212> TYPE: DNA
<213> ORGANISM: Homo sapiens
<220> FEATURE:
<221> NAME/KEY: CDS
<222> LOCATION: (1)..(339)

<400> SEQUENCE: 59 cag gtg tac ttg gta gag tct ggg gga ggc gtg gtc cag cct ggg agg         48
Gln Val Tyr Leu Val Glu Ser Gly Gly Gly Val Val Gln Pro Gly Arg
1               5                   10                  15 tcc ctg aga ctc tcc tgt gca gcg tct gga ttc acc ttc agt aac tat         96
Ser Leu Arg Leu Ser Cys Ala Ala Ser Gly Phe Thr Phe Ser Asn Tyr
                20                  25                  30 ggc atg cac tgg gtc cgc cag gct cca ggc aag ggg ctg gag tgg gtg        144
Gly Met His Trp Val Arg Gln Ala Pro Gly Lys Gly Leu Glu Trp Val
            35                  40                  45 gca ctt ata tgg tat gat gga agt aat aaa tac tat gca gac tcc gtg        192
Ala Leu Ile Trp Tyr Asp Gly Ser Asn Lys Tyr Tyr Ala Asp Ser Val
50                  55                  60 aag ggc cga ttc acc atc tcc aga gac aat tcc aag aac acg ctg tat        240
Lys Gly Arg Phe Thr Ile Ser Arg Asp Asn Ser Lys Asn Thr Leu Tyr
```

```
                65                  70                  75                  80
ctg caa atg acc agt ctg aga gtc gag gac acg gct gtg tat tat tgt     288
Leu Gln Met Thr Ser Leu Arg Val Glu Asp Thr Ala Val Tyr Tyr Cys
                    85                  90                  95 gcg agc aac gtt gac cat tgg ggc cag gga acc ctg gtc acc gtc tcc     336
Ala Ser Asn Val Asp His Trp Gly Gln Gly Thr Leu Val Thr Val Ser
                100                 105                 110 tca                                                                 339
Ser

<210> SEQ ID NO 60
<211> LENGTH: 339
<212> TYPE: DNA
<213> ORGANISM: Homo sapiens
<220> FEATURE:
<221> NAME/KEY: CDS
<222> LOCATION: (1)..(339)

<400> SEQUENCE: 60 cag gtg cag ctg gtg gag tct ggg gga ggc gtg gtc cag cct ggg agg     48
Gln Val Gln Leu Val Glu Ser Gly Gly Gly Val Val Gln Pro Gly Arg
1               5                   10                  15 tcc ctg aga ctc gac tgt aaa gcg tct gga atc acc ttc agt aac tct     96
Ser Leu Arg Leu Asp Cys Lys Ala Ser Gly Ile Thr Phe Ser Asn Ser
                20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
            35                  40                  45 gca gtt att tgg tat gat gga agt aaa aga tac tat gca gac tcc gtg     192
Ala Val Ile Trp Tyr Asp Gly Ser Lys Arg Tyr Tyr Ala Asp Ser Val
        50                  55                  60 aag ggc cga ttc acc atc tcc aga gac aat tcc aag aac acg ctg ttt     240
Lys Gly Arg Phe Thr Ile Ser Arg Asp Asn Ser Lys Asn Thr Leu Phe
65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                    85                  90                  95 gcg aca aac gac gac tac tgg ggc cag gga acc ctg gtc acc gtc tcc     336
Ala Thr Asn Asp Asp Tyr Trp Gly Gln Gly Thr Leu Val Thr Val Ser
                100                 105                 110 tca                                                                 339
Ser

<210> SEQ ID NO 61
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 61 cag ctg cag ctg cag gag tcg ggc cca gga ctg gtg aag cct tcg gag     48
Gln Leu Gln Leu Gln Glu Ser Gly Pro Gly Leu Val Lys Pro Ser Glu
1               5                   10                  15 acc ctg tcc ctc acc tgc act gtc tct ggt ggc tcc ctc agc agg agt     96
Thr Leu Ser Leu Thr Cys Thr Val Ser Gly Gly Ser Leu Ser Arg Ser
                20                  25                  30 agt ttc ttc tgg ggc tgg atc cgt cag ccc cca ggg aag gga ctg gag     144
Ser Phe Phe Trp Gly Trp Ile Arg Gln Pro Pro Gly Lys Gly Leu Glu
            35                  40                  45 tgg att ggg agt atc tat tat agt ggg agc acc tac tac aac ccg tcc     192
Trp Ile Gly Ser Ile Tyr Tyr Ser Gly Ser Thr Tyr Tyr Asn Pro Ser
```

```
Trp Ile Gly Ser Ile Tyr Tyr Ser Gly Ser Thr Tyr Tyr Asn Pro Ser
     50                  55                  60 ctc aag agt cga gtc acc ata tcc gta gac acg tcc aag aac cag ttc      240
Leu Lys Ser Arg Val Thr Ile Ser Val Asp Thr Ser Lys Asn Gln Phe
 65                  70                  75                  80 tcc ctg aag ctg agc tct gtg acc gcc gca gac acg gct gtg tat tac      288
Ser Leu Lys Leu Ser Ser Val Thr Ala Ala Asp Thr Ala Val Tyr Tyr
                 85                  90                  95 tgt gtg aga gat tac gat att ttg act ggc gac gag gac tac tgg ggc      336
Cys Val Arg Asp Tyr Asp Ile Leu Thr Gly Asp Glu Asp Tyr Trp Gly
            100                 105                 110 cag gga acc ctg gtc acc gtg tcc tca                                   363
Gln Gly Thr Leu Val Thr Val Ser Ser
        115                 120

<210> SEQ ID NO 62
<211> LENGTH: 339
<212> TYPE: DNA
<213> ORGANISM: Homo sapiens
<220> FEATURE:
<221> NAME/KEY: CDS
<222> LOCATION: (1)..(339)

<400> SEQUENCE: 62 cag gtg cag ctg gtg gag tct ggg gga ggc gtg gtc cag cct ggg agg       48
Gln Val Gln Leu Val Glu Ser Gly Gly Gly Val Val Gln Pro Gly Arg
  1               5                  10                  15 tcc ctg aga ctc tcc tgt aca acg tct gga atc acc ttc agt agc tat       96
Ser Leu Arg Leu Ser Cys Thr Thr Ser Gly Ile Thr Phe Ser Ser Tyr
             20                  25                  30 ggc ttt cac tgg gtc cgc cag gct cca ggc aag ggg ctg gag tgg gtg      144
Gly Phe His Trp Val Arg Gln Ala Pro Gly Lys Gly Leu Glu Trp Val
         35                  40                  45 gca gta ata tgg tat gat gga agt aaa aaa tac tat gca gac tcc gtg      192
Ala Val Ile Trp Tyr Asp Gly Ser Lys Lys Tyr Tyr Ala Asp Ser Val
     50                  55                  60 aag ggc cga ttc acc ctc tcc aga gac gat tcc aag aac acg ctg tat      240
Lys Gly Arg Phe Thr Leu Ser Arg Asp Asp Ser Lys Asn Thr Leu Tyr
 65                  70                  75                  80 ctg caa atg aac agc ctg aga gcc gag gac acg gct gtg tat tac tgt      288
Leu Gln Met Asn Ser Leu Arg Ala Glu Asp Thr Ala Val Tyr Tyr Cys
                 85                  90                  95 gtt act ggg gat gac tac tgg ggc cag gga acc ctg gtc acc gtc tcc      336
Val Thr Gly Asp Asp Tyr Trp Gly Gln Gly Thr Leu Val Thr Val Ser
            100                 105                 110 tca                                                                   339
Ser

<210> SEQ ID NO 63
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 63 cag ctg cag ctg cag gag tcg ggc cca gga ctg gtg aag cct tcg gag       48
Gln Leu Gln Leu Gln Glu Ser Gly Pro Gly Leu Val Lys Pro Ser Glu
  1               5                  10                  15 acc ctg tcc ctc acc tgc tct gtc tct ggt ggc tcc ctc agc agg agt       96
Thr Leu Ser Leu Thr Cys Ser Val Ser Gly Gly Ser Leu Ser Arg Ser
             20                  25                  30
```

```
agt tac ttc tgg ggc tgg atc cgc cag ccc cca ggg aag ggg ctg gag        144
Ser Tyr Phe Trp Gly Trp Ile Arg Gln Pro Pro Gly Lys Gly Leu Glu
        35                  40                  45 tgg att gcg agt atc ttt tat agt ggg gaa acc tac ttc aat ccg tcc        192
Trp Ile Ala Ser Ile Phe Tyr Ser Gly Glu Thr Tyr Phe Asn Pro Ser
 50                  55                  60 ctc aag agt cga gtc acc ata tcc gta gac acg tcc agg aac cag ttc        240
Leu Lys Ser Arg Val Thr Ile Ser Val Asp Thr Ser Arg Asn Gln Phe
65                  70                  75                  80 tcc ctg aag ctg agc tct gtg acc gcc gca gac acg gct gtg tat tac        288
Ser Leu Lys Leu Ser Ser Val Thr Ala Ala Asp Thr Ala Val Tyr Tyr
             85                  90                  95 tgt gcg aga gat tac gat att ttg act ggc gac gag gac tac tgg ggc        336
Cys Ala Arg Asp Tyr Asp Ile Leu Thr Gly Asp Glu Asp Tyr Trp Gly
            100                 105                 110 cag gga acc ctg gtc acc gtc tcc tca                                    363
Gln Gly Thr Leu Val Thr Val Ser Ser
            115                 120

<210> SEQ ID NO 64
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 64 gaa att gtg ttg aca cag tct cca gcc acc ctg tct ttg tct cca ggg         48
Glu Ile Val Leu Thr Gln Ser Pro Ala Thr Leu Ser Leu Ser Pro Gly
1               5                  10                  15 gaa aga gcc acc ctc tcc tgc agg gcc agt cag agt gtt agc agc tac         96
Glu Arg Ala Thr Leu Ser Cys Arg Ala Ser Gln Ser Val Ser Ser Tyr
             20                  25                  30 tta gcc tgg tac caa cag aaa cct ggc cag gct ccc agg ctc atc atc        144
Leu Ala Trp Tyr Gln Gln Lys Pro Gly Gln Ala Pro Arg Leu Ile Ile
        35                  40                  45 tat gat gca tcc aac agg gcc act ggc atc cca gcc agg ttc agt ggc        192
Tyr Asp Ala Ser Asn Arg Ala Thr Gly Ile Pro Ala Arg Phe Ser Gly
 50                  55                  60 agt ggg tct ggg aca gac ttc act ctc acc atc agc agc cta gag cct        240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg cct ctc        288
Glu Asp Phe Ala Val Tyr Tyr Cys Gln Gln Arg Ser Asn Trp Pro Leu
             85                  90                  95 act ttc ggc gga ggg acc aag gtg gag atc aaa                            321
Thr Phe Gly Gly Gly Thr Lys Val Glu Ile Lys
            100                 105

<210> SEQ ID NO 65
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 65 gaa att gtg ttg aca cag tct cca gcc acc ctg tct ttg tct cca ggg         48
Glu Ile Val Leu Thr Gln Ser Pro Ala Thr Leu Ser Leu Ser Pro Gly
1               5                  10                  15
```

| | | | | | | | | | | | | | | | | |
|---|---|---|---|---|---|---|---|---|---|---|---|---|---|---|---|---|
| gaa | aga | gcc | acc | ctg | tcc | tgc | agg | gcc | agt | cag | agt | gtt | agc | agc | tac | 96 |
| Glu | Arg | Ala | Thr | Leu | Ser | Cys | Arg | Ala | Ser | Gln | Ser | Val | Ser | Ser | Tyr | |
| | | | 20 | | | | | 25 | | | | | 30 | | | |
| tta | gcc | tgg | tac | caa | cag | aaa | cct | ggc | cag | gct | ccc | agg | ctc | ctc | atc | 144 |
| Leu | Ala | Trp | Tyr | Gln | Gln | Lys | Pro | Gly | Gln | Ala | Pro | Arg | Leu | Leu | Ile | |
| | | 35 | | | | | 40 | | | | | 45 | | | | |
| tat | gat | aca | tcc | aac | agg | gcc | act | ggc | atc | cca | gcc | agg | ttc | agt | ggc | 192 |
| Tyr | Asp | Thr | Ser | Asn | Arg | Ala | Thr | Gly | Ile | Pro | Ala | Arg | Phe | Ser | Gly | |
| | 50 | | | | | 55 | | | | | 60 | | | | | |
| agt | ggg | tct | ggg | aca | gac | ttc | act | ctc | acc | atc | agc | agc | cta | gag | cct | 240 |
| Ser | Gly | Ser | Gly | Thr | Asp | Phe | Thr | Leu | Thr | Ile | Ser | Ser | Leu | Glu | Pro | |
| 65 | | | | | 70 | | | | | 75 | | | | | 80 | |
| gaa | gat | ttt | gca | gtt | tat | tac | tgt | cag | cag | cgt | agc | aac | tgg | ccg | ctc | 288 |
| Glu | Asp | Phe | Ala | Val | Tyr | Tyr | Cys | Gln | Gln | Arg | Ser | Asn | Trp | Pro | Leu | |
| | | | 85 | | | | | 90 | | | | | 95 | | | |
| act | ttc | ggc | gga | ggg | acc | aag | gtg | gag | atc | aaa | | | | | | 321 |
| Thr | Phe | Gly | Gly | Gly | Thr | Lys | Val | Glu | Ile | Lys | | | | | | |
| | | 100 | | | | | 105 | | | | | | | | | |

<210> SEQ ID NO 66
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 66

| | | | | | | | | | | | | | | | | |
|---|---|---|---|---|---|---|---|---|---|---|---|---|---|---|---|---|
| gaa | att | gtg | ttg | aca | cag | tct | cca | gcc | acc | ctg | tct | ttg | tct | cca | ggg | 48 |
| Glu | Ile | Val | Leu | Thr | Gln | Ser | Pro | Ala | Thr | Leu | Ser | Leu | Ser | Pro | Gly | |
| 1 | | | | 5 | | | | | 10 | | | | | 15 | | |
| gaa | aga | gcc | acc | ctc | tcc | tgc | agg | gcc | agt | cag | agt | gtt | agt | agt | tac | 96 |
| Glu | Arg | Ala | Thr | Leu | Ser | Cys | Arg | Ala | Ser | Gln | Ser | Val | Ser | Ser | Tyr | |
| | | | 20 | | | | | 25 | | | | | 30 | | | |
| tta | gcc | tgg | tac | caa | cag | aaa | cct | ggc | cag | gct | ccc | agg | ctc | ctc | atc | 144 |
| Leu | Ala | Trp | Tyr | Gln | Gln | Lys | Pro | Gly | Gln | Ala | Pro | Arg | Leu | Leu | Ile | |
| | | 35 | | | | | 40 | | | | | 45 | | | | |
| tat | gat | gca | tcc | aac | agg | gcc | act | ggc | atc | cca | gcc | agg | ttc | agt | ggc | 192 |
| Tyr | Asp | Ala | Ser | Asn | Arg | Ala | Thr | Gly | Ile | Pro | Ala | Arg | Phe | Ser | Gly | |
| | 50 | | | | | 55 | | | | | 60 | | | | | |
| agt | ggg | tct | ggg | aca | gac | ttc | act | ctc | acc | atc | agc | agc | cta | gag | cct | 240 |
| Ser | Gly | Ser | Gly | Thr | Asp | Phe | Thr | Leu | Thr | Ile | Ser | Ser | Leu | Glu | Pro | |
| 65 | | | | | 70 | | | | | 75 | | | | | 80 | |
| gaa | gat | ttt | gca | gtt | tat | tac | tgt | cag | cag | agt | agc | aac | tgg | cct | cgg | 288 |
| Glu | Asp | Phe | Ala | Val | Tyr | Tyr | Cys | Gln | Gln | Ser | Ser | Asn | Trp | Pro | Arg | |
| | | | 85 | | | | | 90 | | | | | 95 | | | |
| acg | ttc | ggc | caa | ggg | acc | aag | gtg | gaa | atc | aaa | | | | | | 321 |
| Thr | Phe | Gly | Gln | Gly | Thr | Lys | Val | Glu | Ile | Lys | | | | | | |
| | | 100 | | | | | 105 | | | | | | | | | |

<210> SEQ ID NO 67
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 67

| | | | | | | | | | | | | | | | | |
|---|---|---|---|---|---|---|---|---|---|---|---|---|---|---|---|---|
| gaa | att | gtg | ttg | aca | cag | tct | cca | gcc | acc | ctg | tct | ttg | tct | cca | ggg | 48 |
| Glu | Ile | Val | Leu | Thr | Gln | Ser | Pro | Ala | Thr | Leu | Ser | Leu | Ser | Pro | Gly | |
| 1 | | | | 5 | | | | | 10 | | | | | 15 | | |
| gaa | aga | gcc | acc | ctc | tcc | tgc | agg | gcc | agt | cag | agt | gtt | agt | agt | tac | 96 |

```
Glu Arg Ala Thr Leu Ser Cys Arg Ala Ser Gln Ser Val Ser Ser Tyr
             20                  25                  30 tta gcc tgg tac caa cag aaa cct ggc cag gct ccc agg ctc ctc atc        144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc        192
Tyr Asp Ala Ser Asn Arg Ala Thr Gly Ile Pro Ala Arg Phe Ser Gly
 50                  55                  60 agt ggg tct ggg aca gac ttc act ctc acc atc agc agc cta gag cct        240
Ser Gly Ser Gly Thr Asp Phe Thr Leu Thr Ile Ser Ser Leu Glu Pro
 65                  70                  75                  80 gaa gat ttt gca gtt tat tac tgt cag cag agt agc aac tgg cct cgg        288
Glu Asp Phe Ala Val Tyr Tyr Cys Gln Gln Ser Ser Asn Trp Pro Arg
                 85                  90                  95 acg ttc ggc caa ggg acc aag gtg gaa atc aaa                            321
Thr Phe Gly Gln Gly Thr Lys Val Glu Ile Lys
            100                 105

<210> SEQ ID NO 68
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 68 gac atc cag atg acc cag tct cca tcc tca ctg tct gca tct gtg gga         48
Asp Ile Gln Met Thr Gln Ser Pro Ser Ser Leu Ser Ala Ser Val Gly
 1               5                  10                  15 gac aga gtc tcc atc act tgt cgg gcg agt cag ggt att agc agc tgg         96
Asp Arg Val Ser Ile Thr Cys Arg Ala Ser Gln Gly Ile Ser Ser Trp
             20                  25                  30 tta gcc tgg tat cag cag aaa cca gag aaa gcc cct aag tcc ctg atc        144
Leu Ala Trp Tyr Gln Gln Lys Pro Glu Lys Ala Pro Lys Ser Leu Ile
         35                  40                  45 tat gct gca tcc aat tta cga agt ggg gtc cca tca agg ttc agc ggc        192
Tyr Ala Ala Ser Asn Leu Arg Ser Gly Val Pro Ser Arg Phe Ser Gly
 50                  55                  60 agt gga tct ggg aca gat ttc act ctc acc atc agc agc ctg cag cct        240
Ser Gly Ser Gly Thr Asp Phe Thr Leu Thr Ile Ser Ser Leu Gln Pro
 65                  70                  75                  80 gaa gat ttt gca act tat tac tgc caa cag tat tat agt tac cct agg        288
Glu Asp Phe Ala Thr Tyr Tyr Cys Gln Gln Tyr Tyr Ser Tyr Pro Arg
                 85                  90                  95 acg ttc ggc caa ggg acc aag gtg gaa atc aaa                            321
Thr Phe Gly Gln Gly Thr Lys Val Glu Ile Lys
            100                 105

<210> SEQ ID NO 69
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 69 gaa att gtg ttg aca cag tct cca gcc acc ctg tct ttg tct cca ggg         48
Glu Ile Val Leu Thr Gln Ser Pro Ala Thr Leu Ser Leu Ser Pro Gly
 1               5                  10                  15 gaa aga gcc acc ctc tcc tgc agg gcc agt cag agt gtt agc agc tac         96
Glu Arg Ala Thr Leu Ser Cys Arg Ala Ser Gln Ser Val Ser Ser Tyr
```

```
tta gcc tgg tac caa cag aaa cct ggc cag gct ccc agg ctc ctc atc    144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc    192
Tyr Asp Ala Ser Asn Arg Ala Thr Gly Ile Pro Ala Arg Phe Ser Gly
 50                  55                  60 agt ggg tct ggg aca gac ttc act ctc acc atc agc agc cta gag cct    240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg cct ctc    288
Glu Asp Phe Ala Val Tyr Tyr Cys Gln Gln Arg Ser Asn Trp Pro Leu
                 85                  90                  95 act ttc ggc gga ggg acc aag gtg gag atc aaa                        321
Thr Phe Gly Gly Gly Thr Lys Val Glu Ile Lys
            100                 105

<210> SEQ ID NO 70
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 70 gac atc cag atg acc cag tct cca tcc tca ctg tct gca tct gta gga     48
Asp Ile Gln Met Thr Gln Ser Pro Ser Ser Leu Ser Ala Ser Val Gly
1               5                   10                  15 gac aga gtc acc atc act tgt cgg gcg agt cag ggt att agc agc tgg     96
Asp Arg Val Thr Ile Thr Cys Arg Ala Ser Gln Gly Ile Ser Ser Trp
            20                  25                  30 tta gcc tgg tat cag cag aaa cca gag aaa gcc cct aag tcc ctg atc    144
Leu Ala Trp Tyr Gln Gln Lys Pro Glu Lys Ala Pro Lys Ser Leu Ile
        35                  40                  45 tat gct gca tcc agt ttg caa agt ggg gtc cca tca agg ttc agc ggc    192
Tyr Ala Ala Ser Ser Leu Gln Ser Gly Val Pro Ser Arg Phe Ser Gly
 50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
65                  70                  75                  80 gaa gat ttt gca act tat tac tgc caa cag tat tat agt tac cct agg    288
Glu Asp Phe Ala Thr Tyr Tyr Cys Gln Gln Tyr Tyr Ser Tyr Pro Arg
                 85                  90                  95 acg ttc ggc caa ggg acc aag gtg gaa atc aaa                        321
Thr Phe Gly Gln Gly Thr Lys Val Glu Ile Lys
            100                 105

<210> SEQ ID NO 71
<211> LENGTH: 98
<212> TYPE: PRT
<213> ORGANISM: Homo sapiens

<400> SEQUENCE: 71

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg
```

<210> SEQ ID NO 72
<211> LENGTH: 95
<212> TYPE: PRT
<213> ORGANISM: Homo sapiens

<400> SEQUENCE: 72

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Ile Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro
                 85                  90                  95
```

<210> SEQ ID NO 73
<211> LENGTH: 99
<212> TYPE: PRT
<213> ORGANISM: Homo sapiens

<400> SEQUENCE: 73

```
Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Ser
                 20                  25                  30

Ser Tyr Tyr Trp Gly Trp Ile Arg Gln Pro Pro Gly Lys Gly Leu Glu
             35                  40                  45

Trp Ile Gly Ser Ile Tyr Tyr Ser Gly Ser Thr Tyr Tyr Asn Pro Ser
         50                  55                  60

Leu Lys Ser Arg Val Thr Ile Ser Val Asp Thr Ser Lys Asn His Phe
 65                  70                  75                  80

Ser Leu Lys Leu Ser Ser Val Thr Ala Ala Asp Thr Ala Val Tyr Tyr
                 85                  90                  95

Cys Ala Arg
```

<210> SEQ ID NO 74
<211> LENGTH: 95
<212> TYPE: PRT
<213> ORGANISM: Homo sapiens

<400> SEQUENCE: 74

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
```

```
                35                  40                  45
Tyr Ala Ala Ser Ser Leu Gln Ser Gly Val Pro Ser Arg Phe Ser Gly
            50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Asn Ser Tyr Pro
                85                  90                  95
```

<210> SEQ ID NO 75
<211> LENGTH: 23
<212> TYPE: PRT
<213> ORGANISM: Homo sapiens

<400> SEQUENCE: 75

```
Glu Ile Val Leu Thr Gln Ser Pro Ala Thr Leu Ser Leu Ser Pro Gly
 1               5                  10                  15
Glu Arg Ala Thr Leu Ser Cys
                20
```

<210> SEQ ID NO 76
<211> LENGTH: 15
<212> TYPE: PRT
<213> ORGANISM: Homo sapiens

<400> SEQUENCE: 76

```
Trp Tyr Gln Gln Lys Pro Gly Gln Ala Pro Arg Leu Leu Ile Tyr
 1               5                  10                  15
```

<210> SEQ ID NO 77
<211> LENGTH: 32
<212> TYPE: PRT
<213> ORGANISM: Homo sapiens

<400> SEQUENCE: 77

```
Gly Ile Pro Ala Arg Phe Ser Gly Ser Gly Ser Gly Thr Asp Phe Thr
 1               5                  10                  15
Leu Thr Ile Ser Ser Leu Glu Pro Glu Asp Phe Ala Val Tyr Tyr Cys
                20                  25                  30
```

<210> SEQ ID NO 78
<211> LENGTH: 10
<212> TYPE: PRT
<213> ORGANISM: Homo sapiens

<400> SEQUENCE: 78

```
Phe Gly Gly Gly Thr Lys Val Glu Ile Lys
 1               5                  10
```

<210> SEQ ID NO 79
<211> LENGTH: 30
<212> TYPE: PRT
<213> ORGANISM: Homo sapiens

<400> SEQUENCE: 79

```
Gln Val Gln Leu Val Glu Ser Gly Gly Asp Val Val Gln Pro Gly Arg
 1               5                  10                  15
Ser Leu Arg Leu Ser Cys Ala Ala Ser Gly Leu Thr Phe Thr
                20                  25                  30
```

<210> SEQ ID NO 80
<211> LENGTH: 14
<212> TYPE: PRT

```
<213> ORGANISM: Homo sapiens

<400> SEQUENCE: 80

Trp Val Arg Gln Ala Pro Gly Lys Gly Leu Glu Trp Val Ala
1               5                   10

<210> SEQ ID NO 81
<211> LENGTH: 32
<212> TYPE: PRT
<213> ORGANISM: Homo sapiens

<400> SEQUENCE: 81

Arg Phe Thr Ile Ser Arg Asp Asn Ser Lys Asn Thr Leu Tyr Leu Gln
1               5                   10                  15

Met Asn Asn Leu Arg Ala Glu Asp Thr Ala Val Tyr Tyr Cys Ala Thr
                20                  25                  30

<210> SEQ ID NO 82
<211> LENGTH: 11
<212> TYPE: PRT
<213> ORGANISM: Homo sapiens

<400> SEQUENCE: 82

Trp Gly Gln Gly Thr Leu Val Thr Val Ser Ser
1               5                   10
```